United States Patent
Gregory et al.

(10) Patent No.: US 9,976,165 B2
(45) Date of Patent: May 22, 2018

(54) METHODS FOR INCREASING MOLECULAR DIVERSITY OF POLYKETIDES AND NON-RIBOSOMAL PROTEINS

(71) Applicant: Isomerase Therapeutics Limited, Cambridge (GB)

(72) Inventors: Matthew Alan Gregory, Cambridge (GB); Steven Gary Kendrew, Cambridge (GB); Steven James Moss, Cambridge (GB); Barrie Wilkinson, Cambridge (GB)

(73) Assignee: ISOMERASE THERAPEUTICS, LTD., Cambridge (GB)

( * ) Notice: Subject to any disclaimer, the term of this patent is extended or adjusted under 35 U.S.C. 154(b) by 1 day.

(21) Appl. No.: 14/903,190

(22) PCT Filed: Jul. 9, 2014

(86) PCT No.: PCT/GB2014/052094
§ 371 (c)(1),
(2) Date: Jan. 6, 2016

(87) PCT Pub. No.: WO2015/004458
PCT Pub. Date: Jan. 15, 2015

(65) Prior Publication Data
US 2017/0101659 A1    Apr. 13, 2017

(30) Foreign Application Priority Data
Jul. 9, 2013  (GB) .................................. 1312318.7

(51) Int. Cl.
| | |
|---|---|
| *C12P 21/02* | (2006.01) |
| *C12P 19/60* | (2006.01) |
| *C12N 15/10* | (2006.01) |
| *C12P 17/08* | (2006.01) |
| *C12P 17/06* | (2006.01) |
| *C12P 17/18* | (2006.01) |
| *C12P 19/62* | (2006.01) |
| *C12P 17/16* | (2006.01) |
| *C12P 17/10* | (2006.01) |
| *C12P 17/12* | (2006.01) |
| *C12N 9/10* | (2006.01) |
| *C12N 15/31* | (2006.01) |
| *C12N 15/52* | (2006.01) |
| *C12N 15/63* | (2006.01) |
| *C40B 10/00* | (2006.01) |
| *C40B 20/00* | (2006.01) |
| *C40B 30/08* | (2006.01) |
| *C40B 40/00* | (2006.01) |
| *C40B 40/02* | (2006.01) |

(52) U.S. Cl.
CPC .......... *C12P 21/02* (2013.01); *C12N 9/1029* (2013.01); *C12N 15/1082* (2013.01); *C12P 17/06* (2013.01); *C12P 17/08* (2013.01); *C12P 17/10* (2013.01); *C12P 17/12* (2013.01); *C12P 17/162* (2013.01); *C12P 17/181* (2013.01); *C12P 17/182* (2013.01); *C12P 17/188* (2013.01); *C12P 17/189* (2013.01); *C12P 19/60* (2013.01); *C12P 19/62* (2013.01); *C12Y 203/01* (2013.01)

(58) Field of Classification Search
None
See application file for complete search history.

(56) References Cited

U.S. PATENT DOCUMENTS

| | | | | |
|---|---|---|---|---|
| 5,962,290 | A * | 10/1999 | Khosla ................ | C07D 309/36 435/183 |
| 6,558,942 | B1 * | 5/2003 | Khosla ................ | C07D 309/36 435/253.5 |

FOREIGN PATENT DOCUMENTS

| | | |
|---|---|---|
| WO | 98/27203 | 6/1998 |
| WO | 98/49315 | 11/1998 |
| WO | 00/09109 | 2/2000 |
| WO | 01/34816 | 5/2001 |
| WO | 2004/007709 | 1/2004 |
| WO | 2006/016167 | 2/2006 |
| WO | 2015/004455 | 1/2015 |

OTHER PUBLICATIONS

Ayuso-Sacido et al., "New PCR Primers for the Screening of NRPS and PKS-I Systems in Actinomycetes: Detection and Distribution of These Biosynthetic Gene Sequences in Major Taxonomic Groups" 49 Microbial Ecology 10-24 (Dec. 21, 2004).*
International Search Report PCT/GB2014/052094 (dated Mar. 4, 2015).*
Chemieret al., Evolution of Efficient Modular Polyketide Synthases by Homologous Recombination, J Am Chem Soc. 2015, 137(33):10603-9.
Chung et al., Deletion of rapQONML from the rapamycin gene cluster of *Streptomyces hygroscopicus* gives production of the 16-O-desmethyl-27-desmethoxy analog, J Antibiot (Tokyo), 2001, 54(3):250-6.
Jenke-Kodama et al., Natural biocombinatorics in the polyketide synthase genes of the actinobacterium *Streptomyces avermitilis*, PLoS Comput Biol, 2006, 2(10):e132.
Menzella et al., Combinatorial polyketide biosynthesis by de novo design and rearrangement of modular polyketide synthase genes, Nat Biotechnol, 2005, 23(9):1171-6.
Reeves et al., Genetic engineering to produce polyketide analogues, Methods Enzymol., 2009, 459:295-318.
Staunton et al., Polyketide biosynthesis: a millennium review., Nat Prod Rep. 2001, 18(4):380-416.
Staunton et al., Combinatorial biosynthesis of polyketides and nonribosomal peptides, Curr Opin Chem Biol. 2001, 5(2):159-64.

(Continued)

*Primary Examiner* — Nancy J Leith
(74) *Attorney, Agent, or Firm* — Robert C. Netter, Jr.; Dann, Dorfman, Herrell & Skillman

(57) ABSTRACT

A method for increasing the molecular diversity of polyketides and non-ribosomal peptides by using recombination to efficiently increase or decrease the number of modules in the polyketide synthase or non-ribosomal peptide synthetase encoding the polyketide or peptide.

18 Claims, 8 Drawing Sheets

(56) References Cited

OTHER PUBLICATIONS

International Search Report and Written Opinion for PCT/GB2014/052091, dated Jan. 23, 2015.

Nelson et al., Manipulation of the C(22)-C(27) region of rapamycin: stability issues and biological implications, Bioorg Med Chem Lett., 1999, 18;9(2):295-300.

Nielson et al., A novel ring contraction of rapamycin, Tetrahedron Letters, 1994, 34(41): 7557-7560.

Holt et al., Structure-activity studies of nonmacrocyclic rapamacin derivatives, Bioorganic & Medicinal Chemistry Letters, 1993, 3(10):1977-1980.

Skotnicki et al., Ring expanded rapamycin derivatives, Tetrahedron Letters, 1994, 35(2):201-202.

International Search Report and Written Opinion for PCT/GB2014/052094, dated Mar. 4, 2015.

Xue et al., A multiplasmid approach to preparing large libraries of polyketides, Proc Natl Acad Sci U S A., 1999, 96(21): 11740-11745.

Kittendorf et al., Developing tools for engineering hybrid polyketide synthetic pathways, Curr Opin Biotechnol., 2006, (6):597-605.

Kim et al., An efficient method for creation and functional analysis of libraries of hybrid type I polyketide synthases, Protein Eng Des Sel., 2004, 17(3):277-84.

De Boer et al., Recent efforts in engineering microbial cells to produce new chemical compounds, Curr Opin Chem Biol., 2003, 7(2):273-8.

Cropp et al., Recent developments in the production of novel polyketides by combinatorial biosynthesis, Biotechnol Genet Eng Rev., 2002, 19:159-72.

Kendrew et al., Recombinant strains for the enhanced production of bioengineered rapalogs, Metab Eng., 2013 15:167-73.

Jung et al. Heterologous expression of tylosin polyketide synthase and production of a hybrid bioactive macrolide in *Streptomyces venezuelae*, Appl Microbiol Biotechnol., 2006, 72(4):763-9.

Yoon et al., Generation of multiple bioactive macrolides by hybrid modular polyketide synthases in *Streptomyces venezuelae*, Chem Biol. 2002, 9(2):203-14.

Menzella et al., Rational design and assembly of synthetic trimodular polyketide synthases, Chem Biol. 2007, (2):143-51.

Starcevic et al., Recombinatorial biosynthesis of polyketides, J Ind Microbiol Biotechnol., 2012, 39(3):503-11.

Hillemann, D., et al., "Gene Disruption and Gene Replacement in *Streptomyces* via Single Stranded DNA Transformation of Integration Vectors," Nuc. Acids Res. (1991) 19(4):727-731.

Herrmann, S., et al., "Site-Specific Recombination Strategies for Engineering Actinomycete Genomes," App. Environ. Miorobiol. (2012) 78(6):1804-1812.

Kao, C.M., et al., "Engineered Biosynthesis of a Triketide Lactone from an Incomplete Modular Polyketide Synthase" J. Am. Chem. Soc. (1994) 116:11612-11613.

Andexer, J.N., et al., "Biosynthesis of the immunosuppressants FK506, FK520, and rapamycin involves a previously undescribed family of enzymes acting on chorismate" Proc. Natl. Acad. Sci. (2011) 108(12):4776-4781.

\* cited by examiner

A: Typical organisation of a PKS module

B: Typical organisation of a NRPS module

Structure of rapamycin:

Tylosin analogues (tylactones)

SEQUENCE LISTING

```
<160> NUMBER OF SEQ ID NOS: 166

<210> SEQ ID NO 1
<211> LENGTH: 32
<212> TYPE: DNA
<213> ORGANISM: Artificial Sequence
<220> FEATURE:
<223> OTHER INFORMATION: primer

<400> SEQUENCE: 1
cgacgaattc catcgcgccc cggcccgcca gg                                32

<210> SEQ ID NO 2
<211> LENGTH: 29
<212> TYPE: DNA
<213> ORGANISM: Artificial Sequence
<220> FEATURE:
<223> OTHER INFORMATION: primer

<400> SEQUENCE: 2
ttgtccggcc gggtgtcgta cgtcttcgg                                    29

<210> SEQ ID NO 3
<211> LENGTH: 30
<212> TYPE: DNA
<213> ORGANISM: Artificial Sequence
<220> FEATURE:
<223> OTHER INFORMATION: primer

<400> SEQUENCE: 3
ccagggacga ggagcacgcc gtgtccatcg                                   30

<210> SEQ ID NO 4
<211> LENGTH: 37
<212> TYPE: DNA
<213> ORGANISM: Artificial Sequence
<220> FEATURE:
<223> OTHER INFORMATION: primer

<400> SEQUENCE: 4
ggggtgtaga ggctagccgc cctggcaccg gccgagc                           37

<210> SEQ ID NO 5
<211> LENGTH: 43
<212> TYPE: DNA
<213> ORGANISM: Artificial Sequence
<220> FEATURE:
<223> OTHER INFORMATION: primer

<400> SEQUENCE: 5
gtatctagaa agatctagta cccggttgt ggcggtgccg agg                     43

<210> SEQ ID NO 6
<211> LENGTH: 38
<212> TYPE: DNA
<213> ORGANISM: Artificial Sequence
```

<220> FEATURE:
<223> OTHER INFORMATION: primer

<400> SEQUENCE: 6
tcaggccgcc tcgggcgtgt cggttgtcat caagatgg    38

<210> SEQ ID NO 7
<211> LENGTH: 33
<212> TYPE: DNA
<213> ORGANISM: Artificial Sequence
<220> FEATURE:
<223> OTHER INFORMATION: primer

<400> SEQUENCE: 7
gacggctcat ccacgtgcag ggtgcgggga acc    33

<210> SEQ ID NO 8
<211> LENGTH: 37
<212> TYPE: DNA
<213> ORGANISM: Artificial Sequence
<220> FEATURE:
<223> OTHER INFORMATION: primer

<400> SEQUENCE: 8
gtctaagctt tccccaccga ccgtggctgg gacgtcg    37

<210> SEQ ID NO 9
<211> LENGTH: 39
<212> TYPE: DNA
<213> ORGANISM: Artificial Sequence
<220> FEATURE:
<223> OTHER INFORMATION: primer

<400> SEQUENCE: 9
cgcgaattcg gagaaaccgg caccgtccgc actgtccgc    39

<210> SEQ ID NO 10
<211> LENGTH: 40
<212> TYPE: DNA
<213> ORGANISM: Artificial Sequence
<220> FEATURE:
<223> OTHER INFORMATION: primer

<400> SEQUENCE: 10
cgtaaagctt ggagacgaca ccgtcaccgg caccgctgtg    40

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
ggccagtgcc aagctgcggc ttcctccacg acgcg    35

<210> SEQ ID NO 12
<211> LENGTH: 37
<212> TYPE: DNA
<213> ORGANISM: Artificial Sequence
<220> FEATURE:
<223> OTHER INFORMATION: primer

<400> SEQUENCE: 12
acatgattac gaattccggc tcgcccggct gctctcc    37

```
<210> SEQ ID NO 13
<211> LENGTH: 40
<212> TYPE: DNA
<213> ORGANISM: Artificial Sequence
<220> FEATURE:
<223> OTHER INFORMATION: primer

<400> SEQUENCE: 13
ggccagtgcc aagctacctc accaccctcc ccacctaccc                           40

<210> SEQ ID NO 14
<211> LENGTH: 33
<212> TYPE: DNA
<213> ORGANISM: Artificial Sequence
<220> FEATURE:
<223> OTHER INFORMATION: primer

<400> SEQUENCE: 14
acatgattac gaattgccgt ccggctcctc ccg                                  33

<210> SEQ ID NO 15
<211> LENGTH: 36
<212> TYPE: DNA
<213> ORGANISM: Artificial Sequence
<220> FEATURE:
<223> OTHER INFORMATION: primer

<400> SEQUENCE: 15
ggccagtgcc aagctcgacc ctgccggcgt acatgg                               36

<210> SEQ ID NO 16
<211> LENGTH: 43
<212> TYPE: DNA
<213> ORGANISM: Artificial Sequence
<220> FEATURE:
<223> OTHER INFORMATION: primer

<400> SEQUENCE: 16
acatgattac gaattgtgta ccagatctgg aacagcgggt ggc                       43

<210> SEQ ID NO 17
<211> LENGTH: 36
<212> TYPE: DNA
<213> ORGANISM: Artificial Sequence
<220> FEATURE:
<223> OTHER INFORMATION: primer

<400> SEQUENCE: 17
ggccagtgcc aagctacccc cacagcagca ccccg                                36

<210> SEQ ID NO 18
<211> LENGTH: 35
<212> TYPE: DNA
<213> ORGANISM: Artificial Sequence
<220> FEATURE:
<223> OTHER INFORMATION: primer

<400> SEQUENCE: 18
acatgattac gaattgtagg cggccaggtc ggtgc                                35

<210> SEQ ID NO 19
<211> LENGTH: 36
<212> TYPE: DNA
<213> ORGANISM: Artificial Sequence
<220> FEATURE:
<223> OTHER INFORMATION: primer
```

<400> SEQUENCE: 19
ggccagtgcc aagctacccc cacagcagca cccccg               36

<210> SEQ ID NO 20
<211> LENGTH: 35
<212> TYPE: DNA
<213> ORGANISM: Artificial Sequence
<220> FEATURE:
<223> OTHER INFORMATION: primer

<400> SEQUENCE: 20
acatgattac gaattgtagg cggccaggtc ggtgc                35

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
ggccagtgcc aagcttccgg ccacgcaggc c                    31

<210> SEQ ID NO 22
<211> LENGTH: 36
<212> TYPE: DNA
<213> ORGANISM: Artificial Sequence
<220> FEATURE:
<223> OTHER INFORMATION: primer

<400> SEQUENCE: 22
acatgattac gaattccaag ctcgccgacc tggagt               36

<210> SEQ ID NO 23
<211> LENGTH: 32
<212> TYPE: DNA
<213> ORGANISM: Artificial Sequence
<220> FEATURE:
<223> OTHER INFORMATION: primer

<400> SEQUENCE: 23
ggccagtgcc aagcttcggc ggaggaaccg ag                   32

<210> SEQ ID NO 24
<211> LENGTH: 31
<212> TYPE: DNA
<213> ORGANISM: Artificial Sequence
<220> FEATURE:
<223> OTHER INFORMATION: primer

<400> SEQUENCE: 24
acatgattac gaattccagc tcacggccga t                    31

<210> SEQ ID NO 25
<211> LENGTH: 42
<212> TYPE: DNA
<213> ORGANISM: Artificial Sequence
<220> FEATURE:
<223> OTHER INFORMATION: primer

<400> SEQUENCE: 25
ggccagtgcc aagctttcgc atggacaacg aagagaagct cg        42

```
<210> SEQ ID NO 26
<211> LENGTH: 34
<212> TYPE: DNA
<213> ORGANISM: Artificial Sequence
<220> FEATURE:
<223> OTHER INFORMATION: primer

<400> SEQUENCE: 26
acatgattac gaattcccga atgcccggcc acca                              34

<210> SEQ ID NO 27
<211> LENGTH: 31
<212> TYPE: DNA
<213> ORGANISM: Artificial Sequence
<220> FEATURE:
<223> OTHER INFORMATION: primer

<400> SEQUENCE: 27
ggccagtgcc aagcttacga gccggtggag g                                 31

<210> SEQ ID NO 28
<211> LENGTH: 32
<212> TYPE: DNA
<213> ORGANISM: Artificial Sequence
<220> FEATURE:
<223> OTHER INFORMATION: primer

<400> SEQUENCE: 28
acatgattac gaattcctca cctcggccca gc                                32

<210> SEQ ID NO 29
<211> LENGTH: 30
<212> TYPE: DNA
<213> ORGANISM: Artificial Sequence
<220> FEATURE:
<223> OTHER INFORMATION: primer

<400> SEQUENCE: 29
ggccagtgcc aagcttgcgc agttgctccg                                   30

<210> SEQ ID NO 30
<211> LENGTH: 34
<212> TYPE: DNA
<213> ORGANISM: Artificial Sequence
<220> FEATURE:
<223> OTHER INFORMATION: primer

<400> SEQUENCE: 30
acatgattac gaattctcac caccccgag ctgg                               34

<210> SEQ ID NO 31
<211> LENGTH: 39
<212> TYPE: DNA
<213> ORGANISM: Artificial Sequence
<220> FEATURE:
<223> OTHER INFORMATION: primer

<400> SEQUENCE: 31
ggccagtgcc aagcttcgca gcaggagatt ctggcgtcg                         39

<210> SEQ ID NO 32
<211> LENGTH: 32
<212> TYPE: DNA
<213> ORGANISM: Artificial Sequence
<220> FEATURE:
<223> OTHER INFORMATION: primer
```

<400> SEQUENCE: 32
acatgattac gaattccgag ggcctccacg gt                                         32

<210> SEQ ID NO 33
<211> LENGTH: 36
<212> TYPE: DNA
<213> ORGANISM: Artificial Sequence
<220> FEATURE:
<223> OTHER INFORMATION: primer

<400> SEQUENCE: 33
ggccagtgcc aagcttgctt cgacgtgaac gcgctc                                    36

<210> SEQ ID NO 34
<211> LENGTH: 29
<212> TYPE: DNA
<213> ORGANISM: Artificial Sequence
<220> FEATURE:
<223> OTHER INFORMATION: primer

<400> SEQUENCE: 34
acatgattac gaattcgcgc ccgcgtcgt                                            29

<210> SEQ ID NO 35
<211> LENGTH: 37
<212> TYPE: DNA
<213> ORGANISM: Artificial Sequence
<220> FEATURE:
<223> OTHER INFORMATION: primer

<400> SEQUENCE: 35
ggccagtgcc aagcttacac cggtctgcgt ctgccgg                                   37

<210> SEQ ID NO 36
<211> LENGTH: 29
<212> TYPE: DNA
<213> ORGANISM: Artificial Sequence
<220> FEATURE:
<223> OTHER INFORMATION: primer

<400> SEQUENCE: 36
acatgattac gaattcgccc ccgcaccgc                                            29

<210> SEQ ID NO 37
<211> LENGTH: 33
<212> TYPE: DNA
<213> ORGANISM: Artificial Sequence
<220> FEATURE:
<223> OTHER INFORMATION: primer

<400> SEQUENCE: 37
ggccagtgcc aagcttggtg tcccgcaccg atg                                       33

<210> SEQ ID NO 38
<211> LENGTH: 31
<212> TYPE: DNA
<213> ORGANISM: Artificial Sequence
<220> FEATURE:
<223> OTHER INFORMATION: primer

<400> SEQUENCE: 38
acatgattac gaattcaacg ccaccacccg c                                         31

<210> SEQ ID NO 39
<211> LENGTH: 31
<212> TYPE: DNA
<213> ORGANISM: Artificial Sequence
<220> FEATURE:
<223> OTHER INFORMATION: primer

<400> SEQUENCE: 39
ggccagtgcc aagcttcccc gcccgaaggc a                             31

<210> SEQ ID NO 40
<211> LENGTH: 35
<212> TYPE: DNA
<213> ORGANISM: Artificial Sequence
<220> FEATURE:
<223> OTHER INFORMATION: primer

<400> SEQUENCE: 40
acatgattac gaattctcgt cctcgtcggg atggc                         35

<210> SEQ ID NO 41
<211> LENGTH: 30
<212> TYPE: DNA
<213> ORGANISM: Artificial Sequence
<220> FEATURE:
<223> OTHER INFORMATION: primer

<400> SEQUENCE: 41
ggccagtgcc aagcttcgca cccatgcggc                               30

<210> SEQ ID NO 42
<211> LENGTH: 34
<212> TYPE: DNA
<213> ORGANISM: Artificial Sequence
<220> FEATURE:
<223> OTHER INFORMATION: primer

<400> SEQUENCE: 42
acatgattac gaattccagt gcggccgctt cttc                          34

<210> SEQ ID NO 43
<211> LENGTH: 30
<212> TYPE: DNA
<213> ORGANISM: Artificial Sequence
<220> FEATURE:
<223> OTHER INFORMATION: primer

<400> SEQUENCE: 43
ggccagtgcc aagcttcggg cgagccgcgt                               30

<210> SEQ ID NO 44
<211> LENGTH: 33
<212> TYPE: DNA
<213> ORGANISM: Artificial Sequence
<220> FEATURE:
<223> OTHER INFORMATION: primer

<400> SEQUENCE: 44
acatgattac gaattccggt tgcacgacgt cga                           33

<210> SEQ ID NO 45
<211> LENGTH: 30
<212> TYPE: DNA
<213> ORGANISM: Artificial Sequence
<220> FEATURE:
<223> OTHER INFORMATION: primer

```
<400> SEQUENCE: 45
ggccagtgcc aagcttgcgc acgtccgcac                                              30

<210> SEQ ID NO 46
<211> LENGTH: 34
<212> TYPE: DNA
<213> ORGANISM: Artificial Sequence
<220> FEATURE:
<223> OTHER INFORMATION: primer

<400> SEQUENCE: 46
acatgattac gaattcccag ctcgccgatc gaat                                          34

<210> SEQ ID NO 47
<211> LENGTH: 37
<212> TYPE: DNA
<213> ORGANISM: Artificial Sequence
<220> FEATURE:
<223> OTHER INFORMATION: primer

<400> SEQUENCE: 47
ggccagtgcc aagcttggag ttcctgctca acctggt                                      37

<210> SEQ ID NO 48
<211> LENGTH: 34
<212> TYPE: DNA
<213> ORGANISM: Artificial Sequence
<220> FEATURE:
<223> OTHER INFORMATION: primer

<400> SEQUENCE: 48
acatgattac gaattctctt gccgtgggtg gtgg                                          34

<210> SEQ ID NO 49
<211> LENGTH: 37
<212> TYPE: DNA
<213> ORGANISM: Artificial Sequence
<220> FEATURE:
<223> OTHER INFORMATION: primer

<400> SEQUENCE: 49
ggccagtgcc aagcttattc gactacccga caccgct                                      37

<210> SEQ ID NO 50
<211> LENGTH: 34
<212> TYPE: DNA
<213> ORGANISM: Artificial Sequence
<220> FEATURE:
<223> OTHER INFORMATION: primer

<400> SEQUENCE: 50
acatgattac gaattctccc agacagccgc cagc                                          34

<210> SEQ ID NO 51
<211> LENGTH: 30
<212> TYPE: DNA
<213> ORGANISM: Artificial Sequence
<220> FEATURE:
<223> OTHER INFORMATION: primer

<400> SEQUENCE: 51
ggccagtgcc aagcttacgc gccggagcag                                              30
```

```
<210> SEQ ID NO 52
<211> LENGTH: 32
<212> TYPE: DNA
<213> ORGANISM: Artificial Sequence
<220> FEATURE:
<223> OTHER INFORMATION: primer

<400> SEQUENCE: 52
acatgattac gaattcacgc tcctgctgga gg                                    32

<210> SEQ ID NO 53
<211> LENGTH: 30
<212> TYPE: DNA
<213> ORGANISM: Artificial Sequence
<220> FEATURE:
<223> OTHER INFORMATION: primer

<400> SEQUENCE: 53
ggccagtgcc aagcttgcgc gtgggcgcga                                       30

<210> SEQ ID NO 54
<211> LENGTH: 33
<212> TYPE: DNA
<213> ORGANISM: Artificial Sequence
<220> FEATURE:
<223> OTHER INFORMATION: primer

<400> SEQUENCE: 54
acatgattac gaattcggct tgctcgcgcc aac                                   33

<210> SEQ ID NO 55
<211> LENGTH: 38
<212> TYPE: DNA
<213> ORGANISM: Artificial Sequence
<220> FEATURE:
<223> OTHER INFORMATION: primer

<400> SEQUENCE: 55
ggccagtgcc aagcttgggt tcaactacat gggccggt                              38

<210> SEQ ID NO 56
<211> LENGTH: 34
<212> TYPE: DNA
<213> ORGANISM: Artificial Sequence
<220> FEATURE:
<223> OTHER INFORMATION: primer

<400> SEQUENCE: 56
acatgattac gaattcaccc tggtcgatga gcca                                  34

<210> SEQ ID NO 57
<211> LENGTH: 35
<212> TYPE: DNA
<213> ORGANISM: Artificial Sequence
<220> FEATURE:
<223> OTHER INFORMATION: primer

<400> SEQUENCE: 57
ggccagtgcc aagcttcacg agatcgacaa ggccc                                 35

<210> SEQ ID NO 58
<211> LENGTH: 31
<212> TYPE: DNA
<213> ORGANISM: Artificial Sequence
<220> FEATURE:
<223> OTHER INFORMATION: primer
```

<400> SEQUENCE: 58
acatgattac gaattcagcg caggaacgcc g    31

<210> SEQ ID NO 59
<211> LENGTH: 32
<212> TYPE: DNA
<213> ORGANISM: Artificial Sequence
<220> FEATURE:
<223> OTHER INFORMATION: primer

<400> SEQUENCE: 59
ggccagtgcc aagcttccgc ccacaacgca gg    32

<210> SEQ ID NO 60
<211> LENGTH: 33
<212> TYPE: DNA
<213> ORGANISM: Artificial Sequence
<220> FEATURE:
<223> OTHER INFORMATION: primer

<400> SEQUENCE: 60
acatgattac gaattccacc tggatctcac cgc    33

<210> SEQ ID NO 61
<211> LENGTH: 42
<212> TYPE: DNA
<213> ORGANISM: Artificial Sequence
<220> FEATURE:
<223> OTHER INFORMATION: primer

<400> SEQUENCE: 61
ggccagtgcc aagcttgatc agctttaact acctgggaca gt    42

<210> SEQ ID NO 62
<211> LENGTH: 33
<212> TYPE: DNA
<213> ORGANISM: Artificial Sequence
<220> FEATURE:
<223> OTHER INFORMATION: primer

<400> SEQUENCE: 62
acatgattac gaattccgga acaatggcac cgc    33

<210> SEQ ID NO 63
<211> LENGTH: 54
<212> TYPE: DNA
<213> ORGANISM: Artificial Sequence
<220> FEATURE:
<223> OTHER INFORMATION: primer

<400> SEQUENCE: 63
ggccagtgcc aagctttatc aaccattcat aaagaactga atgtcaagct gcct    54

<210> SEQ ID NO 64
<211> LENGTH: 34
<212> TYPE: DNA
<213> ORGANISM: Artificial Sequence
<220> FEATURE:
<223> OTHER INFORMATION: primer

<400> SEQUENCE: 64
acatgattac gaattctcct gcggatacgc cgga    34

```
<210> SEQ ID NO 65
<211> LENGTH: 41
<212> TYPE: DNA
<213> ORGANISM: Artificial Sequence
<220> FEATURE:
<223> OTHER INFORMATION: primer

<400> SEQUENCE: 65
ggccagtgcc aagcttttca ccgagttgaa cggaacggaa c        41

<210> SEQ ID NO 66
<211> LENGTH: 32
<212> TYPE: DNA
<213> ORGANISM: Artificial Sequence
<220> FEATURE:
<223> OTHER INFORMATION: primer

<400> SEQUENCE: 66
acatgattac gaattccggt cccgtacggt gt                  32

<210> SEQ ID NO 67
<211> LENGTH: 36
<212> TYPE: DNA
<213> ORGANISM: Artificial Sequence
<220> FEATURE:
<223> OTHER INFORMATION: primer

<400> SEQUENCE: 67
ggccagtgcc aagcttttcg gcgtggactg attccc              36

<210> SEQ ID NO 68
<211> LENGTH: 35
<212> TYPE: DNA
<213> ORGANISM: Artificial Sequence
<220> FEATURE:
<223> OTHER INFORMATION: primer

<400> SEQUENCE: 68
acatgattac gaattcgagg agttgtgccc ccatg               35

<210> SEQ ID NO 69
<211> LENGTH: 33
<212> TYPE: DNA
<213> ORGANISM: Artificial Sequence
<220> FEATURE:
<223> OTHER INFORMATION: primerr

<400> SEQUENCE: 69
ggccagtgcc aagcttggtc acggcggaac tgc                 33

<210> SEQ ID NO 70
<211> LENGTH: 33
<212> TYPE: DNA
<213> ORGANISM: Artificial Sequence
<220> FEATURE:
<223> OTHER INFORMATION: primer

<400> SEQUENCE: 70
acatgattac gaattccgcc ccgacaacac ccg                 33

<210> SEQ ID NO 71
<211> LENGTH: 35
<212> TYPE: DNA
<213> ORGANISM: Artificial Sequence
<220> FEATURE:
<223> OTHER INFORMATION: primer
```

<400> SEQUENCE: 71
ggccagtgcc aagcttcgac cccggtttct tcggg                35

<210> SEQ ID NO 72
<211> LENGTH: 32
<212> TYPE: DNA
<213> ORGANISM: Artificial Sequence
<220> FEATURE:
<223> OTHER INFORMATION: primer

<400> SEQUENCE: 72
acatgattac gaattccagc cggtccggcc at                32

<210> SEQ ID NO 73
<211> LENGTH: 39
<212> TYPE: DNA
<213> ORGANISM: Artificial Sequence
<220> FEATURE:
<223> OTHER INFORMATION: primer

<400> SEQUENCE: 73
ggccagtgcc aagcttgatc gaccagatgg ctcgagcga                39

<210> SEQ ID NO 74
<211> LENGTH: 32
<212> TYPE: DNA
<213> ORGANISM: Artificial Sequence
<220> FEATURE:
<223> OTHER INFORMATION: primer

<400> SEQUENCE: 74
acatgattac gaattcccat gccggggtgc tg                32

<210> SEQ ID NO 75
<211> LENGTH: 30
<212> TYPE: DNA
<213> ORGANISM: Artificial Sequence
<220> FEATURE:
<223> OTHER INFORMATION: primer

<400> SEQUENCE: 75
ggccagtgcc aagcttcccg gccggcacga                30

<210> SEQ ID NO 76
<211> LENGTH: 37
<212> TYPE: DNA
<213> ORGANISM: Artificial Sequence
<220> FEATURE:
<223> OTHER INFORMATION: primer

<400> SEQUENCE: 76
acatgattac gaattccgac accatcaccg cccacaa                37

<210> SEQ ID NO 77
<211> LENGTH: 30
<212> TYPE: DNA
<213> ORGANISM: Artificial Sequence
<220> FEATURE:
<223> OTHER INFORMATION: primer

<400> SEQUENCE: 77
ggccagtgcc aagcttcgcc ctcagccggg                30

<210> SEQ ID NO 78
<211> LENGTH: 35
<212> TYPE: DNA
<213> ORGANISM: Artificial Sequence
<220> FEATURE:
<223> OTHER INFORMATION: primer

<400> SEQUENCE: 78
acatgattac gaattcggag gtggtgttcg gcggt                              35

<210> SEQ ID NO 79
<211> LENGTH: 32
<212> TYPE: DNA
<213> ORGANISM: Artificial Sequence
<220> FEATURE:
<223> OTHER INFORMATION: primer

<400> SEQUENCE: 79
ggccagtgcc aagcttcacc gccacctccg tg                                 32

<210> SEQ ID NO 80
<211> LENGTH: 31
<212> TYPE: DNA
<213> ORGANISM: Artificial Sequence
<220> FEATURE:
<223> OTHER INFORMATION: primer

<400> SEQUENCE: 80
acatgattac gaattccggc actcgcaccc t                                  31

<210> SEQ ID NO 81
<211> LENGTH: 33
<212> TYPE: DNA
<213> ORGANISM: Artificial Sequence
<220> FEATURE:
<223> OTHER INFORMATION: primer

<400> SEQUENCE: 81
ggccagtgcc aagcttccgg ttccagcagg tca                                33

<210> SEQ ID NO 82
<211> LENGTH: 28
<212> TYPE: DNA
<213> ORGANISM: Artificial Sequence
<220> FEATURE:
<223> OTHER INFORMATION: primer

<400> SEQUENCE: 82
acatgattac gaattcgctg cgcgccct                                      28

<210> SEQ ID NO 83
<211> LENGTH: 35
<212> TYPE: DNA
<213> ORGANISM: Artificial Sequence
<220> FEATURE:
<223> OTHER INFORMATION: primer

<400> SEQUENCE: 83
ggccagtgcc aagcttcgac atcgtcgacg gcgaa                              35

<210> SEQ ID NO 84
<211> LENGTH: 30
<212> TYPE: DNA
<213> ORGANISM: Artificial Sequence
<220> FEATURE:
<223> OTHER INFORMATION: primer

<400> SEQUENCE: 84
acatgattac gaattcccgg accgggcctc        30

<210> SEQ ID NO 85
<211> LENGTH: 34
<212> TYPE: DNA
<213> ORGANISM: Artificial Sequence
<220> FEATURE:
<223> OTHER INFORMATION: primer

<400> SEQUENCE: 85
ggccagtgcc aagcttccga caccaccggc acca        34

<210> SEQ ID NO 86
<211> LENGTH: 32
<212> TYPE: DNA
<213> ORGANISM: Artificial Sequence
<220> FEATURE:
<223> OTHER INFORMATION: primer

<400> SEQUENCE: 86
acatgattac gaattccaga ccttcgccag cg        32

<210> SEQ ID NO 87
<211> LENGTH: 31
<212> TYPE: DNA
<213> ORGANISM: Artificial Sequence
<220> FEATURE:
<223> OTHER INFORMATION: primer

<400> SEQUENCE: 87
ggccagtgcc aagcttgccc aactgggccg c        31

<210> SEQ ID NO 88
<211> LENGTH: 37
<212> TYPE: DNA
<213> ORGANISM: Artificial Sequence
<220> FEATURE:
<223> OTHER INFORMATION: primer

<400> SEQUENCE: 88
acatgattac gaattcgacc ttccagtcct gcatcgg        37

<210> SEQ ID NO 89
<211> LENGTH: 35
<212> TYPE: DNA
<213> ORGANISM: Artificial Sequence
<220> FEATURE:
<223> OTHER INFORMATION: primer

<400> SEQUENCE: 89
ggccagtgcc aagcttcggt atcgacccgg agtcc        35

<210> SEQ ID NO 90
<211> LENGTH: 32
<212> TYPE: DNA
<213> ORGANISM: Artificial Sequence
<220> FEATURE:
<223> OTHER INFORMATION: primer

<400> SEQUENCE: 90
acatgattac gaattcagac gctcgcggat ct        32

```
<210> SEQ ID NO 91
<211> LENGTH: 31
<212> TYPE: DNA
<213> ORGANISM: Artificial Sequence
<220> FEATURE:
<223> OTHER INFORMATION: primer

<400> SEQUENCE: 91
ggccagtgcc aagcttgccg gagagcgcca a                           31

<210> SEQ ID NO 92
<211> LENGTH: 31
<212> TYPE: DNA
<213> ORGANISM: Artificial Sequence
<220> FEATURE:
<223> OTHER INFORMATION: primer

<400> SEQUENCE: 92
acatgattac gaattcggtg ccgctgaccc c                           31

<210> SEQ ID NO 93
<211> LENGTH: 33
<212> TYPE: DNA
<213> ORGANISM: Artificial Sequence
<220> FEATURE:
<223> OTHER INFORMATION: primer

<400> SEQUENCE: 93
ggccagtgcc aagcttagct ccttcgtgct ggg                         33

<210> SEQ ID NO 94
<211> LENGTH: 36
<212> TYPE: DNA
<213> ORGANISM: Artificial Sequence
<220> FEATURE:
<223> OTHER INFORMATION: primer

<400> SEQUENCE: 94
acatgattac gaattcgttg cgggttgttc gccaga                      36

<210> SEQ ID NO 95
<211> LENGTH: 33
<212> TYPE: DNA
<213> ORGANISM: Artificial Sequence
<220> FEATURE:
<223> OTHER INFORMATION: primer

<400> SEQUENCE: 95
ggccagtgcc aagcttcgcc atcgtgggca tgg                         33

<210> SEQ ID NO 96
<211> LENGTH: 32
<212> TYPE: DNA
<213> ORGANISM: Artificial Sequence
<220> FEATURE:
<223> OTHER INFORMATION: primer

<400> SEQUENCE: 96
acatgattac gaattctccg cctgtgccac cg                          32

<210> SEQ ID NO 97
<211> LENGTH: 36
<212> TYPE: DNA
<213> ORGANISM: Artificial Sequence
<220> FEATURE:
<223> OTHER INFORMATION: primer
```

<400> SEQUENCE: 97
ggccagtgcc aagcttcacc tgaccccggt tcgaga                        36

<210> SEQ ID NO 98
<211> LENGTH: 31
<212> TYPE: DNA
<213> ORGANISM: Artificial Sequence
<220> FEATURE:
<223> OTHER INFORMATION: primer

<400> SEQUENCE: 98
acatgattac gaattccgtg cttggccgaa c                             31

<210> SEQ ID NO 99
<211> LENGTH: 40
<212> TYPE: DNA
<213> ORGANISM: Artificial Sequence
<220> FEATURE:
<223> OTHER INFORMATION: primer

<400> SEQUENCE: 99
ggccagtgcc aagcttggcg gaaccgggac atcggcatgg                    40

<210> SEQ ID NO 100
<211> LENGTH: 35
<212> TYPE: DNA
<213> ORGANISM: Artificial Sequence
<220> FEATURE:
<223> OTHER INFORMATION: primer

<400> SEQUENCE: 100
acatgattac gaattcagca ttggtcccgc cgata                         35

<210> SEQ ID NO 101
<211> LENGTH: 43
<212> TYPE: DNA
<213> ORGANISM: Artificial Sequence
<220> FEATURE:
<223> OTHER INFORMATION: primer

<400> SEQUENCE: 101
ggccagtgcc aagcttcagc gaggggcgcg agaaggccgt caa                43

<210> SEQ ID NO 102
<211> LENGTH: 35
<212> TYPE: DNA
<213> ORGANISM: Artificial Sequence
<220> FEATURE:
<223> OTHER INFORMATION: primer

<400> SEQUENCE: 102
acatgattac gaattctgag ccgccgccaa ctccc                         35

<210> SEQ ID NO 103
<211> LENGTH: 37
<212> TYPE: DNA
<213> ORGANISM: Artificial Sequence
<220> FEATURE:
<223> OTHER INFORMATION: primer

<400> SEQUENCE: 103
ggccagtgcc aagcttggac tgggcccggt tcgcccc                       37

```
<210> SEQ ID NO 104
<211> LENGTH: 32
<212> TYPE: DNA
<213> ORGANISM: Artificial Sequence
<220> FEATURE:
<223> OTHER INFORMATION: primer

<400> SEQUENCE: 104
acatgattac gaattccgca ccactccggg cg                                    32

<210> SEQ ID NO 105
<211> LENGTH: 32
<212> TYPE: DNA
<213> ORGANISM: Artificial Sequence
<220> FEATURE:
<223> OTHER INFORMATION: primer

<400> SEQUENCE: 105
ggccagtgcc aagcttcgct ggcccgccac cg                                    32

<210> SEQ ID NO 106
<211> LENGTH: 36
<212> TYPE: DNA
<213> ORGANISM: Artificial Sequence
<220> FEATURE:
<223> OTHER INFORMATION: primer

<400> SEQUENCE: 106
acatgattac gaattcgacg aactccagta gtcgct                                36

<210> SEQ ID NO 107
<211> LENGTH: 33
<212> TYPE: DNA
<213> ORGANISM: Artificial Sequence
<220> FEATURE:
<223> OTHER INFORMATION: primer

<400> SEQUENCE: 107
ggccagtgcc aagcttcaga cccggcagcg gct                                   33

<210> SEQ ID NO 108
<211> LENGTH: 32
<212> TYPE: DNA
<213> ORGANISM: Artificial Sequence
<220> FEATURE:
<223> OTHER INFORMATION: primer

<400> SEQUENCE: 108
acatgattac gaattcgcgt gatggccgcc ag                                    32

<210> SEQ ID NO 109
<211> LENGTH: 32
<212> TYPE: DNA
<213> ORGANISM: Artificial Sequence
<220> FEATURE:
<223> OTHER INFORMATION: primer

<400> SEQUENCE: 109
ggccagtgcc aagcttcgac gggcatgggc ag                                    32

<210> SEQ ID NO 110
<211> LENGTH: 32
<212> TYPE: DNA
<213> ORGANISM: Artificial Sequence
<220> FEATURE:
<223> OTHER INFORMATION: primer
```

<400> SEQUENCE: 110
acatgattac gaattcactg cgaaccctgc cc                                32

<210> SEQ ID NO 111
<211> LENGTH: 33
<212> TYPE: DNA
<213> ORGANISM: Artificial Sequence
<220> FEATURE:
<223> OTHER INFORMATION: primer

<400> SEQUENCE: 111
ggccagtgcc aagcttcgca accgcctctc cac                               33

<210> SEQ ID NO 112
<211> LENGTH: 32
<212> TYPE: DNA
<213> ORGANISM: Artificial Sequence
<220> FEATURE:
<223> OTHER INFORMATION: primer

<400> SEQUENCE: 112
acatgattac gaattccctc cggcggctcc tc                                32

<210> SEQ ID NO 113
<211> LENGTH: 33
<212> TYPE: DNA
<213> ORGANISM: Artificial Sequence
<220> FEATURE:
<223> OTHER INFORMATION: primer

<400> SEQUENCE: 113
ggccagtgcc aagcttctcg accccgacca ggc                               33

<210> SEQ ID NO 114
<211> LENGTH: 32
<212> TYPE: DNA
<213> ORGANISM: Artificial Sequence
<220> FEATURE:
<223> OTHER INFORMATION: primer

<400> SEQUENCE: 114
acatgattac gaattcggct gcgcagggcg ac                                32

<210> SEQ ID NO 115
<211> LENGTH: 34
<212> TYPE: DNA
<213> ORGANISM: Artificial Sequence
<220> FEATURE:
<223> OTHER INFORMATION: primer

<400> SEQUENCE: 115
ggccagtgcc aagctttgtc gaggcactgc gagc                              34

<210> SEQ ID NO 116
<211> LENGTH: 37
<212> TYPE: DNA
<213> ORGANISM: Artificial Sequence
<220> FEATURE:
<223> OTHER INFORMATION: primer

<400> SEQUENCE: 116
acatgattac gaattctccg gtcaaggtcg acacgat                           37

```
<210> SEQ ID NO 117
<211> LENGTH: 38
<212> TYPE: DNA
<213> ORGANISM: Artificial Sequence
<220> FEATURE:
<223> OTHER INFORMATION: primer

<400> SEQUENCE: 117
ggccagtgcc aagcttcacc gatggagtga ccggccac                              38

<210> SEQ ID NO 118
<211> LENGTH: 35
<212> TYPE: DNA
<213> ORGANISM: Artificial Sequence
<220> FEATURE:
<223> OTHER INFORMATION: primer

<400> SEQUENCE: 118
acatgattac gaattcaccc gatcgtgatc gtcgg                                 35

<210> SEQ ID NO 119
<211> LENGTH: 31
<212> TYPE: DNA
<213> ORGANISM: Artificial Sequence
<220> FEATURE:
<223> OTHER INFORMATION: primer

<400> SEQUENCE: 119
ggccagtgcc aagcttactg cggctccccg c                                     31

<210> SEQ ID NO 120
<211> LENGTH: 31
<212> TYPE: DNA
<213> ORGANISM: Artificial Sequence
<220> FEATURE:
<223> OTHER INFORMATION: primer

<400> SEQUENCE: 120
acatgattac gaattccgtg gcgggttccc c                                     31

<210> SEQ ID NO 121
<211> LENGTH: 35
<212> TYPE: DNA
<213> ORGANISM: Artificial Sequence
<220> FEATURE:
<223> OTHER INFORMATION: primer

<400> SEQUENCE: 121
ggccagtgcc aagcttggat tcgagcaacc gggac                                 35

<210> SEQ ID NO 122
<211> LENGTH: 34
<212> TYPE: DNA
<213> ORGANISM: Artificial Sequence
<220> FEATURE:
<223> OTHER INFORMATION: primer

<400> SEQUENCE: 122
acatgattac gaattcctgg ctgacctgcc cgaa                                  34

<210> SEQ ID NO 123
<211> LENGTH: 35
<212> TYPE: DNA
<213> ORGANISM: Artificial Sequence
<220> FEATURE:
<223> OTHER INFORMATION: primer
```

```
<400> SEQUENCE: 123
ggccagtgcc aagcttgaag tggcgtccga ccggc                              35

<210> SEQ ID NO 124
<211> LENGTH: 33
<212> TYPE: DNA
<213> ORGANISM: Artificial Sequence
<220> FEATURE:
<223> OTHER INFORMATION: primer

<400> SEQUENCE: 124
acatgattac gaattcgacg ccattgacgt cgg                                33

<210> SEQ ID NO 125
<211> LENGTH: 32
<212> TYPE: DNA
<213> ORGANISM: Artificial Sequence
<220> FEATURE:
<223> OTHER INFORMATION: primer

<400> SEQUENCE: 125
ggccagtgcc aagcttgtgc acagtgctgc gg                                 32

<210> SEQ ID NO 126
<211> LENGTH: 31
<212> TYPE: DNA
<213> ORGANISM: Artificial Sequence
<220> FEATURE:
<223> OTHER INFORMATION: primer

<400> SEQUENCE: 126
acatgattac gaattcaggc ggccagacgc c                                  31

<210> SEQ ID NO 127
<211> LENGTH: 32
<212> TYPE: DNA
<213> ORGANISM: Artificial Sequence
<220> FEATURE:
<223> OTHER INFORMATION: primer

<400> SEQUENCE: 127
ggccagtgcc aagcttggct cccgtccgca gg                                 32

<210> SEQ ID NO 128
<211> LENGTH: 32
<212> TYPE: DNA
<213> ORGANISM: Artificial Sequence
<220> FEATURE:
<223> OTHER INFORMATION: primer

<400> SEQUENCE: 128
acatgattac gaattcccctt cggaggcggc ca                                32

<210> SEQ ID NO 129
<211> LENGTH: 33
<212> TYPE: DNA
<213> ORGANISM: Artificial Sequence
<220> FEATURE:
<223> OTHER INFORMATION: primer

<400> SEQUENCE: 129
ggccagtgcc aagcttcatg gacccgcagc agc                                33
```

<210> SEQ ID NO 130
<211> LENGTH: 32
<212> TYPE: DNA
<213> ORGANISM: Artificial Sequence
<220> FEATURE:
<223> OTHER INFORMATION: primer

<400> SEQUENCE: 130
acatgattac gaattcagac ccgaccccat cc                              32

<210> SEQ ID NO 131
<211> LENGTH: 33
<212> TYPE: DNA
<213> ORGANISM: Artificial Sequence
<220> FEATURE:
<223> OTHER INFORMATION: primer

<400> SEQUENCE: 131
ggccagtgcc aagcttccgc cttcgtcgtg ctc                             33

<210> SEQ ID NO 132
<211> LENGTH: 29
<212> TYPE: DNA
<213> ORGANISM: Artificial Sequence
<220> FEATURE:
<223> OTHER INFORMATION: primer

<400> SEQUENCE: 132
acatgattac gaattcgcga gcgcgatgc                                  29

<210> SEQ ID NO 133
<211> LENGTH: 29
<212> TYPE: DNA
<213> ORGANISM: Artificial Sequence
<220> FEATURE:
<223> OTHER INFORMATION: primer

<400> SEQUENCE: 133
acatgattac gaattctcgc gcggtgcgg                                  29

<210> SEQ ID NO 134
<211> LENGTH: 36
<212> TYPE: DNA
<213> ORGANISM: Artificial Sequence
<220> FEATURE:
<223> OTHER INFORMATION: primer

<400> SEQUENCE: 134
ggccagtgcc aagcttttcc cctctcttac gcgcag                          36

<210> SEQ ID NO 135
<211> LENGTH: 30
<212> TYPE: DNA
<213> ORGANISM: Artificial Sequence
<220> FEATURE:
<223> OTHER INFORMATION: primer

<400> SEQUENCE: 135
ggccagtgcc aagcttgcgg tcacgcacgg                                 30

<210> SEQ ID NO 136
<211> LENGTH: 31
<212> TYPE: DNA
<213> ORGANISM: Artificial Sequence
<220> FEATURE:
<223> OTHER INFORMATION: primer

```
<400> SEQUENCE: 136
acatgattac gaattctccg tgcgcggcca c                                    31

<210> SEQ ID NO 137
<211> LENGTH: 45
<212> TYPE: DNA
<213> ORGANISM: Artificial Sequence
<220> FEATURE:
<223> OTHER INFORMATION: primer

<400> SEQUENCE: 137
ggccagtgcc aagcttattt atggatgttt atgcagcccg ccgga                     45

<210> SEQ ID NO 138
<211> LENGTH: 41
<212> TYPE: DNA
<213> ORGANISM: Artificial Sequence
<220> FEATURE:
<223> OTHER INFORMATION: primer

<400> SEQUENCE: 138
acatgattac gaattcccgg ctttttgata agcgcttttc a                         41

<210> SEQ ID NO 139
<211> LENGTH: 33
<212> TYPE: DNA
<213> ORGANISM: Artificial Sequence
<220> FEATURE:
<223> OTHER INFORMATION: primer

<400> SEQUENCE: 139
ggccagtgcc aagcttcggc accatgaccg agg                                  33

<210> SEQ ID NO 140
<211> LENGTH: 33
<212> TYPE: DNA
<213> ORGANISM: Artificial Sequence
<220> FEATURE:
<223> OTHER INFORMATION: primer

<400> SEQUENCE: 140
acatgattac gaattcgcca gcgcttcgag gat                                  33

<210> SEQ ID NO 141
<211> LENGTH: 34
<212> TYPE: DNA
<213> ORGANISM: Artificial Sequence
<220> FEATURE:
<223> OTHER INFORMATION: primer

<400> SEQUENCE: 141
ggccagtgcc aagcttgccc tgcacctggc gatc                                 34

<210> SEQ ID NO 142
<211> LENGTH: 33
<212> TYPE: DNA
<213> ORGANISM: Artificial Sequence
<220> FEATURE:
<223> OTHER INFORMATION: primer

<400> SEQUENCE: 142
acatgattac gaattcgccg ttgctggtgg gga                                  33
```

```
<210> SEQ ID NO 143
<211> LENGTH: 29
<212> TYPE: DNA
<213> ORGANISM: Artificial Sequence
<220> FEATURE:
<223> OTHER INFORMATION: primer

<400> SEQUENCE: 143
ggccagtgcc aagcttgcgc acggcgcac                                   29

<210> SEQ ID NO 144
<211> LENGTH: 31
<212> TYPE: DNA
<213> ORGANISM: Artificial Sequence
<220> FEATURE:
<223> OTHER INFORMATION: primer

<400> SEQUENCE: 144
acatgattac gaattcggac tgggcggcca g                                31

<210> SEQ ID NO 145
<211> LENGTH: 48
<212> TYPE: DNA
<213> ORGANISM: Artificial Sequence
<220> FEATURE:
<223> OTHER INFORMATION: primer

<400> SEQUENCE: 145
ggccagtgcc aagcttttcg gaatcaactc acttatgatc atgtcact              48

<210> SEQ ID NO 146
<211> LENGTH: 44
<212> TYPE: DNA
<213> ORGANISM: Artificial Sequence
<220> FEATURE:
<223> OTHER INFORMATION: primer

<400> SEQUENCE: 146
acatgattac gaattcaaag ttctcagttt ctcctttagt tccg                  44

<210> SEQ ID NO 147
<211> LENGTH: 33
<212> TYPE: DNA
<213> ORGANISM: Artificial Sequence
<220> FEATURE:
<223> OTHER INFORMATION: primer

<400> SEQUENCE: 147
ggccagtgcc aagcttctcg agcagtggct gct                              33

<210> SEQ ID NO 148
<211> LENGTH: 35
<212> TYPE: DNA
<213> ORGANISM: Artificial Sequence
<220> FEATURE:
<223> OTHER INFORMATION: primer

<400> SEQUENCE: 148
acatgattac gaattcgcct cgacatagcc cacat                            35

<210> SEQ ID NO 149
<211> LENGTH: 32
<212> TYPE: DNA
<213> ORGANISM: Artificial Sequence
<220> FEATURE:
<223> OTHER INFORMATION: primer
```

<400> SEQUENCE: 149
ggccagtgcc aagcttagcc gctcgctgat cg                          32

<210> SEQ ID NO 150
<211> LENGTH: 32
<212> TYPE: DNA
<213> ORGANISM: Artificial Sequence
<220> FEATURE:
<223> OTHER INFORMATION: primer

<400> SEQUENCE: 150
acatgattac gaattcgcct ccaaacgacc cg                          32

<210> SEQ ID NO 151
<211> LENGTH: 36
<212> TYPE: DNA
<213> ORGANISM: Artificial Sequence
<220> FEATURE:
<223> OTHER INFORMATION: primer

<400> SEQUENCE: 151
ggccagtgcc aagcttccga ccccgctgga cgcggc                     36

<210> SEQ ID NO 152
<211> LENGTH: 31
<212> TYPE: DNA
<213> ORGANISM: Artificial Sequence
<220> FEATURE:
<223> OTHER INFORMATION: primer

<400> SEQUENCE: 152
acatgattac gaattcccac gaccacggcc c                          31

<210> SEQ ID NO 153
<211> LENGTH: 38
<212> TYPE: DNA
<213> ORGANISM: Artificial Sequence
<220> FEATURE:
<223> OTHER INFORMATION: primer

<400> SEQUENCE: 153
ggccagtgcc aagcttgcac ggtagcctcc aggaactt                    38

<210> SEQ ID NO 154
<211> LENGTH: 33
<212> TYPE: DNA
<213> ORGANISM: Artificial Sequence
<220> FEATURE:
<223> OTHER INFORMATION: primer

<400> SEQUENCE: 154
acatgattac gaattcggtt cggtgggggg tgt                         33

<210> SEQ ID NO 155
<211> LENGTH: 34
<212> TYPE: DNA
<213> ORGANISM: Artificial Sequence
<220> FEATURE:
<223> OTHER INFORMATION: primer

<400> SEQUENCE: 155
ggccagtgcc aagcttaccg gctcgacacc gcac                       34

```
<210> SEQ ID NO 156
<211> LENGTH: 31
<212> TYPE: DNA
<213> ORGANISM: Artificial Sequence
<220> FEATURE:
<223> OTHER INFORMATION: primer

<400> SEQUENCE: 156
acatgattac gaattcgacc atcaccgccc g                              31

<210> SEQ ID NO 157
<211> LENGTH: 36
<212> TYPE: DNA
<213> ORGANISM: Artificial Sequence
<220> FEATURE:
<223> OTHER INFORMATION: primer

<400> SEQUENCE: 157
ggccagtgcc aagcttctcg acggcttcgg catcga                         36

<210> SEQ ID NO 158
<211> LENGTH: 32
<212> TYPE: DNA
<213> ORGANISM: Artificial Sequence
<220> FEATURE:
<223> OTHER INFORMATION: primer

<400> SEQUENCE: 158
acatgattac gaattctgaa cggggtggcc gc                             32

<210> SEQ ID NO 159
<211> LENGTH: 35
<212> TYPE: DNA
<213> ORGANISM: Artificial Sequence
<220> FEATURE:
<223> OTHER INFORMATION: primer

<400> SEQUENCE: 159
ggccagtgcc aagcttggac ctggacgccc tctac                          35

<210> SEQ ID NO 160
<211> LENGTH: 39
<212> TYPE: DNA
<213> ORGANISM: Artificial Sequence
<220> FEATURE:
<223> OTHER INFORMATION: primer

<400> SEQUENCE: 160
acatgattac gaattccttc ggcttcggtg gcttggagg                      39

<210> SEQ ID NO 161
<211> LENGTH: 37
<212> TYPE: DNA
<213> ORGANISM: Artificial Sequence
<220> FEATURE:
<223> OTHER INFORMATION: primer

<400> SEQUENCE: 161
ggccagtgcc aagcttaact tcttttccgt gggcgga                        37

<210> SEQ ID NO 162
<211> LENGTH: 32
<212> TYPE: DNA
<213> ORGANISM: Artificial Sequence
<220> FEATURE:
<223> OTHER INFORMATION: primer
```

```
<400> SEQUENCE: 162
acatgattac gaattcgacg cggttggacc ag                                  32

<210> SEQ ID NO 163
<211> LENGTH: 37
<212> TYPE: DNA
<213> ORGANISM: Artificial Sequence
<220> FEATURE:
<223> OTHER INFORMATION: primer

<400> SEQUENCE: 163
ggccagtgcc aagcttaccg tgtaggagaa gcaccga                             37

<210> SEQ ID NO 164
<211> LENGTH: 32
<212> TYPE: DNA
<213> ORGANISM: Artificial Sequence
<220> FEATURE:
<223> OTHER INFORMATION: primer

<400> SEQUENCE: 164
acatgattac gaattcccag ttccggcacg gt                                  32

<210> SEQ ID NO 165
<211> LENGTH: 33
<212> TYPE: DNA
<213> ORGANISM: Artificial Sequence
<220> FEATURE:
<223> OTHER INFORMATION: primer

<400> SEQUENCE: 165
ggccagtgcc aagcttcgtc cggtcagctc ggc                                 33

<210> SEQ ID NO 166
<211> LENGTH: 34
<212> TYPE: DNA
<213> ORGANISM: Artificial Sequence
<220> FEATURE:
<223> OTHER INFORMATION: primer

<400> SEQUENCE: 166
acatgattac gaattcgccg gggcgcatcc ggaa                                34
```

METHODS FOR INCREASING MOLECULAR DIVERSITY OF POLYKETIDES AND NON-RIBOSOMAL PROTEINS

This application is a § 371 application of PCT/GB2014/052094, filed Jul. 9, 2014, which in turn claims priority to GB Application 1312318.7, filed Jul. 9, 2013. The entire disclosure of each of the foregoing applications is incorporated by reference herein.

BACKGROUND OF THE INVENTION

Polyketides, non-ribosomal peptides and other related natural products cover a region of chemical space that interacts very effectively with targets in biological systems, leading to very high hit rates on HTS and phenotypic screens (Koehn et al., 2005, Koehn, 2008, Carter, 2011). They have also been very successful commercially, with around 50 approved products with peak sales of the six most successful totalling $15 billion. The molecular diversity of polyketides and non-ribosomal peptides is very high, with macrocyclic, linear, mixed polyketide/peptide and glycosylated examples. For example, just over 7000 known polyketide structures have led to >20 commercial drugs. This 0.3% 'hit rate' compares very favourably with the <0.001% hit rate for synthetic compound libraries (Li and Vederas 2009). However, it is getting increasingly difficult to discover new natural product chemotypes from natural sources and new methods for increasing this 'naturally available' diversity are required.

Although polyketides are structurally diverse, they are produced by a common biosynthetic pathway. These pathways involve large enzymes, containing multiple modules each involved in one (or more) rounds of chain extension with Ketosynthase (KS), Acyl Transferase (AT) and Acyl Carrier Protein (ACP) domains with optional Dehydratase (DH), Enoyl Reductase (ER) and Ketoreductase (KR) (and sometimes other, such as methylase) domains. The polyketides are assembled in the producer organism by stepwise condensation of carboxylic acids (see Staunton et al., 2001 for review) followed by potential cyclisation and further processing of the beta-ketone function in a manner analogous to fatty acid biosynthesis, and generally exhibit a direct one to one correspondence between the genes encoding the polyketide synthase (PKS), the active sites of the biosynthetic proteins, the chemical reactions performed and the structure of the product molecule. Bioengineering techniques have been used to alter the genetic architecture coding for production of the PKS that generates the polyketide. However, the majority of previously described bioengineering techniques are only effective at making simple structural changes to the molecular structure of the parent polyketide (see Reeves et al., 2009 for review). A single genetic alteration leads to a specific chemical change in the polyketide produced. This is useful for lead optimisation and improvement of properties to make the polyketide of interest more drug-like, but has not been very successful at increasing the chemical space that naturally available polyketides cover, especially for generating new chemotypes.

Non-ribosomal peptides are produced by non-ribosomal peptide synthetases (NRPS), multimodular assembly lines which are analogous to polyketide synthases (see FIG. 1). In place of the KR, AT and ACP domains found in PKSs, there are Condensation, Adenylation and Thiolation (or Peptidyl Carrier Protein) domains (see Strieker et al., 2010 for review). Similar issues have been faced to those in PKS engineering (Giessen et al., 2012).

Thus, there remains a need to discover methods for more efficiently accessing novel analogues of natural products, in particular with significant alterations in gross structure.

SUMMARY OF THE INVENTION

We describe herein an efficient method for vastly increasing the molecular diversity available from polyketides and related natural products, by using a recombineering method to add or remove modules from the PKS or NRPS, following a single initial integration event. The presence of a selective pressure, such as an controllable origin of replication, on the integrated vector can substantially increase the frequency of the secondary recombination event between homologous regions on the DNA coding for the PKS or NRPS, which leads to a mixture of strains with increased and reduced numbers of modules on the PKS or NRPS. Surprisingly, the secondary recombination event leads to a very high ratio of productive strains (those producing isolatable quantities) to non-productive strains. With this knowledge, this mixture of strains can then be easily separated into multiple individual strains each producing specific new products. The productivity of the strains following this event are also usually similar to the parent strain, and the production titre of an average isolated strain following recombineering is much higher than the production titre of average strain isolated following a typical biosynthetic engineering technique leading to a hybrid PKS. As the position of the initial integration event can be selected, it gives a controllable way to generate clusters coding for and producing polyketides with expanded and/or contracted macrocyclic ring sizes and or linear chain lengths (see FIG. 2). A single recombineering experiment therefore efficiently leads to generation of multiple novel polyketides or peptides with vastly divergent structures (see FIG. 3 for example). This methodology can therefore be used to significantly expand the available diversity in an efficient and predictable way. In the described case study on rapamycin (Examples and FIG. 4), a single plasmid and integration event led to isolation of 7 strains with altered genetic architecture, all producing multiple novel polyketides. Following combination with feeding of precursors as described in Examples 4, 5.1-5.5, 6 and 17, over 300 novel polyketides were observed analytically. In another case study using the tylosin gene cluster, a series of analogues were generated and analysed. Numerous other recombineering examples of PKS, NRPS and mixed PKS/NRPS gene clusters are also described. These types of methods, along with the discussion in the general methods, can be used to design studies to recombineer any type I modular PKS, NRPS or mixed PKS/NRPS system.

In a first aspect, the present invention provides a method for increasing or reducing the number of modules in a modular polyketide synthase produced by a cell, comprising recombining in a cell population DNA encoding a first polyketide synthase with DNA encoding at least part of a second polyketide synthase thereby to generate a mixture of two or more cells expressing two or more polyketide synthases, each different from the first polyketide synthase in respect of having an increased or reduced number of modules.

In a second aspect, the present invention provides a method for increasing the molecular diversity of polyketides produced by polyketide synthase expressing cells, comprising recombining in a cell population DNA encoding a first polyketide synthase with DNA encoding at least part of a second polyketide synthase thereby to generate a mixture of two or more cells expressing two or more polyketide synthases, each different from the first polyketide synthase in respect of having an increased or reduced number of modules, and isolating said two or more cells. Said isolated cells may be cultured to produce polyketides which are different from the polyketide produced by the first polyketide synthase.

In a third aspect, the present invention provides a method for producing a library of two or more polyketide synthase expressing cells comprising recombining in a cell population DNA encoding a first polyketide synthase with DNA encoding at least part of a second polyketide synthase thereby to generate a mixture of two or more cells expressing two or more polyketide synthases, each different from the first polyketide synthase in respect of having an increased or reduced number of modules, and generating a library by isolating said two or more cells. Said isolated cells may be cultured to produce polyketides which are different from the polyketide produced by the first polyketide synthase.

In the first, second and third aspects, a mixture of three or four or five or six or more cells may be generated. In the second aspect, a mixture of three or four or five or six or more cells may be isolated. In the third aspect, a library of three or four or five or six or more cells may be generated.

In the first, second and third aspects, the first polyketide synthase may be the same as the second polyketide synthase. In the first, second and third aspects, the first polyketide synthase may be different from the second polyketide synthase (this is less favoured).

In a fourth aspect, the present invention provides a method for increasing or reducing the number of modules in a modular non-ribosomal peptide synthetase produced by a cell, comprising recombining in a cell population DNA encoding a first non-ribosomal peptide synthetase with DNA encoding at least part of a second non-ribosomal peptide synthetase thereby to generate a mixture of two or more cells expressing two or more non-ribosomal peptide synthetases, each different from the first non-ribosomal peptide synthetase in respect of having an increased or reduced number of modules.

In a fifth aspect, the present invention provides a method for increasing the molecular diversity of non-ribosomal peptides produced by non-ribosomal peptide synthetase expressing cells, comprising recombining in a cell population DNA encoding a first non-ribosomal peptide synthetase with DNA encoding at least part of a second non-ribosomal peptide synthetase thereby to generate a mixture of two or more cells expressing two or more non-ribosomal peptide synthetases, each different from the first non-ribosomal peptide synthetase in respect of having an increased or reduced number of modules, and isolating said two or more cells. Said isolated cells may be cultured to produce non-ribosomal peptides which are different from the non-ribosomal peptide produced by the first non-ribosomal peptide synthetase.

In a sixth aspect, the present invention provides a method for producing a library of two or more non-ribosomal peptide synthetase expressing cells comprising recombining in a cell population DNA encoding a first non-ribosomal peptide synthetase with DNA encoding at least part of a second non-ribosomal peptide synthetase thereby to generate a mixture of two or more cells expressing two or more non-ribosomal peptide synthetases, each different from the first non-ribosomal peptide synthetase in respect of having an increased or reduced number of modules, and generating a library by isolating said two or more cells. Said isolated cells may be cultured to produce non-ribosomal peptides which are different from the non-ribosomal peptide produced by the first non-ribosomal peptide synthetase.

In the fourth, fifth and sixth aspects, a mixture of three or four or five or six or more cells may be generated. In the fifth aspect, a mixture of three or four or five or six or more cells may be isolated. In the sixth aspect, a library of three or four or five or six or more cells may be generated.

In the fourth, fifth and sixth aspects, the first non-ribosomal peptide synthetase may be the same as the second non-ribosomal peptide synthetase. In the fourth, fifth and sixth aspects, the first non-ribosomal peptide synthetase may be different from the second non-ribosomal peptide synthetase (this is less favoured).

In the first, second, third, fourth, fifth and sixth aspects the number of modules may be reduced. Alternatively, the number of modules may be increased.

In another aspect, the invention provides methods for selecting and identifying strains containing polyketide synthase genes which have undergone recombination to increase or reduce the number of modules. In particular, methods are described for manipulating the rapamycin polyketide synthase, and other polyketide synthases containing co-linear modules.

In another aspect, the invention provides methods for selecting and identifying strains containing non-ribosomal peptide synthetase genes which have undergone recombination to increase or reduce the number of modules.

In another embodiment, heterologous DNA, containing modules or part modules from other PKS or NRPS-encoding clusters can be included the vector.

Definitions

The articles "a" and "an" are used herein to refer to one or to more than one (i.e. at least one) of the grammatical objects of the article. By way of example "an analogue" means one analogue or more than one analogue.

As used herein the term "analogue(s)" refers to chemical compounds that are structurally similar to another but which differ slightly in composition (as in the replacement of one atom by another or in the presence or absence of a particular functional group).

As used herein the term "strain(s)" refers to bacterial strains including, but not limited to, *Streptomyces rapamycinicus* NRRL 5491 and other strains such as *Streptomyces lasaliensis, Actinosynnema pretiosum, Streptomyces bikiniensis, Streptomyces graminofaciens, Streptomyces sp., Streptomyces virginiae, Sorangium cellulosum, Micromonospora megalomicea, Streptomyces halstedii, Streptomyces spiroverticillatus, Streptomyces avermitilis, Streptomyces aureofaciens, Streptomyces hygroscopicus, Streptomyces geldanamycininus, Streptomyces sahachiroi, Xanthomonas albilineans, Amycolatopsis balhimycina, Streptomyces verticillus, Acinetobacter baumannii, Bacillus amyloliquefaciens, Bacillus licheniformis, Streptomyces lohii, Streptomyces nanchangensis, Streptomyces caelestis, Streptomyces violaceusniger, Streptomyces noursei, Streptomyces* sp. HK803, *Streptomyces piomogenus, Streptomyces venezuelae, Saccharopolyspora erythraea, Streptomyces natalensis, Streptomyces platensis, Pseudomonas fluorescens, Streptomyces* sp. SN-593, *Amycolatopsis mediterranei, Streptomyces achromogenes, Streptomyces albus, Streptomyces* sp. CK4412, *Streptomyces spiroverticillatus, Streptomyces* sp. NRRL 11266, *Streptomyces griseus, Streptomyces ambofaciens, Saccharopolyspora spinosa, Streptomyces flaveolus, Nocardiopsis* sp. FU40, *Streptomyces violaceoru-* ber, *Streptomyces* sp. ATCC 39366, *Streptomyces bottropensis*, *Streptomyces* sp. CS40, *Streptomyces lavendulae*, *Streptomyces triostinicus*, *Bacillus amyloliquefaciens*, *Actinomadura kijaniata*, *Streptomyces rochei*, *Bacillus amyloliquefaciens*, *Pseudomonas fluorescens*, *Micromonospora griseorubida*, *Streptomyces cyaneogriseus*, *Streptomyces antibioticus*, *Streptomyces platensis*, *Stigmatella aurantiaca*, *Streptomyces lasaliensis*, *Streptomyces* sp. MK498-98 F14, *Streptomyces fungicidicus*, *Streptomyces pristinaespiralis*, *Streptomyces lividans*, *Streptomyces coelicolor*, *Streptomyces roseosporus*, *Streptomyces actuosus*, *Streptoverticillium* sp. ATCC33160, *Streptomyces fradiae*, *Streptomyces mycarofaciens*, *Streptomyces longisporoflavus*, *Streptomyces parvulus*, *Streptomyces antibioticus*, *Streptomyces incamates*, *Streptomyces tsukubaensis*, *Streptomyces rimosus*, *Streptomyces cinnamonensis*, *Streptomyces parvulus*, *Micromonospora megalomicea*, *Streptomyces diastatochromogenes*, *Streptomyces nodosus*, *Streptomyces varsoviensis*, *Streptomyces setae* and their derivatives.

As used herein the term "polyketide synthase" or "PKS" refers to a protein with modular enzymatic activities which can lead to production of a polyketide under certain conditions.

As used herein the term "non-ribosomal peptide synthetase" or "NRPS" refers to a protein with modular enzymatic activities which can lead to production of a non-ribosomal peptide under certain conditions.

As used herein the term "module" refers to a section of a polyketide synthase or non-ribosomal peptide synthetase protein containing one or more domains, involved in at least one round (typically one round) of chain extension or chain transfer (more commonly chain extension), including but not limited to a ketosynthase, ketoreductase, dehydratase, enoyl reductase, acyl carrier protein, acyl transferase, thioesterase, condensation, thiolation, peptidyl carrier protein, methylation or adenylation domain. See FIG. 1 for the organisation of a typical PKS and NRPS module and FIGS. 6 and 7 for organisation of modules within a typical PKS and NRPS.

As used herein the term "domain" refers to a section of a polyketide synthase or non-ribosomal peptide synthetase protein containing a single enzymatic activity, including but not limited to a ketosynthase, ketoreductase, dehydratase, enoyl reductase, acyl carrier protein, acyl transferase, thioesterase, condensation, thiolation, peptidyl carrier protein, methylation or adenylation domain. See FIG. 1 for the organisation of domains within a typical PKS and NRPS module and FIGS. 6 and 7 for organisation of domains within a typical PKS and NRPS.

Percentage identity determinations can be performed for nucleic acids using BLASTN or standard nucleotide BLAST using default settings (Match/Mismatch scores 1, −2) Gap costs linear, Expect threshold 10, Word size 28 and match matches in a query range 0) and for proteins using BLAST using default settings (Expect threshold 10, Word size 3, Max matches in a query range 0, Matrix Blosum62, Gap costs Existence 11, extension 1 and conditional compositional score matrix adjustment).

As used herein the term "co-linear" refers to open reading frames coding for one or more modules of PKS or NRPS which are transcribed in the same direction.

As used herein the term "heterologous host" refers to an organism, usually a bacterial strain, which can express one or more genes from a PKS or NRPS gene cluster from another organism and has the potential to produce PKS or NRPS when cultured under the correct conditions.

As used herein the term "homologous host" refers to an organism, usually a bacterial strain, which can express one or more genes from a PKS or NRPS gene cluster from an identical organism and has the potential to produce a PKS or NRPS when cultured under the correct conditions.

As used herein the term "post PKS genes" refers to open reading frames coding for one or more gene products which act on the product of a PKS after chain assembly. Examples include genes encoding methylases, hydroxylases and glycosyltransferases.

As used herein the term "post NRPS genes" refers to open reading frames coding for one or more gene products which act on the product of a NRPS after chain assembly. Examples include genes encoding methylases, hydroxylases and glycosyltransferases.

As used herein the term "temperature sensitive plasmid" refers to a plasmid with an origin of replication that can be active or inactive depending on the temperature the strain containing the plasmid is grown at. The example used in most references is pKC1139, which is based on the pSG5 temperature sensitive origin (Bierman et al., 1992). Other examples are pE194 and related plasmids in *Bacillus* sp. (Hofemeister et al., 1983), pBD95 and related plasmids in *Bacillus* sp. (Youngman et al., 1983), pB264 and related plasmids in *Rhodococcus* sp. (Lessard et al., 2004), pMM101 and derivatives in *Pseudomonas* sp. (Chen et al., 2010), pMQ113, pVE6002 and pWV101 and related temperature sensitive plasmids in *Lactococcus* sp., *Streptococcus* sp., *Bacillus* sp., and other gram positive and gram negative strains (Shanks et al., 2009, Maguin et al., 1992).

As used herein the term "gene cluster" refers to a collection of genes within an organism coding for gene products, such as PKS and/or NRPS, required for production of a particular secondary metabolite, such as a polyketide or non-ribosomal peptide.

As used herein the term "polyketide" refers to a secondary metabolite which which is biosynthesised by a modular enzyme which has exclusively or mostly PKS domains, for example rapamycin or tylosin.

As used herein the term "non-ribosomal peptide" refers to a secondary metabolite which is biosynthesised by a modular enzyme which has exclusively or mostly NRPS domains, for example daptomycin or calcium dependent antibiotic.

Figure 1:
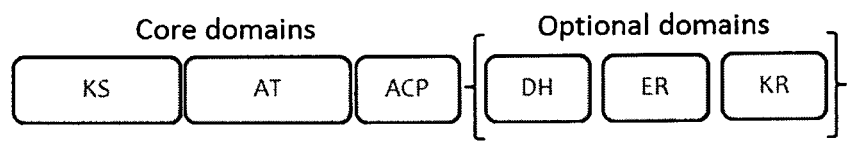
FIG. 1: A: Pictorial representation of a typical PKS module with core Ketosynthase (KS), Acyl Transferase (AT), Acyl Carrier Protein (ACP) domains and optional Ketoreductase (KR), Enoyl Transferase (ER) and Dehydratase (DH) domains. B: Pictorial representation of a typical NRPS module with core Condensation (C), Adenylation (A), Thiolation or Peptidyl Carrier Protein (T) domains and optional Epimerization (E) and Methylation (M) domains.
Figure 1:
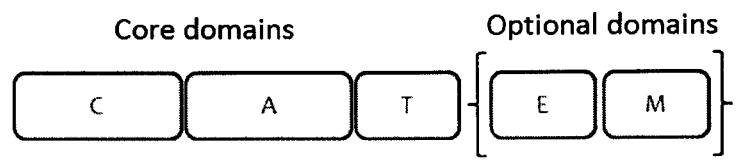
Figure 2:
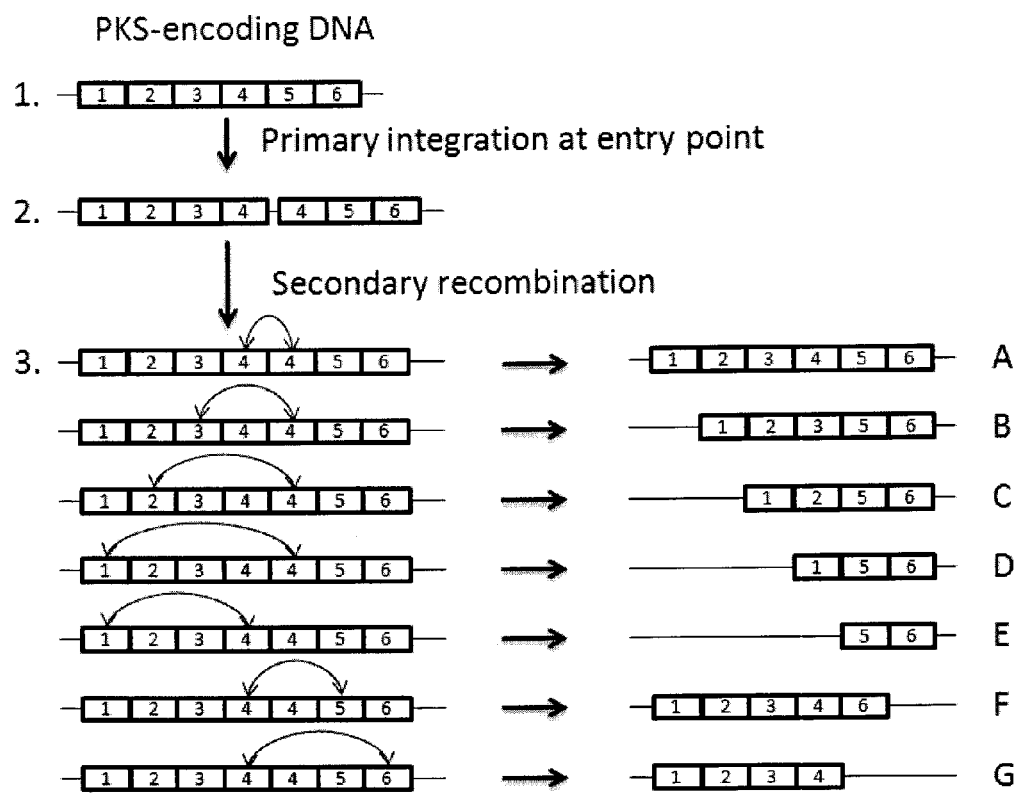
FIG. 2: Pictorial representation of recombineering process with primary integration using entry point DNA (1) in DNA encoding module 4 of the PKS, followed by representation of a series of different potential secondary recombination outputs: wild type (a) and removal of 1 (B, F) 2 (C, G), 3 (D) and 4 (E) modules.
Figure 3:
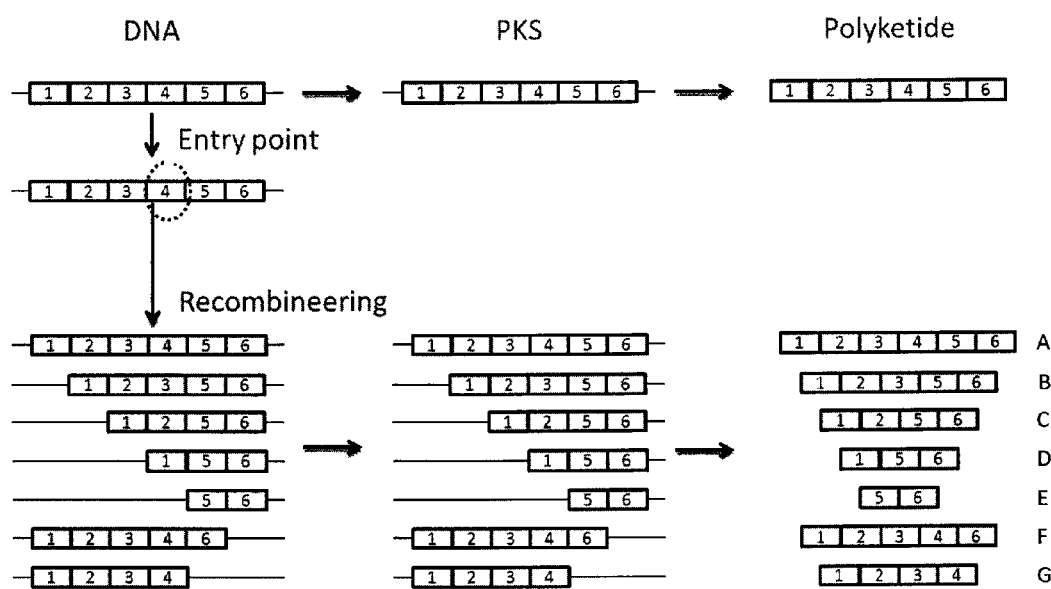
FIG. 3: Pictorial representation of recombineering process and one to one correspondence of DNA, PKS modules and the final polyketide, following a series of different potential secondary recombination outputs: wild type (a) and removal of 1 (B, F) 2 (C, G), 3 (D) and 4 (E) modules.
Figure 4:
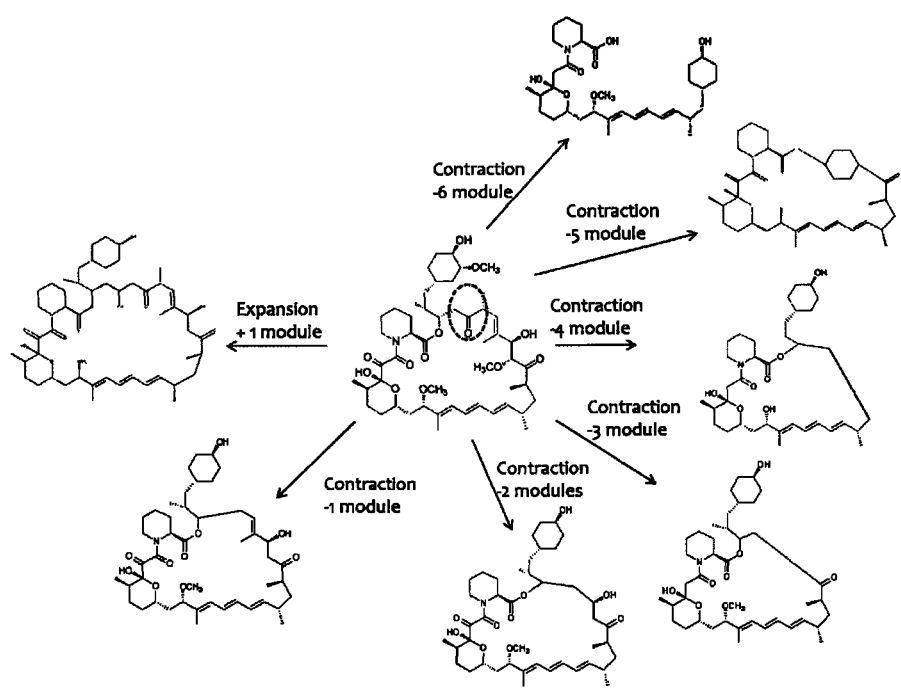
FIG. 4: Representation of the outputs from recombineering on the rapamycin PKS following initial recombination into DNA encoding module 3 of the rapamycin PKS.
Figure 5:
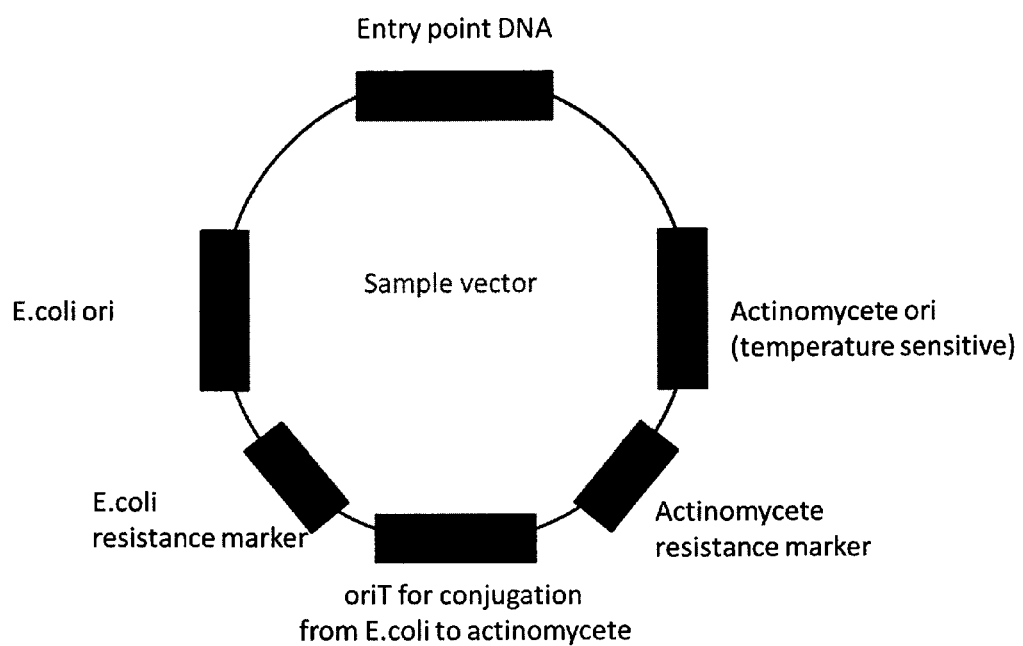
FIG. 5: Representation of a sample vector to carry out recombineering in an actinomycete host containing a PKS or NRPS cluster, with conjugation from *E. coli* to the actinomycete.
Figure 6:
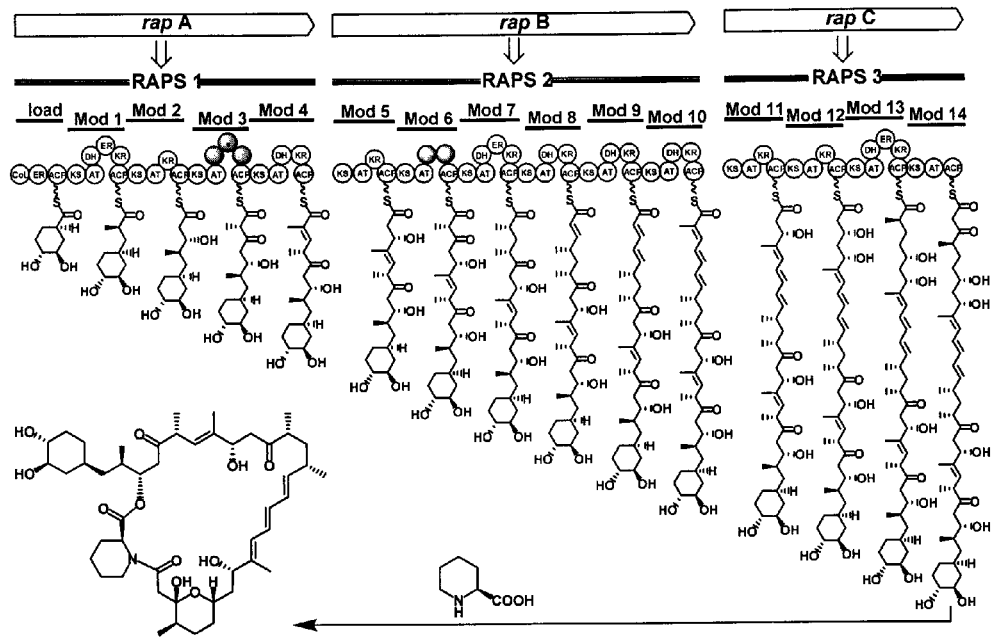
FIG. 6: Representation of the rapamycin PKS, showing modular arrangement of KS, AT, ACP, DH, ER, KR and Thioesterase (TE) domains, together with the structure of rapamycin
Figure 6:
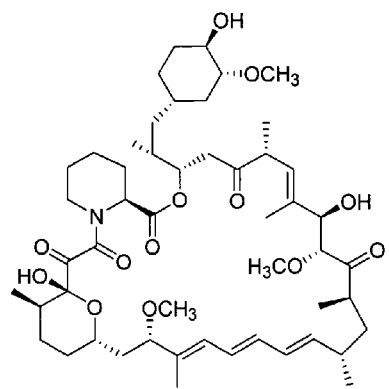
Figure 7:
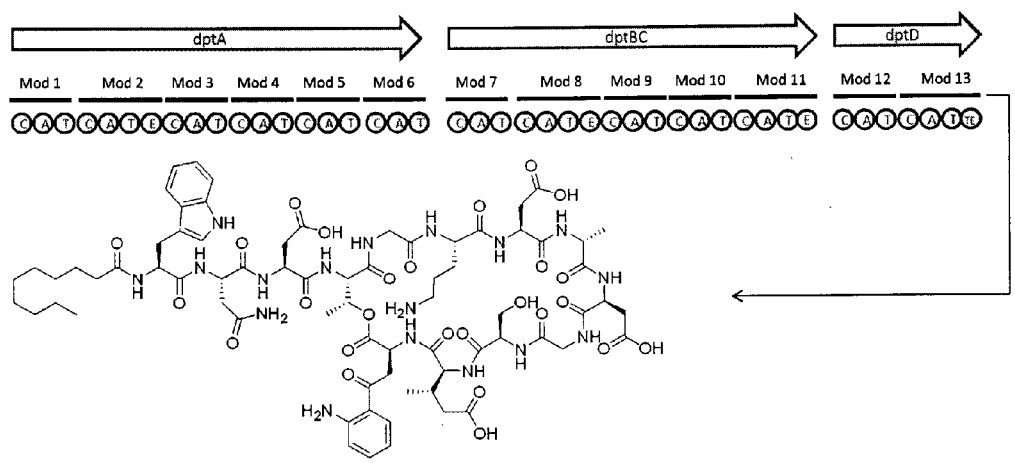
FIG. 7: Representation of the daptomycin NRPS, showing modular arrangement of C, A, T, E and Thioesterase (TE) domains.

| Seq ID No | PRIMER NAME |
| --- | --- |
| 11 | MG101 |
| 12 | MG102 |
| 13 | MG103 |
| 14 | MG104 |
| 15 | MG109 |
| 16 | MG110 |
| 17 | MG105 |
| 18 | MG106 |
| 19 | IR014.FOR |
| 20 | IR014.REV |
| 21 | IR015.FOR |
| 22 | IR015.REV |
| 23 | IR016.FOR |
| 24 | IR016.REV |
| 25 | IR017.FOR |
| 26 | IR017.REV |
| 27 | IR018.FOR |
| 28 | IR018.REV |
| 29 | IR019.FOR |
| 30 | IR019.REV |
| 31 | IR020.FOR |
| 32 | IR020.REV |
| 33 | IR021.FOR |
| 34 | IR021.REV |
| 35 | IR022.FOR |
| 36 | IR022.REV |
| 37 | IR023.FOR |
| 38 | IR023.REV |
| 39 | IR024.FOR |
| 40 | IR024.REV |
| 41 | IR025.FOR |
| 42 | IR025.REV |
| 43 | IR026.FOR |
| 44 | IR026.REV |
| 45 | IR027.FOR |
| 46 | IR027.REV |
| 47 | IR028.FOR |
| 48 | IR028.REV |
| 49 | IR029.FOR |
| 50 | IR029.REV |
| 51 | IR030.FOR |
| 52 | IR030.REV |
| 53 | IR031.FOR |
| 54 | IR031.REV |
| 55 | IR032.FOR |
| 56 | IR032.REV |
| 57 | IR033.FOR |
| 58 | IR033.REV |
| 59 | IR034.FOR |
| 60 | IR034.REV |
| 61 | IR035.FOR |
| 62 | IR035.REV |
| 63 | IR036.FOR |
| 64 | IR036.REV |
| 65 | IR037.FOR |
| 66 | IR037.REV |
| 67 | IR038.FOR |
| 68 | IR038.REV |
| 69 | IR039.FOR |
| 70 | IR039.REV |
| 71 | IR040.FOR |
| 72 | IR040.REV |
| 73 | IR041.FOR |
| 74 | IR041.REV |
| 75 | IR042.FOR |
| 76 | IR042.REV |
| 77 | IR043.FOR |
| 78 | IR043.REV |
| 79 | IR044.FOR |
| 80 | IR044.REV |
| 81 | IR045.FOR |
| 82 | IR045.REV |
| 83 | IR046.FOR |
| 84 | IR046.REV |
| 85 | IR047.FOR |
| 86 | IR047.REV |
| 87 | IR048.FOR |
| 88 | IR048.REV |
| 89 | IR049.FOR |
| 90 | IR049.REV |
| 91 | IR050.FOR |
| 92 | IR050.REV |
| 93 | IR051.FOR |
| 94 | IR051.REV |
| 95 | IR052.FOR |
| 96 | IR052.REV |
| 97 | IR053.FOR |
| 98 | IR053.REV |
| 99 | IR054.FOR |
| 100 | IR054.REV |
| 101 | IR055.FOR |
| 102 | IR055.REV |
| 103 | IR056.FOR |
| 104 | IR056.REV |
| 105 | IR057.FOR |
| 106 | IR057.REV |
| 107 | IR058.FOR |
| 108 | IR058.REV |
| 109 | IR059.FOR |
| 110 | IR059.REV |
| 111 | IR060.FOR |
| 112 | IR060.REV |
| 113 | IR061.FOR |
| 114 | IR061.REV |
| 115 | IR062.FOR |
| 116 | IR062.REV |
| 117 | IR063.FOR |
| 118 | IR063.REV |
| 119 | IR064.FOR |
| 120 | IR064.REV |
| 121 | IR065.FOR |
| 122 | IR065.REV |
| 123 | IR066.FOR |
| 124 | IR066.REV |
| 125 | IR067.FOR |
| 126 | IR067.Rev |
| 127 | IR068.FOR |
| 128 | IR068.Rev |
| 129 | IR069.FOR |
| 130 | IR069.REV |
| 131 | IR070.FOR |
| 132 | IR070.REV |
| 133 | IR071.FOR |
| 134 | IR071.REV |
| 135 | IR072.FOR |
| 136 | IR072.REV |
| 137 | IR073.FOR |
| 138 | IR073.REV |
| 139 | IR074.FOR |
| 140 | IR074.REV |
| 141 | IR075.FOR |
| 142 | IR075.REV |
| 143 | IR076.FOR |

-continued

| Seq ID No | PRIMER NAME |
|---|---|
| 144 | IR076.REV |
| 145 | IR077.FOR |
| 146 | IR077.REV |
| 147 | IR078.FOR |
| 148 | IR078.REV |
| 149 | IR079.FOR |
| 150 | IR079.REV |
| 151 | IR080.FOR |
| 152 | IR080.REV |
| 153 | IR081.FOR |
| 154 | IR081.REV |
| 155 | IR082.FOR |
| 156 | IR082.REV |
| 157 | IR083.FOR |
| 158 | IR083.REV |
| 159 | IR084.FOR |
| 160 | IR084.REV |
| 161 | IR085.FOR |
| 162 | IR085.REV |
| 163 | IR086.FOR |
| 164 | IR086.REV |
| 165 | IR087.FOR |
| 166 | IR087.REV |

DETAILED DESCRIPTION OF THE INVENTION

The present invention provides methods for specifically inducing recombination between DNA encoding PKS or NRPS modules and then identifying polyketide synthase or NRPS genes which have undergone recombination to increase or reduce the number of modules.

Surprisingly, the inventors have found that by carrying out their process, strains containing PKS gene clusters where recombination events increasing or reducing the number of PKS modules can be obtained, and these strains grown to allow production and isolation of novel polyketides. NRPS have analogous organisation and similar methods are taught to induce similar expansion and contraction of modules in these systems.

Thus, according to the invention there is provided a process for preparing a strain containing a novel PKS or NRPS gene cluster and optionally isolating the polyketide or peptide which comprises:

a) Selecting or synthesising (by DNA synthesis) an appropriate PKS or NRPS
  a. This cluster contains more than one PKS or NRPS module, and within the cluster at least 2 modules are preferably co-linear, preferably with ≥1 stretches of >100 bases of homologous DNA. This co-linearity can be generated synthetically (using synthetic DNA) with expression of the PKS or NRPS encoding DNA in a homologous or heterologous system, by recombination within an existing system or by other methods appreciated by those skilled in the art. Homologous DNA is preferably >80% identical e.g. >85% or >90% or >95 or >98 or >99% identical. For example it may be 100% identical.

b) Selecting for the occurrence of a recombination event by:
  a. Integrating into the desired region of the PKS or NRPS a vector including a selectable marker [and optionally an origin of replication, that may be inducible], via a single crossover.
  b. Isolating strains containing the integrated vector
  c. Screening or selecting for loss of the vector c) Analysis of recombinants
  a. Analysing the products from strains which have now lost the selectable marker
  b. Isolating strains which produce compounds from expanded or contracted PKS or NRPS and are derived from recombination events which remove the selectable marker [and origin of replication if present].
  c. Optionally isolating the polyketide or peptide produced
  d. Optionally obtaining all or part of the sequence of the resulting polyketide synthase or NRPS The modularity observed in PKS and NRPS systems is an important aspect and cause of this invention. The modular nature of functional protein domains in a type I polyketide synthase (including but not limited to KS, AT, ACP plus optional reductive functions KR, DH and ER) or NRPS (including but not limited to C, A and T plus optional functions E, M) (see FIG. 1) arranged in a repetitive manner (module1-module2-module3 . . . ) leads to repeating segments of DNA on the genome. Thus there is a high homology in the encoding DNA of different modules of a PKS. Within PKS systems there are areas of DNA encoding different modules that display very high homology over 100s and sometimes ~1000 bp stretches. It is this degree of similarity that allows the observed recombination events to occur.

Our experiments have shown that, when forced, this recombination surprisingly frequently results in functional PKS being produced. That a novel in-frame module is produced by the recombinations observed relies on the modularity of the system.

In conventional PKS or NRPS biosynthetic engineering, the sites are typically chosen at or close to the domain boundaries or at linkers between the modules. However, this process of genetic engineering coupled with (in some cases) limited replacement domain compatibility is thought to result in some cases in poor productivity from the resultant strains. The process described here removes the need to artificially determine domain boundaries but instead allows the process of recombination to occur and only productive events are screened for.

Furthermore, as illustrated by the Examples such as with the rapamycin and tylosin systems, because a strain can undergo a whole series of recombinations with different pieces of DNA encoding parts of domains and inserting into a range of equivalent homologous regions of DNA in downstream modules, multiple stable strains that have one or more module deleted or inserted are produced from a single experiment. This results in a range of stable strains and multiple novel compounds from a single genetic engineering experiment. In rational PKS or NRPS engineering a single designed DNA construct results in the production of a single strain that produces the desired compound and sometimes intermediates or shunt metabolites of the desired compound which are closely related in structure and often predictable.

In another embodiment, it may be possible for the methodology to be used on non-co-linear PKSs, either by generating co-linear versions of the PKS or NRPS encoding DNA via synthetic DNA or using recombination or other targeted methods to re-organise the PKS into a co-linear form.

The Examples describe the targeted insertion of vector to an area of a PKS followed by the removal of vector through secondary recombination. Because of the extensive repeating homologies observed in the PKS we observe removal of the vector through recombination events between homologous regions in a series of downstream modules. This results in the removal of the individual PKS modules of a co-linear PKS and production of a series of functional modified PKS. The repetitive, modular nature of the PKS or NRPS ensure that in-frame joining of modules is achieved.

In this process a vector is placed into the polyketide cluster of interest (primary recombination event). The secondary recombination event that follows involves the removal of the vector and in some resulting strains the recombination provides a strain containing a PKS that has one or more module deleted or duplicated. Therefore the site of the recombination should preferably include the region into which the vector was originally integrated. Therefore in this process one cluster within the strain is targeted and the analysis is then directed towards identification of analogues of that polyketide containing metabolite—in this first case, the polyketide-containing metabolite is rapamycin. This allows the analytical techniques used to be appropriate for the target molecule. Although the resulting molecule may contain significant different features to the parent, obviously much of the molecule remains the same so that analysis can be carried out by identifying specific features that are retained in the products eg a UV chromophore, or a specific molecular ion and its daughters as observed by mass spectrometry.

In further embodiments the stress causing the recombination event could be expression of a recombinase, heat shock, exposure to UV or chemical mutagens. In order to guide analysis it is an advantage to carry out integration of a vector into a known region of a polyketide-coding biosynthetic gene cluster followed by secondary recombination during which one or more modules may be deleted or duplicated. The expression of a recombinase or the exposure to a mutagen either UV or chemical is incorporated during or following the subculturing steps.

One aspect of this invention is the analysis of the strains isolated from the recombination event. Once the vector is lost, and the stress is removed (whether that stress is associated with an element on the vector, or an external influence such as sucrose, streptomycin, a chemical mutagen, UV or a co-expressed recombinase) the isolates are screened for loss of the vector. Those isolates that have lost the vector could fall into 4 separate classes:

1. Reverting to wild type
2. Having undergone a recombination event that leaves the same number of PKS modules but if the integration vector carried more than one region of homology and was designed appropriately this could result in a different sequence to the wild type, eg the desired result of a domain swap experiment.
3. Having undergone a recombination event that leaves a larger or smaller number or modules by recombination to delete or expand the PKS by one or more module.
4. Some other event causing 'damage' may occur in the genome during the genetic engineering.

In the first case, the wild type revertants are readily de-selected by production of the expected product of the parent strain under appropriate conditions. In the second case the resulting PKS may be functional to give a compound of the correct predicted structure. There may be a number of possible related compounds produced, particularly if there are post-PKS steps involved in the biosynthetic pathway that may be rate-limiting or have substrate specificity issues with the new PKS product, however these are generally predictable. In the third case the isolates may either be un-productive in which case they are discarded, or produce new compounds of different PKS size to the parent. While this is a more complicated analysis, once the motivation exists to screen for them there are a number of approaches that can be used. For example in the case of the rapamycin analogues in the Examples described herein they all retain a triene functionality and were identified by their recognizable UV chromophore. In the fourth case the strains are discarded as unproductive and therefore under this analysis approach indistinguishable from other unproductive strains made.

A person of skill in the art will appreciate that there are a number of ways to generate a strain that contains the biosynthetic gene cluster expressing the PKS or NRPS prior to carrying out the described recombineering methodology.

A person of skill in the art will appreciate that a polyketide or non-ribosomal peptide may be biosynthesised by a modular enzyme which contains regions containing both NRPS and PKS domains (for example pederin and rapamycin). The recombineering methods disclosed herein for generation of a mutant PKS or mutant NRPS may be performed in respect of biosynthetic gene clusters that contain only PKS or NRPS modules or contain both PKS and NRPS models (so-called "mixed PKS/NRPS systems" or "mixed PKS/NRPS clusters"). Both the PKS and the NRPS of a mixed PKS/NRPS system may be mutated by performing the recombineering methods disclosed herein on the PKS and the NRPS (simultaneously or successively in either order).

It is well known to those skilled in the art that polyketide gene clusters may be expressed in heterologous hosts (Pfeifer and Khosla, 2001). Accordingly, the present invention includes the transfer of the biosynthetic gene cluster, with or without resistance and regulatory genes, either otherwise complete or containing additional deletions, into a heterologous host. Alternatively, the biosynthetic gene cluster could be generated with synthetic DNA and transferred to a strain. Methods and vectors for the transfer as defined above of such large pieces of DNA are well known in the art (Rawlings, 2001; Staunton and Weissman, 2001) or are provided herein in the methods disclosed. In this context a preferred host cell strain is a eukaryote or prokaryote, more preferably an actinomycete or *Escherichia coli*, still more preferably include, but are not limited to *Actinosynnema mirum* (*A. mirum*), *Actinosynnema pretiosum* subsp. *pretiosum* (*A. pretiosum*), *Streptomyces hygroscopicus*, *Streptomyces hygroscopicus* sp., *Streptomyces hygroscopicus* var. *ascomyceticus*, *Streptomyces tsukubaensis*, *Streptomyces coelicolor*, *Streptomyces lividans*, *Streptomyces rapamycinicus*, *Saccharopolyspora erythraea*, *Streptomyces fradiae*, *Streptomyces avermitilis*, *Streptomyces cinnamonensis*, *Streptomyces rimosus*, *Streptomyces albus*, *Streptomyces griseofuscus*, *Streptomyces longisporoflavus*, *Streptomyces venezuelae*, *Streptomyces albus*, *Micromonospora* sp., *Micromonospora griseorubida*, *Amycolatopsis mediterranei* or *Actinoplanes* sp. N902-109. Further examples include *Streptomyces hygroscopicus* subsp. *geldanus* and *Streptomyces violaceusniger*.

In one embodiment the entire biosynthetic cluster is transferred into a heterologous host. In an alternative embodiment the entire PKS is transferred without any of the associated post-PKS genes (such as methylases, hydroxylases and glycosyltransferases). Optionally this can be carried out step-wise. Optionally some of the post-PKS genes can be introduced appropriately. Optionally additional genes from other biosynthetic gene clusters can be introduced appropriately. Likewise the entire NRPS with or without associated post-NRPS genes (such as methylases, hydroxylases and glycosyltransferases) may be transferred.

Typical PKS Recombineering Experiment This is a description of a sample methodology taught by this disclosure which can be used on any strain containing a suitable PKS:

1. Generate (for example by DNA synthesis or excision from cloned DNA or PCR) a section of DNA homologous ((preferably >90% identity, more preferably >98% identity, most preferably 100% identity)) to the desired entry point on the DNA coding for the PKS. The entry point should be a section of the PKS from which the contraction or expansion of modules is desired. Preferably this DNA should include >500 bp of homologous DNA, more preferably >1000 bp of DNA or >2000 bp of DNA. Preferably this DNA should include at least all or part of a KS or ACP module. In another embodiment it includes all or part of another domain which is repeated within the PKS, such as an AT, KR, ER or DH domain. Optionally, this DNA can also include heterologous DNA from the same or other PKS-encoding gene clusters. This is the ENTRY POINT DNA.
2. This DNA should be joined with a vector DNA (using standard techniques for example by PCR cloning, ligation or Gateway cloning). This vector DNA should preferably include one or more selective markers for the parent hosts (such as *E. coli*) and PKS CONTAINING HOST such as the actinomycete host, such as apramycin resistance, and sequence coding for an *E. coli* origin of replication. Most preferably this vector should also include a controllable origin of replication for the PKS CONTAINING HOST, such as a temperature sensitive replicon, such as the pSG5 origin. An example vector sequence is pKC1139 (Bierman et al., 1992). THIS IS THE VECTOR DNA.
3. The combined ENTRY POINT DNA and the VECTOR DNA should be introduced into the PKS CONTAINING HOST by standard methods (for example conjugation, protoplast transformation or electroporation).
4. The primary recombinant should be selected for using the selective marker.
5. Once strains have been isolated containing the combined ENTRY POINT DNA and the VECTOR DNA integrated into the PKS CONTAINING HOST, the secondary selection should be initiated. This is most preferably a temperature sensitive replicon, by altering the temperature from a non-replicative temperature to a replicative temperature. This induces the recombination event.
6. The mixture of strains/cells generated by this recombination should then be separated into clonal populations by standard methods, e.g. single spore isolation.
7. Each of the isolated strains should then be tested for production of polyketides. In particular strains producing polyketides coded for by PKS with one or more modules added or removed should be analysed for.

The strain could be a strain containing a rapamycin PKS. An example strain is *Streptomyces rapamycinicus* NRRL 5491. More generally, any strain containing one or more genes encoding a modular (type I) polyketide synthase could be used with the methodology described herein. Examples of suitable PKS include, but are not limited to: Actinopyrone, Anguinomycin, Ansatrienin, Antibiotic L 681,217, Antibiotic RK-682, Antibiotic TAN 420, Antibiotic TPU-0037, Antibiotic UCN-01, Antibiotic UCN-02, Apoptolidin, Aureothin, Avermectin, Bafilomycin, Blasticidin, Chlorothricin, Concanamycin, Conglobatin, Ellaiophylin, Fostriecin, Herbimycin, Isoapoptolidin, Kazusamycin, Kendomycin, Leptomycin, Luteoreticulin, Lydicamycin, Milbemycin, Nemadectin, Neoaureothin, Oligomycin, Pestalotin, Piericidin, Reveromycin, Saccharocarcin, Sultriecin, Tetromycin, Trichostatin, Venturicidin, Ikarugamycin, Nigericin, Pimaricin, Pseudomonic acid, Amphotericin, Aurodox, Batumin, Ionomycin, Josamycin, Naphthomycin, Nargenicin, Virustomycin, X-206, Borrelidin, Sanglifehrin, Tylosin, FK506, FK520, Macbecin, Versipelostatin, Kijinamycin, Spinosyn, Epothilone, Monensin, Nystatin, Factumycin, Rosamicin, Lonomycin, Methymycin, Phenelfamycin, Angolamycin, Antascomicin, Rifamycin, Kanchanamycin, Yokonolide, Partricin, Niphimycin, Ammocidin, Erythromycin, Irumamycin, Heinicomycin, Calyculin, Albatansine, Malolactomycin, Clethramycin, Notonesomycin, Cymbimicin, Magnamycin, Narbomycin, Megalomycin, Pladienolide, Bongkrekic acid, Mathemycin, Pironetin, Meridamycin, Ebelactone, Copiamycin, Hygrolydin, Lankamycin, Desertomycin, CP-60993, Vancoresmycin, Perimycin, Halomycin, Aculeximycin, Albocycline, Cytovaricin, Ossamycin, Antibiotic A59770A, Antibiotic A 82548A, Antibiotic SS49, Dunaimycin, Ushkulide, Antibiotic IB 96212, Maclafungin, Antibiotic S 541, UK86956, VM 54339, Meilingmycin, Picromycin, Narbomycin and Methymycin.

Typical NRPS Recombineering Experiment

This is a description of a sample methodology taught by this disclosure which can be used on any strain containing a suitable NRPS:

1. Generate (for example by DNA synthesis or excision from cloned DNA or PCR) a section of DNA homologous ((preferably >90% identity, more preferably >98% identity, most preferably 100% identity)) to the desired entry point on the DNA coding for the NRPS. The entry point should be a section of the NRPS from which the contraction or expansion of modules is desired. Preferably this DNA should include >250 bp of homologous DNA, more preferably >500 bp, most preferably >1000 bp of DNA or >2000 bp of DNA. Preferably this DNA should include all or part of the condensation (C) domain or Thiolation/Peptidyl Carrier Protein (PCP) domain. Optionally, this DNA can also include heterologous DNA from the same or other NRPS-encoding gene clusters. This is the ENTRY POINT DNA.
2. This DNA should be joined with a vector DNA (using standard techniques for example by PCR cloning, ligation or Gateway cloning). This vector DNA should preferably include one or more selective markers for the parent hosts, if used (such as *E. coli* for conjugation) and NRPS CONTAINING HOST such as the actinomycete host, such as apramycin resistance, and if required, sequence coding for an *E. coli* (or other initial host) origin of replication. Most preferably this vector should also include a controllable origin of replication for the NRPS CONTAINING HOST, such as a temperature sensitive replicon, such as the pSG5 origin. An example vector sequence is pKC1139 (Bierman et al., 1992). THIS IS THE VECTOR DNA.
3. The combined ENTRY POINT DNA and the VECTOR DNA should be introduced into the NRPS CONTAINING HOST by standard methods (for example conjugation, protoplast transformation or electroporation).
4. The primary recombinant should be selected for using the NRPS CONTAINING HOST selective marker.
5. Once strains have been isolated containing the combined ENTRY POINT DNA and the VECTOR DNA integrated into the NRPS CONTAINING HOST, the secondary selection should be initiated. This is most preferably a temperature sensitive replicon, by altering the temperature from a non-replicative temperature to a replicative temperature. This induces the recombination event. Alternatively, repeated growth without selection could be used.

6. The mixture of strains/cells generated by this recombination should then be separated into clonal populations by standard methods, e.g. single spore isolation.

7. Each of the isolated strains should then be tested for production of peptides. In particular, strains producing peptides coded for by NRPS with one or more modules added or removed should be analysed for.

Any strain containing one or more genes encoding a non-ribosomal peptide synthetase could be used with the methodology described herein. Examples of suitable NRPS include, but are not limited to: Calcium dependent antibiotic, Berninamycin, Geninthiocin, Ostreogrycin, Quinaldopeptin, Quinomycin, Siomycin, Desotamide, Daptomycin, Virginiamycin, Aurantimycin, Tubulysin. Other examples include Azinomycin, Albicidin, Balhimycin, Bleomycin, Bacillomycin, Bacitracin, Complestatin, Triostin, Polyoxypeptin, Enduracidin, Telomycin and Pristinamycin.

As noted above, the strain of cells may be a heterologous host for the polyketide synthase or the non-ribosomal peptide synthetase and said host may optionally express one or more PKS or post NRPS genes. Alternatively, the strain of cells may be a homologous host for the polyketide synthase or the non-ribosomal peptide synthetase.

Further aspects of the invention are defined as follows:

There is provided a process for producing a library of two or more mutant modular polyketide synthase encoding cells which express mutant functional polyketide synthases having an increased or reduced number of domains and which have been formed by recombination events which process comprises the steps of:

(i) contacting a modular polyketide synthase encoding strain of cells with a vector which includes a selectable marker and a portion of DNA homologous (preferably >90% identity, more preferably >98% identity, most preferably 100% identity) to a portion of DNA within the polyketide synthase such that the vector integrates into cells of the strain via a single crossover event;

(ii) applying selective pressure to the cells into which the vector has been integrated so that the cells eliminate the selectable marker through one or more recombination events; and (iii) screening for or selecting two or more cells that lack the selectable marker and which express mutant functional polyketide synthases having an increased or reduced number of domains.

Said process may be a process for producing a library of three or four or five or six or more mutant modular polyketide synthase encoding cells and wherein step (iii) consists of screening for or selecting three or four or five or six or more cells that lack the selectable marker and which express mutant functional polyketide synthases having an increased or reduced number of domains.

There is also provided a process for producing a library of two or more mutant modular non-ribosomal peptide synthetase encoding cells which express mutant functional non-ribosomal peptide synthetases having an increased or reduced number of domains and which have been formed by recombination events which process comprises the steps of:

(i) Contacting a modular non-ribosomal peptide synthetase encoding strain of cells with a vector which includes a selectable marker and a portion of DNA homologous to a portion of DNA within the non-ribosomal peptide synthetase such that the vector integrates into cells of the strain via a single crossover event;

(ii) Applying selective pressure to the cells into which the vector has been integrated so that the cells eliminate the selectable marker through one or more recombination events; and (iii) Screening for or selecting two or more cells that lack the selectable marker and which express mutant functional non-ribosomal peptide synthetase having an increased or reduced number of domains.

Said process may be a process for producing a library of three or four or five or six or more mutant modular non-ribosomal peptide synthetase encoding cells and wherein step (iii) consists of screening for or selecting three or four or five or six or more cells that lack the selectable marker and which express mutant functional non-ribosomal peptide synthetases having an increased or reduced number of domains.

Suitably the portion of DNA in the vector of the aforementioned processes homologous to a portion of DNA within the polyketide synthase/non-ribosomal peptide synthetase has length >250 bg e.g. >500 bp e.g. >1000 bp>2000 bp. Suitably the homology is >90% sequence identity e.g. >98% sequence identity e.g. 100% sequence identity.

Suitably the vector of the aforementioned processes includes an origin of replication for the organism containing the PKS or NRPS DNA. Suitably the origin of replication is a controllable origin of replication and the selective pressure comprises inducing the origin of replication. For example, the inducible origin of replication is a temperature sensitive origin of replication. Alternatively, the vector may include a dominant sensitivity marker which is lethal if expressed by the strain and the selective pressure is the lethality of the expressed dominant sensitivity marker. Exemplary dominant sensitivity markers are selected from rpsL and sacB.

Suitably the strain of cells is an actinomycete strain, for example, *Streptomyces hygroscopicus*. Alternative suitable strains are mentioned elsewhere in this document.

In an embodiment, the polyketide synthase is a polyketide synthase capable of producing rapamycin, tylosin, concanamycin, clethramycin, monensin or an analogue thereof.

In an embodiment, the vector includes a portion of DNA homologous to a portion of DNA within the polyketide synthase or non-ribosomal peptide synthetase such that the vector integrates into the strain within a linker region between modules. Alternatively, the vector includes a portion of DNA homologous to a portion of DNA within the polyketide synthase or non-ribosomal peptide synthetase such that the vector integrates into the strain within a module.

Suitably the vector includes a portion of DNA homologous to a portion of DNA within the polyketide synthase such that the vector integrates into the strain within the KS or ACP domain of a module. The KS domain of a module is an advantageous choice because a relatively long sequence (>1000 bp) of DNA may be chosen from a given KS domain which has high homology to a corresponding sequence in the KS domain of other modules. All modules of a typical modular polyketide synthase also have a KS domain. Thus all or part of the KS or ACP domains may be used as the portion of DNA homologous to a portion of DNA within the polyketide synthase. Alternatively, all or part of another domain repeated within the PKS can be used, such as an AT, KR, ER or DH domain. Suitably the vector includes a portion of DNA homologous to a portion of DNA within the non-ribosomal peptide synthetase such that the vector integrates into the strain within the C domain or the PCP domain of a module. Thus all or part of C or PCP domains may be used as the portion of DNA homologous to a portion of DNA within the non-ribosomal peptide synthetase. Alternatively, all or part of another domain repeated within the NRPS can be used, such as an A, M or E domain.

Suitably the vector is a plasmid. Suitably the selectable marker is an antibiotic resistance gene, such as the apramycin resistance gene, the thiostrepton resistance gene, the hygromycin resistance gene or the kanamycin resistance gene.

The invention provides a process for producing a library of two or more mutant modular polyketide synthase encoding cells which express mutant functional polyketide synthases having a reduced number of domains, alternatively, the cells express mutant functional polyketide synthases having an increased number of domains.

The invention provides a process for producing a library of two or more mutant modular non-ribosomal peptide synthetase encoding cells which express mutant functional non-ribosomal peptide synthetase having a reduced number of domains, alternatively, the cells express mutant functional non-ribosomal peptide synthetases having an increased number of domains.

A process according to the invention may further comprise the step of isolating at least one cell that lacks the selectable marker and which expresses a mutant functional polyketide synthases or a mutant non-ribosomal peptide synthetase having an increased or reduced number of domains and culturing that at last one cell to obtain a strain.

In an embodiment, the polyketide synthase is a rapamycin synthase, a tylosin synthase, a concanamycin synthase, a clethramycin synthase, or a monensin synthase.

The invention provides a strain obtained or obtainable according to the process of the invention as described herein. Thus there is provided a process for producing a polyketide which comprises culturing a polyketide synthase expressing strain according to the invention in the presence of one or more starter acids and other necessary feed materials (e.g. carbon and nitrogen sources and sources of other trace elements; see e.g. production media components as described in General Methods) and optionally isolating the polyketide. Thus there is provided a polyketide obtained or obtainable by means of a process according to the invention which has an increased or reduced number of modules than the polyketide(s) naturally produced by the strain prior to the one or more recombination events following selective pressure. In one embodiment the polyketide has a reduced number of modules. Alternatively it has an increased number of modules. For example the polyketide is a rapamycin analogue. In another example, the polyketide is a tylosin analogue.

The invention also provides a process for producing a non-ribosomal peptide which comprises culturing a expressing a non-ribosomal peptide synthetase expressing strain according to the invention in the presence of necessary feed materials (e.g. carbon and nitrogen sources and sources of other trace elements; see e.g. production media components as described in General Methods) and optionally isolating the non-ribosomal peptide. Thus there is provided a non-ribosomal peptide obtained or obtainable by means of a process according to the invention which has a reduced or increased number of modules than the non-ribosomal peptide(s) naturally produced by the strain prior to the one or more recombination events following selective pressure. In an embodiment it has a reduced number of modules. Alternatively it has an increased number of modules.

The novel polyketide synthase enzymes and non-ribosomal peptide synthetase enzymes described herein may be used to synthesis new and useful compounds e.g. compounds useful in therapy.

In one embodiment, the gene cluster for recombineering is chosen from the following list of PKS, NRPS and mixed PKS/NRPS clusters: 9-Methylstreptimidone, A40926, A-500359, A-503083, A-74528, abyssomicin, Acinetobactin, Actinomycin, Actinopyrone, Aculeximycin, Acutiphycin, Aflastatin, Albatansine, Albicidin, Albocycline, Aldgamycin, Aldgamycin, Alpha-lipomycin, Altamycin, Ammocidin, Amphotericin, Amycomycin, Angolamycin, Anguinomycin, Ansamitocin, Ansatrienin, Antascomicin, Antibiotic3874H1, Antibiotic67-121A, AntibioticA82548A, AntibioticA83016F, AntibioticA130C, AntibioticA59770A, AntibioticA73A, AntibioticA90720A, AntibioticAB023A, AntibioticAH758, AntibioticCP91243, AntibioticHA-1-92, AntibioticIB96212, AntibioticL681, AntibioticNFAT68, AntibioticRS22A, AntibioticS541, AntibioticTAN1323, AntibioticTAN420, AntibioticTPU-0037, AntibioticTS155-2, AntibioticVM54168, AntibioticX14952B, AntibioticX206, Apicidin, Amphomycin, Apoptolidin, Ascomycin, Aurodox, Avermectin, Azalomycin, Azinomycin, Bacillaene, Bacillomycin, Bacitracin, Bafilomycin, Balhimycin, Barbamide, Batumin, BE-14106, BlasticidinA, Bleomycin, Bongkrekic acid, Boromycin, Borrelidin, Bottromycin, Bryostatin, Bundlin, Butyrolactol, C-1027, Caerulomycin, Calicheamicin, Calyculin, Candicidin, Capreomycin, Carbomycin, Carriomycin, Cationomycin, Cephalosporin, Chalcomycin, Chivosazol, Chondramide, Chondrochlorens, Chrolactomycin, Cinnamycin, Clethramycin, Collismycin, Complestatin, Concanamycin, Conglobatin, Copiamycin, Corallopyronin, Coronatine, Crocacin, Cryptophycin, Cryptophycin, CSG104-175L, Curacin, Curromycin, Cyclomarin, Cyclosporine, Cylindrospermosin, Cymbimicin, Cytovaricin, Dalbavancin, Daptomycin, Decatromycin, Dermostatin, Desertomycin, Dhanyabadomycin, Diastovaricin, Difficidin, Disorazole, Dorrigocin, Dunaimycin, Ebelactone, Elansolid, Ellaiophylin, Enacyloxin, Enduracidin, Endusamycin, Epothilone, Equisetin, Erythromycin, Esperamicin, Etheromycin, Etnangien, Factumycin, FD-594, FD-891, Feglymycin, Fengycin, Fidaxomicin, FK228, FK506, FK520, Flavofungin, Fluvirucin, Fostriecin, FR-008, FR901464, Friulimicin, Fusarin, Geldanamycin, Gephyronic Acid, Gramicidin, Grisorixin, Guadinomine, Halomicin, Halochondrine, Halstoctacosanolide, Hectochlorin, Heinicomycin, Herbimycin, Herboxidiene, Heronamide, Hygrolydin, Ikarugamycin, Indanomycin, Ionomycin, Irumamycin, Isoapoptolidin, Iso-migrastatin, Iturin, Jamaicamide, Jerangolid, Josamycin, Kaimonolide, Kalimantacin, Kanchanamycin, Kazusamycin, Kedarcidin, Kendomycin, Kijinamycin, Kirromycin, Kirrothricin, Labilomycin, Lactimidomycin, Laidlomycin, Lajollamycin, Langkolide, Lankacidin, Lankamycin, Lasalocid, Lavendofuseomycin, Leinamycin, Leptomycin, Leucomycin, Leustroducsin, Lichenysin, Lienomycin, Lincomycin, Lipomycin, Lonomycin, Luteoreticulin, Lydicamycin, MA2664-

I, Macbecin, Madafungin, Macrolactin, Maduropeptin, Magnamycin, Malolactomycin, Manumycin, Massetolide, Mathemycin, Mediomycin, Megalomicin, Meilingmycin, Mepartricin, Meridamycin, Methymycin, Microcystin, Micromonospolide, Micropeptin, Midecamycin, Milbemycin, ML-449, Monensin, Mupirocin, Mutalomycin, Mycinamycin, Mycobactin, Mycolactone, Mycosubtilin, Myxalamid, Myxothiazol, Nanchangmycin, Naphthomycin, Napsamycin, Napthomycin, Narbomycin, Nargenicin, Nemadectin, Neoaureothin, Neomethymycin, Niddamycin, Nigericin, Niphimycin, Notonesomycin, Nystatin, Okadaicacid, Okilactomycin, Oleandomycin, Oleficin, Oligomycin, Onnamide, Orevactaene, Ossamycin, Oxazolomycin, Oxyhygrolidin, Pacidamycin, Paenibactin, Partricin, Pederin, Pellasoren, Perimycin, Phenelfamycin, Phoslactomycin, Picromycin, Piericidin, Pikromycin, Pimaricin, Pironetin, Pladienolide, Platenomycin, Primycin, Pristinamycin, Prodigiosin, Pseudomonic acid, Psymberin, Pyochelin, Pyoluteorin, Pyoverdin, Pyrrolomycin, Quartromicin, Rapamycin, Reveromycin, Rhizopodin, Rhizoxin, Rifamycin, Rimocidin, Roflamycoin, Rosamicin, Roseofungin, Roxaticin, Rubradirin, Rubradirin, Saccharocarcin, Safracin, Saframycin, Salinilactam, Sanglifehrin, Semduramycin, Septamycin, Simocyclinone, Sorangicin, Soraphen, Spinosad, Spinosyn, Spiramycin, Spirangien, Sporaviridin, Stambomycin, Streptolydigin, Streptothricin, Sultriecin, Surfactin, Syringomycin, Tautomycetin, Tautomycetin, Tautomycin, Teicoplanin, Tetromycin, Tetronasin, Tetronomycin, Thailandamide, Thailanstatin, Thiazinotrienomycin, TMC135A, TrichostatinC, Triedimycin, Tubulysin, Tylactone, Tylosin, Tyrocydine, UK86956, Ushkulide, Vacidin, Valinomycin, Vancomycin, Vancoresmycin, Venturicidin, Versipelostatin, Vibriobactin, Vicenistatin, Vicenistatin, Viranamycin, Virginiamycin, Virustomycin, X-206, Yersiniabactin, Yokonolide, Zorbamycin, Zwittermicin and Ambruticin.

A suitable host for expression of a mutant rapamycin PKS is *Streptomyces hydroscopicus*. A suitable host for expression of a mutant tylosin PKS is *S. fradiae*. A suitable host for expression of a mutant daptomycin NRPS is *S. roseosporus*. A suitable host for expression of a mutant Calcium Dependent Antibiotic NRPS is *S. coelicolor*. A suitable host for expression of a mutant lasalocid PKS is *Streptomyces lasaliensis*. A suitable host for expression of a mutant ansamitosin PKS is *Actinosynnema pretiosum* (e.g. ATCC 31565). A suitable host for expression of a mutant chalcomycin PKS is *Streptomyces bikiniensis* (e.g. NRRL 2737). A suitable host for expression of a mutant FD-891 PKS is *Streptomyces graminofaciens* (e.g. A-8890). A suitable host for expression of a mutant FR-008 PKS is *Streptomyces* sp. FR-008. A suitable host for expression of a mutant virginiamycin M PKS is *Streptomyces virginiae* (e.g. MAFF 116014). A suitable host for expression of a mutant virginiamycin S NRPS is *Streptomyces virginiae* (e.g. MAFF 116014). A suitable host for expression of a mutant soraphen PKS is *Sorangium cellulosum* (e.g. So ce26). A suitable host for expression of a mutant megalomycin PKS is *Micromonospora megalomicea* (e.g. subsp. *nigra*). A suitable host for expression of a mutant viceniastatin PKS is *Streptomyces halstedii* (e.g. HC34). A suitable host for expression of a mutant tautomycin PKS is *Streptomyces spiroverticillatus*. A suitable host for expression of a mutant avermectin PKS is *Streptomyces avermitilis* (e.g. ATCC 31267). A suitable host for expression of a mutant alpha-lipomycin PKS is *Streptomyces aureofaciens* (e.g. Tü117). A suitable host for expression of a mutant ascomycin/FK520 PKS is *Streptomyces hygroscopicus* (e.g. subsp. *Ascomyceticus* ATCC14891). A suitable host for expression of a mutant geldanamycin PKS is *Streptomyces geldanamycinnus* (e.g. NRRL 3602). A suitable host for expression of a mutant halstoctacosanolide PKS is *Streptomyces halstedii* (e.g. HC34). A suitable host for expression of a mutant azinomyin NRPS is *Streptomyces sahachiroi* (e.g. NRRL 2485). A suitable host for expression of a mutant albicidin NRPS is *Xanthomonas albilineans*. A suitable host for expression of a mutant balhimycin NRPS is *Amycolatopsis balhimycina* (e.g. DSM 5908). A suitable host for expression of a mutant bleomycin NRPS is *Streptomyces verticillus* (e.g. ATCC15003). A suitable host for expression of a mutant borrelidin PKS is *Streptomyces parvulus* (e.g. Tu4055). A suitable host for expression of a mutant bacillomycin NRPS is *Bacillus amyloliquefaciens* (e.g. FZB42). A suitable host for expression of a mutant bacitracin NRPS is *Bacillus licheniformis* (e.g. ATCC 10716). A suitable host for expression of a mutant bafilomycin PKS is *Streptomyces lohii* (e.g. strain ATCC BAA-1276). A suitable host for expression of a mutant herbimycin A PKS is *Streptomyces hygroscopicus* (e.g. strain AM 3672). A suitable host for expression of a mutant nanchangmycin PKS is *Streptomyces nanchangensis* (e.g. NS3226). A suitable host for expression of a mutant meilingmycin PKS is *Streptomyces nanchangensis* (e.g. strain NS3226). A suitable host for expression of a mutant niddamycin PKS is *Streptomyces caelestis*. A suitable host for expression of a mutant nigericin PKS is *Streptomyces violaceusniger* (e.g. DSM 4137). A suitable host for expression of a mutant nystatin PKS is *Streptomyces noursei* (e.g. ATCC 11455). A suitable host for expression of a mutant oligomycin PKS is *Streptomyces avermitilis* (e.g. ATCC 31267). A suitable host for expression of a mutant phoslactomycin PKS is *Streptomyces* sp. HK803. A suitable host for expression of a mutant piericidin PKS is *Streptomyces piomogenus* (e.g. var. *Hangzhouwanensis*). A suitable host for expression of a mutant pikromycin PKS is *Streptomyces venezuelae* (e.g. ATCC 15439). A suitable host for expression of a mutant erythromycin PKS is *Saccharopolyspora erythraea* (e.g. NRRL 2338). A suitable host for expression of a mutant pimaracin PKS is *Streptomyces natalensis* (e.g. ATCC 27448). A suitable host for expression of a mutant pladienolide PKS is *Streptomyces platensis* (e.g. Mer-11107). A suitable host for expression of a mutant pyoluteorin PKS is *Pseudomonas fluorescens* (e.g. Pf-5). A suitable host for expression of a mutant reveromycin PKS is *Streptomyces* sp. SN-593. A suitable host for expression of a mutant rifamycin PKS is *Amycolatopsis mediterranei* (e.g. S699). A suitable host for expression of a mutant rubradirin PKS is *Streptomyces achromogenes* var. *rubradiris* (e.g. NRRL3061). A suitable host for expression of a mutant salinomycin PKS is *Streptomyces albus* (e.g. DSM 41398). A suitable host for expression of a mutant tautomycetin PKS is *Streptomyces* sp. CK4412. A suitable host for expression of a mutant tautomycin PKS is *Streptomyces spiroverticillatus*. A suitable host for expression of a mutant tetronomycin PKS is *Streptomyces* sp. NRRL 11266. A suitable host for expression of a mutant vicenistatin PKS is *Streptomyces halstedii* (e.g. HC34). A suitable host for expression of a mutant monensin PKS is *Streptomyces cinnamonensis* (e.g. ATCC 15413). A suitable host for expression of a mutant spiramycin PKS is *Streptomyces ambofaciens*. A suitable host for expression of a mutant spinosyn PKS is *Saccharopolyspora spinosa* (e.g. NRRL 18538). A suitable host for expression of a mutant amphotericin B PKS is *Streptomyces nodosus* (e.g. ATCC 14899). A suitable host for expression of a mutant mycotrienin PKS is *Streptomyces flaveolus* (e.g. DSM40061). A suitable host for expression of a mutant apoptolidin PKS is *Nocardiopsis* sp. FU40. A suitable host for expression of a mutant kendomycin PKS is *Streptomyces violaceoruber*. A suitable host for expression of a mutant angolamycin PKS is *Streptomyces eurythermus* (e.g. ATCC 23956). A suitable host for expression of a mutant meridamycin PKS is *Streptomyces violaceusniger* (e.g. DSM 4137). A suitable host for expression of a mutant concanamcyin A PKS is *Streptomyces neyagawaensis* (e.g. ATCC 27449). A suitable host for expression of a mutant complestatin NRPS is *Streptomyces lavendulae*. A suitable host for expression of a mutant Triostin NRPS is *Streptomyces triostinicus*. A suitable host for expression of a mutant ambruticin PKS is *Sorangium cellulosum* (e.g. So ce10). A suitable host for expression of a mutant difficidin PKS is *Bacillus amyloliquefaciens* (e.g. strain FZB42). A suitable host for expression of a mutant filipin PKS is *Streptomyces avermitilis*. A suitable host for expression of a mutant kijanimicin PKS is *Actinomadura kijaniata*. A suitable host for expression of a mutant lankamycin PKS is *Streptomyces rochei*. A suitable host for expression of a mutant macrolactin PKS is *Bacillus amyloliquefaciens* (e.g strain FZB42). A suitable host for expression of a mutant mupirocin PKS is *Pseudomonas fluorescens* (e.g. NCIMB 10586). A suitable host for expression of a mutant mycinamicin PKS is *Micromonospora griseorubida*. A suitable host for expression of a mutant macbecin PKS is *Actinosynnema pretiosum* (e.g. ATCC 31280). A suitable host for expression of a mutant nemadectin PKS is *Streptomyces cyaneogriseus* (e.g. subsp. *Noncyanogenus*). A suitable host for expression of a mutant oleandomycin PKS is *Streptomyces antibioticus*. A suitable host for expression of a mutant iso-migrastatin PKS is *Streptomyces platensis* (e.g. NRRL 18993). A suitable host for expression of a mutant chlorothricin PKS is *Streptomyces antibioticus* (e.g. DSM 40725). A suitable host for expression of a mutant Quinomycin NRPS is *Streptomyces lasaliensis*. A suitable host for expression of a mutant Polyoxypeptin NRPS is *Streptomyces sp.* MK498-98 F14. A suitable host for expression of a mutant enduracidin NRPS is *Streptomyces fungicidicus* (e.g. ATCC 21013).

Further aspects of the invention include:

1) Strain BIOT-2437 having deposit number NCIMB 42152.
2) A process for preparing a polyketide which comprises culturing such a strain in the presence of one or more starter acids and other necessary feed materials (including carbon and nitrogen sources and sources of other trace elements; see e.g. production media components as described in General Methods) and optionally isolating the polyketide. Example starter acids are listed in Table 1.
3) A polyketide obtained or obtainable by means of said process. Such a polyketide will have an increased or reduced number of modules as compared with rapamycin.
4) A strain having a mutant polyketide synthase and a mutant non-ribosomal peptide synthetase which is obtained or obtainable according to the recombineering process described herein.
5) A process for preparing a polyketide and a non-ribosomal peptide which comprises culturing such a strain in the presence of one or more starter acids and other necessary feed materials and optionally isolating the polyketide or the non-ribosomal peptide.
6) A polyketide or a non-ribosomal peptide obtained or obtainable by means of a process comprising the steps of such a process.

EXAMPLES

General Methods
Media
Water used for preparing media was prepared using Millipore Elix Analytical Grade Water purification System
2×TY

| Yeast extract | 10 g/L |
| Tryptone | 16 g/L |
| Sodium Chloride | 5 g/L |

R6 Conjugation Media.
For 700 ml

| Sucrose | 200 g |
| Dextrin | 10 g |
| Casamino acids | 1 g |
| $MgSO_4 \cdot 7H_2O$ | 0.05 g |
| $K_2SO_4$ | 0.1 g |
| Trace Elements | 1 mL (1g/L each of $FeSO_4 \cdot 7H_2O$, $MnCl_2 \cdot 4H_2O$, $ZnSO_4 \cdot 7H_2O$, sterilized by filter and stored at room temperature). |
| Agar | 20 g |

Autoclaved at 121 C, 20 minutes.
Sterile additions (added to 700 mL of well-tempered mixture prepared as above)

| 0.65M L-glutamic acid, mono sodium salt | 100 mL (filter sterilised) |
| 0.48M $CaCl_2 \cdot 2H2O$ | 100 mL |
| 0.1M MOPS pH 7.2 | 100 mL |

Plates are poured (~30 mL) and dried extensively in a laminar flow hood before use
ISP3 Agar

| Oatmeal | 20 g/L |
| Bacto Agar | 18 g/L |
| Trace element solution | 1 mL/L (1 g/L each of $FeSO_4 \cdot 7H_2O$, $MnCl_2 \cdot 4H_2O$, $ZnSO_4 \cdot 7H_2O$, sterilized by filter and stored at room temperature). |

Oatmeal is cooked/steamed in the water for 20 min, strained through a muslin and more water added to replace lost volume. Trace elements solution is added and pH adjusted to 7.2 with NaOH. Agar is added before autoclaving at 121° C., 15 minutes.
MMAM Agar (MAM Agar)

| Wheat Starch | 10 g/L |
| Corn steep powder | 2.5 g/L |
| Yeast extract | 3 g/L |
| $CaCO_3$ | 3 g/L |
| $FeSO_4$ | 0.3 g/L |

Adjust to pH 5.8 if needed before sterilisation

| Agar | 20 g/L |

RapV7

| Corn steep solids | 4.0 g/L |
| Nutrisoy | 5.0 g/l |

-continued

| | |
|---|---|
| Dextrin | 35 g/L |
| Ammonium sulphate | 2.0 g/L, |
| Lactic acid | 1.6 mL/L, |
| Calcium carbonate | 7.0 g/L |

Adjust to pH7.5 and Autoclave 121° C., 1 bar, 20 minutes
Add 25 mL/L 40% w/v sterile glucose post sterilisation
MD6

| | |
|---|---|
| Nutrisoy | 30 g/L |
| Corn starch | 30 g/L |
| Dextrin | 19 g/L |
| Yeast (whole Allinson) | 3 g/L |
| Corn steep powder | 1 g/L |
| $KH_2PO_4$ | 2.5 g/L |
| $K_2HPO_4$ | 2.5 g/L |
| Ammonium sulphate | 10 g/L |
| Sodium chloride | 5 g/L |
| Calcium carbonate | 10 g/L |
| $MnCl_2 \cdot 4H_2O$ | 10 mg/L |
| $MgSO_4 \cdot 7H_2O$ | 2.5 mg/L |
| $FeSO_4 \cdot 7H_2O$ | 120 mg/L |
| $ZnSO_4 \cdot 7H_2O$ | 50 mg/L |
| MES | 21.2 g/L |

Adjust to pH6.0 and add α-amylase 0.4 mL/L prior to sterilisation (121° C., 1 bar, 20 minutes).
Add 50 ml/L 40% w/v sterile fructose and 14 mL/L 14% L-lysine (filter sterilised)
MD6/5-1

| | |
|---|---|
| Nutrisoy | 15 g/L |
| Dextrin | 50 g/L |
| Yeast (whole Allinson) | 3 g/L |
| Corn steep powder | 1 g/L |
| $KH_2PO_4$ | 2.5 g/L |
| $K_2HPO_4$ | 2.5 g/L |
| Ammonium sulphate | 10 g/L |
| Sodium chloride | 13 g/L |
| Calcium carbonate | 10 g/L |
| $MnCl_2 \cdot 4H_2O$ | 3.5 mg/L |
| $MgSO_4 \cdot 7H_2O$ | 15 mg/L |
| $FeSO_4 \cdot 7H_2O$ | 150 mg/L |
| $ZnSO_4 \cdot 7H_2O$ | 60 mg/L |
| SAG471 | 0.5 ml/L |

Add 15 g/L (28.1% w/v sterile) fructose and 0.5 ml/L sterile 3.75% L-lysine after sterilisation Materials All molecular biology enzymes and reagents were from commercial sources.

Bacterial Strains and Growth Conditions

*Escherichia coli* DH10B (GibcoBRL) was grown in 2×TY medium or 2×TY agar media as described by Sambrook et al. (1989) and *E. coli* ET12567 (pUZ8002) as described in Paget et al. (1999) in 2×TY medium with kanamycin (25 µg/ml) and chloramphenicol (10 µg/ml). The vector pUC19 was obtained from New England Biolabs. Vector pKC1139 is described in (Bierman et al., 1992). *E. coli* transformants were typically selected for with either 100 µg/mL ampicillin or 50 µg/mL apramycin depending on resistance marker

*Streptomyces rapamycinicus* Biot-4010 (*Streptomyces rapamycinicus* NRRL5491 in which the rapK gene has been deleted using methodology as described in WO2004/00709 and as described in Kendrew et al., 2013) and its derivatives were maintained on ISP3 agar plates or MAM agar plates at 28° C. Where necessary for selection apramycin was used at 50 µg/mL. Spore stocks of these strains were prepared by growth on ISP3 agar medium for approximately 14-21 days and preserved in 20% w/v glycerol in distilled water at −80° C.

Listing of Phenotypes in BIOT-4827

The following phenotypes are for when grown as described below with the addition of feed A1.

Phenotype A—produces metabolites including one with molecular formula $C_{51}H_{79}NO_{12}$ Phenotype B—produces metabolites including one with molecular formula $C_{46}H_{71}NO_{10}$ Phenotype C—produces metabolites including one with molecular formula $C_{43}H_{67}NO_{10}$ Phenotype D—produces metabolites including one with molecular formula $C_{41}H_{65}NO_8$ Phenotype E—produces metabolites including one with molecular formula $C_{37}H_{59}NO_7$ Phenotype F—produces metabolites including one with molecular formula $C_{36}H_{53}NO_8$ Phenotype G—produces metabolites including one with molecular formula $C_{33}H_{53}NO_7$ BIOT-4827, a mixture of strains, has been submitted to the NCIMB strain collection and has deposit number NCIMB 42152. A method for splitting the constituent strains, should it be required, is taught as follows:

*S. rapamycinicus* BIOT-4827 Separation Method

1) Streak Out the Strain to Obtain Single Colonies.

The spore suspension is streaked out on ISP3 agar at 28° C. for 7-14 days to reveal single colonies. Single colonies are then patched onto fresh ISP3 agar at 28° C. for 7-14 days to achieve good sporulation.

2) Grow Individual Colonies to Prepare to Assess Phenotype

Take a number of individual colonies, prepared as in step 1 and use the fresh spores to inoculate 7 ml seed medium RapV7 (50 mL polypropylene centrifuge tubes (falcon tubes) (cat no. 227261, purchased from Greiner Bio-One Ltd, Stonehouse, Gloucestershire, UK)) closed with foam plugs by transferring an agar plug (5 mm diameter). The inoculated seed medium is incubated with shaking at 300 rpm, 2.5 cm throw at 28° C. for 48 hours. This seed culture (0.5 ml) is transferred to the fermentation medium MD6 (7 mL in falcon tube as before) using a wide bore tip and incubated with shaking at 300 rpm, 2.5 cm throw at 26° C. After 24 hours feed A1 (0.05 ml of stock solution, prepared as described below) is added to the growing cultures. The cultures are incubated with shaking at 300 rpm, 2.5 cm throw at 26° C. for a further 5 days (i.e. a total of 6 days). The broth is then extracted by aliquoting 0.9 ml into a 2 ml eppendorf tube and adding methanol (0.9 ml). The eppendorf is then shaken on a vibrax bed for 30 minutes before the cell debris is removed by centrifugation (13,200 rpm, 10 minutes). An aliquot of the supernatant is then transferred to an LC-vial for LC-MS analysis by the methods described below.

3) Phenotype Analysis

The strain extracts may be analysed by HPLC or LC-MS. The HPLC system comprises an Agilent HP1100 equipped with a Hyperclone 3 micron BDS C18 130 A column 150 mm×4.6 mm (Phenomenex) heated to 50° C. The gradient elution is from 55% mobile phase B to 95% mobile phase B over 10 minutes followed by an isocratic hold at 95% mobile phase B for 2 minutes with a flow rate of 1 mL/min. Mobile phase A is 10% acetonitrile:90% water, containing 10 mM ammonium acetate and 0.1% trifluoroacetic acid, mobile phase B is 90% acetonitrile:10% water, containing 10 mM ammonium acetate and 0.1% trifluoroacetic acid.

LC-MS system comprised an Agilent HP1100 equipped with a Hyperclone 3 micron BDS C18 130 A column 150 mm×4.6 mm (Phenomenex) heated to 50° C. coupled to a Bruker Daltonics Esquire 3000 electrospray mass spectrometer. The gradient elution was from 50% mobile phase B to 100% mobile phase B over 10 minutes followed by an isocratic hold at 100% mobile phase B for 3 minutes with a flow rate of 1 mL/min. Mobile phase A was water containing 0.1% formic acid, mobile phase B was acetonitrile containing 0.1% formic acid. Positive negative switching was used over a scan range of 500 to 1000 Dalton.

Isolatable strains may be annotated as follows:

Phenotype A—produces metabolites including one with molecular formula $C_{51}H_{79}NO_{12}$ Phenotype B—produces metabolites including one with molecular formula $C_{46}H_{71}NO_{10}$ Phenotype C—produces metabolites including one with molecular formula $C_{43}H_{67}NO_{10}$ Phenotype D—produces metabolites including one with molecular formula $C_{41}H_{65}NO_8$ Phenotype E—produces metabolites including one with molecular formula $C_{37}H_{59}NO_7$ Phenotype F—produces metabolites including one with molecular formula $C_{36}H_{53}NO_8$ Phenotype G—produces metabolites including one with molecular formula $C_{33}H_{53}NO_7$ Alternatively, the BIOT-4827 mixture could be grown and separate metabolites isolated from a single mixed culture broth, using standard methods.

DNA Manipulation and Sequencing

DNA manipulations, PCR and electroporation procedures were carried out as described in Sambrook et al. (1989). Automated DNA sequencing was carried out at a contract service provider.

Conjugation of *Streptomyces rapamycinicus* or Similar Strains

*Escherichia coli* ET12567, harbouring the plasmid pUZ8002 was transformed with the desired plasmid by electroporation to generate the *E. coli* donor strain for conjugation. This strain was used to transform *Streptomyces rapamycinicus* by spore conjugation as described below.

Fresh spores were harvested in water or 20% glycerol from plates of *Streptomyces rapamycinicus*. Alternatively frozen spore stocks were used. These spores were washed in 2TY and then resuspended in 0.25 ml 2T×Y and were heat-shocked at 50° C. for 10 minutes in a water bath. These were then mixed with the *E. coli* donor strain which had been grown (with appropriate antibiotics) to an optical density of approximately 0.4 and washed twice with 2TY before resuspending in 0.25 ml 2T×Y. The mixture of strains was plated onto R6 medium and incubated at 37° C. (for plasmids with pKC1139 background). After 2-3 hours the plates were overlaid with nalidixic acid (final in-plate concentration 25 µg/mL) and after a further 18 hours with apramycin sulphate (final in-plate concentration 50 µg/mL). For conjugation of plasmids to an attachment site conjugation plates were incubated at 28° C. overnight before and overlaying sequentially with first nalidixic acid (final in-plate concentration 25 µg/mL) and apramycin sulphate (final in-plate concentration 50 µg/mL).

General Transformation Methods

Conjugation is a process of a direct cell-to-cell transfer of a plasmid, usually carrying an oriT sequence from an *E. coli* donor strain (such as *E. coli* ET12567 pUZ8002 (Kieser et al 2000), *E. coli* Et12567 pUB307 or *E. coli* S17-1 (Flett et al., 1997)) to the recipient strain (containing the biosynthetic gene cluster).

It can be performed through conjugation with either spores or mycelia. In both cases, the donor strain is transformed with the plasmid of choice and grown in liquid medium with antibiotic selection. In case of the spore conjugation route, the donor strain is combined with the recipient strain spores (freshly harvested or thawed) preconditioned with heat-shock at 50° C. In case of mycelial conjugation route, the recipient strain is grown in liquid culture, the mycelium is collected by centrifugation, washed with 10% glycerol, and then mixed with the donor strain cells as above.

In both cases, after mixing, the strains are plated on a non-selective medium, and after a given time of growth (e.g. ~24 hours) the antibiotic selection is imposed to remove the donor strain (e.g. with nalidixic acid) and the recipient cells that have not accepted the plasmid (e.g. Apramycin for pKC1139). Resulting antibiotic-resistant exconjugants are usually observed within a few days. Antibiotic resistant exconjugants are transferred to a medium with antibiotics and nalidixic acid to retain the transformed plasmid, and are maintained in 'patches' for use in further work. Further details are discussed in Kieser et al. 2000. Conjugation, or transformation of other strains is also known to those skilled in the art. For example transformation of *Bacillus* (Lotareva and Prosorov 2005), *Mycobacteria* (Garbe et al., 1994), *Myxobacteria* (Wenzel et al., 2005), *Xanthomonas* (Atkins et al., 1987), *Acetinobacter* (Aranda et al., 2010), *Amycolatopsis* (Dhingra et al., 2003), *Pseudomonas* (Choi et al., 2006), *Micromonospora* (Love et al., 1992), *Actinosynemma* (Goh et al., 2007), *Nocardia* (Vasant Kumar et al., 1994) and *Nocardiopsis* (Du et al., 2011).

In addition to conjugation, electroporation can be used to transfer plasmids into bacterial strains. Examples of this are known to those skilled in the art and include electroporation of *Rhodococcus* sp. (Desomer et al., 1990), *Bacillus* sp. (Stephenson and Jarrett 1991), *Mycobacteria* sp. (Goude and Parish 2009), *Sorangium* sp. (Kopp et al., 2005).

Infusion Cloning

The vector for InFusion cloning (BioTechniques 43:354-359 (September 2007)) is linearised using restriction enzymes as directed by enzymes supplier. After digestion, the vector is purified by a PCR purification kit of choice.

InFusion cloning primers should contain at least 15 base pairs at the 5' end that are homologous to the bases at one end of the vector and the 3' end complementary to the target gene. SnapGene software (from GSL Biotech; available at snapgene.com) can be used to help automate the design process. PCR is then performed using the designed primers on genomic DNA. The fragment is then excised from the gel, purified and mixed with the linearized vector in 1:5-1:1 ratio and the 5× In-Fusion HD Enzyme Premix up to 10 uL volume. The reaction is performed for 15 minutes at 50° C., and then placed on ice. Afterwards, the *E. coli* cells are transformed with 2.5 uL of the reaction mixture.

Temperature Sensitive Plasmids

The secondary recombination event often occurs via the change in temperature (e.g. 37° C. for primary recombination and 28° C. for secondary recombination or initial plasmid replication) when using a temperature sensitive plasmid, such as the pSG5 based conjugative plasmid pKC1139. Other temperature sensitive plasmids are known to those skilled in the art, such as pGM1190, pMT660 (Birch and Cullum 1985) and others described in Kieser et el. 2000.

Heterologous Expression

Biosynthetic NRPS and PKS gene clusters may be heterologously expressed in *Saccharopolyspora* and *Streptomyces* sp. and other strains which are easier to manipulate. Methods for this are known to this skilled in the art and are discussed in Wenzel et al. 2005 and Pfeifer and Khosla 2001.

FKBP12 PPIase Assay

The assay was conducted at 10° C. in 50 mM Tris buffer at pH8.0, 50 µM DTT, 100 mM NaCl, 0.005% NP40 with 6 nM FKBP12 and 60 µM substrate (SUC-ALPF-pNA, diluted from 20 mg/ml stock in 0.5M LiCl/TFE). The $K_m$ for the substrate was determined to be approximately 188 µM. The first order rate equation was fitted to the absorbance data to obtain a rate constant. A catalytic rate ($K_{enz}$) was calculated from the enzymatic rate minus the background rate. $K_{enz}$ v inhibitor concentration was plotted to obtain the Ki value.

Murine PLP T Cell Proliferation Assay

Activity of mTOR inhibitors was measured in two different antigen-specific murine T cell proliferation assays (as described in Young et al., 2000). In the first assay, lymph nodes obtained from SJL/J mice immunized with PLP 139-151 encephalitogenic peptide, are re-stimulated in culture and assayed for a secondary proliferation response to the same peptide. In a second type of assay, lymph nodes obtained from PLP TCR transgenic mice are simulated with PLP peptide in culture in a primary stimulation assay.

Production and Isolation of Rapamycin Analogs and Contracted Rapamycins

TABLE 1

| | | Starting materials | | |
|---|---|---|---|---|
| Feed code | Name | | structure | Source |
| A | cyclohexanecarboxylic acid | | | Sigma (10,183-4) |
| B | cyclohex-1-enecarboxylic acid | | | Alfa Aesar (A10741) |
| C | cyclohex-3-enecarboxylic acid | | | Alfa Aesar (A15229) |
| D | 3-methoxycyclohexanecarboxylic acid | | | Sigma (332836) |
| E | Ethyl 5-hydroxycyclohex-3-enecarboxylic acid | | | Synthesised as described below |
| F | (1S*,3S*,4R*)-4-fluoro-3-hydroxycyclohexanecarboxylic acid | | | Synthesised as per Goss et al. 2010 |
| G | 4-methylcyclohexanecarboxylic acid | | | Sigma (330620) |
| H | cyclopentanecarboxylic acid | | | Sigma (328324) |
| I | cycloheptanecarboxylic acid | | | Sigma (C98500) |

TABLE 1-continued

| Feed code | Name | structure | Source |
|---|---|---|---|
| J | (1R*,2S*,4S*)-bicyclo[2.2.1]heptane-2-carboxylic acid | 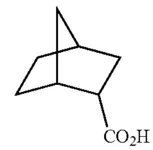 | Alfa Aesar (32482) |
| K | (1S*,2R*,5R*,6S*)-2-hydroxybicyclo[3.2.1]octane-6-carboxylic acid | 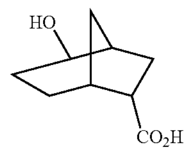 | Fisher (BTBG00035DA) |
| L | tetrahydro-2H-pyran-4-carboxylic acid | 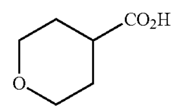 | Parkway Scientific (BX-103) |
| M | tetrahydro-2H-thiopyran-4-carboxyl acid | 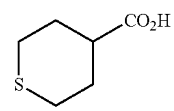 | Synthesis as per Strassler et al. 1997 |
| N | 3-hydroxybenzoic acid | 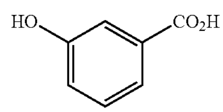 | Sigma (H20008) |
| O | 4-methylthiophene-2-carboxylic acid | 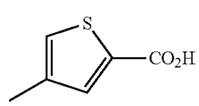 | Sigma (633550) |
| P | 3-amino-5-hydroxybenzoic acid | 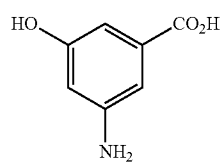 [SMILES: Nc1cc(O)cc(C(=O)O)c1] | Synthesised as per Becker and Rickards, 1984 |
| Q | 4-hydroxy-3,3-dimethylcyclohexanecarboxylic acid | 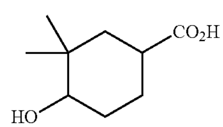 | Synthesised as described below |
| R | 4-methylenecyclohexanecarboxylic acid | 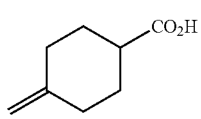 | Synthesised as described below |
| S | 4-methylcyclohex-3-enecarboxylic acid | 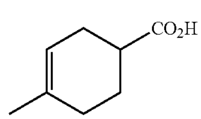 | Synthesised as described below |
| T | (1S*,4S*)-4-methylcyclohexanecarboxylic acid | 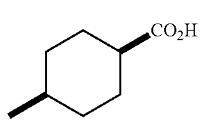 | Synthesised as described below |

TABLE 1-continued

Starting materials

| Feed code | Name | structure | Source |
|---|---|---|---|
| U | (1S*,3S*,4S*)-3,4-dihydroxycyclohexanecarboxylic acid | 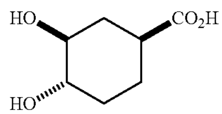 [SMILES: O=C(O)[C@H]1CC[C@H](O)[C@@H](O)C1] | Synthesised as described below |
| V | 3-methylcyclohexanecarboxylic acid | 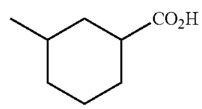 | Sigma (330612) |
| W | isonicotinic acid | 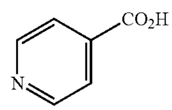 | Sigma (I17508) |
| X | 5-methylthiophene-2-carboxylic acid | 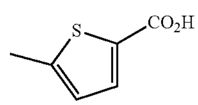 | Sigma (M84429) |
| A1 | (1R*,4R*)-4-hydroxycyclohexanecarboxylic acid | 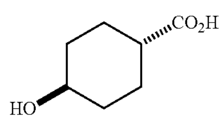 | TCI (UK) Ltd (H1175) |
| B1 | (2S*)-bicyclo[2.2.1]heptane-2-carboxylic acid | 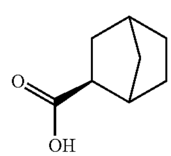 | Synthesised as described below |
| C1 | (1S*,3S*)-3-hydroxycyclohexanecarboxylic acid | 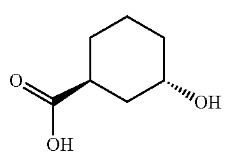 | Synthesised as described below |
| D1 | (1S*,3R*,4S*)-methyl 3-fluoro-4-hydroxycyclohexanecarboxylate | 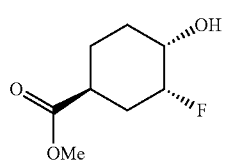 [SMILES: COC(=O)[C@H]1CC[C@H](O)[C@H](F)C1] | Synthesised as described below |
| E1 | (1S*,3R*,4S*)-3-ethyl-4-hydroxycyclohexanecarboxylic acid | 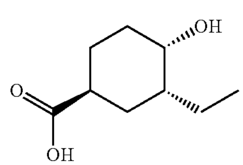 | Synthesised as described below |
| F1 | methyl 3,3-difluoro-4-hydroxycyclohexanecarboxylate | 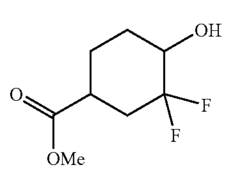 [SMILES: COC(=O)C1CCC(O)C(F)(F)C1] | Synthesised as described below |

TABLE 1-continued

Starting materials

| Feed code | Name | structure | Source |
|---|---|---|---|
| G1 | (1S*,3R*)-3-hydroxycyclohexanecarboxylic acid | 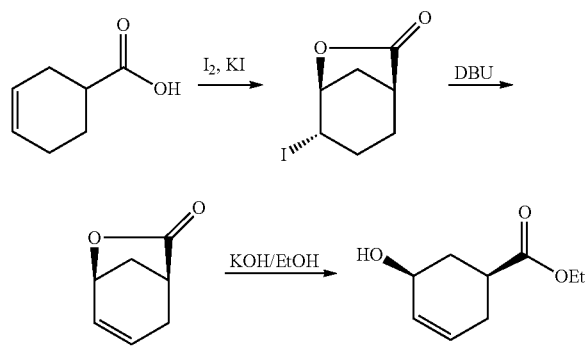 | Synthesised as described below |

5-hydroxycyclohex-3-enecarboxylic Acid—Feed E

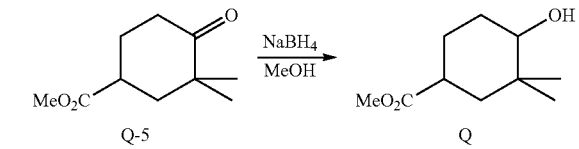

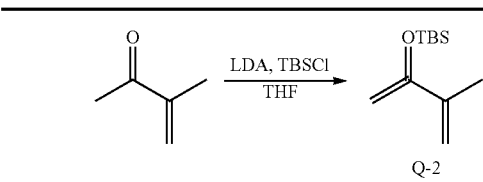

The title compound was prepared, in racemic form, by generating (1R*, 3R*, 4R*)-4-iodocyclohexane-1,3-carbolactone from cyclohex-3-ene carboxylic acid, which was then treated with the base DBU (1,8-diazabicyclo[5.4.0]undec-7-ene) to eliminate HI. The resultant (1R*, 5S*) cyclohex-3-ene-1,5-carbolactone was then treated with potassium hydroxide dissolved in ethanol to yield the title compound (Marshall, J. A., and Shiping, X., 1995)

4-hydroxy-3,3-dimethylcyclohexanecarboxylic Acid—Feed Q

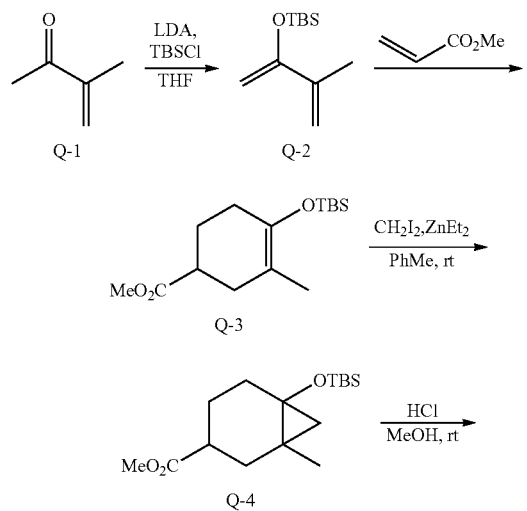

Synthesis of Q-2:

| Chemicals/Reagents & Solvents | moles | Eq. | Qty. |
|---|---|---|---|
| 3-Methyl-3-butene-2-one | 0.0595 | 1.0 | 5.00 g |
| n-Butyl Lithium | 0.0654 | 1.1 | 40.5 mL, 4.1 g |
| Diisopropyl amine | 0.0654 | 1.1 | 9.25 mL, 6.66 g |
| HMPA | 0.0119 | 0.2 | 2.13 mL |
| TBDMSCl | 0.0654 | | 9.85 g |
| THF | | | (50 + 25) mL |

Brief procedure: n-BuLi was added to a solution of diisopropyl amine in tetrahydrofuran at −78° C. over a period of 15 minutes and stirred for 1 h at same temperature and at 0° C. for 30 minutes. The reaction mixture was cooled to −78° C., 3-methyl-3-butene-2-one in 25 mL of THF was added and stirring continued at −78° C. for 30 minutes. HMPA followed by TBDMSCl were added and stirring continued at same temperature for 2 h.

Work up: Reaction mixture was quenched with 100 mL of water and extracted with ethyl acetate, dried over $Na_2SO_4$, concentrated under reduced pressure to give crude product Purification: This compound was purified by distillation (87° C.-90° C.)

TLC system: 10% ethyl acetate in Hexane

Nature of the compound: Yellowish Brown solid, Yield: 3.99 g

Synthesis of Q-3:

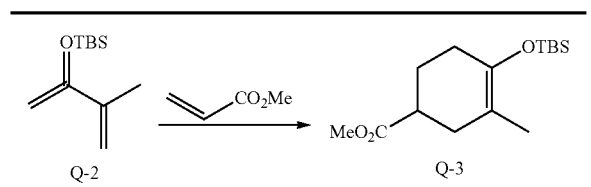

| Chemicals/Reagents & Solvents | moles | Eq. | Qty. |
| --- | --- | --- | --- |
| Q-2 | 0.040 | 1.0 | 8.0 g |
| Methyl acrylate | 0.032 | 0.8 | 2.752 g |
| Toluene | | | 240 mL |

Brief procedure: A mixture of Q-2 and methyl acrylate in toluene was heated (120° C.) with stirring in a sealed tube for 48-72 h.

Work up: Reaction mixture was extract with ethyl acetate, washed with 100 mL of water and dried over sodium sulfate. Solvent evaporation under reduced pressure afforded crude product.

Purification: The crude compound was purified by column chromatography using ethyl acetate in hexane to give pure product.

TLC system: 10% ethyl acetate in Hexane, $R_f$ Value: 0.8

Nature of the compound: Yellowish Brown solid, Yield: 3.19 g

Synthesis of Q-4:

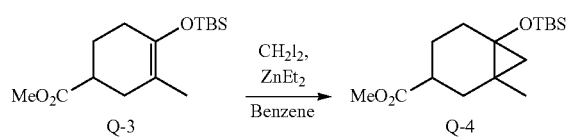

| Chemicals/Reagents & Solvents | Moles | Eq. | Qty. |
| --- | --- | --- | --- |
| Q-3 | 0.7 mmol | 1.0 | 0.2 g |
| ZnEt$_2$ | 10.5 mmol | 15 | 1.29 g |
| CH$_2$I$_2$ | 10.5 mmol | 15 | 2.81 g |
| dry Benzene | | | 20.0 mL |

Brief procedure: Q-3 was taken in dry benzene and to which were added diethyl zinc and diiodomethane simultaneously. The reaction mixture was stirred at 65° C. for 16 h under nitrogen atmosphere.

Work up: The reaction mixture was quenched with NH$_4$Cl (aqueous) and extracted into ethyl acetate. Solvent evaporated under reduced pressure afforded desired product as yellowish brown solid.

Purification: This crude was directly used for next step without further purification.

TLC system: 10% ethyl acetate in Hexane, $R_f$ value: 0.8

Nature of the compound: Yellowish Brown solid, Yield: 0.31 g (crude)

Synthesis of Q-5:

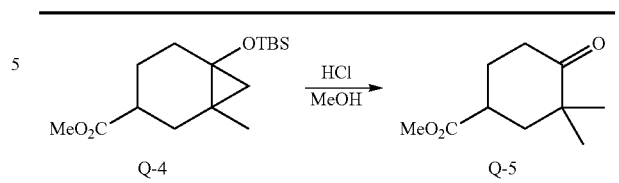

| Chemicals/Reagents & Solvents | moles | Eq. | Qty. |
| --- | --- | --- | --- |
| Q-4 | 0.0026 | 1.0 | 0.8 g |
| methanol | — | | 8 mL |
| HCl in ether | — | | 8 mL |

Brief procedure: HCl in ether (saturated) was added to a solution of Q-4 in dry methanol and the reaction mixture was stirred at room temperature for 30 min.

Work up: Reaction mixture was neutralised with NaHCO$_3$ (to pH 7) and extracted with ethyl acetate (three times). Combined organic layer was washed with brine and dried over Na$_2$SO$_4$. Solvent evaporated under reduced pressure afforded crude product.

Purification: The crude compound was purified by column chromatography over silica gel using ethyl acetate in hexane as solvent to yield pure desired product.

TLC system: 20% ethyl acetate in Hexane $R_f$ value: 0.5

Nature of the compound: Yellowish Brown solid Yield: 0.27 g

Synthesis of Q:

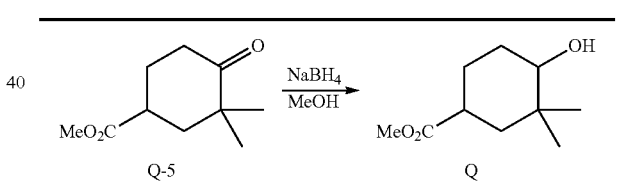

| Chemicals/Reagents & Solvents | mmol | Eq. | Qty. |
| --- | --- | --- | --- |
| Q-5 | 0.5 | 1.0 | 0.1 g |
| NaBH$_4$ | 0.5 | | 0.0189 g |
| Methanol | | | 1.0 mL |

Brief procedure: Q-5 was taken in methanol and was added sodium borohydride. The reaction mixture was stirred at −15° C. for 30 min.

Work up: Reaction mixture was quenched with 0.1 mL Acetic acid and extracted into ethyl acetate. Organic layer was washed with brine, dried over Na$_2$SO$_4$ and concentrated under reduced pressure to give crude product.

Purification: The compound was purified by column chromatography over silica gel using ethyl acetate in hexane as eluent to give desired product.

TLC system: 20% ethyl acetate in Hexane $R_f$ value: 0.3

Nature of the compound: Yellowish Brown solid Yield: 0.072 g

4-methylenecyclohexanecarboxylic Acid—Feed R

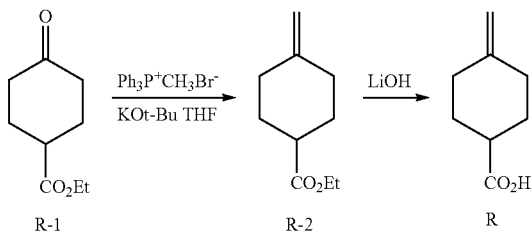

Synthesis of R-2:

| Chemicals/Reagents & Solvents | Wt./Vol. | mmol | Eq. |
|---|---|---|---|
| ethyl 4-oxocyclohexane carboxylate | 5 g | 29.37 | 1 |
| methyltriphenylphosphonium bromide | 16.8 g | 47.02 | 1.6 |
| potassium tert-butoxide | 4.95 g | 44.08 | 1.5 |
| THF | 90 mL | — | — |

Brief procedure: KO-tBu was added to a solution of methyltriphenylphosponium bromide at 0° C. under nitrogen atmosphere and stirred for 30 min. To the above yellow colored reaction, a solution of ethyl 4-oxocyclohexane carboxylate in THF was added dropwise and the resulting mixture was stirred at the same temperature for 16 h.

Work up: The reaction mixture was quenched with water and extracted with diethyl ether. The combined ethereal extract was dried and concentrated under reduced pressure.

Purification: The crude residue was purified by silica gel (100-200 mesh) column chromatography by gradual elution from 5% to 10% EtOAc-petroleum ether.

TLC system: 20% Ethyl acetate-petroleum ether, $R_f$ value: 0.6

Nature of the compound: Colorless liquid, Yield: 3.5 g

Synthesis of R:

| Chemicals/Reagents & Solvents | Wt./Vol. | mmol | Eq. |
|---|---|---|---|
| R-2 | 6.7 g | 39.88 | 1 |
| LiOH•H$_2$O | 3.35 g | 79.76 | 2 |
| H$_2$O | 100 mL | — | — |
| THF | 100 mL | — | — |

Brief procedure: An aqueous solution of LiOH was added to R-2 in THF at room temperature and resulting mixture stirred at room temperature for 12 h.

Work up: The reaction mixture was diluted with pentane. The phases were separated and the aqueous layer was acidified with 4 N HCl at ice bath temperature and extracted with diethyl ether. The combined organic extract was dried and concentrated under reduced pressure to furnish the compound R as a solid.

Purification: No purification done.

TLC system: 30% Ethyl acetate-petroleum ether, $R_f$ value: 0.3

Nature of the compound: White solid, Yield: 3.9 g

4-methylcyclohex-3-enecarboxylic Acid—Feed S

| Chemicals/Reagents & Solvents | Wt. | mmol. | Eq. |
|---|---|---|---|
| Isoprene | 6 g | 88.07 | 1.0 |
| Acrylic acid | 6.3 g | 88.07 | 1.0 |

Brief procedure: A mixture of isoprene and acrylic acid was taken in a 50 mL sealed tube and heated to 110° C. for 15 h.

Work up: The reaction mass was dissolved in ether and basified with saturated NaHCO$_3$ solution. The organic layer was discarded and the aqueous layer was washed with diethyl ether (3×50 mL) to remove polymeric material. The aqueous layer was then acidified with 20% HCl and extracted with DCM. The combined organic extract was dried over NaSO$_4$ and concentrated.

Purification: The product was repeatedly recrystallized from hexane at 0° C.

TLC system: 20% EtOAc in pet ether, $R_f$ value: 0.51

Nature of the compound: White solid, Yield: 1.1 g

(1S*,4S*)-4-methylcyclohexanecarboxylic Acid—Feed T

| Chemicals/Reagents & Solvents | Wt | mol | Eq. |
|---|---|---|---|
| p-Toluic acid | 10 g | 0.0734 | 1 |
| Platinum oxide | 3.31 g | 0.014 | 0.2 |
| Diethyl ether | 100 mL | — | — |

Brief procedure: A mixture of p-Toluic acid and PtO$_2$ in ether was placed in a 250 mL Parr hydrogenation apparatus overnight under 60 psi hydrogen pressure at room temperature.

Work-up: The reaction mixture was then filtered and concentrated under reduced pressure.

Purification: WG-433 was obtained as cis & trans isomers (84% & 15% respectively), the mixture was purified by column chromatography.

TLC system: 50% Diethyl ether/Hexane, $R_f$ value: 0.54

Nature of the compound: Light yellow color liquid, Yield: 5.0 g (1S*,3S*,4S*)-3,4-dihydroxycyclohexanecarboxylic Acid—Feed U

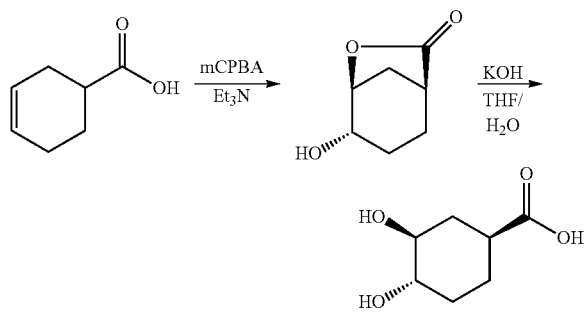

Racemic 3-cis,4-trans-dihydroxycyclohexane carboxylic acid was readily attainable from commercially available racemic 3-cyclohexene carboxylic acid. This acid was epoxidised through treatment with meta-chloroperbenzoic acid and converted to the lactone in situ by the addition of base (triethylamine), thus setting up the relative stereochemistries. This lactone was then hydrolysed by the action of aqueous potassium hydroxide, and the final product purified over ion exchange resin (see PAS Lowden Thesis 1997, Corey, E. J. and Huang, H., 1989).

(2S)-bicyclo[2.2.1]heptane-2-carboxylic Acid—Feed B1

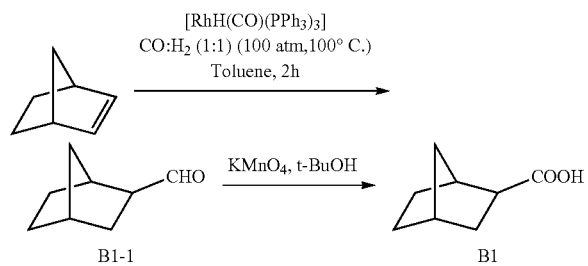

Synthesis of B1-1:

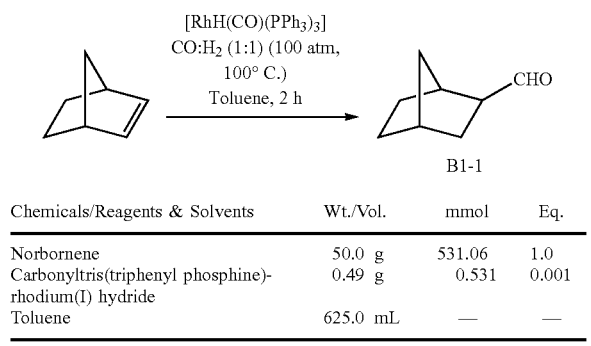

| Chemicals/Reagents & Solvents | Wt./Vol. | mmol | Eq. |
|---|---|---|---|
| Norbornene | 50.0 g | 531.06 | 1.0 |
| Carbonyltris(triphenyl phosphine)-rhodium(I) hydride | 0.49 g | 0.531 | 0.001 |
| Toluene | 625.0 mL | — | — |

Procedure: Norbornene was placed in a 2 L stainless steel autoclave together with toluene and carbonyl tris (triphenyl phosphine)-rhodium (I) hydride. The reactor was pressurized to 1250 Psi with synthesis gas (CO/$H_2$=1:1) and heated to 100° C.

Work up: The reactor was cooled to room temperature; the residual gases removed by purging $N_2$ gas for 15-20 min and the solvent was concentrated under reduced pressure to give the crude B1-1.

Purification: B1-1 was purified by column chromatography using 60-120 mesh silica (eluent: 15% DCM-petroleum ether).

Nature of the compound: Pale yellow liquid Yield: 25 g (37.9%)

Synthesis of B1:

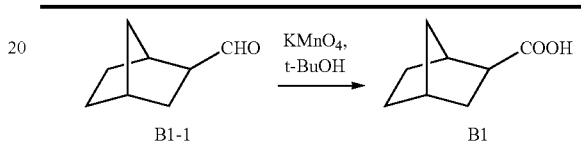

| Chemicals/Reagents & Solvents | Wt./Vol. | mmol | Eq. |
|---|---|---|---|
| B1-1 | 125.0 g | 1006.6 | 1.0 |
| Potassium permanganate | 154.0 g | 1006.6 | 1.0 |
| t-Butanol | 125.0 mL | — | — |
| Water | 125.0 mL | — | — |

Reaction time: 1 min Reaction temperature: rt

Brief procedure: To a solution of B1-1 in t-butanol was added water. To the resulting mixture an aq $KMnO_4$ solution was added with vigorous stirring at room temperature.

Work up: The reaction mixture was quenched by the addition of a saturated solution of sodium sulfite and the pH of the resulting mixture was adjusted to 3 with cold dilute HCl to dissolve the colloidal $MnO_2$. The reaction mixture was extracted with ethyl acetate, washed with water, dried over anhydrous $Na_2SO_4$ and concentrated under reduced pressure to yield crude B1.

Purification The crude B1 was purified by column chromatography using 100-200 mesh silica (eluent: 3% EtOAc-petroleum ether).

TLC system: 10% EtOAc-petroleum ether, $R_f$ value: 0.1

Nature of the compound: White crystalline solid, Yield: 100 g (1S*,3S*)-3-hydroxycyclohexanecarboxylic Acid—Feed C1

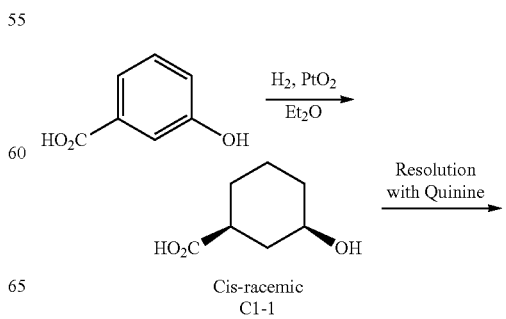

-continued

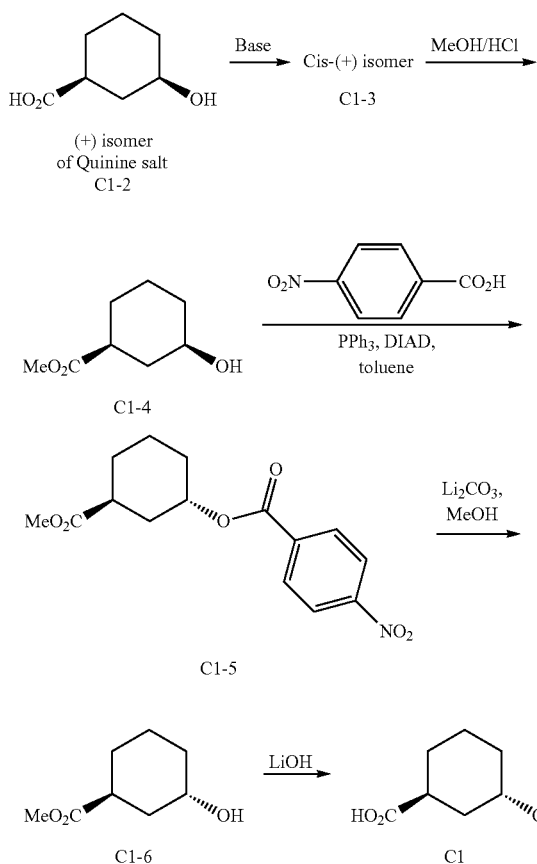

Synthesis of C1-2:

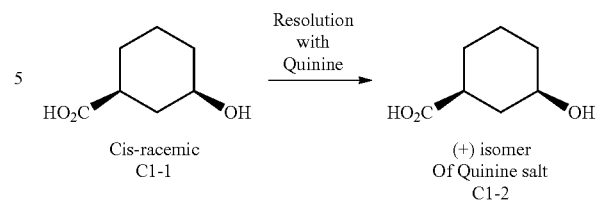

| Chemicals/Reagents & Solvents | Wt./Vol. | mol | Eq. |
|---|---|---|---|
| C1-1 | 26 g | 0.18 | 1 |
| Quinine trihydrate | 35 g | 1.08 | 0.6 |
| Methanol | 500 mL | — | — |

Brief procedure: Quinine trihydrate was dissolved in warm methanol, to this solution C1-1 in methanol was added portion wise. The combined solution was placed in a water bath at 50° C. and allowed to cool slowly to room temperature and then placed in ice bath for 3 h. The resulting mixture was filtered.

Purification: Recrystallisation from ethanol.

Nature of the compound: Off white solid, Yield: 40 g

Synthesis of C1-3:

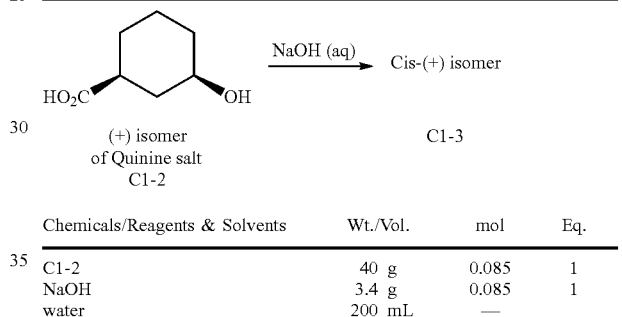

| Chemicals/Reagents & Solvents | Wt./Vol. | mol | Eq. |
|---|---|---|---|
| C1-2 | 40 g | 0.085 | 1 |
| NaOH | 3.4 g | 0.085 | 1 |
| water | 200 mL | — | — |

Brief procedure: Quinine salt was suspended in a stirred solution of NaOH in water. The mixture was stirred at 80° C. for 2 h.

Work up: Water was added and washed with chloroform. The aq layer was acidified with $H_2SO_4$ and extracted with ethyl acetate. Combined ethyl acetate layer was dried and concentrated.

Purification: Recrystallization from ethyl acetate.

TLC system: 10% MeOH/DCM $R_f$ value: 0.12

Nature of the compound: Off white solid. Yield: 9.1 g

Synthesis of C1-4:

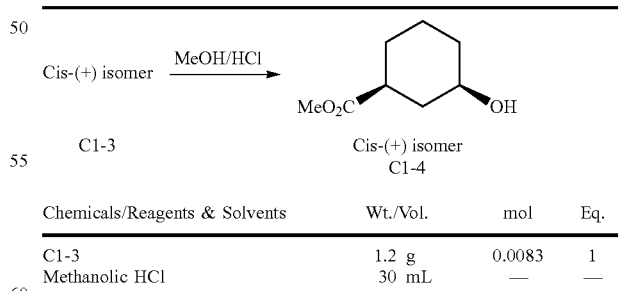

| Chemicals/Reagents & Solvents | Wt./Vol. | mol | Eq. |
|---|---|---|---|
| C1-3 | 1.2 g | 0.0083 | 1 |
| Methanolic HCl | 30 mL | — | — |

Brief procedure: A solution of C1-3 in methanolic HCl was heated under refluxed overnight.

Work up: After completion of the reaction, organic layer was removed under reduced pressure.

Purification: The residue was extracted with ethyl acetate, washed with water, brine, dried over $Na_2SO_4$ and concentrated to yield light yellow oil.

Synthesis of C1-1:

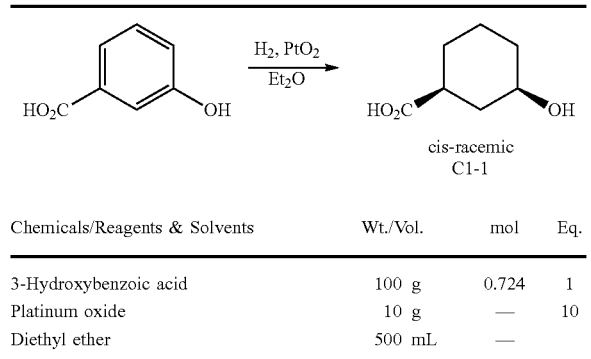

| Chemicals/Reagents & Solvents | Wt./Vol. | mol | Eq. |
|---|---|---|---|
| 3-Hydroxybenzoic acid | 100 g | 0.724 | 1 |
| Platinum oxide | 10 g | — | 10 |
| Diethyl ether | 500 mL | — | — |

Brief procedure: A solution of 3-hydroxybenzoic acid in diethyl ether was hydrogenated at 60 Psi with platinum oxide for 10 days.

Work up: After completion of the reaction, the catalyst was removed by filtration and washed with methanol under nitrogen; the organic layer was distilled under reduced pressure.

Purification: The residue was washed with petroleum ether (3×100 mL), the mixture on recrystallization four times with ethyl acetate gave pure compound.

TLC system: 10% MeOH/DCM, $R_f$ value: 0.12

Nature of the compound: Off white solid, Yield: 26 g

TLC system: 10% MeOH/DCM, $R_f$ value: 0.4
Nature of the compound: Light yellow oil, Yield: 1.2 g
Synthesis of C1-5:

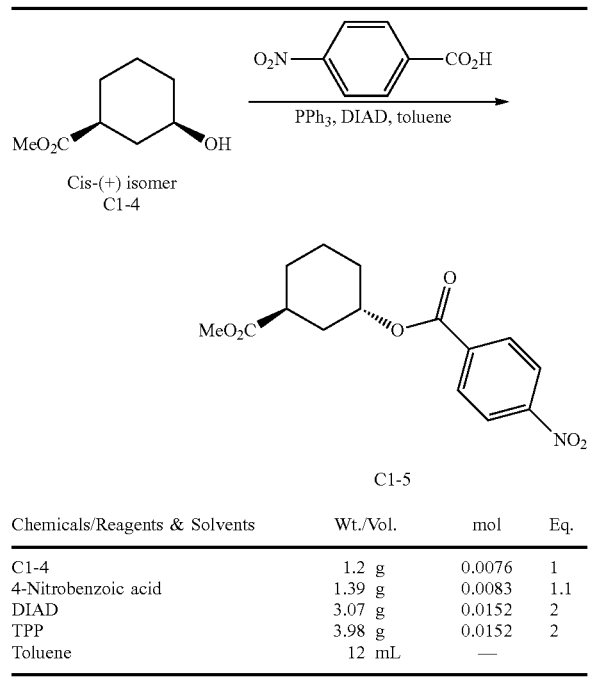

Cis-(+) isomer
C1-4

C1-5

| Chemicals/Reagents & Solvents | Wt./Vol. | mol | Eq. |
|---|---|---|---|
| C1-4 | 1.2 g | 0.0076 | 1 |
| 4-Nitrobenzoic acid | 1.39 g | 0.0083 | 1.1 |
| DIAD | 3.07 g | 0.0152 | 2 |
| TPP | 3.98 g | 0.0152 | 2 |
| Toluene | 12 mL | — | |

Reaction time: 2 days Temperature conditions: r.t
Brief procedure: A solution of C1-4, 4-nitrobenzoic acid, TPP in Toluene was cooled to −78° C. then DIAD was added at 50° C. and stirred at r.t for 2 days.
Work up: After completion of the reaction, the reaction mixture was concentrated.
Purification: The residue on purification by column chromatography using hexane/ethyl acetate (10% to 40% ethyl acetate gradient) gave off white solid.
TLC system: 30% ethyl acetate/petroleum ether, $R_f$ value: 0.7
Nature of the compound: Off white solid, Yield: 700 mg
Synthesis of C1-6:

C1-5

C-16

| Chemicals/Reagents & Solvents | Wt./Vol. | mol | Eq. |
|---|---|---|---|
| C1-5 | 1 g | 0.0032 | 1 |
| Li$_2$CO$_3$ | 0.84 g | 0.0128 | 4 |
| MeOH | 10 mL | — | |

Reaction time: Overnight Temperature conditions: r.t
Brief procedure: A solution of C1-5 and Li$_2$CO$_3$ in MeOH was stirred overnight at r.t.
Work up: After completion of the reaction, organic layer was distilled under reduced pressure, extracted with ethyl acetate, washed with water, brine, dried over Na$_2$SO$_4$. and concentrated to yield light yellow oil.
Purification: The residue was washed with petroleum ether (3×100 mL), recrystallized four times with ethyl acetate to obtain pure compound.
TLC system: 30% ethyl acetate/petroleum ether, $R_f$ value: 0.3
Nature of the compound: Light yellow oil, Yield: 330 mg
Synthesis of C1:

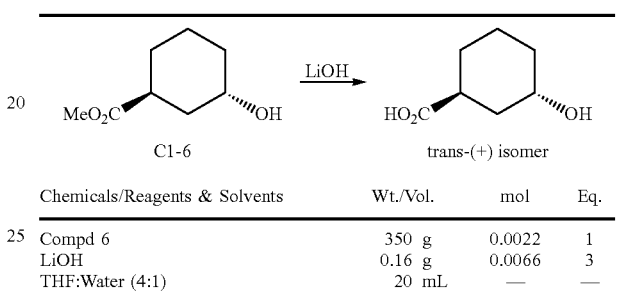

C1-6 trans-(+) isomer

| Chemicals/Reagents & Solvents | Wt./Vol. | mol | Eq. |
|---|---|---|---|
| Compd 6 | 350 g | 0.0022 | 1 |
| LiOH | 0.16 g | 0.0066 | 3 |
| THF:Water (4:1) | 20 mL | — | — |

Brief procedure: A solution of C1-6 and LiOH in THF: Water (4:1) was stirred for overnight.
Work up: After completion of the reaction, the organic layer was distilled under reduced pressure, extracted with ethyl acetate, washed with water, brine, dried over Na$_2$SO$_4$ and concentrated to afford light yellow oil.
Purification: Crude on Recrystallisation with ethyl acetate afforded pure compound.
TLC system: 10% MeOH/DCM, $R_f$ value: 0.25
Nature of the compound: Off white solid, Yield: 300 mg (1S*,3R*,4S*)-methyl 3-fluoro-4-hydroxycyclohexanecarboxylate—Feed D1

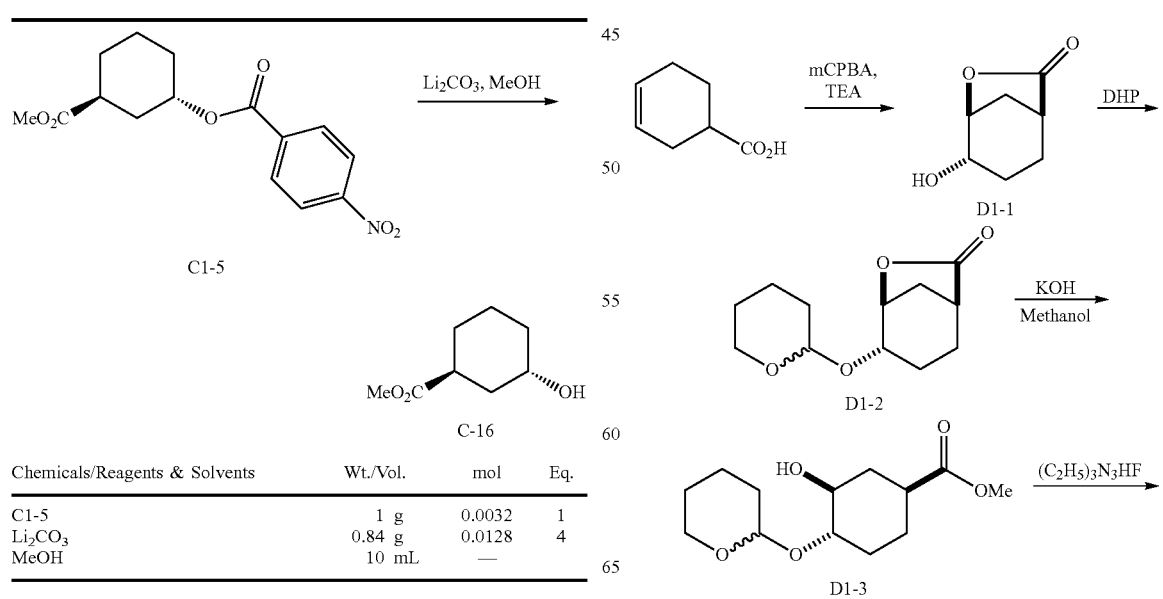

-continued

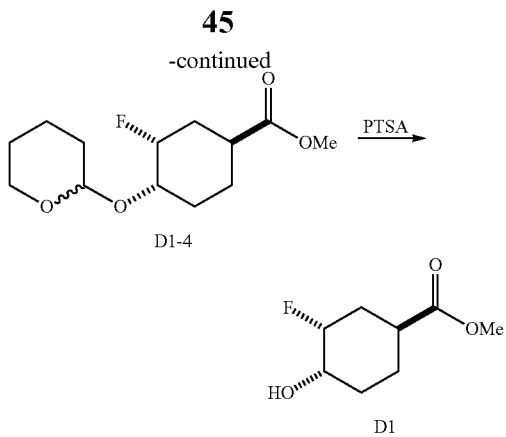

Synthesis of D1-1:

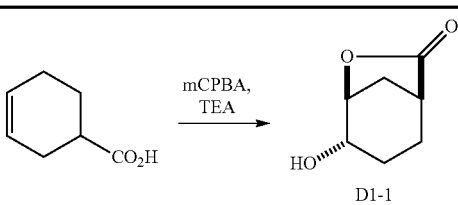

| Chemicals/Reagents & Solvents | Wt. | Mol | Eq. |
|---|---|---|---|
| Cyclohex-3-enecarboxylic acid | 5 g | 0.0396 | 1 |
| m-CPBA | 10.4 g | 0.059 | 1.5 |
| TEA | 16.5 g | — | 4.13 |
| CCl$_4$ | 131.5 mL | — | |

Reaction time: 8 h, Reaction temperature: 65° C.

Procedure: m-CPBA was added to a solution of cyclohex-3-enecarboxylic acid in CCl$_4$ and the reaction mixture was stirred for 4 h. Triethyl amine was added and the resulting reaction mixture was stirred at 65° C. for 4 h.

Work up: The reaction mixture was concentrated under reduced pressure to get crude residue.

Purification: The crude product was purified by flash column chromatography using ethyl acetate and petroleum ether as eluents.

TLC system: 50% Ethyl acetate in pet ether, R$_f$ value: 0.3

Nature of the compound: Light brown color solid, Yield: 50%

Synthesis of D1-2:

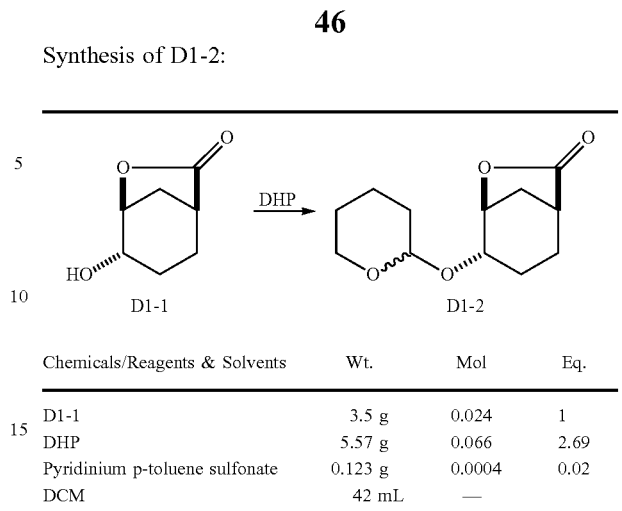

| Chemicals/Reagents & Solvents | Wt. | Mol | Eq. |
|---|---|---|---|
| D1-1 | 3.5 g | 0.024 | 1 |
| DHP | 5.57 g | 0.066 | 2.69 |
| Pyridinium p-toluene sulfonate | 0.123 g | 0.0004 | 0.02 |
| DCM | 42 mL | — | |

Reaction time: 2 h Reaction temperature: RT

Procedure: To a solution of D1-1 in DCM, was added dihydropyran followed by pyridinium p-toluene sulfonate. The resulting reaction mixture was stirred for 2 h at room temperature.

Work up: The reaction mixture was cooled to 0° C., quenched with aqueous 5% NaHCO$_3$ solution. Organic layer separated, aqueous layer re-extracted with dichloromethane and combined organic layer was washed with brine. Finally, organic layer was dried over sodium sulfate and concentrated under reduced pressure to give crude product.

Purification: The compound was directly taken for next step without further purification.

TLC system: 50% Ethyl acetate in pet ether, R$_f$ value: 0.8

Nature of the compound: Brown color liquid, Yield: 77%

Synthesis of D1-3:

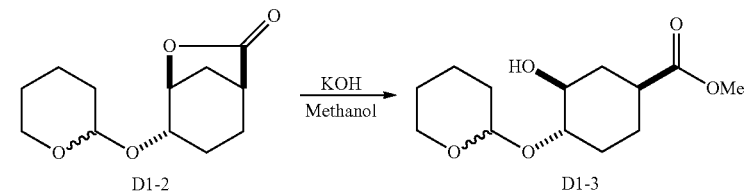

| Chemicals/Reagents & Solvents | Wt. | Mol | Eq. |
|---|---|---|---|
| D1-2 | 6.3 g | 0.176 | 1 |
| KOH in methanol | 0.012 g + 0.315 mL | 0.0002 | 0.0012 |
| Methanol | 12.6 mL | — | |

Reaction time: 1 h Reaction temperature: RT

Procedure: KOH in methanol was added to a solution of D1-2 in methanol and the resulting reaction mixture stirred at room temperature over a period of 1 h.

Work up: The reaction mixture was diluted with chloroform and water, organic layer separated and aqueous layer was re-extracted with chloroform. The combined organic layer was washed with saturated NH$_4$Cl solution and brine, dried over sodium sulfate and solvent evaporated under reduced pressure.

Purification: The crude product was directly used in next step without further purification.

TLC system: 50% Ethyl acetate in pet ether, R$_f$ value: 0.4

Nature of the compound: Yellow color liquid, Yield: 70%

Synthesis of D1-4

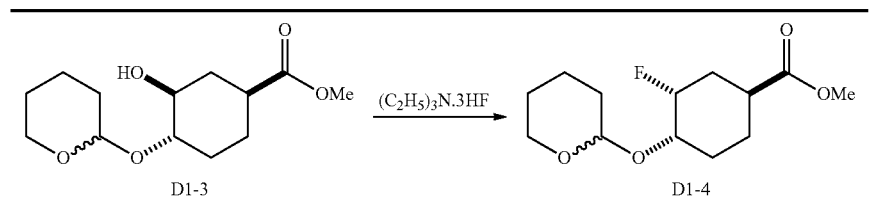

| Chemicals/Reagents & Solvents | Wt. | Mol | Eq. |
| --- | --- | --- | --- |
| D1-3 | 1 g | 0.0038 | 1 |
| Perfluorobutane sulfonylfluoride | 2.341 g | 0.0077 | 2 |
| Triethylamine tri hydrofluoride | 1.24 g | 0.0077 | 2 |
| TEA | 3.28 mL | 0.023 | 6 |
| THF | 6.2 mL | — | |

Reaction time: 12 h, Reaction temperature: RT

Procedure: D1-3 was dissolved in THF and were added perfluorobutanesulfonylfluoride, triethyl amine and triethylamine-trihydrofluoride. The resulting reaction mixture was stirred overnight under nitrogen atmosphere.

Work up: The reaction mixture was filtered, solid washed with ethyl acetate-hexane (1:3) and solvent evaporated under reduced pressure.

Purification: The crude product was purified by flash column chromatography using ethyl acetate and petroleum ether as eluents.

TLC system: 50% Ethyl acetate in petroleum ether, $R_f$ value: 0.8

Nature of the compound: Brown color liquid, Yield: 69%.

Synthesis of D1

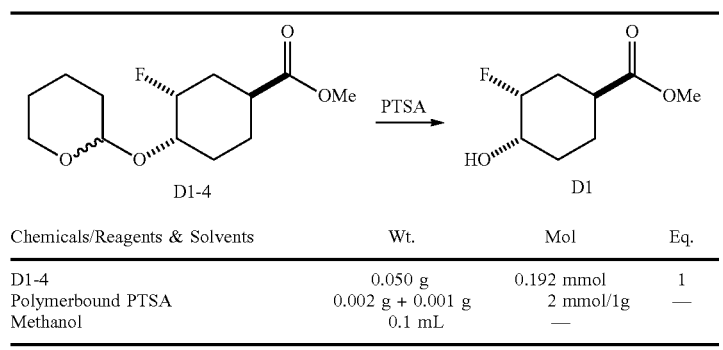

| Chemicals/Reagents & Solvents | Wt. | Mol | Eq. |
| --- | --- | --- | --- |
| D1-4 | 0.050 g | 0.192 mmol | 1 |
| Polymerbound PTSA | 0.002 g + 0.001 g | 2 mmol/1g | — |
| Methanol | 0.1 mL | — | |

Reaction time: 3 h, Reaction temperature: 50° C.

Procedure: Polymerbound PTSA was added to a solution of D1-4 in methanol and the resulting suspension was stirred at 50° C. over a period of 2 h. Another portion of polymerbound PTSA was added and stirring continued for another 1 h at same temperature.

Work up: The reaction mixture was filtered through a sintered funnel and solvent removed under reduced pressure.

Purification: The crude product was purified by flash column chromatography using ethyl acetate and petroleum ether as eluents.

TLC system: 50% Ethyl acetate in pet ether, $R_f$ value: 0.3

Nature of the compound: Yellow color liquid, Yield: 60%

(1S*,3R*,4S*)-3-ethyl-4-hydroxycyclohexanecarboxylic Acid—Feed E1

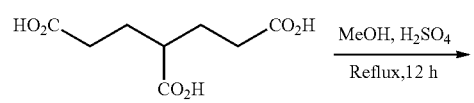

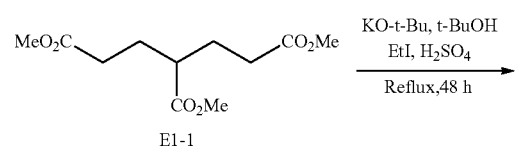

-continued

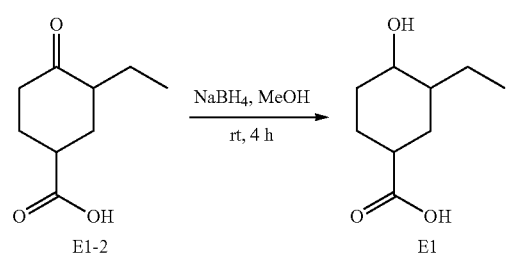

Synthesis of E1-1

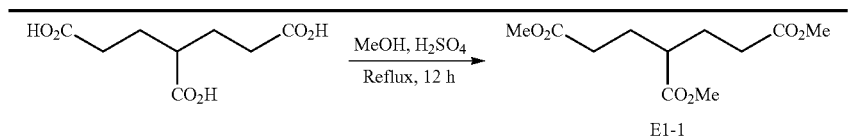

| Chemicals/Reagents &Solvents | Wt. | mol | Eq. |
|---|---|---|---|
| pentane-1,3,5-tricarboxylic acid | 100 g | 490 | 1.0 |
| H$_2$SO$_4$ | 20 mL | 245 | 0.5 |
| Methanol | 1500 mL | — | 15V |

Reaction time: 12 h, Reaction temperature: reflux

Brief procedure: A mixture of pentane-1,3,5-tricarboxylic acid in dry methanol and sulfuric acid was heated under refluxed for 12 h.

Work up: The reaction mixture was concentrated in vacuo, diluted with ethyl acetate and washed repeatedly with water followed by 10% NaHCO$_3$. The combined organic extract was dried, filtered and concentrated under reduced pressure to give a residue.

Purification: The crude residue was purified by silica gel (60-100 mesh) column chromatography using 15% ethyl acetate-petroleum ether as eluent.

TLC system: 30% Ethyl acetate-petroleum ether, R$_f$ value: 0.8

Nature of the compound: Colorless sticky liquid, Yield: 110 g (95%)

Synthesis of E1-2:

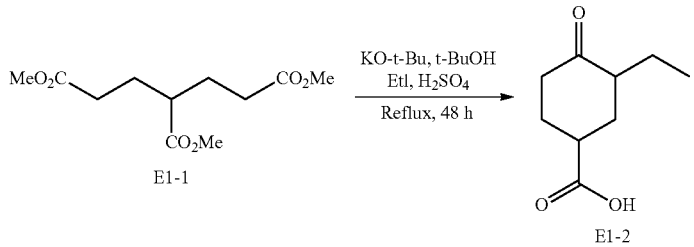 [SMILES: COC(=O)CCC(CCC(=O)OC)C(=O)OC ; CCC1CC(C(=O)O)CCC1=O]

| Chemicals/Reagents & Solvents | Wt. | mol | Eq. |
|---|---|---|---|
| E1-1 | 110.0 g | 447.1 | 1.0 |
| Potassium t-butoxide | 150.28 g | 1341 | 3.0 |
| ethyl iodide | 288 mL | 3577 | 8.0 |
| t-Butyl alcohol | 770 mL | — | — |
| 10% sulfuric acid | 288 mL | — | — |

Brief procedure: To a solution of potassium t-butoxide in dry t-butyl alcohol, under argon atmosphere was added in one portion a solution of E1-1 to afford a viscous orange solution. The reaction mixture was heated at reflux for 3 h, then cooled to RT and ethyl iodide was added with stirring. The reaction mixture was stirred at reflux for 10 h, and then t-butyl alcohol was removed in vacuo. To the residue was mixed with 10% sulfuric acid and the mixture was refluxed for further 48 h.

Work up: The reaction mixture extracted with three portions of diethyl ether, the combined extract was washed successively with water and saturated ammonium sulfate, dried over Na$_2$SO$_4$, filtered and concentrated in vacuo to give the crude product.

Purification: The crude residue was purified by silica gel (100-200 mesh) column chromatography using 30% ethyl acetate-petroleum ether as eluent.

TLC system: 30% Ethyl acetate-petroleum ether, R$_f$ value: 0.14

Nature of the compound: Colorless sticky liquid, Yield: 50 g

Synthesis of E1:

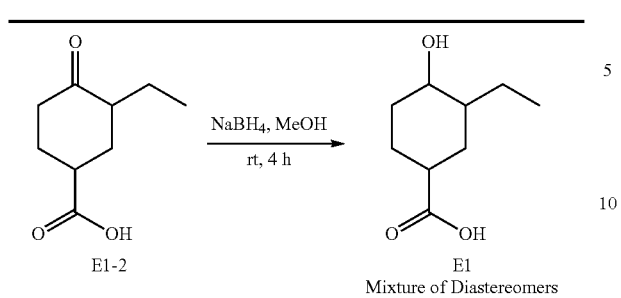

| Chemicals/Reagents & Solvents | Wt. | M. Mol | Eq. |
|---|---|---|---|
| E1-2 | 30 g | 176.47 | 1.0 |
| NaBH$_4$ | 10.1 g | 264.7 | 1.5 |
| Methanol | 300 mL | — | |

Brief procedure: NaBH$_4$ was added portion-wise to a stirred solution of E1-2 in methanol at 0° C. and further stirred at room temperature for 4 h.

Work up: The reaction mixture was concentrated in vacuo to give the crude product.

Purification: The crude residue was purified by silica gel (100-200 mesh) column chromatography using 28% ethyl acetate-petroleum ether as eluent.

TLC system: 90% Ethyl acetate-petroleum ether, R$_f$ value: 0.6

Nature of the compound: Light yellow viscous liquid, Yield: 15 g

Methyl 3,3-difluoro-4-hydroxycyclohexanecarboxylate—Feed F1

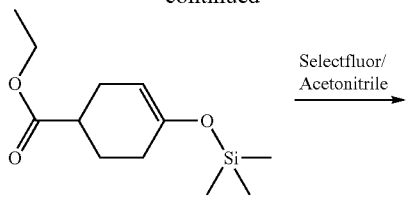

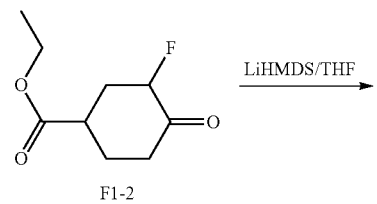

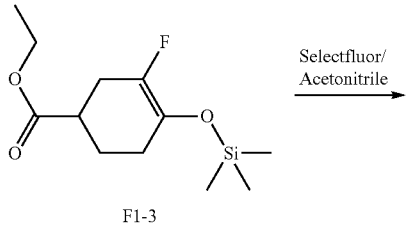

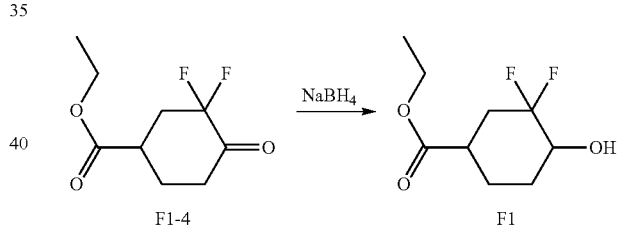

Synthesis of F1-1

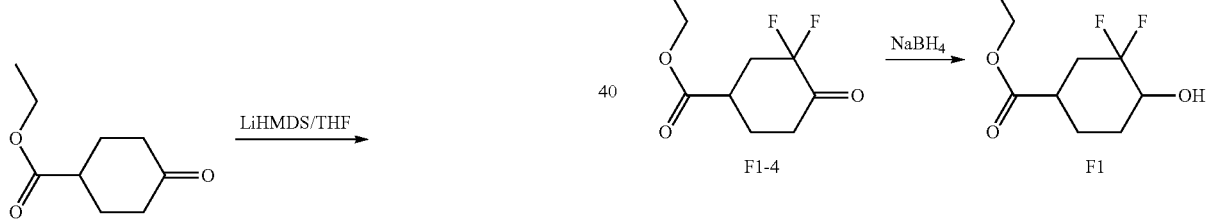

| Chemicals/Reagents & Solvents | Wt. | Mol | Eq. |
|---|---|---|---|
| Ethyl-4-oxocyclohexane carboxylate | 25 g | 0.146 | 1 |
| LiHMDS | 29.73 g | 0.177 | 1.21 |
| TMS-Cl | 24.1 g | 0.22 | 1.51 |
| THF | 567 + 567 mL | — | — |

Ethyl-4-oxocyclohexane carboxylate in THF was added dropwise at −78° C. to a stirred solution of lithium hexamethyldisilazide in THF. The reaction mixture was stirred for 1 h at same temperature and TMS-Cl was added. It was stirred for 10 minutes at same temperature and then for 1 hour at room temperature. The reaction was monitored by TLC. The reaction mixture was concentrated under reduced pressure, added hexane and filtered off. Filtrate was concentrated under reduced pressure to get crude product. The crude product was purified by column chromatography over silica gel using diethyl ether in hexane.

TLC system: 30% Ethyl acetate in petroleum ether, Rf value: 0.8

Nature of the compound: Yellow liquid, Yield: 19.5 g

Synthesis of F1-2

| Chemicals/Reagents & Solvents | Wt. | Mol | Eq. |
|---|---|---|---|
| F1-1 | 19 g | 0.0785 | 1 |
| Selectfluor | 40.4 g | 0.0942 | 1.19 |
| Acetonitrile | 337.5 mL | — | — |

Selectfluor was added to a solution of F1-1 in acetonitrile at 0° C. under nitrogen atmosphere and stirred for 1.5 hours. The reaction mixture was partitioned between water and ethyl acetate. Organic layer separated, washed with NaHCO$_3$ followed by brine and dried over sodium sulfate. Solvent was removed under reduced pressure to get crude product. The crude product was purified by column chromatography over silica gel using diethyl ether in hexane.

TLC system: 30% Ethyl acetate in petroleum ether, Rf value: 0.3

Nature of the compound: Light Yellow Liquid, Yield: 6.7 g

Synthesis of F1-3

| Chemicals/Reagents & Solvents | Wt. | Mol | Eq. |
|---|---|---|---|
| F1-2 | 6.02 g | 0.0320 | 1 |
| LiHMDS | 6.48 g | 0.038 | 1.21 |
| TMS-Cl | 5.25 g | 0.483 | 1.51 |
| THF | 136.6 + 136.6 mL | — | — |

F1-2 in THF was added dropwise at −78° C. to a stirred solution of lithium hexamethyldisilazide in THF. The reaction mixture was stirred for 1 hour at same temperature and TMS-Cl was added. It was stirred for 10 min at same temperature and 1 h at room temperature.

Work up: The reaction mixture was concentrated under reduced pressure, added hexane and filtered off. Filtrated was concentrated under reduced pressure to get crude desired product.

Purification: The crude product was purified by column chromatography over silica gel using diethyl ether in hexane.

TLC system: 30% Ethyl acetate in petroleum ether, Rf value: 0.8

Nature of the compound: Yellow liquid, Yield: 2.8 g

Synthesis of F1-4

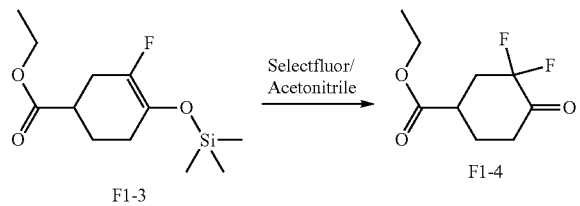 [SMILES: CCOC(=O)C1CCC(O[Si](C)(C)C)=C(F)C1 ; CCOC(=O)C1CCC(=O)C(F)(F)C1]

| Chemicals/Reagents & Solvents | Wt. | Mol | Eq. |
| --- | --- | --- | --- |
| F1-3 | 2.5 g | 0.00962 | 1 |
| Selectfluor | 4.05 g | 11.442 | 1.19 |
| Acetonitrile | 30 mL | — | — |

Selectfluor was added to a solution of F1-3 in acetonitrile at 0° C. under nitrogen atmosphere and stirred for 1.5 h.

Work up: The reaction mixture was partitioned between water and ethyl acetate. Organic layer separated, washed with $NaHCO_3$ followed by brine and dried over sodium sulfate. Solvent was removed under reduced pressure to get crude desired product.

Purification: The crude product was purified by column chromatography over silica gel using diethyl ether in hexane.

TLC system: 30% Ethyl acetate in petroleum ether, Rf value: 0.3

Nature of the compound: Light Yellow Liquid, Yield: 0.0.5 g

Synthesis of F1

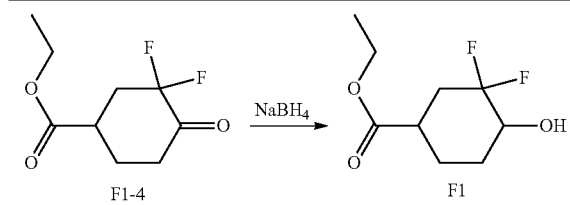

| Chemicals/Reagents & Solvents | Wt. | Mol | Eq. |
| --- | --- | --- | --- |
| F1-4 | 0.45 g | 0.00218 | 1.0 |
| Sodium Borohydride | 0.0908 g | 0.0024 | 1.1 |
| Ethanol | 4.5 mL | — | — |

F1-4 was dissolved in EtOH and sodium borohydride was added at 0° C. The mixture was stirred for 30 min at same temperature.

Work up: The reaction was quenched with water, extracted with dichloromethane, dried over sodium sulfate and solvent evaporated under reduced pressure to get crude product.

Purification: The crude product was purified by column chromatography over silica gel using diethyl ether in petroleum ether as eluent TLC system: 30% Ethyl acetate in petroleum ether, Rf value: 0.5

Nature of the compound: Light Yellow Liquid, Yield: 0.170 g (1S*,3R*)-3-hydroxycyclohexanecarboxylic Acid—Feed G1

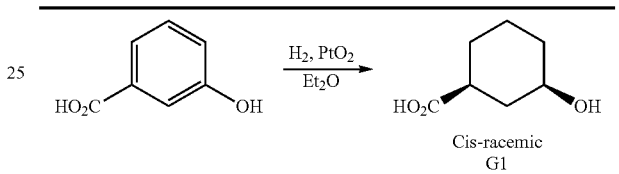

| Chemicals/Reagents & Solvents | Wt./Vol. | Mol | Eq. |
| --- | --- | --- | --- |
| 3-Hydroxybenzoic acid | 10 g | 0.072 | 1 |
| Platinum oxide | 1 g | 0.004 | 0.6 |
| Diethyl ether | 250 mL | — | 25 V |

Brief procedure: A solution of 3-hydroxybenzoic acid in diethyl ether was hydrogenated with platinum oxide at 60 psi for 10 days.

Work up: After completion of the reaction, the catalyst was removed by filtration and washed with methanol under nitrogen; the organic layer was distilled under reduced pressure.

Purification: The residue was washed with petroleum ether (3×100 mL), the mixture was recrystallized four times with ethyl acetate to afford pure compound.

TLC system: 10% MeOH/DCM, $R_f$ value: 0.25

Nature of the compound: Off white solid, Yield: 2.6 g (25%)

Methods

Analytical Biotransformations

Production of rapamycin analogs and contracted rapamycins was carried out by fermentation of *Streptomyces rapamycinicus*. Typically strains were grown on ISP3 agar at 28° C. for 10-14 days to achieve good sporulation and used to inoculate 7 ml seed medium RapV7 (50 mL polypropylene centrifuge tubes (falcon tubes) (cat no. 227261, purchased from Greiner Bio-One Ltd, Stonehouse, Gloucestershire, UK)) closed with foam plugs by transferring an agar plug (5 mm diameter). Alternatively 35 μL of a thawed spore stock was used for the inoculation. The inoculated seed medium was incubated with shaking at 300 rpm, 2.5 cm throw at 28° C. for 48 hours. For production the fermentation medium MD6 (7 mL in falcon tube as before) was inoculated with 0.5 mL of the seed culture using a wide bore tip and incubated with shaking at 300 rpm, 2.5 cm throw at 26° C. for six days. The culture was then harvested for extraction. A selected starter unit feed (corresponding to the desired starting unit for biosynthesis of the target compound) was fed to the production medium 24 hours post inoculation. Typically feed was dissolved in methanol (0.05 mL) and added to culture to give final concentration of 2 mM. The broth was extracted by aliquoting 0.9 ml into an eppendorf tube (2 ml) and adding methanol (0.9 ml). The eppendorf was then shaken on a vibrax bed for 30 minutes before the cell debris was removed by centrifugation (13,200 rpm, 10 minutes). An aliquot of the supernatant was then transferred to an LC-vial for analysis by the methods described below.

Preparative Biotransformations

Spore stocks of the strains for fermentation were prepared after growth on ISP3 agar medium and preserved in 20% w/v glycerol in distilled water and stored at −80° C. Spore stocks were recovered onto plates of MAM or ISP3 medium and incubated for 10-11 days at 28° C.

Vegetative cultures (seed cultures) were prepared using working spore stocks of at 0.05% inoculum and inoculating into 400 ml medium RapV7 in 2 liter Erlenmeyer flasks with foam plugs. Cultivation was carried out for 48 hours at 28° C., 250 rpm (2.5 cm throw). The entire seed culture in one flask was transferred into 15 liters of medium MD6/5-1 pre-adjusted at 25 pH 6.0-7.0 in a V7 Braun 22 L fermenter. The fermentation was carried out for 6 days at 26° C., with starting agitation at 200 rpm, aeration rate at 0.5 V/V/VM and dissolved oxygen (DO) level controlled with the agitation cascade at 30% air saturation. The starting agitation was set at 200 rpm. For production of compound, the selected precursor to feed (starting unit for biosynthesis of target compound) was fed to the production medium 24 hours post inoculation. Feed was dissolved in 3 mL to 5 mL methanol and added to the culture to give final concentration of 2 mM of the feed compound. The amount of methanol does not exceed 1% of the total volume. Fermentation was continued for further five days post-feeding, before harvesting.

Harvested whole broth was centrifuged at 3500 rpm (RCF 3300 g) for 25 mins. The clarified broth was assayed and discarded if less than 5% target compound detected. The cell pellet was removed from the centrifuge pots with acetonitrile and decanted into a 10 L glass duran. Further acetonitrile is added to give a ratio of 2 volumes of solvent to 1 volume of cells. The mixture was then stirred for 1 hour using an overhead electric paddle stirrer at 600 rpm.

After 1 hour the stirring was stopped and the mixture left to settle under gravity for 15 mins. The solvent layer was removed as extract_1 and a further 2 volumes of acetonitrile added to the remaining cells. This was stirred again as above to obtain extract_2. Any remaining rapatractins in the cell pellet can be removed by a third extraction if required.

Any target compound in the clarified broth can be recovered by adding an equal volume of ethyl acetate and stirring for 1 hour in a glass duran using an overhead electric paddle stirrer at 600 rpm. The organic solvent was then separated by centrifugation at 3500 rpm (RCF 3300 g) for 15 mins.

The combined extracts from both the cell pellet and, if required clarified broth, were concentrated in vacuo to a residual aqueous extract which was then extracted into an equal volume of ethyl acetate. A second ethyl acetate extraction can be performed as necessary. The ethyl acetate extract containing the target rapatractin is then concentrated in vacuo to yield a final often oily crude.

The crude extract was dissolved in methanol, and silica gel added (approximately equal amount to the extract by weight) and the solvent removed in vacuo to a free-flowing powder. The impregnated silica is loaded on to a silica gel column (20×5 cm) and eluted with 100% $CHCl_3$, and gradually increases polarity by adding MeOH (to a maximum 5% MeOH). Approximately 20×250 ml fractions were collected and monitored by TLC and analytical HPLC. The fractions containing the rapatractins were loaded onto a second silica gel column (15×2 cm) and eluted with a mixture of hexane and ethyl acetate (1:1). First 1 L of (1:1) mixture was passed through, then 1 L of (40:60), and continued to 100% of EtOAc. Approximately 20×250 mL fractions were collected and individually checked by tlc and analytical HPLC. Fractions found to contain rapatractins were combined and the solvents were removed in vacuo. This bulk was then dissolved in acetonitrile and multiple injections (about 100 mg crude per injection) made to preparative HPLC using a water acetonitrile gradient mixture for 30 minutes (actual methods depend on compound polarity). The solvent from the resulting pure rapatractin containing fractions was removed in vacuo and the compound analysed by LC-MS and NMR for characterisation.

NMR Structure Elucidation Methods

NMR spectra were recorded on a Bruker Advance 500 spectrometer at 298 K operating at 500 MHz and 125 MHz for $^1H$ and $^{13}C$ respectively. Standard Bruker pulse sequences were used to acquire $^1H$-$^1H$ COSY, APT, HMBC and HMQC spectra. NMR spectra were referenced to the residual proton or standard carbon resonances of the solvents in which they were run.

Assessment of Compound Purity

Purified compounds were analysed using LCMS method 2 described. LCMS method 2: chromatography was achieved over a Phenomenex HyperClone $C_{18}$-BDS column (4.6×150 mm, 3 micron particle size) eluting with a gradient of water+0.1% formic acid:acetonitrile+0.1% formic acid, (90:10) to (0:100), at 1 mL/min over 20 min. Purity was assessed by MS and at multiple wavelengths (210, 254 & 276 nm). All compounds were >95% pure at all wavelengths. Purity was finally confirmed by inspection of the $^1H$ and $^{13}C$ NMR spectra.

HPLC Analysis of Rapamycin Analogs and Contracted or Expanded Rapamycins in Fermentation Broths An aliquot of whole culture broth (0.9 mL) was added to methanol (0.9 mL) in a 2 mL eppendorf, and then shaken for 30 minutes. The sample was centrifuged (10 minutes, 13000 rpm) and the supernatant (0.15 ml) was transferred to a HPLC vial for analysis by HPLC with diode array detection. The HPLC system comprised an Agilent HP1100 equipped with a Hyperclone 3 micron BDS C18 130 A column 150 mm×4.6 mm (Phenomenex) heated to 50° C. The gradient elution was from 55% mobile phase B to 95% mobile phase B over 10 minutes followed by an isocratic hold at 95% mobile phase B for 2 minutes with a flow rate of 1 mL/min. Mobile phase A was 10% acetonitrile:90% water, containing 10 mM ammonium acetate and 0.1% trifluoroacetic acid, mobile phase B was 90% acetonitrile:10% water, containing 10 mM ammonium acetate and 0.1% trifluoroacetic acid. Rapamycin analogues were identified by the presence of the characteristic rapamycin triene, centred on $\lambda$=278 nm or by LC-MS.

LC-MS—method 1 (fermentation broths)—The HPLC system described above was coupled to a Bruker Daltonics Esquire3000 electrospray mass spectrometer. The gradient elution was from 50% mobile phase B to 100% mobile phase B over 10 minutes followed by an isocratic hold at 100% mobile phase B for 3 minutes with a flow rate of 1 mL/min. Mobile phase A was water containing 0.1% formic acid, mobile phase B was acetonitrile containing 0.1% formic acid. Positive negative switching was used over a scan range of 500 to 1000 Dalton.

LC-MS—method 2 (purified samples)—LC-MS—method 1 (fermentation broths)—The HPLC system described above was coupled to a Bruker Daltonics Esquire3000 electrospray mass spectrometer. Chromatography was achieved over a Phenomenex HyperClone $C_{18}$-BDS column (4.6×150 mm, 3 micron particle size) eluting with a gradient of water+0.1% formic acid:acetonitrile+0.1% formic acid, (90:10) to (0:100), at 1 mL/min over 20 min. Purity was assessed by MS and at multiple wavelengths (210, 254 & 276 nm). All compounds were >95% pure at all wavelengths Example 1: Generation of Constructs Able to Induce Deletion or Expansion of the Rapamycin PKS Modules and Transfer to S. rapamycinicus To construct a downstream region of homology two PCR products were ligated together.

The first of these two PCR products was obtained using two oligonucleotides

```
                                    (SEQ ID NO: 1)
(CGACGAATTCCATCGCGCCCCGGCCCGCCAGG (SEQ ID NO: 2)
and TTGTCCGGCCGGGTGTCGTACGTCTTCGG
``` to amplify a ~1.5 kb region of the rapamycin gene cluster using Cos25 (Schwecke et al., 1995) as the template. The second of the two products was obtained using oligonucleotides

```
                                    (SEQ ID NO: 3)
(CCAGGGACGAGGAGCACGCCGTGTCCATCG
and
                                    (SEQ ID NO: 4))
GGGGTGTAGAGGCTAGCCGCCCTGGCACCGGCCGAGC
``` to amplify a ~0.8 kb region of the rapamycin gene cluster again using Cos25 as the template. Each of these PCR products was treated with T4 polynucleotide kinase and cloned into pUC19 before sequencing to verify the amplified fragment. The first fragment was excised using EcoRI and ApaI and the second fragment excised using ApaI and XbaI (from the pUC19 polylinker) and ligated together with pUC19 that had been digested with EcoRI and XbaI. This plasmid was designated intermediate plasmid 1.

Similarly, to construct the upstream region of homology a further two PCR products were ligated together The first of these two PCR products was obtained using two oligonucleotides

```
                                    (SEQ ID NO: 5)
(GTATCTAGAAAGATCTAGTACCCGGGTTGTGGCGGTGCCGAGG
and
                                    (SEQ ID NO: 6))
TCAGGCCGCCTCGGGCGTGTCGGTTGTCATCAAGATGG
``` to amplify a ~1.5 kb region of the rapamycin gene cluster using Cos25 as the template. The second of the two products was obtained using oligonucleotides

```
                                    (SEQ ID NO: 7)
(GACGGCTCATCCACGTGCAGGGTGCGGGGAACC (SEQ ID NO: 8))
and GTCTAAGCTTTCCCCACCGACCGTGGCTGGGACGTCG
``` to amplify a ~1 kb region of the rapamycin gene cluster again using Cos25 as the template. Each of these PCR products was kinased using T4 polynucleotide kinase and cloned into pUC19 before sequencing to verify the amplified fragment. The first fragment was excised using XbaI and PstI and the second fragment excised using PstI and HindIII and ligated together with pUC19 that had been digested with XbaI and HindIII. This plasmid was designated intermediate plasmid 2.

The region of downstream homology from intermediate plasmid 1 was excised using EcoRI and XbaI. The region of upstream homology from intermediate plasmid 2 was excised using XbaI and HindIII. These two fragments were ligated together with pUC19 that had been digested with EcoRI and HindIII. The resulting vector was then digested with NheI and BglII to insert the desired reductive loop. Two loops were used, the reductive loop from module 13 of the rapamycin cluster and the reductive loop from module 11 of the rapamycin cluster. NheI/BglII sites were utilised. The reductive loop of module 13 of the rapamycin cluster was excised from plasmid pPF137 (Gaisser et al., 2003) using NheI and BglII. The reductive loop of module 11 of the rapamycin cluster was excised from plasmid pWV165 (a plasmid containing the rapamycin PKS module 11 reductive loop engineered to have NheI and BglII sites surrounding the reductive loop encoding DNA.

The resulting constructs were transferred to the conjugative vector pKC1139 (Bierman et al 1992) by digesting with EcoRI and HindIII and ligating with pKC1139 that had been digested with the same enzymes. The resulting plasmids were named pSGK210 (containing rapamycin PKS module 13 loop) and pSGK212 (containing rapamycin PKS module 11 loop). Plasmids pSGK210 and pSGK212 were transferred to S. rapamycinicus BIOT-4010 (Kendrew et al., 2013) by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 ml 2TY liquid medium containing apramycin (50 µg/mL), kanamycin (25 µg/mL) and chloramphenicol (25 µg/ml). 0.7 ml of this culture was used to inoculate 10 ml liquid medium containing apramycin (50 µg/ml), kanamycin (25 µg/ml) and chloramphenicol (25 µg/mL) and grown at 37 C to reach an OD of approximately 0.5. Cells were pelleted at 4000 rpm for 10 minutes and washed twice with 10 ml 2×TY before resuspending in 0.25 mL 2 TY. Spores of S. rapamycinicus BIOT-4010 grown on ISP3 for 2-3 weeks were harvested using 20% glycerol and stored at −80° C. (1 plate gives about 1 mL spore stock). For the conjugation approximately 0.3-0.5 mL of these spores are needed for each conjugation. Spores were unfrozen and pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 mL of washed E. coli cells to the heat shocked spores, mixing and spreading the mixture onto a R6 plate and transferring to 37° C. The plate was overlaid with 2 mL water containing 15 µL naladixic acid (stock 50 mg/mL) after 2-3 hours and with 2 mL water containing 15 µL apramycin (stock 100 mg/mL) after an overnight incubation.

Plates were incubated at 37° C. until single exconjugant colonies were visible. Colonies (approximately 15-20) were patched to MAM containing apramycin and naladixic acid and reincubated at 37° C. Usually this colony was then repatched to the same media (containing apramycin and nalidixic acid) to ensure there was no *E. coli* contamination. Once stabilised approximately 10-15 of the strains were patched to solid ISP3 media lacking antibiotics and incubated at 37° C. for approximately 3 days before repatching to ISP3 media and growing for a further 3 or 4 days. A final round of subculture at 37° C. on ISP3 was performed before plating to ISP3 and leaving at 28° C. for to allow the strain to sporulate (~10-14 days). Spores were harvested in 20% glycerol and a dilution series prepared in water and spread onto ISP3 media before incubating at 28° C. Once individual sporulating colonies were visible they were patched to ISP3 media plus and minus apramycin to assess for loss of plasmid. The vast majority of strains had lost the apramycin marker. Strains that had lost the marker were tested by growing in production media to assess whether they still produced 39-desmethoxy rapamycin (i.e. had reverted to original strain). Among the strains that no longer produced the original compound 39-desmethoxy rapamycin strains that produced novel compounds were identified (see Example 3).

Example 2: Generation of an Alternative Construct Able to Induce Deletion of the Rapamycin PKS Modules and Transfer to *S. rapamycinicus*

A series of alternative constructs were prepared to assess the effect of smaller regions (~1 kb) of homology for recombination.

Two oligonucleotides

```
                                           (SEQ ID NO: 9)
CGCGAATTCGGAGAAACCGGCACCGTCCGCACTGTCCGC
and
                                           (SEQ ID NO: 4)
     GGGGTGTAGAGGCTAGCCGCCCTGGCACCGGCCGAGC
``` were used to amplify a ~1 kb region of homology using intermediate plasmid 1 as a template. The resulting PCR product was kinased using T4 polynucleotide kinase and cloned into pUC19 before sequencing to verify the amplified fragment. The fragment was then excised using EcoR1 and XbaI.

```
                                          (SEQ ID NO: 10)
CGTAAAGCTTGGAGACGACACCGTCACCGGCACCGCTGTG
and
                                           (SEQ ID NO: 5)
GTATCTAGAAAGATCTAGTACCCGGGTTGTGGCGGTGCCGAGG
``` were used to amplify a ~1 kb region of homology using intermediate plasmid 2 as a template. The resulting PCR product was kinased using T4 polynucleotide kinase and cloned into pUC19 before sequencing to verify the amplified fragment. The fragment was then excised using HindIII and XbaI.

The excised fragments were ligated together with pUC19 that had been digested with EcoRI and HindIII. The resulting vector was then digested with NheI and BglII to insert the desired rapamycin PKS module 11 reductive loop as outlined previously (see Example 1).

The resulting construct was transferred to the conjugative replacement vector pKC1139 (Bierman et al., 1992) by digesting with EcoRI and HindIII and ligating with pKC1139 that had been digested with the same enzymes.

Plasmid pSGK234 was transferred to *S. rapamycinicus* BIOT-4010 by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 mL 2×TY liquid medium containing apramycin (50 µg/mL), kanamycin (25 µg/mL) and chloroamphenicol (25 µg/mL). 0.7 mL of this culture was used to inoculate 10 mL liquid medium containing apramycin (50 µg/mL), kanamycin (25 µg/mL) and chloramphenicol (25 µg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. rapamycinicus* BIOT-4010 grown on ISP3 for 2-3 weeks were harvested using 20% glycerol and stored at −80° C. (1 plate gives about 1 mL spore stock). For the conjugation approximately 0.3-0.5 mL of these spores are needed for each conjugation. Spores were unfrozen and pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 ml of washed *E. coli* cells to the heat shocked spores, mixing and spreading the mixture onto a R6 plate and transferring to 37 C. The plate was overlaid with 2 ml water containing 15 µL naladixic acid (stock 50 mg/ml) after 2-3 hours and with 2 mL water containing 15 µL apramycin (stock 100 mg/mL) after an overnight incubation.

Plates were incubated at 37° C. until single exconjugant colonies were visible. Colonies (approximately 10-20) were patched to MAM containing apramycin and naladixic acid and reincubated at 37° C. Usually this colony was then repatched to the same media (containing apramycin and nalidixic acid) to ensure there was no *E. coli* contamination. Once stabilised approximately 10-15 of the strains were patched to solid ISP3 media lacking antibiotics and incubated at 37° C. for approximately 3 days before repatching to ISP3 media and growing for a further 3 or 4 days. A final round of subculture at 37° C. on ISP3 was performed before plating to ISP3 and leaving at 28° C. for to allow the strain to sporulate (~10-14 days). Spores were harvested in 20% glycerol and a dilution series prepared in water and spread onto ISP3 media before incubating at 28° C. Once individual sporulating colonies were visible they were patched to ISP3 media plus and minus apramycin to assess for loss of plasmid. The vast majority of strains had lost the apramycin marker. Strains that had lost the marker were tested by growing in production media to assess whether they still produced 39-desmethoxy rapamycin (i.e. had reverted to original strain). Among the strains that no longer produced the original compound 39-desmethoxy rapamycin strains that produced novel compounds were identified (see Example 3).

Example 3: Testing the Genetically Engineered Strains for Production of Novel Contracted Compounds Typically 10-15 colonies displaying apramycin sensitivity and derived from each of the primaries were taken forward. Patches were typically grown for around 10-14 days to allow significant mycelial growth and sporulation. An agar plug (about 5 mM in diameter) from each patch was used to inoculate a seed falcon tube containing 7 ml RapV7 media (in a falcon tube) and incubated at 28° C., 300 rpm (1 inch throw) for 48 hours. 0.5 mL of this seed culture was used to inoculate 7 mL MD6 media and incubated at 26° C. and 300 rpm for 6 days; 24 hours into this time each culture was supplemented with 50 μl of 0.32M cyclohexane carboxylic acid (CHCA) in methanol (final concentration in media 2 mM).

For harvest and product analysis 0.9 ml of culture was aliquoted into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS.

Example 4: Diversifying Compounds Produced from Module Deleted Strains by Mutasynthetic Experiments As the strains were constructed in a *S. rapamycinicus* strain that had previously had the rapK gene deleted to interrupt starter unit provision we were able to use a mutasynthetic-feeding approach to further diversify the range of compounds from these strains and produce compounds that possessed the expected contracted polyketide skeleton but bore an altered starter unit. We could also often observe compounds with masses corresponding to different levels of post PKS processing.

Example 5.1 Diversifying Compounds from the −1 PKS Module Strain (Phenotype B) by Mutasynthetic Experiments The isolated strain with phenotype B was grown on ISP3 media for approximately 2-3 weeks to allow significant mycelial growth and sporulation. Spores were harvested in 20% glycerol and aliquoted to produce a working stock of spores that was frozen at 80 C. 0.25 ml of the spore stock was used to inoculate 50 mL RapV7 in a 250 mL flask and incubated at 28° C. at 250 rpm? for 48 hours. 0.5 mL of this seed culture was used to inoculate 7 mL MD6 media in a falcon tube and incubated at 26° C. and 300 rpm for 6 days, 24 hours into this time each culture was supplemented with 50 μl of 0.32M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 2 illustrates the amounts produced (mg/L using 39-desmethoxy rapamycin callibration curve) and range of compounds and masses observed in these mutasynthetic experiments. Where a mass was not recorded, NR replaces the number.

Example 5.2 Diversifying Compounds from the −2 PKS Module Strain (Phenotype C) by Mutasynthetic Experiments The isolated strain with phenotype C was grown on ISP3 media for approximately 2-3 weeks to allow significant mycelial growth and sporulation. Spores were harvested in 20% glycerol and aliquoted to produce a working stock of spores that was frozen at 80 C. 0.25 ml of the spore stock was used to inoculate 50 mL RapV7 in a 250 mL flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 μL of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 3 illustrates the amounts produced (mg/L using 39-desmethoxy rapamycin callibration curve) and range of compounds and masses observed in these mutasynthetic experiments. Where a mass was not recorded, NR replaces the number.

Example 5.3 Diversifying Compounds from the −3 PKS Module Strain (Phenotype D) by Mutasynthetic Experiments The isolated strain with phenotype D was grown on ISP3 media for approximately 2-3 weeks to allow significant mycelial growth and sporulation. Spores were harvested in 20% glycerol and aliquoted to produce a working stock of spores that was frozen at 80° C. 0.25 mL of the spore stock was used to inoculate 50 mL RapV7 in a 250 ml flask and incubated at 28° C. at 250 rpm for 48 hours. 0.5 ml of this seed culture was used to inoculate 7 mL MD6 media in a falcon tube and incubated at 26° C. and 300 rpm for 6 days, 24 hours into this time each culture was supplemented with 50 μl of 0.32M novel starter unit (see Table 1) dissolved in methanol (final concentration in media 2 mM). Each starter acid was tested in duplicate for each strain. After the 6 days of production 0.9 mL of culture was transferred into a 2 ml eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 4 illustrates the amounts produced (mg/L using 39-desmethoxy rapamycin callibration curve) and range of compounds and masses observed in these mutasynthetic experiments. Where a mass was not recorded, NR replaces the number.

Example 5.4 Diversifying Compounds from the 4 PKS Module Strain (Phenotype E) by Mutasynthetic Experiments The isolated strain with phenotype E was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 mL flask and incubated at 28° C. at 250 rpm for 48 hours. 0.5 ml of this seed culture was used to inoculate 7 mL MD6 media in a falcon tube and incubated at 26° C. and 300 rpm for 6 days, 24 hours into this time each culture was supplemented with 50 ml of 0.32M novel starter unit (see Table 1) dissolved in methanol (final concentration in media 2 mM). Each starter acid was tested in duplicate for each strain. After the 6 days of production 0.9 ml of culture was aliquoted into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 5 illustrates the amounts produced (mg/L using 39-desmethoxy rapamycin callibration curve) and range of compounds and masses observed in these mutasynthetic experiments. Where a mass was not recorded, NR replaces the number.

Example 5.5 Diversifying Compounds from the −6 PKS Module Strain (Phenotype F) by Mutasynthetic Experiments The isolated strain with phenotype F was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 ml flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 µl of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS. Table 6 illustrates the amounts produced (mg/L using 39-desmethoxy rapamycin callibration curve) and range of compounds and masses observed in these mutasynthetic experiments. Where a mass was not recorded, NR replaces the number.

Example 6 Diversifying Compounds from the +1 PKS Module Strain (Phenotype A) by Mutasynthetic Experiments The isolated strain with phenotype A was grown on ISP3 media for approximately 2-3 weeks to allow significant mycelial growth and sporulation. Spores were harvested in 20% glycerol and aliquoted to produce a working stock of spores that was frozen at 80 C. 0.25 mL of the spore stock was used to inoculate 50 ml RapV7 in a 250 ml flask and incubated at 28° C. at 250 rpm for 48 hours. 0.5 mL of this seed culture was used to inoculate 7 mL MD6 media in a falcon tube and incubated at 26° C. and 300 rpm for 6 days, 24 hours into this time each culture was supplemented with 50 µl of 0.32 M novel starter unit (see Table 1) dissolved in methanol (final concentration in media 2 mM). Each starter acid was tested in duplicate for each strain. After the 6 days of production 0.9 mL of culture was transferred into a 2 mL eppendorf tube and 0.9 mL methanol was added and mixed for ~30 minutes. Cell debris was pelleted by centrifugation and the liquid fraction analysed for the presence of novel rapalogs by LC (screening for presence of triene) and subsequently LCMS.

Example 7: Isolation of Compounds 2 and 3

Strain: Phenotype G from BIOT-4827
Feed: 4-trans-hydroxylcyclohexanecarboxylic acid (final concentration 2 mM)
1×15 liter fermentation
The fermentation was as described above except that the vegetative cultures (seed cultures) were prepared using 12×5 mm plugs from an agar plate and inoculating into 400 ml medium RapV7 in 2 liter Erlenmeyer flasks with foam plugs. Cultivation was carried out for 48 hours at 28° C., 250 rpm (2.5 cm throw).

DSP was as described in the general section, both the cell mass and clarified broth were extracted and the crude extracts combined.

The crude extract (13.8 g) was dissolved in 1:1 methanol/acetonitrile and C18 reverse-phase silica added (26 g). The solvent was removed in vacuo and the silica added to a C18 reverse-phase silica open column (70 mm×50 mm diameter) and the column eluted with 3:2 water/acetonitrile (600 ml), 1:1 water/acetonitrile (400 ml), 2:3 water/acetonitrile (1000 ml). Fractions combining compound 2 were pooled and taken to dryness (6.0 g) and fractions containing compound 3 were combined and taken to dryness (9.4 g).

Compound 2 was then purified by dissolving the 6.0 g enriched extract in methanol (5 ml) and separating the mixture by size-exclusion chromatography over sephadex LH-20 (column dimensions 1000 mm×30 mm diameter) eluted with methanol. Fractions containing compound 2 were combined and taken to dryness (210 mg), before the being adsorbed onto C18 reverse-phase silica (dissolved in 20 ml methanol, add 2 g C18 silica and remove the solvent in vacuo). This was then added to a C18 silica column (100 mm×30 mm diameter) and eluted with 3:2 acetonitrile/water. The fractions containing compound 2 were combined and taken to dryness to yield compound 2 as a white, amorphous solid.

QC data. RT=10.7 minutes, m/z=584.2 ([M+Na]$^+$) and 560.2 ([M−H]$^-$)

NMR was shown to be consistent with the structure shown:

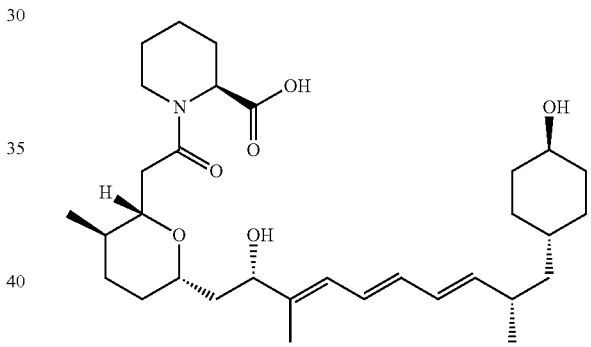

Compound 3 was then purified by dissolving the 9.4 g enriched extract in methanol (5 ml) and separating the mixture by size-exclusion chromatography over sephadex LH-20 (column dimensions 1000 mm×30 mm diameter) eluted with methanol. Fractions containing compound 3 were combined and taken to dryness.

QC data. RT 13.5 minutes, m/z=598.2 ([M+Na]$^+$) and 574.1 ([M−H]$^-$)

NMR was shown to be consistent with the structure shown:

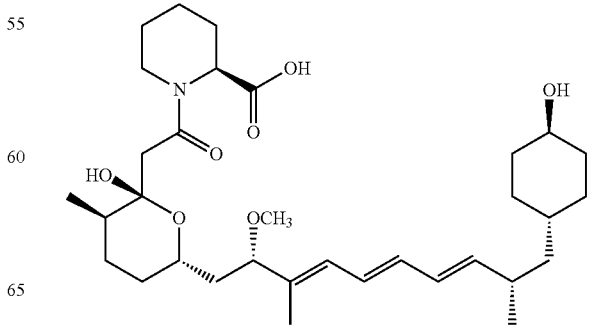

Example 8: Isolation of Compound 4

Strain: Phenotype C from BIOT-4827
Feed: 4-trans-hydroxylcyclohexanecarboxylic acid (final concentration 2 mM)
80×7 ml fermentation (in falcon tubes)
The broths from the individual falcons were combined and the cell mass separated by centrifugation. The DSP was carried out as described above, with only the cell mass extracted.

The crude extract (1.2 g) was dissolved in ethyl acetate and silica gel added (10 g). the solvent was removed in vacuo and the adsorbed silica was applied to a flash silica column (180 mm×55 mm diameter). The column was eluted with 4:5 ethyl acetate/hexanes (1.3 liters) then 1:1 ethyl acetate/hexanes (3.4 liters). The fractions containing compound 4 were combined and reduced in vacuo (65 mg). This material was further purified by reverse-phase HPLC (Phenomenex Xterra C18 column, 10 micron, 19 mm diameter× 250 mm, mobile phase at 20 ml/min, A=water, B=acetonitrile, t=0 min, B=50%; t=22 mins, B=80%). Fractions containing compound 4 were combined and taken to dryness to yield the target compound as a white amorphous solid (47 mg).

QC data. RT=15.5 minutes, m/z=780.3 ([M+Na]$^+$) and 756.2 ([M–H]$^-$)

NMR was shown to be consistent with the structure shown:

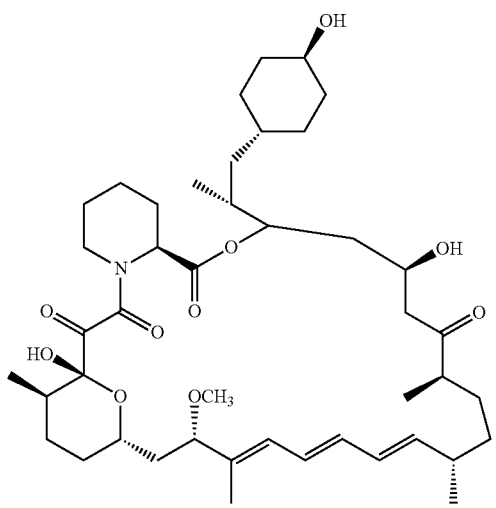 [SMILES: CO[C@H]1C[C@@H]2CC[C@@H](C)[C@@](O)(O2)C(=O)C(=O)N2CCCC[C@H]2C(=O)OC([C@H](C)C[C@H]2CC[C@H](O)CC2)C[C@@H](O)CC(=O)[C@H](C)CC[C@H](C)/C=C/C=C/C=C/1C]

Example 9: Isolation of Compound 5

Strain: Phenotype B from BIOT-4827
Feed: 4-trans-hydroxylcydohexanecarboxylic acid (final concentration 2 mM)
1×15 liter fermentation
The fermentation was as described above.
The fermentation broth at the end of the fermentation was separated by centrifugation and the cell paste processed as described above.

The crude extract was dissolved in ethyl acetate and silica gel added (7.5 g). The solvent was removed in vacuo and the adsorbed silica was applied to a flash silica column (200 mm×55 mm diameter). The column was eluted with 4:5 ethyl acetate/hexanes (1.8 liters), 1:1 ethyl acetate/hexanes (3.0 liters), 3:2 ethyl acetate/hexanes (1.5 liters) and then 2:1 ethyl acetate/hexanes (0.9 liters). The fractions containing compound 5 were combined and reduced in vacuo (44 mg). This material was further purified by reverse-phase HPLC (Phenomenex Xterra C18 column, 10 micron, 19 mm diameter×250 mm, mobile phase at 20 ml/min, A=water, B=acetonitrile, t=0 min, B=50%; t=22 mins, B=80%). Fractions containing compound 5 were combined and taken to dryness to yield the target compound as a white amorphous solid (32.6 mg).

QC data. RT=14.8 minutes, m/z=820.7 ([M+Na]$^+$) and 796.4 ([M–H]$^-$)

NMR was shown to be consistent with the structure shown:

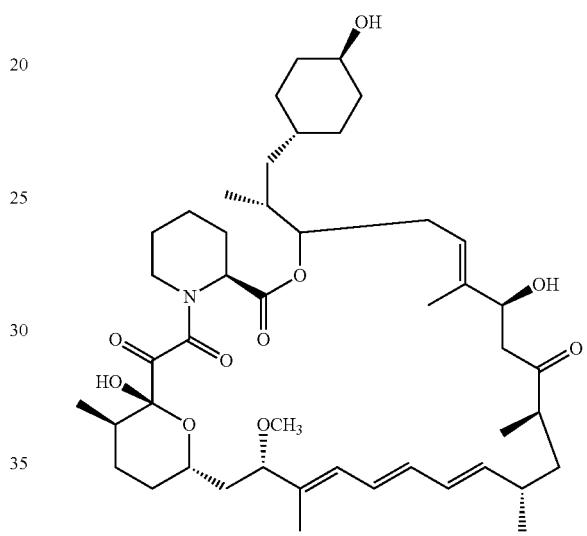

Example 10: Isolation of Compound 6

Strain: Phenotype D from BIOT-4827
Feed: 4-trans-hydroxylcyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract (8 g) was dissolved in ethyl acetate and silica gel added (15 g). The solvent was removed in vacuo and the adsorbed silica was applied to a flash silica column (200 mm×55 mm diameter). The column was eluted with 1:2 ethyl acetate/hexanes (0.9 liters), 4:5 ethyl acetate/hexanes (1.8 liters), 1:1 ethyl acetate/hexanes (3.0 liters), 3:2 ethyl acetate/hexanes (1.0 liters), 2:1 ethyl acetate/hexanes (1.8 liters) and then 100% ethyl acetate (0.4 liters). The fractions containing compound 6 were combined and reduced in vacuo. This material was dissolved in 2:3 acetonitrile/water and applied to a C18 SPE cartridge (20 g). This was eluted with 100 ml of each of 2:3, 1:1, 3:2, 7:3, 4:1 acetonitrile/water. The fractions containing compound 6 were combined and reduced in vacuo (150 mg). This material was further purified by reverse-phase HPLC (Phenomenex Xterra C18 column, 10 micron, 19 mm diameter×250 mm, mobile phase at 20 ml/min, A=water, B=acetonitrile, t=0 min, B=50%; t=22 mins, B=80%). Fractions containing compound 6 were combined and taken to dryness to yield the target compound as a white amorphous solid (93 mg).

QC data. RT=14.3 minutes, m/z=722.6 ([M+Na]$^+$) and 698.5 ([M–H]$^-$)

NMR was shown to be consistent with the structure shown:

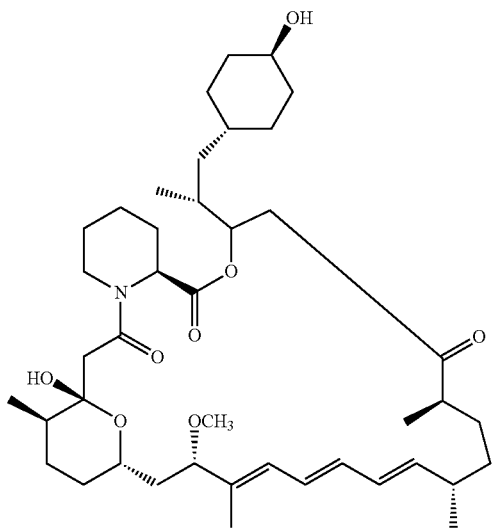 [SMILES: CO[C@H]1C[C@@H]2CC[C@@H](C)[C@](O)(CC(=O)N3CCCC[C@H]3C(=O)OC([C@H](C)C[C@H]3CC[C@H](O)CC3)CC(=O)[C@H](C)CC[C@H](C)/C=C/C=C/C=C/1C)O2]

Example 11: Isolation of Compound 7

Strain: Phenotype E from BIOT-4827
Feed: 4-trans-hydroxylcydohexanecarboxylic acid (final concentration 2 mM)
1×15 liter fermentation
The fermentation was as described above.
The fermentation broth at the end of the fermentation was separated by centrifugation and the cell paste processed as described above.

The crude extract (9.8 g) was dissolved in 1:1 methanol/acetonitrile and C18 reverse-phase silica gel added. The solvent was removed in vacuo and the adsorbed silica was applied to a flash reverse-phase C18 silica column (70 mm×55 mm diameter). The column was eluted with 6:4 water/acetonitrile (0.8 liters), 1:1 water/acetonitrile (0.2 liters), 4:6 water/acetonitrile (0.8 liters), and then 3:7 water/acetonitrile (0.2 liters). The fractions containing compound 7 were combined and reduced in vacuo (404 mg). This material was further purified by reverse-phase HPLC (Phenomenex Xterra C18 column, 10 micron, 19 mm diameter× 250 mm, mobile phase at 20 ml/min, A=water, B=acetonitrile, t=0 min, B=30%; t=30 mins, B=80%). Fractions containing compound 7 were combined and taken to dryness in vacuo. This material was by size-exclusion chromatography over sephadex LH-20 (column dimensions 1000 mm×30 mm diameter) eluted with methanol. Fractions containing compound 7 were combined and taken to dryness to yield the target compound as a white amorphous solid (47 mg).

QC data. RT=12.7 minutes, m/z=652.6 ([M+Na]$^+$) and 628.5 ([M–H]$^-$)

NMR was shown to be consistent with the structure shown:

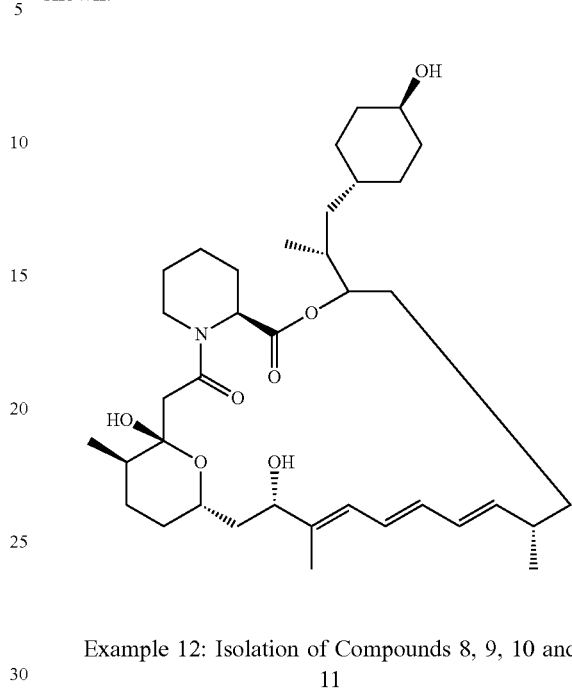

Example 12: Isolation of Compounds 8, 9, 10 and 11

Strain: Phenotype B from BIOT-4827
Feed: 3,4-trans-dihydroxylcydcohexanecarboxylic acid (final concentration 2 mM)
1×15 liter fermentation
The fermentation was as described above.
The fermentation broth at the end of the fermentation was separated by centrifugation and the cell paste processed as described above.

The crude extract (8.5 g) was dissolved in 80% aqueous methanol (250 ml) and washed with hexanes (2×250 ml). The aqueous methanol was reduced in vacuo to yield an enriched extract (6.8 g). The crude extract was dissolved in methanol and silica added. The solvent was removed in vacuo and the adsorbed silica added added to a flash silica column (20 cm×5 cm diameter) and eluted with 100% chloroform, and the polarity gradually increased by adding MeOH (to a maximum 5% MeOH). Fractions contain compound 8 were combined and taken to dryness (3.1 g). Fractions contain compound 9 were combined and taken to dryness (196 mg). Fractions contain compound 10 were combined and taken to dryness (480 mg). Fractions contain compound 11 were combined and taken to dryness (304 mg). The extract containing compound 8 was then purified further by flash silica column chromatography eluted with ethyl acetate/hexane. Fractions contain compound 8 were combined and taken to dryness to yield the target compound as a white amorphous solid (65 mg).

QC data. RT=15.9 minutes, m/z=850.8 ([M+Na]$^+$) and 826.5 ([M–H]$^-$)

NMR was shown to be consistent with the structure shown:

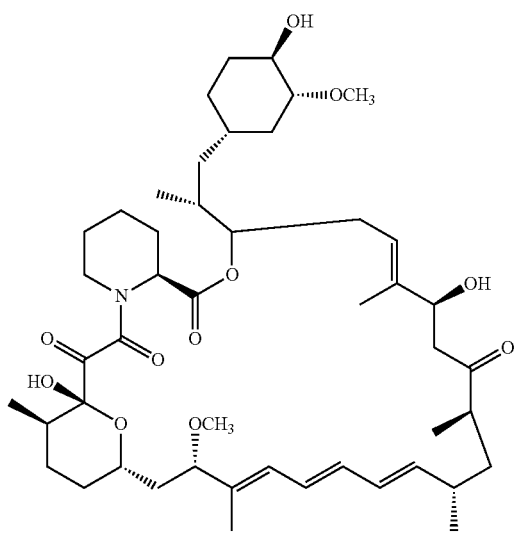 [SMILES: CO[C@H]1C[C@@H]2CC[C@@H](C)[C@@](O)(O2)C(=O)C(=O)N2CCCC[C@H]2C(=O)OC([C@H](C)C[C@@H]2CC[C@@H](O)[C@H](OC)C2)C/C=C(\C)[C@@H](O)CC(=O)[C@H](C)C[C@H](C)/C=C/C=C/C=C/1C]

The extract containing compound 9 was then purified further by reverse-phase HPLC (Phenomenex Xterra C18 column, 10 micron, 19 mm diameter×250 mm, mobile phase at 20 ml/min, A=water, B=acetonitrile) to yield the target compound as a white amorphous solid (55 mg).

QC data. RT=14.7 minutes, m/z=822.8 ([M+Na]$^+$) and 798.6 ([M−H]$^−$)

NMR was shown to be consistent with the structure shown:

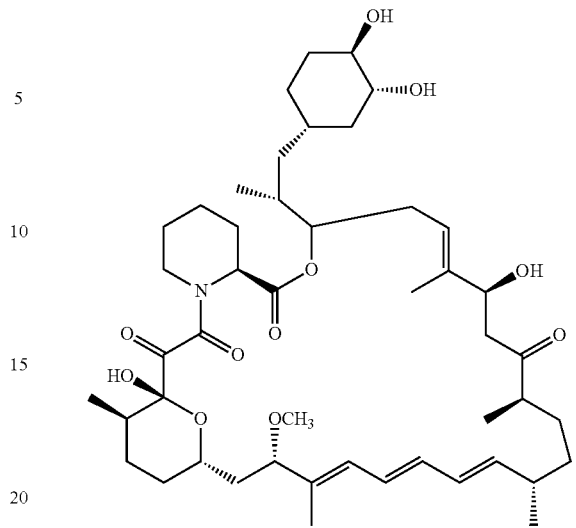

The extract containing compound 11 was then purified further by reverse-phase HPLC (Phenomenex Xterra C18 column, 10 micron, 19 mm diameter×250 mm, mobile phase at 20 ml/min, A=water, B=acetonitrile) to yield the compound 11 as a white amorphous solid (55 mg).

QC data. RT=13.0 minutes and 14.2 minutes, m/z=822.6 ([M+Na]$^+$) and 798.5 ([M−H]$^−$)

NMR was shown to be consistent with the structure shown:

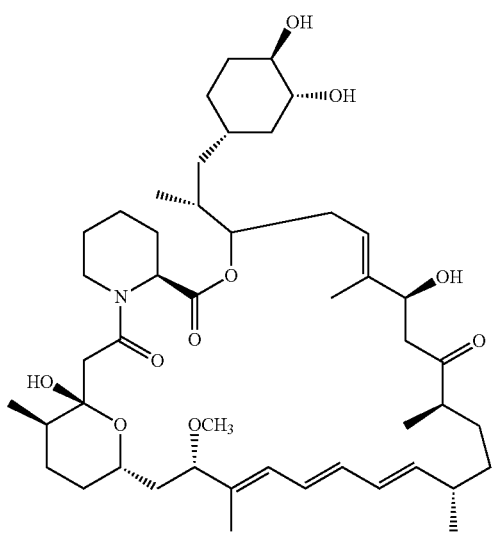 [SMILES: CO[C@H]1C[C@@H]2CC[C@@H](C)[C@](O)(CC(=O)N3CCCC[C@H]3C(=O)OC([C@H](C)C[C@@H]3CC[C@@H](O)[C@H](O)C3)C/C=C(\C)[C@@H](O)CC(=O)[C@H](C)CC[C@H](C)/C=C/C=C/C=C/1C)O2]

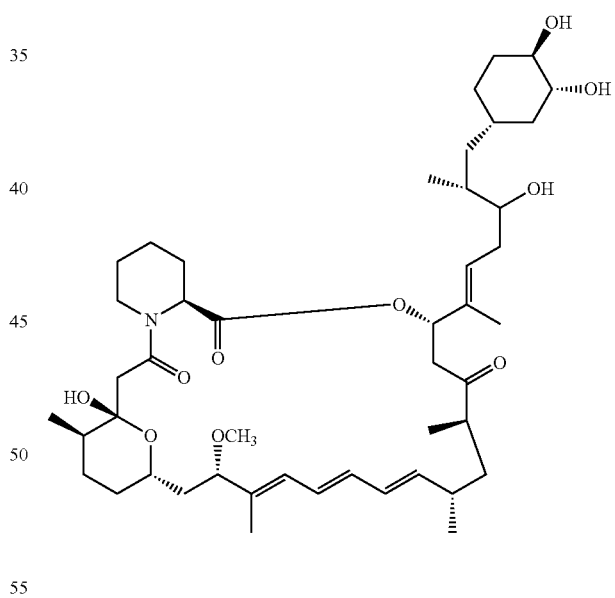

Example 13: Isolation of Compound 12

Strain: Phenotype B from BIOT-4827
Feed: 5-methylthiophene-2-carboxylic acid (final concentration 2 mM)
1×15 liter fermentation
The fermentation was as described above.
The fermentation broth at the end of the fermentation was separated by centrifugation and the cell paste processed as described above.
The crude extract (6.7 g) was dissolved in methanol and silica added. The solvent was removed in vacuo and the The extract containing compound 10 was then purified further by reverse-phase HPLC (Phenomenex Xterra C18 column, 10 micron, 19 mm diameter×250 mm, mobile phase at 20 ml/min, A=water, B=acetonitrile) to yield the target compound as a white amorphous solid (211 mg).

QC data. RT=14.2 minutes, m/z=836.8 ([M+Na]$^+$) and 812.5 ([M−H]$^−$)

NMR was shown to be consistent with the structure shown:

adsorbed silica added added to a flash silica column (20 cm×5 cm diameter) and eluted with 100% chloroform. Fractions containing the target compound were combined and dried in vacuo (2.14 g). This enriched extract was loaded onto a second silica column, pre-conditioned in 1:1 ethyl acetate/hexanes. The column was eluted with the same solvent mixture and fractions containing the target compound were combined and dried in vacuo (0.42 g). The extract containing compound 12 was then purified further by reverse-phase HPLC (Phenomenex Xterra C18 column, 10 micron, 19 mm diameter×250 mm, mobile phase at 20 ml/min, A=water, B=acetonitrile, t=0 minutes, B=50%, t=30 minutes, B=100%) to yield the compound 12 as a white amorphous solid (256 mg).

QC data. RT=12.7 minutes, m/z=834.4 ([M+Na]$^+$) and 810.2 ([M–H]$^-$)

NMR was shown to be consistent with the structure shown:

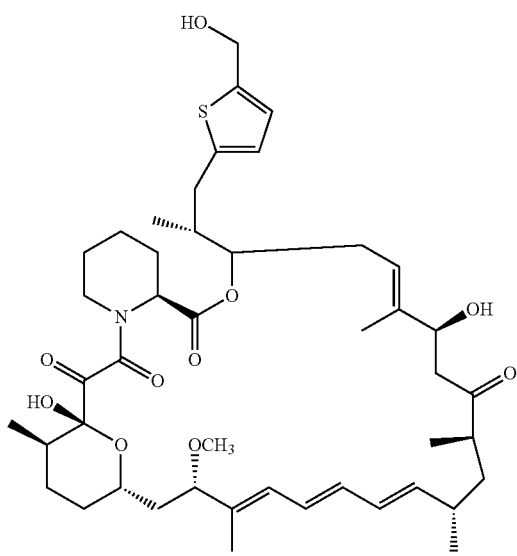 [SMILES: CO[C@H]1C[C@@H]2CC[C@@H](C)[C@@](O)(O2)C(=O)C(=O)N2CCCC[C@H]2C(=O)OC([C@H](C)Cc2ccc(CO)s2)C/C=C(\C)[C@@H](O)CC(=O)[C@H](C)C[C@H](C)/C=C/C=C/C=C/1C]

Example 14: Isolation of Compound 13

Strain: Phenotype B from BIOT-4827
Feed: isonicotinic acid (final concentration 2 mM)
1×15 liter fermentation
The fermentation was as described above.
The fermentation broth at the end of the fermentation was separated by centrifugation and the cell paste processed as described above.

The crude extract (5.3 g) was dissolved in methanol and silica added. The solvent was removed in vacuo and the adsorbed silica added added to a flash silica column (20 cm×5 cm diameter) and eluted with 100% chloroform, 1% methanol/chloroform, 2% methanol/chloroform, 3% methanol/chloroform, 4% methanol/chloroform and 5% methanol/chloroform. Fractions containing the target compound were combined and dried in vacuo (1.99 g). This enriched extract was loaded onto a second silica column, pre-conditioned in 1:1 ethyl acetate/hexanes. The column was eluted with the same solvent mixture and then 60:40, 70:30, 80:20, 90:10 mixtures followed by 100% ethyl acetate. Fractions containing the target compound were combined and dried in vacuo to yield the compound 13 as an amorphous solid (0.124 g).

All analytics for compound 13 were performed using an Agilent Zorbax, Eclipse XDB-C8 column (150×4.6 mm, 5 micron). All of the LC-timetables were the same as in the other Examples.

QC data. RT=11.6 minutes, m/z=777.7 ([M+H]$^+$) and 775.4 ([M–H]$^-$)

NMR was shown to be consistent with the structure shown:

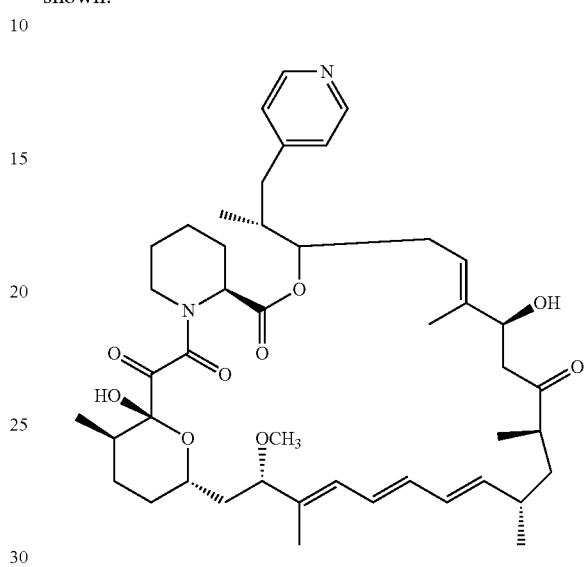

Example 15: Isolation of Compound 14

Strain: Phenotype A from BIOT-4827
Feed: 4-trans-hydroxycyclohexanecarboxylic acid (final concentration 2 mM)
1×15 liter fermentation
The fermentation was as described above.
The fermentation broth at the end of the fermentation was separated by centrifugation and the cell paste processed as described above.

The crude extract (5.3 g) was dissolved in methanol and silica added. The solvent was removed in vacuo and the adsorbed silica added added to a flash silica column (20 cm×5 cm diameter) and eluted with the 50:50 ethyl acetate/hexanes and then 60:40, 70:30, 80:20, 90:10 mixtures followed by 100% ethyl acetate. Fractions containing the target compound were combined and dried in vacuo to yield an enriched extract of 0.05 g. This material was loaded onto a second silica column (10 cm×2 cm) and eluted with 45% ethyl acetate/55% hexanes. Fractions containing the target compound were combined and dried in vacuo (32 mg). This was then purified further by reverse-phase HPLC (Phenomenex Xterra C18 column, 10 micron, 19 mm diameter×250 mm, mobile phase at 20 ml/min, A=water, B=acetonitrile, t=0 minutes, B=50%, t=30 minutes, B=100%) and then by further reverse-phase HPLC (Phenomenex Gemini NX C18 column, 10 micron, 21 mm diameter×150 mm, mobile phase at 20 ml/min, A=water, B=acetonitrile, t=0 minutes, B=50%, t=30 minutes, B=100%) to yield compound 14 as a white amorphous solid (14.5 mg).

QC data. RT=15.2 minutes, m/z=920.6 ([M+Na]$^+$) and 896.5 ([M–H]$^-$)

NMR was shown to be consistent with the structure shown:

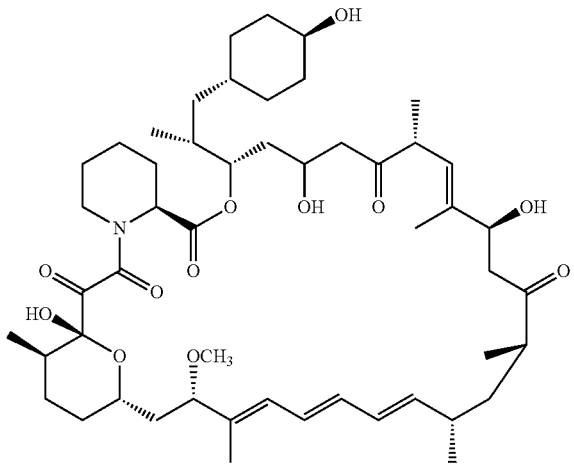 [SMILES: CO[C@H]1C[C@@H]2CC[C@@H](C)[C@@](O)(O2)C(=O)C(=O)N2CCCC[C@H]2C(=O)O[C@H]([C@H](C)C[C@H]2CC[C@H](O)CC2)CC(O)CC(=O)[C@H](C)/C=C(\C)[C@@H](O)CC(=O)[C@@H](C)C[C@H](C)/C=C/C=C/C=C/1C]

Example 16: Isolation of Compounds 15, 16 and 17

Strain: Phenotype F from BIOT-4827

Feed: 4-trans-hydroxycyclohexanecarboxylic acid (final concentration 2 mM)

1×15 liter fermentation

The fermentation was as described above.

The fermentation broth at the end of the fermentation was separated by centrifugation and the cell paste and clarified broth processed as described above.

The crude extract (20.7 g) was dissolved in methanol and silica added. The solvent was removed in vacuo and the adsorbed silica added added to a flash silica column (20 cm×5 cm diameter) and eluted with the 40:60 ethyl acetate/hexanes and then 50:50, 60:40, 70:30, 80:20, 90:10 mixtures followed by 100% ethyl acetate. Fractions containing the target compounds X+14 and X+15 were combined and dried in vacuo to yield an enriched extract of 0.96 g. Fractions containing the target compounds 17 were combined and dried in vacuo to yield an enriched extract of 3.1 g.

Compounds 15 and 16 were then purified by preparative HPLC (Phenomenex Gemini NX C18 column, 10 micron, 21 mm diameter×150 mm, mobile phase at 20 ml/min, A=water, B=acetonitrile, t=0 minutes, B=60%, t=30 minutes, B=100%) to yield compound X+15 as a white amorphous solid (152 mg). Fractions containing compound 16 was defatted (dissolved in 80% aqueous methanol and extracted into hexanes, the solvent was then removed from the aqueous methanol layer to reveal the target compound) to yield a white amorphous solid (164 mg)

Compound 15

QC data. RT=16.3 minutes, m/z=650.3 ([M+Na]$^+$) and 626.2 ([M–H]$^-$)

NMR was shown to be consistent with the structure shown:

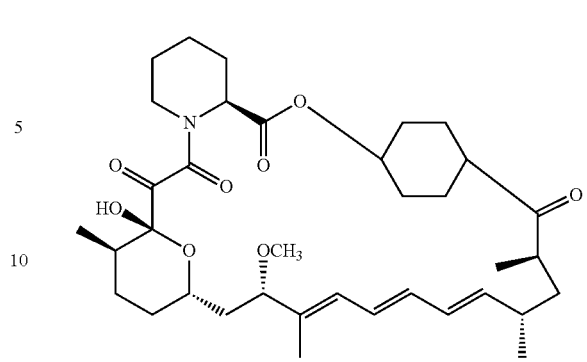

Compound 16

QC data. RT=14.9 minutes, m/z=636.2 ([M+Na]$^+$) and 612.2 ([M–H]$^-$)

NMR was shown to be consistent with the structure shown:

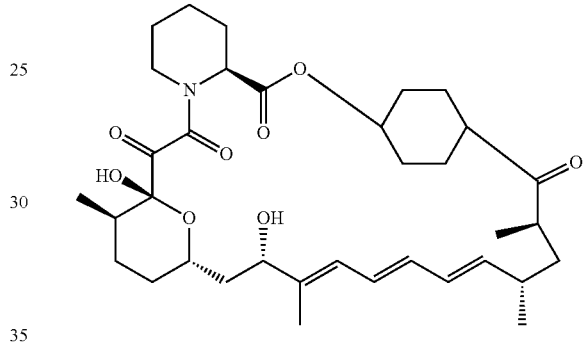

Compound 17

QC data. RT=13.5 minutes, m/z=654.3 ([M+Na]$^+$) and 630.1 ([M–H]$^-$)

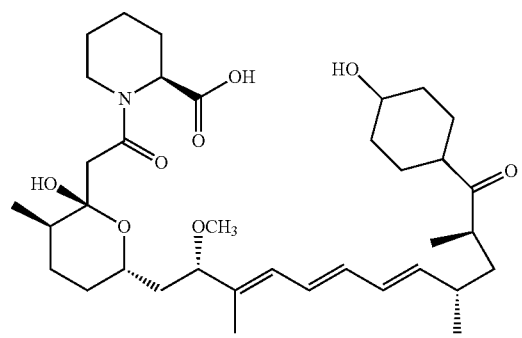 [SMILES: CO[C@@H](C[C@@H]1CC[C@@H](C)[C@](O)(CC(=O)N2CCCC[C@H]2C(=O)O)O1)/C(C)=C/C=C/C=C/[C@@H](C)C[C@@H](C)C(=O)C1CCC(O)CC1]

Example 17: Analytical Biotransformations

List of Substrate Carboxylic Acids and Carboxylic Acid Analogs Used in the Analytical Biotransformations Analytical biotransformations were conducted as described above in the general methods section and Example 5. In each case the strain being tested was fed each of the compounds above separately. After a total of 6 days growth the broths were extracted as described above and analysed for the production of rapamycin analogues as indicated by observing the rapamycin triplet at 278 nm and/or mass ions that derive from the predicted combination of starter unit and strain. Results are shown in Tables 2 to 6 below.

Results of Mutasynthetic Feeding to −1 PKS Module Strain Phenotype B

TABLE 2

| Feed | major product peaks RT/mins | molecular weight |
|---|---|---|
| unfed | 9.1 | NR |
|  | 10.4 | 791.5 |
| A | 9.4 | NR |
|  | 10.1 | 797.5 |
| B | 8.7 | 813.5 |
|  | 9.6 | 797.5 |
|  | 10.6 | 781.5 |
| C | 8.2 | 813.5 |
|  | 9.8 | 795.5 |
|  | 10.1 | 813.5 |
| D | 8.2 | NR |
|  | 8.7 | NR |
|  | 9.6 | NR |
|  | 10.6 | 797.5 |
|  | 10.8 | 813.5 |
|  | 11.3 | 797.5 |
| E | 8.3 | 811.6 |
|  | 10.2 | 795.5 |
| F | 9.7 | 831.6 |
| G | 8.9 | 843.5 |
|  | 9.5 | 827.5 |
|  | 10.1 | 811.5 |
|  | 10.7 | 811.5 |
| H | 10.1 | 783.5 |
|  | 10.4 | 791.6 |
| I | 7.7 | NR |
|  | 10.1 | 827.2 |
|  | 10.4 | 827.2 |
|  | 10.9 | 811.6 |
| J | 7.1 | NR |
|  | 9.2 | NR |
|  | 9.3 | 825.6 |
|  | 9.8 | 825.6 |
|  | 10.5 | 809.5 |
| K | 7.6 | NR |
|  | 8.2 | NR |
|  | 8.9 | 839.5 |
|  | 9.9 | 839.5 |
|  | 10.4 | 839.5 |
|  | 11.1 | 823.5 |
| L | 9.9 | 769.5 |
|  | 11.7 | 783.4 |
| M | 7.5 | NR |
|  | 8.2 | NR |
|  | 10.4 | 815.5 |
|  | 12.9 | NR |
|  | 13.8 | NR |
| N | 10.4 | 791.5 |
| O | 9.9 | 811.5 |
| P | 5.2 | NR |
|  | 6.2 | NR |
|  | 6.8 | NR |
|  | 7.1 | NR |
| Q | 10.4 | 827.5 |
|  | 10.9 | 811.5 |
|  | 11.6 | 825.5 |
| R | 10.5 | 827.5 |
|  | 11.2 | 825.5 |
|  | 11.7 | 809.5 |
| S | 8.5 | NR |
|  | 10.4 | 825.7 |
|  | 10.7 | 809.5 |
| T | 8.9 | 827.6 |
|  | 9.5 | 843.5 |
|  | 10.1 | 827.6 |
|  | 10.7 | 811.5 |
| A1 | 8.3 | NR |
|  | 9.4 | NR |
|  | 10.1 | 797.9 |
|  | 11.5 | 784.1 |

TABLE 2-continued

| Feed | major product peaks RT/mins | molecular weight |
|---|---|---|
| B1 | 8.7 | NR |
|  | 9.7 | NR |
|  | 10.4 | NR |
|  | 11.9 | 796.2 |
| C1 | 8.2 | NR |
|  | 10.7 | 814.9 |
|  | 11.3 | 726 |
|  | 12.6 | NR |
| D1 | 7.9 | NR |
|  | 9.7 | 816.9 |
|  | 10.8 | 802 |
| F1 | 8.2 | NR |
|  | 9.9 | 833.9 |
|  | 10.9 | 819.9 |
| G1 | 8.7 | 784.1 |
|  | 9.6 | NR |
|  | 10.5 | NR |
|  | 11.7 | 772.1 |

Results of Mutasynthetic Feeding to −2 PKS Module Strain Phenotype C

TABLE 3

| Feed | major product peaks RT/mins | molecular weight |
|---|---|---|
| unfed | 9.7 | NR |
|  | 9.9 | NR |
| A | 7.5 | NR |
|  | 9.6 | 757.5 |
|  | 11.2 | NR |
| B | 7.8 | 743.6 |
|  | 9.6 | 757.5 |
|  | 9.9 | 781.6 |
|  | 11.2 | NR |
| C | 5.4 | 773.6 |
|  | 7.5 | 757.6 |
|  | 10.5 | NR |
|  | 11.2 | NR |
| D | 7.9 | 743.5 |
|  | 9.9 | 756.7 |
|  | 11.2 | NR |
|  | 11.5 | NR |
| E | 7.5 | 741.6 |
|  | 9.5 | 755.6 |
|  | 9.9 | NR |
|  | 11.2 | NR |
| F | 7.0 | NR |
|  | 9.2 | 775.6 |
|  | 10.3 | NR |
| G | 6.6 | 787.8 |
|  | 8.9 | 757.8 |
|  | 9.2 | NR |
|  | 10.2 | 771.6 |
|  | 11.3 | 771.6 |
| H | 9.8 | 751.5 |
|  | 9.9 | NR |
| I | 7.9 | 751.6 |
|  | 9.8 | NR |
|  | 10.6 | 771.7 |
| J | 7.8 | 769.6 |
|  | 9.9 | 755.8 |
| K | 8.5 | 769.8 |
|  | 9.1 | 783.5 |
|  | 10.6 | 783.5 |
|  | 11.1 | NR |
| L | 8.9 | NR |
|  | 10.1 | 685.7 |
| M | 7.5 | 751.6 |
|  | 2.9 | NR |
|  | 9.8 | NR |
|  | 9.9 | NR |
| N | 7.3 | NR |
|  | 9.8 | 751.6 |

TABLE 3-continued

| Feed | major product peaks RT/mins | molecular weight |
|---|---|---|
| O | 9.3 | 771.6 |
| P | 5.7 | NR |
| Q | 9.7 | 757.4 |
|  | 10 | 751.6 |
|  | 10.5 | 771.7 |
|  | 11.4 | NR |
| R | 9.7 | NR |
|  | 10.8 | NR |
|  | 11.6 | 769.6 |
| S | 5.8 | NR |
|  | 10.6 | 769.6 |
| T | 6.6 | 787.6 |
|  | 8.1 | NR |
|  | 8.9 | NR |
|  | 10.3 | 771.7 |
| U | 5.4 | NR |
|  | 7.2 | 759.7 |
|  | 7.5 | 773.7 |
|  | 9.2 | NR |
| V | 5.7 | NR |
|  | 6.7 | 787.6 |
|  | 8.5 | 787.6 |
|  | 9 | NR |
|  | 10.6 | 771.7 |
| W | 4.7 | NR |
|  | 6.1 | NR |
| X | 9.3 | 771.6 |
| A1 | 6.7 | NR |
|  | 7.3 | 757.6 |
|  | 9.3 | NR |
|  | 10.3 | NR |
|  | 10.6 | NR |
| B1 | 6.3 | NR |
|  | 7.7 | NR |
|  | 8.1 | NR |
|  | 9.6 | 769.9 |
| C1 | 7.7 | NR |
|  | 8.3 | NR |
|  | 10.9 | 757.9 |
|  | 11.2 | 757.9 |
|  | 11.8 | NR |
| D1 | 5.86 | NR |
|  | 6.8 | NR |
|  | 8.9 | NR |
|  | 8.9 | 776.1 |
|  | 9.4 | NR |
|  | 9.8 | NR |
|  | 10 | NR |
| F1 | 6.1 | NR |
|  | 7.3 | NR |
|  | 9.2 | 793.9 |
|  | 9.9 | NR |
|  | 10.1 | NR |
| G1 | 6.6 | NR |
|  | 7.1 | NR |
|  | 7.3 | NR |
|  | 7.7 | NR |
|  | 9.7 | 775.9 and 759.0 |

Results of Mutasynthetic Feeding to −3 PKS Module Strain Phenotype D

TABLE 4

| Feed | major product peaks RT/mins | molecular weight |
|---|---|---|
| unfed | 8.7 | NR |
| A | 6 | NR |
|  | 7.4 | NR |
|  | 8.4 | 699.5 |
|  | 10.8 | 713.6 |
| B | 8.4 | NR |
|  | 8.8 | 699.6 |
| C | 5.4 | NR |
|  | 6.1 | NR |
|  | 7.7 | NR |
|  | 8.3 | 697.6 |
|  | 8.7 | NR |
| D | 6.1 | NR |
|  | 8.4 | NR |
|  | 8.8 | 699.7 |
|  | 9.4 | 699.7 |
| E | 6.1 | NR |
|  | 8.3 | 697.6 |
|  | 8.8 | NR |
|  | 11.6 | NR |
|  | 11.9 | NR |
| F | 6.1 | NR |
|  | 6.9 | 717.6 |
|  | 7.8 | 731.6 |
|  | 10.2 | NR |
| G | 7.5 | 729.6 |
|  | 9.2 | 713.7 |
|  | 10.1 | 713.7 |
| H | 8.3 | 709.5 |
|  | 8.7 | 693.5 |
| I | 8.2 | NR |
|  | 8.5 | NR |
|  | 8.6 | 713.6 |
|  | 9.3 | NR |
|  | 9.7 | NR |
| J | 8.9 | 711.6 |
| K | 7 | 741.6 |
|  | 9.6 | 725.5 |
|  | 10.2 | 725.5 |
| L | 7.3 | NR |
|  | 8.7 | 743.6 |
|  | 9.6 | 711.5 |
|  | 11.2 | 713.5 |
|  | 12 | NR |
|  | 12.4 | NR |
| M | 6.1 | 717.6 |
|  | 7.2 | 693.6 |
|  | 8.7 | NR |
| N | 8.6 | 693.6 |
|  | 11.8 | 693.6 |
| O | 6.5 | 713.5 |
|  | 8.1 | NR |
|  | 8.6 | NR |
| P | 4.5 | NR |
|  | 4.8 | NR |
|  | 6 | NR |
|  | 8.7 | NR |
| Q | 8.7 | 723.6 |
|  | 9.4 | 713.6 |
| R | 8.4 | 723.6 |
|  | 8.7 | 693.6 |
|  | 9.8 | 711.7 |
| S | 6.6 | NR |
|  | 8.7 | NR |
|  | 9.3 | NR |
|  | 9.5 | 711.5 |
|  | 12.2 | 725.5 |
| T | 6.6 | NR |
|  | 7.4 | 729.6 |
|  | 9.2 | 713.6 |
|  | 9.8 | NR |
|  | 11.5 | NR |
| U | 5.4 | 731.9 |
|  | 6.1 | 717.5 |
|  | 7.1 | 729.7 |
|  | 7.7 | NR |
|  | 8.7 | NR |
| V | 7 | NR |
|  | 8.4 | 729.5 |
|  | 9.5 | 713.7 |
|  | 9.9 | 743.6 |
| W | 4.8 | 693.5 |
|  | 8.7 | NR |

TABLE 4-continued

| Feed | major product peaks RT/mins | molecular weight |
|---|---|---|
| X | 6.4 | NR |
|  | 8.1 | 713.5 |
| A1 | 7.4 | NR |
|  | 7.7 | NR |
|  | 8.4 | 699.8 |
|  | 10.8 | 713.7 |
|  | 12.1 | NR |
| B1 | 7.4 | NR |
|  | 8.8 | 711.9 |
|  | 12.5 | NR |
| C1 | 6.1 | NR |
|  | 8.2 | NR |
|  | 8.8 | NR |
|  | 9.4 | 699.9 |
|  | 12.9 | NR |
| D1 | 6.9 | 717.9 |
|  | 7.9 | 717.9 |
|  | 8.4 | NR |
|  | 8.9 | NR |
|  | 10.1 | NR |
|  | 11.5 | NR |
| E1 | 8.4 | NR |
|  | 10.4 | NR |
|  | 13.2 | NR |
| F1 | 7.33 | 735.8 |
|  | 7.7 | NR |
|  | 8.2 | 749.9 |
|  | 8.7 | NR |
|  | 10.3 | 735.8 |
|  | 10.8 | NR |
| G1 | 6.1 | NR |
|  | 8.8 | 699.9 |
|  | 9.3 | 699.9 |
|  | 12.3 | NR |

Results of Mutasynthetic Feeding to −4 PKS Module Strain Phenotype E

TABLE 5

| Feed | major product peaks RT/mins | molecular weight |
|---|---|---|
| unfed | 5.1 | NR |
| A | 4.6 | 629.7 |
|  | 8.8 | 671.9 |
| B | 5.3 | 629.7 |
| C | 8.4 | 655.8 |
| D | 5.4 | NR |
| E | 4.8 | NR |
|  | 12 | NR |
| F | 4.1 | 647.7 |
|  | 7.2 | 689.9 |
| G | 5.2 | 643.5 |
| H | 5.1 | NR |
| I | 5.5 | 643.8 |
| J | 5.2 | NR |
|  | 9 | NR |
| K | 6.02 | 655.5 |
|  | 9.9 | NR |
| L | 6.3 | NR |
| M | 5.1 | NR |
| N | 5.1 | 623.5 |
| O | 11.2 | NR |
| Q | 5.1 | NR |
| R | 5.1 | NR |
| S | 5.1 | NR |
| T | 5.2 | NR |
| U | 4.1 | NR |
|  | 4.8 | NR |
|  | 8.4 | 673.6 |

TABLE 5-continued

| Feed | major product peaks RT/mins | molecular weight |
|---|---|---|
| V | 5.7 | NR |
|  | 9.8 | 687.7 |
|  | 10.1 | 703.7 |
|  | 10.5 | 703.7 |
| W | 3.8 | 608.8 |
| X | 3.2 | NR |
|  | 6.7 | 689.3 |
|  | 11.1 | 671.8 |
|  | 11.6 | 686.7 |
| A1 | 4.6 | NR |
|  | 5.5 | NR |
|  | 7.6 | NR |
|  | 8.7 | NR |
|  | 9.3 | NR |
|  | 9.5 | NR |
| B1 | 5.1 | NR |
|  | 8.3 | NR |
|  | 8.8 | NR |
|  | 9.8 | NR |
| C1 | 5.4 | NR |
|  | 10 | NR |
| D1 | 4.1 | NR |
|  | 4.6 | NR |
|  | 5.7 | NR |
|  | 6.9 | NR |
|  | 7.1 | NR |
|  | 8.1 | NR |
|  | 8.5 | NR |
| E1 | 4.6 | NR |
|  | 7.7 | 647.7 |
|  | 10.7 | NR |
|  | 13.4 | NR |
| F1 | 4.3 | 697.6 |
|  | 4.4 | NR |
|  | 7.3 | NR |
|  | 8.7 | NR |
| G1 | 5.3 | NR |
|  | 6.7 | NR |
|  | 9.7 | NR |
|  | 12.5 | NR |

Results of Mutasynthetic Feeding to −6 PKS Module Strain Phenotype G

TABLE 6

| Feed | major product peaks RT/mins | MW (difference from truncated pre-rap) |
|---|---|---|
| unfed | nd | NR |
| A | 5.1 | 561.5 |
|  | 6.7 | 575.5 |
|  | 8.1 | 557.9 |
|  | 9.2 | NR |
| B | 5.07 | 561.5 |
|  | 6.7 | 575.5 |
|  | 8.1 | 557.9 |
|  | 9.3 | NR |
| C | 5.1 | 561.4 |
|  | 6.1 | 573.7 |
|  | 8.6 | NR |
| D | 5 | 561.4 |
|  | 6 | NR |
|  | 6.7 | 575.5 |
|  | 7.8 | NR |
|  | 9.2 | NR |
|  | 10.3 | NR |
| E | 4.5 | NR |
|  | 6.1 | 574 |
|  | 7.5 | NR |
|  | 8.6 | NR |
| F | 4.4 | NR |
|  | 5.9 | NR |
|  | 7.2 | NR |
|  | 8.2 | NR |

TABLE 6-continued

| Feed | major product peaks RT/mins | MW (difference from truncated pre-rap) |
|---|---|---|
| G | 6.3 | NR |
| | 7.6 | NR |
| | 8.1 | NR |
| | 10.2 | NR |
| | 10.7 | NR |
| I | 6.1 | NR |
| | 7.8 | 590 |
| | 9.3 | NR |
| | 10.3 | 604.5 |
| J | 5.4 | 573.4 |
| | 7.1 | 587.9 |
| | 8.5 | NR |
| | 9.7 | 602 |
| K | 6.1 | NR |
| | 6.3 | NR |
| | 7.8 | 601.8 |
| | 8.2 | NR |
| L | 6.2 | 547.4 |
| | 8.1 | 561.9 |
| | 9.7 | NR |
| | 10.8 | NR |
| M | 9 | NR |
| | 10.9 | NR |
| N | 4.8 | 622.7 |
| | 6.4 | 569.9 |
| O | nd | NR |
| Q | 7.6 | 612.9 |
| | 8.01 | NR |
| | 8.9 | 603.8 |
| R | 8.4 | NR |
| | 7.6 | NR |
| S | 12.2 | 557 |
| T | 7.6 | 589.9 |
| U | 3.9 | 591.9 |
| | 4.2 | NR |
| | 6.05 | 605.7 |
| V | 6.3 | 575.6 |
| | 8.02 | 589.9 |
| | 10.6 | NR |
| X | 6.8 | NR |
| | 9.05 | NR |
| | 10.8 | NR |
| A1 | 4.4 | NR |
| | 5.1 | 561.7 |
| | 6.7 | 575.8 |
| | 7.1 | NR |
| | 7.5 | 557.8 |
| | 7.7 | NR |
| B1 | 5.4 | 575.9 |
| | 7.1 | 587.9 |
| | 7.6 | NR |
| | 9.6 | 569.8 |
| C1 | 3.3 | NR |
| | 4.7 | NR |
| | 5 | NR |
| | 5 | NR |
| | 6 | NR |
| | 6.7 | NR |
| | 7.8 | 575.6 |
| | 8.6 | 577.8 |
| | 9 | NR |
| | 10.2 | 589.1 |
| | 10.8 | NR |
| D1 | 3.7 | NR |
| | 4.5 | 579.8 |
| | 5.1 | NR |
| | 5.9 | 593.7 |
| | 6.6 | NR |
| | 7.1 | NR |
| | 7.7 | NR |
| | 8.2 | 575.6 |
| | 8.8 | NR |
| E1 | 5.1 | NR |
| | 6.7 | NR |
| | 7.3 | NR |
| | 8.6 | 603.7 |
| F1 | 3.9 | NR |
| | 4.7 | 597.6 |
| | 5.5 | NR |
| | 6.1 | 611.8 |
| | 6.8 | NR |
| | 7.3 | NR |
| | 7.6 | NR |
| | 8.4 | 593.8 |
| | 8.9 | NR |
| G1 | 4.1 | NR |
| | 5 | 561.7 |
| | 5.9 | NR |
| | 6.7 | 575.8 |
| | 7.5 | NR |
| | 7.7 | NR |
| | 8.2 | NR |
| | 8.4 | NR |
| | 9.3 | NR |

Example 18: Isolation of Compounds 18, 19, 20, 21 & 22

Strain: Phenotype B from BIOT-4827

Feed: 4-trans-hydroxylcyclohexanecarboxylic acid (final concentration 2 mM)

2×60 liter fermentation

The fermentation was as described above.

The fermentation broth at the end of the fermentation was collected and standard techniques were used to isolate the following compounds:

18

19

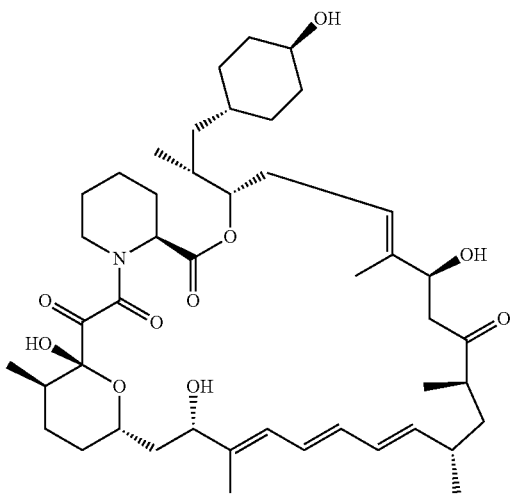

20

21

22

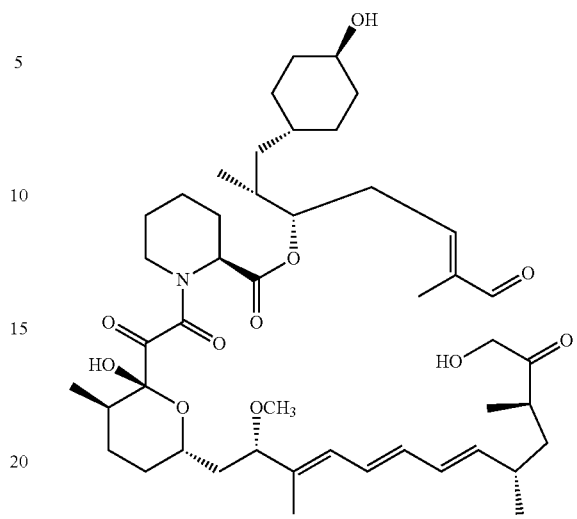

Example 19: Biological Data: Inhibition of FKBP12 PPIase Activity

The rapamycin analogues were tested for their ability to inhibit FKBP12, using a peptidyl-prolyl isomerase (PPIase) assay. All compounds were assayed at 6 concentrations in duplicate and the data fitted to a Ki curve to afford a Ki value with standard error (SE).

| Compound no. | MW | Ki (nM) | SE (nM) |
|---|---|---|---|
| Rapamycin | 914.17 | 5.4 | 0.35 |
| FK506 | 804.02 | 10 | 1.1 |
| Meridamycin | 870.1193 | 10 | 1.1 |
| 2 | 561.7498 | 19% at 1 uM | |
| 5 | 798.06 | 7.9 | 0.69 |
| 6 | 699.96 | 370 | 43 |
| 3 | 575.78 | 25% at 1 uM | |
| 8 | 828.08 | 5.9 | 0.66 |
| 9 | 800.0725 | 180 | 11 |
| 10 | 814.06 | 4.2 | 0.28 |
| 11 | 800.0725 | 430 | 32 |
| 12 | 812.06 | 9.5 | 0.73 |
| 13 | 777 | 13 | 1.4 |
| 14 | 898.17 | 6.5 | 0.66 |
| 15 | 627.81 | 31% at 1 uM | |
| 16 | 613.78 | 460 | 34 |
| 18 | 784.07 | 45 | 4.1 |
| 19 | 784.03 | 7.7 | 0.74 |
| 20 | 814.06 | 18 | 1.3 |
| 21 | 798.06 | 95 | 7.2 |
| 22 | 814.06 | 12 | 0.97 |

As can be seen, the majority of the rapamycin analogues tested show potent inhibition of FKBP12 (Ki<1 μM) in this assay.

Example 20: Biological Data: Inhibition of the PLP T-Cell Proliferation Assay (PLP Assay)

The immunosuppressive potency of rapamycin analogues can be tested using a PLP T-cell proliferation assay. mTOR is known to regulate the expression of Proteo Lipo Protein (Tyler et al. 2009), and activity of rapamycin analogues in this assay is driven by mTOR inhibition, so for rapamycin analogues where the aim is to inhibit FKBPs, this is an off-target activity. Therefore we also calculated the ratio of the FKBP12 IC50 to the PLP assay IC50, with a comparison to rapamycin. Larger ratios therefore relate to compounds with an improved window of activity.

| Compound number | PLP IC50 (nM) | Ratio (PLP/FKBP*) |
|---|---|---|
| Rapamycin | 0.024 | 0.004444 |
| 2 | 113.4 | N/A |
| 4 | 4464 | N/A |
| 6 | 2625 | 7.094595 |
| 3 | 1453 | |
| 8 | 490 | 83.05085 |
| 10 | 14021 | 3338.333 |
| 11 | 4180 | 9.72093 |
| 12 | 2865 | 301.5789 |
| 13 | 6586 | 506.6154 |

*data from Example 19 (Ki values)

As can be seen, all of the rapamycin analogues tested show higher (and therefore improved) ratios of PLP IC50 to FKBP12 Ki as compared to rapamycin.

Example 21

Generation of constructs able to induce deletion or expansion of the tylosin PKS modules and transfer to *S. fradiae*.

Primers MG101 ggccagtgccaagctgcggcttcctccacgacgcg (SEQ ID NO: 11) and MG102 acatgattacgaattccggctcgcccg-gctgctctcc (SEQ ID NO: 12) were used to amplify a 2154 kb region of homology from *S. fradiae* genomic DNA to yield product PCR101. The first 15 bp of MG101 and MG102 contain homology to pKC1139 digested with HindIII and EcoRI. Plasmid pKC1139 was digested with HindIII and EcoRI and used as a vector for Infusion cloning. PCR product PCR101 was ligated with pKC1139 digested with HindIII and EcoRI using Infusion Cloning technology to generate plasmid pISOM01. The insert in plasmid pISOM01 was sequenced to confirm it contained the correct DNA sequence. Plasmid pISOM01 was transferred to *S. fradiae* NRRL2702 by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 mL 2×TY liquid medium containing apramycin (50 µg/mL), kanamycin (25 µg/mL) and chloroamphenicol (25 µg/mL). 0.7 mL of this culture was used to inoculate 10 mL liquid medium containing apramycin (50 µg/mL), kanamycin (25 µg/mL) and chloramphenicol (25 µg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. fradiae* NRRL2702 grown on MAM medium for 2-3 weeks were harvested using 20% glycerol and stored at −80° C. (1 plate gives about 1 mL spore stock). For the conjugation approximately 0.3-0.5 mL of these spores are needed for each conjugation. Spores were pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 mL of washed *E. coli* cells to the heat shocked spores, mixing and spreading the mixture on to MAM agar and transferring to 37° C. The plate was overlaid with 2 ml water containing 15 µL naladixic acid (stock 50 mg/ml) after 2-3 hours and with 2 mL water containing 15 µL apramycin (stock 100 mg/mL) after an overnight incubation.

Plates were incubated at 37° C. until single exconjugant colonies were visible. Colonies (approximately 10-20) were patched to MAM agar containing apramycin and naladixic acid and reincubated at 37° C. Colonies were repatched to the same media (containing apramycin and nalidixic acid) to ensure there was no *E. coli* contamination. Once stabilised, approximately 10-15 of the strains were patched to solid MAM agar lacking antibiotics and incubated at 37° C. for approximately 3 days before repatching to MAM agar and growing for a further 3 or 4 days at 37° C. Samples of patches were then inoculated into TylB media and incubated at 30° C. for 7 days. 0.8 mL samples of culture broth were mixed with 0.8 mL of methanol, centrifuged for 5 minutes and samples of the supernatant analysed for production of tylosin.

Figure 8:
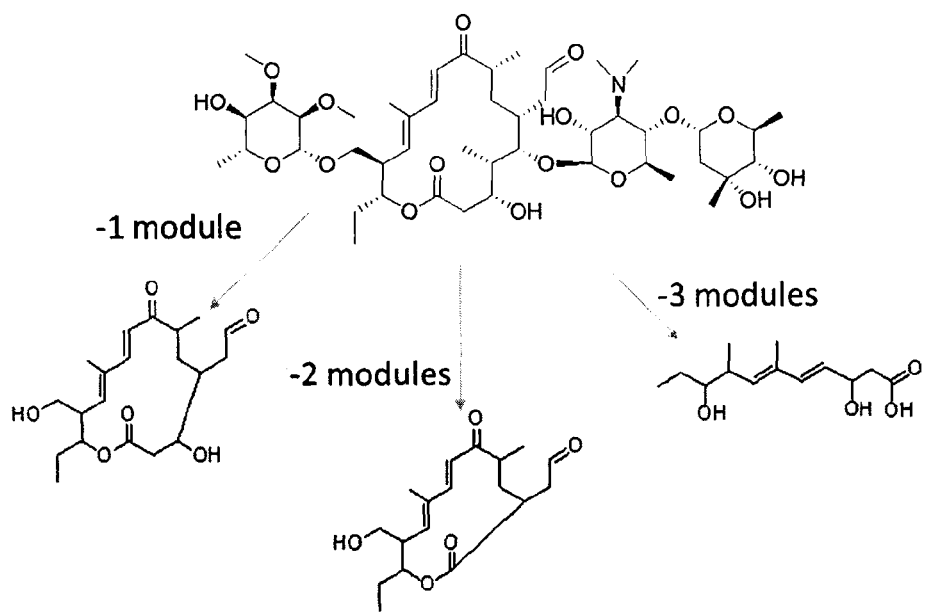
FIG. 8: Representation of the outputs from recombineering on the tylosin PKS following initial recombination into DNA encoding module 3 of the rapamycin PKS.

Those patches showing no production of tylosin (due to primary recombination into the tylosin PKS) were then inoculated into 7 mL TSB media and incubated with shaking at 250 rpm for 48 hours. A 0.5 mL sample was then used to inoculate a second 7 mL of TSB media and incubated with shaking at 250 rpm for a further 48 hours. Finally, another 0.5 mL sample was then used to inoculate a third 7 mL of TSB media and incubated with shaking at 250 rpm for 48 hours. Samples of this third growth were then diluted with sterile water and spread onto MAM plates to generate single colonies when incubated at 28° C. for 5 days. These colonies were patched onto MAM agar and incubated at 28° C. for 5 days. Patches were tested by growing in TylB production media to assess whether they still produced tylosin (i.e. had reverted to original strain). Among the strains that no longer produced tylosin, strains that produced novel compounds were identified. Analysis suggested that these included molecules with structures presumed to be those shown in FIG. 8.

Example 22

Generation of constructs able to induce deletion or expansion of the tylosin PKS modules and transfer to *S. fradiae*.

Primers MG103 ggccagtgccaagctacctcaccaccctccccac-ctaccc (SEQ ID NO: 13) and MG104 acatgattacgaattgccgtc-cggctcctcccg (SEQ ID NO: 14) were used to amplify a 1995 bp region of homology from *S. fradiae* genomic DNA to yield product PCR102. The first 15 bp of MG103 and MG104 contain homology to pKC1139 digested with HindIII and EcoRI. Plasmid pKC1139 was digested with HindIII and EcoRI and used as a vector for Infusion cloning. PCR product PCR102 was ligated with pKC1139 digested with HindIII and EcoRI using Infusion Cloning technology to generate plasmid pISOM02. The insert in plasmid pISOM02 was sequenced to confirm it contained the correct DNA sequence.

Plasmid pISOM02 was transferred to *S. fradiae* NRRL2702 by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 mL 2×TY liquid medium containing apramycin (50 µg/mL), kanamycin (25 µg/mL) and chloroamphenicol (25 µg/mL). 0.7 mL of this culture was used to inoculate 10 mL liquid medium containing apramycin (50 µg/mL), kanamycin (25 µg/mL) and chloramphenicol (25 µg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. fradiae* NRRL2702 grown on MAM medium for 2-3 weeks were harvested using 20% glycerol and stored at −80° C. (1 plate gives about 1 mL spore stock). For the conjugation approximately 0.3-0.5 mL of these spores are needed for each conjugation. Spores were pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 ml of washed *E. coli* cells to the heat shocked spores, mixing and spreading the mixture on to MAM agar and transferring to 37° C. The plate was overlaid with 2 ml water containing 15 µL naladixic acid (stock 50 mg/ml) after 2-3 hours and with 2 mL water containing 15 µL apramycin (stock 100 mg/mL) after an overnight incubation.

Plates were incubated at 37° C. until single exconjugant colonies were visible. Colonies (approximately 10-20) were patched to MAM agar containing apramycin and naladixic acid and reincubated at 37° C. Colonies were repatched to the same media (containing apramycin and nalidixic acid) to ensure there was no *E. coli* contamination. Once stabilised, approximately 10-15 of the strains were patched to solid MAM agar lacking antibiotics and incubated at 37° C. for approximately 3 days before repatching to MAM agar and growing for a further 3 or 4 days at 37° C. Samples of patches were then inoculated into TylB media and incubated at 30° C. for 7 days. 0.8 mL samples of culture broth were mixed with 0.8 mL of methanol, centrifuged for 5 minutes and samples of the supernatant analysed for production of tylosin.

Those patches showing no production of tylosin (due to primary recombination into the tylosin PKS) were then inoculated into 7 mL TSB media and incubated with shaking at 250 rpm for 48 hours. A 0.5 mL sample was then used to inoculate a second 7 mL of TSB media and incubated with shaking at 250 rpm for a further 48 hours. Finally, another 0.5 mL sample was then used to inoculate a third 7 mL of TSB media and incubated with shaking at 250 rpm for 48 hours. Samples of this third growth were then diluted with sterile water and spread onto MAM plates to generate single colonies when incubated at 28° C. for 5 days. These colonies were patched onto MAM agar and incubated at 28° C. for 5 days. Patches are tested by growing in TylB production media to assess whether they still produce tylosin (i.e. had reverted to original strain). Among the strains that no longer produced tylosin, strains that produce novel compounds are identified.

Example 23

Generation of constructs able to induce deletion or expansion of the daptomycin NRPS modules and transfer to *S. roseosporus*.

Primers MG109 ggccagtgccaagctcgaccctgccggcgtacatgg (SEQ ID NO: 15) and MG110 acatgattacgaattgtgtacca-gatctggaacagcgggtggc (SEQ ID NO: 16) were used to amplify a 1447 kb region of homology from *S. roseosporus* ATCC31568 genomic DNA (prepared using standard techniques) to yield product PCR105. The first 15 bp of MG109 and MG110 contain homology to pKC1139 digested with HindIII and EcoRI. Plasmid pKC1139 was digested with HindIII and EcoRI and used as a vector for Infusion cloning. PCR product PCR105 was ligated with pKC1139 digested with HindIII and EcoRI using Infusion Cloning technology to generate plasmid pISOM05. The insert in plasmid pISOM05 was sequenced to confirm it contained the correct DNA sequence. Plasmid pISOM05 was transferred to *S. roseosporus* ATCC31568 by conjugation using standard methods. Briefly, plasmid was electroporated into ET12567: pUZ8002 and selected on 2TY agar medium containing apramycin (50 µg/mL), kanamycin (25 µg/mL), and chloramphenicol (25 µg/mL). Single colonies were grown overnight in 3 mL 2×TY liquid medium containing apramycin (50 µg/mL), kanamycin (25 µg/mL) and chloroamphenicol (25 µg/mL). 0.7 mL of this culture was used to inoculate 10 mL liquid medium containing apramycin (50 µg/mL), kanamycin (25 µg/mL) and chloramphenicol (25 µg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. roseosporus* ATCC31568 grown on MAM medium for 2-3 weeks were harvested using 20% glycerol and stored at −80° C. (1 plate gives about 1 mL spore stock). For the conjugation approximately 0.3-0.5 mL of these spores are needed for each conjugation. Spores were pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 ml of washed *E. coli* cells to the heat shocked spores, mixing and spreading the mixture on to MAM agar and transferring to 37° C. The plate was overlaid with 2 ml water containing 15 µL naladixic acid (stock 50 mg/ml) after 2-3 hours and with 2 mL water containing 15 µL apramycin (stock 100 mg/mL) after an overnight incubation. Plates were incubated at 37° C. until single exconjugant colonies were visible. Colonies (approximately 10-20) were patched to MAM agar containing apramycin and naladixic acid and reincubated at 37° C. Colonies were repatched to the same media (containing apramycin and nalidixic acid) to ensure there was no *E. coli* contamination. Once stabilised, approximately 10-15 of the strains were patched to solid MAM agar lacking antibiotics and incubated at 37° C. for approximately 3 days before repatching to MAM agar and growing for a further 3 or 4 days at 37° C. Samples of patches were then inoculated into TylB media and incubated at 30° C. for 7 days. 0.8 mL samples of culture broth were mixed with 0.8 mL of methanol, centrifuged for 5 minutes and samples of the supernatant analysed for production of daptomycin and related congeners. Those patches showing no production of daptomycin or related congeners (due to primary recombination into the daptomycin NRPS) were then inoculated into 7 mL TSB media and incubated with shaking at 250 rpm for 48 hours. A 0.5 mL sample was then used to inoculate a second 7 mL of TSB media and incubated with shaking at 250 rpm for a further 48 hours. Finally, another 0.5 mL sample was then used to inoculate a third 7 mL of TSB media and incubated with shaking at 250 rpm for 48 hours. Samples of this third growth were then diluted with sterile water and spread onto MAM plates to generate single colonies when incubated at 28° C. for 5 days. These colonies were patched onto MAM agar and incubated at 28° C. for 5 days. Patches were tested by growing in F10A production media to assess whether they still produced daptomycin or related congeners (i.e. had reverted to original strain). Among the strains that no longer produce daptomycin or related congeners, strains that produce novel compounds are identified.

Example 24

Generation of constructs able to induce deletion or expansion of the Calcium Dependent Antibiotic NRPS modules and transfer to *S. coelicolor*.

Primers MG105 ggccagtgccaagctaccccacagcagcaccccg (SEQ ID NO: 17) and MG106 acatgattacgaattgtaggcggcca-ggtcggtgc (SEQ ID NO: 18) were used to amplify a 1649 bp region of homology from *S. coelicolor* DSM40783 genomic DNA (prepared using standard techniques) to yield product PCR103. The first 15 bp of MG105 and MG106 contain homology to pKC1139 digested with HindIII and EcoRI. Plasmid pKC1139 was digested with HindIII and EcoRI and used as a vector for Infusion cloning. PCR product PCR103 was ligated with pKC1139 digested with HindIII and EcoRI using Infusion Cloning technology to generate plasmid pISOM03. The insert in plasmid pISOM03 was sequenced to confirm it contained the correct DNA sequence. Plasmid pISOM03 was transferred to *S. coelicolor* DSM40783 by conjugation using standard methods. Briefly, plasmid was electroporated into ET12567:pUZ8002 and selected on 2TY agar medium containing apramycin (50 µg/mL), kanamycin (25 µg/mL), and chloramphenicol (25 µg/mL). Single colonies were grown overnight in 3 mL 2×TY liquid medium containing apramycin (50 µg/mL), kanamycin (25 µg/mL) and chloroamphenicol (25 µg/mL). 0.7 mL of this culture was used to inoculate 10 mL liquid medium containing apramycin (50 µg/mL), kanamycin (25 µg/mL) and chloramphenicol (25 µg/mL) and grown at 37 C to reach an OD of approximately 0.5. Cells were pelleted at 4000 rpm for 10 minutes and washed twice with 10 mL 2×TY before resuspending in 0.25 mL 2×TY. Spores of *S. coelicolor* DSM40783 grown on MAM medium for 2-3 weeks were harvested using 20% glycerol and stored at −80° C. (1 plate gives about 1 mL spore stock). For the conjugation approximately 0.3-0.5 mL of these spores are needed for each conjugation. Spores were pelleted by centrifugation (4000 rpm, 10 minutes) before washing with 2×TY. The spores were then repelleted and resuspended in 0.25 mL 2×TY and heat shocked in a water bath at 50° C. for 10 minutes before cooling immediately on ice. The conjugation was performed by adding 0.25 ml of washed *E. coli* cells to the heat shocked spores, mixing and spreading the mixture on to MAM agar and transferring to 37° C. The plate was overlaid with 2 ml water containing 15 µL naladixic acid (stock 50 mg/ml) after 2-3 hours and with 2 mL water containing 15 µL apramycin (stock 100 mg/mL) after an overnight incubation. Plates were incubated at 37° C. until single exconjugant colonies were visible. Colonies (approximately 10-20) were patched to MAM agar containing apramycin and naladixic acid and reincubated at 37° C. Colonies were repatched to the same media (containing apramycin and nalidixic acid) to ensure there was no *E. coli* contamination. Once stabilised, approximately 10-15 of the strains were patched to solid MAM agar lacking antibiotics and incubated at 37° C. for approximately 3 days before repatching to MAM agar and growing for a further 3 or 4 days at 37° C. Samples of patches were then inoculated onto Oxoid nutrient agar and incubated at 30° C. for 7 days. 0.8 mL samples of agar were mixed with 0.8 mL of methanol, centrifuged for 5 minutes and samples of the supernatant analysed for production of CDA and related congeners. Those patches showing no production of CDA and related congeners (due to primary recombination into the CDA NRPS) were then inoculated into 7 mL TSB media and incubated with shaking at 250 rpm for 48 hours. A 0.5 mL sample was then used to inoculate a second 7 mL of TSB media and incubated with shaking at 250 rpm for a further 48 hours. Finally, another 0.5 mL sample was then used to inoculate a third 7 mL of TSB media and incubated with shaking at 250 rpm for 48 hours. Samples of this third growth were then diluted with sterile water and spread onto MAM plates to generate single colonies when incubated at 28° C. for 5 days. These colonies were patched onto MAM agar and incubated at 28° C. for 5 days. Patches were tested by growing in F10A production media and Oxoid nutrient agar to assess whether they still produced CDA (i.e. had reverted to original strain). Among the strains that no longer produce CDA, strains that produce novel compounds are identified.

Example 25

Generation of constructs able to induce deletion and/or expansion of the lasalocid PKS modules and transfer to *Streptomyces lasaliensis* ATCC35851. Primers IR014.FOR ggccagtgccaagctaccccacagcagcaccccg (SEQ ID NO: 19) and IR014.REV acatgattacgaattgtaggcggccaggtcggtgc (SEQ ID NO: 20) are used to amplify a region of homology from *Streptomyces lasaliensis* ATCC35851 genomic DNA (prepared using standard techniques) to yield 2627 bp PCR product, IR014. The first 15 bp of primers IR014.FOR and IR014.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR014 is ligated with pKC1139 digested with HindIII and EcoRI using Infusion Cloning technology to generate plasmid pIR014. Plasmid pIR014 is transferred to *Streptomyces lasaliensis* ATCC35851 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of lasalocid as described in Sherman 1986. Samples of culture broth are mixed with methanol, centrifuged for 5 minutes and samples of the supernatant analysed by HPLC-UV and LCMS for production of lasalocid. Those patches showing no production of lasalocid (due to primary recombination into the lasalocid PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Sherman 1986 to assess whether they still produce lasalocid (i.e. have reverted to original strain). Among the strains that no longer produce lasalocid, strains that produce novel compounds are identified by LCMS and HPLC-UV.

Example 26

Generation of constructs able to induce deletion and/or expansion of the ansamitocin PKS modules and transfer to

*Actinosynnema pretiosum* ATCC 31565. Primers IR015.FOR ggccagtgccaagcttccggccacgcaggcc (SEQ ID NO: 21) and IR015.REV acatgattacgaattccaagctcgccgacctggagt (SEQ ID NO: 22) are used to amplify a region of homology from *Actinosynnema pretiosum* ATCC 31565 genomic DNA (prepared using standard techniques) to yield 1907 bp PCR product, IR015. The first 15 bp of primers IR015.FOR and IR015.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR015 is ligated with pKC1139 digested with HindIII and EcoRI using Infusion Cloning technology to generate plasmid pIR015. Plasmid pIR015 is transferred to *Actinosynnema pretiosum* ATCC 31565 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of ansamitocin as described in Jia 2011. Samples of culture broth are mixed with methanol, centrifuged for 5 minutes and samples of the supernatant analysed by HPLC-UV and LCMS for production of ansamitocin. Those patches showing no production of ansamitocin (due to primary recombination into the ansamitocin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Jia 2011 to assess whether they still produce ansamitocin (i.e. have reverted to original strain). Among the strains that no longer produce ansamitocin, strains that produce novel compounds are identified by LCMS and HPLC-UV.

Example 27

Generation of constructs able to induce deletion and/or expansion of the chalcomycin PKS modules and transfer to *Streptomyces bikiniensis* NRRL 2737. Primers IR016.FOR ggccagtgccaagcttcggcggaggaaccgag (SEQ ID NO: 23) and IR016.REV acatgattacgaattccagctcacggccgat (SEQ ID NO: 24) are used to amplify a region of homology from *Streptomyces bikiniensis* NRRL 2737 genomic DNA (prepared using standard techniques) to yield 1989 bp PCR product, IR016. The first 15 bp of primers IR016.FOR and IR016.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR016 is ligated with pKC1139 digested with HindIII and EcoRI using Infusion Cloning technology to generate plasmid pIR016. Plasmid pIR016 is transferred to *Streptomyces bikiniensis* NRRL 2737 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of chalcomycin as described in U.S. Pat. No. 3,065,137. Samples of culture broth are mixed with methanol, centrifuged for 5 minutes and samples of the supernatant analysed by HPLC-UV and LCMS for production of chalcomycin. Those patches showing no production of chalcomycin (due to primary recombination into the chalcomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in U.S. Pat. No. 3,065,137 to assess whether they still produce chalcomycin (i.e. have reverted to original strain). Among the strains that no longer produce chalcomycin, strains that produce novel compounds are identified by LCMS and HPLC-UV.

Example 28

Generation of constructs able to induce deletion and/or expansion of the FD-891 PKS modules and transfer to *Streptomyces graminofaciens* A-8890. Primers IR017.FOR ggccagtgccaagctttcgcatggacaacgaagagaagctcg (SEQ ID NO: 25) and IR017.REV acatgattacgaattcccgaatgcccggccacca (SEQ ID NO: 26) are used to amplify a region of homology from *Streptomyces graminofaciens* A-8890 genomic DNA (prepared using standard techniques) to yield 1985 bp PCR product, IR017. The first 15 bp of primers IR017.FOR and IR017.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR017 is ligated with pKC1139 digested with HindIII and EcoRI using Infusion Cloning technology to generate plasmid pIR017. Plasmid pIR017 is transferred to *Streptomyces graminofaciens* A-8890 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of FD-891 as described in Kudo 2010. Samples of culture broth are mixed with methanol, centrifuged for 5 minutes and samples of the supernatant analysed by HPLC-UV and LCMS for production of FD-891. Those patches showing no production of FD-891 (due to primary recombination into the FD-891 PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kudo 2010 to assess whether they still produce FD-891 (i.e. have reverted to original strain). Among the strains that no longer produce FD-891, strains that produce novel compounds are identified by LCMS and HPLC-UV.

Example 29

Generation of constructs able to induce deletion and/or expansion of the FR-008 PKS modules and transfer to *Streptomyces* sp. FR-008. Primers IR018.FOR ggccagtgccaagcttacgagccggtggagg (SEQ ID NO: 27) and IR018.REV acatgattacgaattcctcacctcggcccagc (SEQ ID NO: 28) are used to amplify a region of homology from *Streptomyces* sp. FR-008 genomic DNA (prepared using standard techniques) to yield 1846 bp PCR product, IR018. The first 15 bp of primers IR018.FOR and IR018.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR018 is ligated with pKC1139 digested with HindIII and EcoRI using Infusion Cloning technology to generate plasmid pIR018. Plasmid pIR018 is transferred to *Streptomyces* sp. FR-008 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of FR-008 as described in Chen 2003. Samples of culture broth are mixed with methanol, centrifuged for 5 minutes and samples of the supernatant analysed by HPLC-UV and LCMS for production of FR-008. Those patches showing no production of FR-008 (due to primary recombination into the FR-008 PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Chen 2003 to assess whether they still produce FR-008 (i.e. have reverted to original strain). Among the strains that no longer produce FR-008, strains that produce novel compounds are identified by LCMS and HPLC-UV.

Example 30

Generation of constructs able to induce deletion and/or expansion of the virginiamycin M PKS modules and transfer to *Streptomyces virginiae* MAFF 116014. Primers IR019.FOR ggccagtgccaagcttgcgcagttgctccg (SEQ ID NO: 28) and IR019.REV acatgattacgaattctcaccaccccgagctgg (SEQ ID NO: 30) are used to amplify a region of homology from *Streptomyces virginiae* MAFF 116014 genomic DNA (prepared using standard techniques) to yield 2101 bp PCR product, IR019. The first 15 bp of primers IR019.FOR and IR019.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR019 is ligated with pKC1139 digested with HindIII and EcoRI using Infusion Cloning technology to generate plasmid pIR019. Plasmid pIR019 is transferred to *Streptomyces virginiae* MAFF 116014 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of virginiamycin M as described in Yang 1996. Samples of culture broth are mixed with methanol, centrifuged for 5 minutes and samples of the supernatant analysed by HPLC-UV and LCMS for production of virginiamycin M. Those patches showing no production of virginiamycin M (due to primary recombination into the virginiamycin M PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested

Example 31

Generation of constructs able to induce deletion and/or expansion of the virginiamycin S NRPS modules and transfer to *Streptomyces virginiae* MAFF 116014. Primers IR020.FOR ggccagtgccaagcttcgcagcaggagattctggcgtcg (SEQ ID NO: 31) and IR020.REV acatgattacgaattccgagggc-ctccacggt (SEQ ID NO: 32) are used to amplify a region of homology from *Streptomyces virginiae* MAFF 116014 genomic DNA (prepared using standard techniques) to yield 1538 bp PCR product, IR020. The first 15 bp of primers IR020.FOR and IR020.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR020 is ligated with pKC1139 digested with HindIII and EcoRI using Infusion Cloning technology to generate plasmid pIR020. Plasmid pIR020 is transferred to *Streptomyces virginiae* MAFF 116014 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of virginiamycin S as described in Yang 1996. Samples of culture broth are mixed with methanol, centrifuged for 5 minutes and samples of the supernatant analysed by HPLC-UV and LCMS for production of virginiamycin S. Those patches showing no production of virginiamycin S (due to primary recombination into the virginiamycin S NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Yang 1996 to assess whether they still produce virginiamycin S (i.e. have reverted to original strain). Among the strains that no longer produce virginiamycin S, strains that produce novel compounds are identified by LCMS and HPLC-UV.

Example 32

Generation of constructs able to induce deletion and/or expansion of the Soraphen PKS modules and transfer to *Sorangium cellulosum* so Ce26. Primers IR021.FOR ggcca-gtgccaagcttgcttcgacgtgaacgcgctc (SEQ ID NO: 33) and IR021.REV acatgattacgaattcgcgcccgcgtcgt (SEQ ID NO: 34) are used to amplify a region of homology from *Sorangium cellulosum* So ce26 genomic DNA (prepared using standard techniques) to yield 1934 bp PCR product, IR021. The first 15 bp of primers IR021.FOR and IR021.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR021 is ligated with pKC1139 digested with HindIII and EcoRI using Infusion Cloning technology to generate plasmid pIR021. Plasmid pIR021 is transferred to *Sorangium cellulosum* So ce26 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of soraphen as described in Hill 2003. Samples of culture broth are mixed with methanol, centrifuged for 5 minutes and samples of the supernatant analysed by HPLC-UV and LCMS for production of soraphen. Those patches showing no production of soraphen (due to primary recombination into the soraphen PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Hill 2003 to assess whether they still produce soraphen (i.e. have reverted to original strain). Among the strains that no longer produce soraphen, strains that produce novel compounds are identified by LCMS and HPLC-UV.

Example 33

Generation of constructs able to induce deletion and/or expansion of the megalomycin PKS modules and transfer to *Micromonospora megalomicea* subsp. *nigra*. Primers IR022.FOR acatgattacgaattcgcccccgcaccgc (SEQ ID NO: 35) and IR022.REV ggccagtgccaagcttacaccggtctgcgtctgc-cgg (SEQ ID NO: 36) are used to amplify a region of homology from *Micromonospora megalomicea* subsp. *nigra* genomic DNA (prepared using standard techniques) to yield 2006 bp PCR product, IR022. The first 15 bp of primers IR022.FOR and IR022.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR022 is ligated with pKC1139 digested with HindIII and EcoRI using Infusion Cloning technology to generate plasmid pIR022. Plasmid pIR022 is transferred to *Micromonospora megalomicea* subsp. *nigra* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of megalomycin as described in Peiru 2007. Samples of culture broth are mixed with methanol, centrifuged for 5 minutes and samples of the supernatant analysed by HPLC-UV and LCMS for production of megalomycin. Those patches showing no production of megalomycin (due to primary recombination into the megalomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Peiru 2007 to assess whether they still produce megalomycin (i.e. have reverted to original strain). Among the strains that no longer produce megalomycin, strains that produce novel compounds are identified by LCMS and HPLC-UV.

Example 34

Generation of constructs able to induce deletion and/or expansion of the viceniastatin PKS modules and transfer to *Streptomyces halstedii* HC34. Primers IR023.FOR ggccagtgccaagcttggtgtcccgcaccgatg (SEQ ID NO: 37) and IR023.REV acatgattacgaattcaacgccaccacccgc (SEQ ID NO: 38) are used to amplify a region of homology from *Streptomyces halstedii* HC34 genomic DNA (prepared using standard techniques) to yield 1994 bp PCR product, IR023. The first 15 bp of primers IR023.FOR and IR023.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR023 is ligated with pKC1139 digested with HindIII and EcoRI using Infusion Cloning technology to generate plasmid pIR023. Plasmid pIR023 is transferred to *Streptomyces halstedii* HC34 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of viceniastatin as described in Otsuka 2000. Samples of culture broth are mixed with methanol, centrifuged for 5 minutes and samples of the supernatant analysed by HPLC-UV and LCMS for production of viceniastatin. Those patches showing no production of viceniastatin (due to primary recombination into the viceniastatin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Otsuka 2000 to assess whether they still produce viceniastatin (i.e. have reverted to original strain). Among the strains that no longer produce viceniastatin, strains that produce novel compounds are identified by LCMS and HPLC-UV.

Example 35

Generation of constructs able to induce deletion and/or expansion of the tautomycin PKS modules and transfer to *Streptomyces spiroverticillatus*. Primers IR024.FOR ggccagtgccaagcttccccgcccgaaggca (SEQ ID NO: 39) and IR024.REV acatgattacgaattctcgtcctcgtcgggatggc (SEQ ID NO: 40) are used to amplify a region of homology from *Streptomyces spiroverticillatus* genomic DNA (prepared using standard techniques) to yield 2012 bp PCR product, IR024. The first 15 bp of primers IR024.FOR and IR024.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR024 is ligated with pKC1139 digested with HindIII and EcoRI using Infusion Cloning technology to generate plasmid pIR024. Plasmid pIR024 is transferred to *Streptomyces spiroverticillatus* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of tautomycin as described in Chen 2010. Samples of culture broth are mixed with methanol, centrifuged for 5 minutes and samples of the supernatant analysed by HPLC-UV and LCMS for production of tautomycin. Those patches showing no production of tautomycin (due to primary recombination into the tautomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Chen 2010 to assess whether they still produce tautomycin (i.e. have reverted to original strain). Among the strains that no longer produce tautomycin, strains that produce novel compounds are identified by LCMS and HPLC-UV.

Example 36

Generation of constructs able to induce deletion and/or expansion of the avermectin PKS modules and transfer to *Streptomyces avermitilis* ATCC 31267. Primers IR025.FOR ggccagtgccaagcttcgcacccatgcggc (SEQ ID NO: 41) and IR025.REV acatgattacgaattccagtgcggccgcttcttc (SEQ ID NO: 42) are used to amplify a region of homology from *Streptomyces avermitilis* ATCC 31267 genomic DNA (prepared using standard techniques) to yield 2204 bp PCR product, IR025. The first 15 bp of primers IR025.FOR and IR025.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR025 is ligated with pKC1139 digested with HindIII and EcoRI using Infusion Cloning technology to generate plasmid pIR025. Plasmid pIR025 is transferred to *Streptomyces avermitilis* ATCC 31267 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of avermectin as described in Ikeda 1988. Samples of culture broth are mixed with methanol, centrifuged for 5 minutes and samples of the supernatant analysed by HPLC-UV and LCMS for production of avermectin. Those patches showing no production of avermectin (due to primary recombination into the avermectin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Ikeda 1988 to assess whether they still produce avermectin (i.e. have reverted to original strain). Among the strains that no longer produce avermectin, strains that produce novel compounds are identified by LCMS and HPLC-UV.

Example 37

Generation of constructs able to induce deletion and/or expansion of the alpha-lipomycin PKS modules and transfer to *Streptomyces aureofaciens* Tü117. Primers IR026.FOR ggccagtgccaagcttcgggcgagccgcgt (SEQ ID NO: 43) and IR026.REV acatgattacgaattccggttgcacgacgtcga (SEQ ID NO: 44) are used to amplify a region of homology from *Streptomyces aureofaciens* Tü117 genomic DNA (prepared using standard techniques) to yield 2022 bp PCR product, IR026. The first 15 bp of primers IR026.FOR and IR026.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR026 is ligated with pKC1139 digested with HindIII and EcoRI using Infusion Cloning technology to generate plasmid pIR026. Plasmid pIR026 is transferred to *Streptomyces aureofaciens* Tü117 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of alpha-lipomycin as described in Horbal 2010. Samples of culture broth are mixed with methanol, centrifuged for 5 minutes and samples of the supernatant analysed by HPLC-UV and LCMS for production of alpha-lipomycin. Those patches showing no production of alpha-lipomycin (due to primary recombination into the alpha-lipomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Horbal 2010 to assess whether they still produce alpha-lipomycin (i.e. have reverted to original strain). Among the strains that no longer produce alpha-lipomycin, strains that produce novel compounds are identified by LCMS and HPLC-UV.

Example 38

Generation of constructs able to induce deletion and/or expansion of the ascomycin/FK520 PKS modules and transfer to *Streptomyces hygroscopicus* subsp. *Ascomyceticus*

ATCC 14891. Primers IR027.FOR ggccagtgccaagcttgcgcacgtccgcac (SEQ ID NO: 45) and IR027.REV acatgattacgaattcccagctcgccgatcgaat (SEQ ID NO: 46) are used to amplify a region of homology from *Streptomyces hygroscopicus* subsp. *Ascomyceticus* ATCC 14891 genomic DNA (prepared using standard techniques) to yield 2092 bp PCR product, IR027. The first 15 bp of primers IR027.FOR and IR027.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR027 is ligated with pKC1139 digested with HindIII and EcoRI using Infusion Cloning technology to generate plasmid pIR027. Plasmid pIR027 is transferred to *Streptomyces hygroscopicus* subsp. *Ascomyceticus* ATCC 14891 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of ascomycin/FK520 as described in U.S. Pat. No. 3,244,592. Samples of culture broth are mixed with methanol, centrifuged for 5 minutes and samples of the supernatant analysed by HPLC-UV and LCMS for production of ascomycin/FK520. Those patches showing no production of ascomycin/FK520 (due to primary recombination into the ascomycin/FK520 PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in U.S. Pat. No. 3,244,592 to assess whether they still produce ascomycin/FK520 (i.e. have reverted to original strain). Among the strains that no longer produce ascomycin/FK520, strains that produce novel compounds are identified by LCMS and HPLC-UV.

Example 39

Generation of constructs able to induce deletion and/or expansion of the geldanamycin PKS modules and transfer to *Streptomyces geldanamycininus* NRRL 3602. Primers IR028.FOR ggccagtgccaagcttggagttcctgctcaacctggt (SEQ ID NO: 47) and IR028.REV acatgattacgaattctcttgccgtgggtggtgg (SEQ ID NO: 48) are used to amplify a region of homology from *Streptomyces geldanamycininus* NRRL 3602 genomic DNA (prepared using standard techniques) to yield 1945 bp PCR product, IR028. The first 15 bp of primers IR028.FOR and IR028.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR028 is ligated with pKC1139 digested with HindIII and EcoRI using Infusion Cloning technology to generate plasmid pIR028. Plasmid pIR028 is transferred to *Streptomyces geldanamycininus* NRRL 3602 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of geldanamycin as described in CA2449601. Samples of culture broth are mixed with methanol, centrifuged for 5 minutes and samples of the supernatant analysed by HPLC-UV and LCMS for production of geldanamycin. Those patches showing no production of geldanamycin (due to primary recombination into the geldanamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in CA2449601 to assess whether they still produce geldanamycin (i.e. have reverted to original strain). Among the strains that no longer produce geldanamycin, strains that produce novel compounds are identified by LCMS and HPLC-UV.

Example 40

Generation of constructs able to induce deletion and/or expansion of the halstoctacosanolide PKS modules and transfer to *Streptomyces halstedii* HC34. Primers IR029.FOR ggccagtgccaagcttattcgactacccgacaccgct (SEQ ID NO: 49) and IR029.REV acatgattacgaattctcccagacagccgccagc (SEQ ID NO: 50) are used to amplify a region of homology from *Streptomyces halstedii* HC34 genomic DNA (prepared using standard techniques) to yield 1982 bp PCR product, IR029. The first 15 bp of primers IR029.FOR and IR029.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR029 is ligated with pKC1139 digested with HindIII and EcoRI using Infusion Cloning technology to generate plasmid pIR029. Plasmid pIR029 is transferred to *Streptomyces halstedii* HC34 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of halstoctacosanolide as described in Tohyama 2006. Samples of culture broth are mixed with methanol, centrifuged for 5 minutes and samples of the supernatant analysed by HPLC-UV and LCMS for production of halstoctacosanolide. Those patches showing no production of halstoctacosanolide (due to primary recombination into the halstoctacosanolide PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown.

Samples of this third growth are then diluted and spread onto agar plates to generate single colonies when incubated at this lower temperature. These colonies are patched onto solid agar plates and incubated until good growth is seen. Patches are tested by growing as described in Tohyama 2006 to assess whether they still produce halstoctacosanolide (i.e. have reverted to original strain). Among the strains that no longer produce halstoctacosanolide, strains that produce novel compounds are identified by LCMS and HPLC-UV.

Example 41

Generation of constructs able to induce deletion and/or expansion of the azinomycin B NRPS modules and transfer to *Streptomyces sahachiroi* NRRL 2485. Primers IR030.FOR ggccagtgccaagcttacgcgccggagcag (SEQ ID NO: 51) and IR030.REV acatgattacgaattcacgctcctgctggagg (SEQ ID NO: 52) are used to amplify a region of homology from *Streptomyces sahachiroi* NRRL 2485 genomic DNA (prepared using standard techniques) to yield 1841 bp PCR product, IR030. The first 15 bp of primers IR030.FOR and IR030.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR030 is ligated with pKC1139 digested with HindIII and EcoRI using Infusion Cloning technology to generate plasmid pIR030. Plasmid pIR030 is transferred to *Streptomyces sahachiroi* NRRL 2485 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of azinomycin B as described in Kelly 2008. Samples of culture broth are mixed with methanol, centrifuged for 5 minutes and samples of the supernatant analysed by HPLC-UV and LCMS for production of azinomycin B. Those patches showing no production of azinomycin B (due to primary recombination into the azinomycin B NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kelly 2008 to assess whether they still produce azinomycin B (i.e. have reverted to original strain). Among the strains that no longer produce azinomycin B, strains that produce novel compounds are identified by LCMS and HPLC-UV.

Example 42

Generation of constructs able to induce deletion and/or expansion of the pristinamycin NRPS modules and transfer to *Streptomyces pristinaespiralis*. Primers IR031.FOR ggccagtgccaagctttgcagcgcaccccg (SEQ ID NO: 53) and IR031.REV acatgattacgaattcgtcggcgacggcgt (SEQ ID NO: 54) are used to amplify a region of homology from *Streptomyces pristinaespiralis* genomic DNA (prepared using standard techniques) to yield 1600 bp PCR product, IR031. The first 15 bp of primers IR031.FOR and IR031.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR031 is ligated with pKC1139 digested with HindIII and EcoRI using Infusion Cloning technology to generate plasmid pIR031. Plasmid pIR031 is transferred to *Streptomyces pristinaespiralis* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of pristinamycin as described in Zhang 2012. Samples of culture broth are mixed with methanol, centrifuged for 5 minutes and samples of the supernatant analysed by HPLC-UV and LCMS for production of pristinamycin. Those patches showing no production of pristinamycin (due to primary recombination into the pristinamycin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Zhang 2012 to assess whether they still produce pristinamycin (i.e. have reverted to original strain). Among the strains that no longer produce pristinamycin, strains that produce novel compounds are identified by LCMS and HPLC-UV.

Example 43

Generation of constructs able to induce deletion and/or expansion of the balhimycin NRPS modules and transfer to *Amycolatopsis balhimycina* DSM 5908. Primers IR032.FOR ggccagtgccaagcttgggttcaactacatgggccggt (SEQ ID NO: 55) and IR032.REV acatgattacgaattcaccctggtcgatgagcca (SEQ ID NO: 56) are used to amplify a region of homology from *Amycolatopsis balhimycina* DSM 5908 genomic DNA (prepared using standard techniques) to yield 1892 bp PCR product, IR032. The first 15 bp of primers IR032.FOR and IR032.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR032 is ligated with pKC1139 digested with HindIII and EcoRI using Infusion Cloning technology to generate plasmid pIR032. Plasmid pIR032 is transferred to *Amycolatopsis balhimycina* DSM 5908 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of balhimycin as described in Nadkami 1994. Samples of culture broth are mixed with methanol, centrifuged for 5 minutes and samples of the supernatant analysed by HPLC-UV and LCMS for production of balhimycin. Those patches showing no production of balhimycin (due to primary recombination into the balhimycin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Nadkami 1994 to assess whether they still produce balhimycin (i.e. have reverted to original strain). Among the strains that no longer produce balhimycin, strains that produce novel compounds are identified by LCMS and HPLC-UV.

Example 44

Generation of constructs able to induce deletion and/or expansion of the bleomycin NRPS modules and transfer to *Streptomyces verticillus* ATCC15003. Primers IR033.FOR ggccagtgccaagcttcacgagatcgacaaggccc (SEQ ID NO: 57) and IR033.REV acatgattacgaattcagcgcaggaacgccg (SEQ ID NO: 58) are used to amplify a region of homology from *Streptomyces verticillus* ATCC15003 genomic DNA (prepared using standard techniques) to yield 2012 bp PCR product, IR033. The first 15 bp of primers IR033.FOR and IR033.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR033 is ligated with pKC1139 digested with HindIII and EcoRI using Infusion Cloning technology to generate plasmid pIR033. Plasmid pIR033 is transferred to *Streptomyces verticillus* ATCC15003 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of bleomycin as described in Matsuo 1997. Samples of culture broth are mixed with methanol, centrifuged for 5 minutes and samples of the supernatant analysed by HPLC-UV and LCMS for production of bleomycin. Those patches showing no production of bleomycin (due to primary recombination into the bleomycin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Matsuo 1997 to assess whether they still produce bleomycin (i.e. have reverted to original strain). Among the strains that no longer produce bleomycin, strains that produce novel compounds are identified by LCMS and HPLC-UV.

Example 45

Generation of constructs able to induce deletion and/or expansion of the borrelidin PKS modules and transfer to *Streptomyces parvulus* Tu4055. Primers IR034.FOR ggccagtgccaagcttccgcccacaacgcagg (SEQ ID NO: 59) and IR034.REV acatgattacgaattccacctggatctcaccgc (SEQ ID NO: 60) are used to amplify a region of homology from *Streptomyces parvulus* Tu4055 genomic DNA (prepared using standard techniques) to yield 2547 bp PCR product, IR034. The first 15 bp of primers IR034.FOR ggccagtgccaagcttccgcccacaacgcagg (SEQ ID NO: 59) and IR034.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR034 is ligated with pKC1139 digested with HindIII and EcoRI using Infusion Cloning technology to generate plasmid pIR034. Plasmid pIR034 is transferred to *Streptomyces parvulus* Tu4055 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of borrelidin as described in Olano 2004. Samples of culture broth are mixed with methanol, centrifuged for 5 minutes and samples of the supernatant analysed by HPLC-UV and LCMS for production of borrelidin. Those patches showing no production of borrelidin (due to primary recombination into the borrelidin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Olano 2004 to assess whether they still produce borrelidin (i.e. have reverted to original strain). Among the strains that no longer produce borrelidin, strains that produce novel compounds are identified by LCMS and HPLC-UV.

Example 46

Generation of constructs able to induce deletion and/or expansion of the bacillomycin NRPS modules and transfer to *Bacillus amyloliquefaciens* FZB42. Primers IR035.FOR ggccagtgccaagcttgatcagctttaactacctgggacagt (SEQ ID NO: 61) and IR035.REV acatgattacgaattccggaacaatggcaccgc (SEQ ID NO: 62) are used to amplify a region of homology from *Bacillus amyloliquefaciens* FZB42 genomic DNA (prepared using standard techniques) to yield 2001 bp PCR product, IR035. The first 15 bp of primers IR035.FOR and IR035.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR035 is ligated with pKC1139 digested with HindIII and EcoRI using Infusion Cloning technology to generate plasmid pIR035. Plasmid pIR035 is transferred to *Bacillus amyloliquefaciens* FZB42 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of bacillomycin as described in Yuan 2012. Samples of culture broth are mixed with methanol, centrifuged for 5 minutes and samples of the supernatant analysed by HPLC-UV and LCMS for production of bacillomycin. Those patches showing no production of bacillomycin (due to primary recombination into the bacillomycin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Yuan 2012 to assess whether they still produce bacillomycin (i.e. have reverted to original strain). Among the strains that no longer produce bacillomycin, strains that produce novel compounds are identified by LCMS and HPLC-UV.

Example 47

Generation of constructs able to induce deletion and/or expansion of the bacitracin NRPS modules and transfer to *Bacillus licheniformis* ATCC 10716. Primers IR036.FOR ggccagtgccaagctttatcaaccattcataaagaactgaatgtcaagctgcct (SEQ ID NO: 63) and IR036.REV acatgattacgaattctcctgcggatacgccgga (SEQ ID NO: 64) are used to amplify a region of homology from *Bacillus licheniformis* ATCC 10716 genomic DNA (prepared using standard techniques) to yield 1767 bp PCR product, IR036. The first 15 bp of primers IR036.FOR and IR036.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR036 is ligated with pKC1139 digested with HindIII and EcoRI using Infusion Cloning technology to generate plasmid pIR036. Plasmid pIR036 is transferred to *Bacillus licheniformis* ATCC 10716 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of bacitracin as described in Haavik 1978. Samples of culture broth are mixed with methanol, centrifuged for 5 minutes and samples of the supernatant analysed by HPLC-UV and LCMS for production of bacitracin. Those patches showing no production of bacitracin (due to primary recombination into the bacitracin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Haavik 1978 to assess whether they still produce bacitracin (i.e. have reverted to original strain). Among the strains that no longer produce bacitracin, strains that produce novel compounds are identified by LCMS and HPLC-UV.

Example 48

Generation of constructs able to induce deletion and/or expansion of the bafilomycin PKS modules and transfer to *Streptomyces lohii* strain ATCC BAA-1276. Primers IR037.FOR ggccagtgccaagcttttcaccgagttgaacggaacggaac (SEQ ID NO: 65) and IR037.REV acatgattacgaattccggtc-ccgtacggtgt (SEQ ID NO: 66) are used to amplify a region of homology from *Streptomyces lohii* strain ATCC BAA-1276 genomic DNA (prepared using standard techniques) to yield 1864 bp PCR product, IR037. The first 15 bp of primers IR037.FOR and IR037.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR037 is ligated with pKC1139 digested with HindIII and EcoRI using Infusion Cloning technology to generate plasmid pIR037. Plasmid pIR037 is transferred to *Streptomyces lohii* strain ATCC BAA-1276 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of bafilomycin as described in Zhang 2013.

Samples of culture broth are mixed with methanol, centrifuged for 5 minutes and samples of the supernatant analysed by HPLC-UV and LCMS for production of bafilomycin. Those patches showing no production of bafilomycin (due to primary recombination into the bafilomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Zhang 2013 to assess whether they still produce bafilomycin (i.e. have reverted to original strain). Among the strains that no longer produce bafilomycin, strains that produce novel compounds are identified by LCMS and HPLC-UV.

Example 49

Generation of constructs able to induce deletion and/or expansion of the herbimycin A PKS modules and transfer to *Streptomyces hygroscopicus* strain AM 3672. Primers IR038.FOR ggccagtgccaagcttttcggcgtggactgattccc (SEQ ID NO: 67) and IR038.REV acatgattacgaattcgaggagttgtgc-ccccatg (SEQ ID NO: 68) are used to amplify a region of homology from *Streptomyces hygroscopicus* strain AM 3672 genomic DNA (prepared using standard techniques) to yield 1877 bp PCR product, IR038. The first 15 bp of primers IR038.FOR and IR038.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR038 is ligated with pKC1139 digested with HindIII and EcoRI using Infusion Cloning technology to generate plasmid pIR038. Plasmid pIR038 is transferred to *Streptomyces hygroscopicus* strain AM 3672 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of herbimycin A as described in Omura 1979. Samples of culture broth are mixed with methanol, centrifuged for 5 minutes and samples of the supernatant analysed by HPLC-UV and LCMS for production of herbimycin A. Those patches showing no production of herbimycin A (due to primary recombination into the herbimycin A PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Omura 1979 to assess whether they still produce herbimycin A (i.e. have reverted to original strain). Among the strains that no longer produce herbimycin A, strains that produce novel compounds are identified by LCMS and HPLC-UV.

Example 50

Generation of constructs able to induce deletion and/or expansion of the nanchangmycin PKS modules and transfer to *Streptomyces nanchangensis* NS3226. Primers IR039.FOR ggccagtgccaagcttggtcacggcggaactgc (SEQ ID NO: 69) and IR039.REV acatgattacgaattccgccccgacaacac-ccg (SEQ ID NO: 70) are used to amplify a region of homology from *Streptomyces nanchangensis* NS3226 genomic DNA (prepared using standard techniques) to yield 2066 bp PCR product, IR039. The first 15 bp of primers IR039.FOR and IR039.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR039 is ligated with pKC1139 digested with HindIII and EcoRI using Infusion Cloning technology to generate plasmid pIR039. Plasmid pIR039 is transferred to *Streptomyces nanchangensis* NS3226 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of nanchangmycin as described in Sun 2002. Samples of culture broth are mixed with methanol, centrifuged for 5 minutes and samples of the supernatant analysed by HPLC-UV and LCMS for production of nanchangmycin. Those patches showing no production of nanchangmycin (due to primary recombination into the nanchangmycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Sun 2002 to assess whether they still produce nanchangmycin (i.e. have reverted to original strain). Among the strains that no longer produce nanchangmycin, strains that produce novel compounds are identified by LCMS and HPLC-UV.

Example 51

Generation of constructs able to induce deletion and/or expansion of the meilingmycin PKS modules and transfer to *Streptomyces nanchangensis* strain NS3226. Primers IR040.FOR ggccagtgccaagcttcgaccccggtttcttcggg (SEQ ID NO: 71) and IR040.REV acatgattacgaattccagccggtccggccat (SEQ ID NO: 72) are used to amplify a region of homology from *Streptomyces nanchangensis* strain NS3226 genomic DNA (prepared using standard techniques) to yield 1920 bp PCR product, IR040. The first 15 bp of primers IR040.FOR and IR040.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR040 is ligated with pKC1139 digested with HindIII and EcoRI using Infusion Cloning technology to generate plasmid pIR040. Plasmid pIR040 is transferred to *Streptomyces nanchangensis* strain NS3226 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of meilingmycin as described in Zhuang 2006. Samples of culture broth are mixed with methanol, centrifuged for 5 minutes and samples of the supernatant analysed by HPLC-UV and LCMS for production of meilingmycin. Those patches showing no production of meilingmycin (due to primary recombination into the meilingmycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Zhuang 2006 to assess whether they still produce meilingmycin (i.e. have reverted to original strain). Among the strains that no longer produce meilingmycin, strains that produce novel compounds are identified by LCMS and HPLC-UV.

Example 52

Generation of constructs able to induce deletion and/or expansion of the niddamycin PKS modules and transfer to *Streptomyces caelestis*. Primers IR041.FOR ggccagtgc-caagcttgatcgaccagatggctcgagcga (SEQ ID NO: 73) and IR041.REV acatgattacgaattcccatgccggggtgctg (SEQ ID NO: 74) are used to amplify a region of homology from *Streptomyces caelestis* genomic DNA (prepared using standard techniques) to yield 2072 bp PCR product, IR041. The first 15 bp of primers IR041.FOR and IR041.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR041 is ligated with pKC1139 digested with HindIII and EcoRI using Infusion Cloning technology to generate plasmid pIR041. Plasmid pIR041 is transferred to *Streptomyces caelestis* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of niddamycin as described in Kakavas 1997. Samples of culture broth are mixed with methanol, centrifuged for 5 minutes and samples of the supernatant analysed by HPLC-UV and LCMS for production of niddamycin. Those patches showing no production of niddamycin (due to primary recombination into the niddamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kakavas 1997 to assess whether they still produce niddamycin (i.e. have reverted to original strain). Among the strains that no longer produce niddamycin, strains that produce novel compounds are identified by LCMS and HPLC-UV.

Example 53

Generation of constructs able to induce deletion and/or expansion of the nigericin PKS modules and transfer to *Streptomyces violaceusniger* DSM 4137. Primers IR042.FOR ggccagtgccaagcttcccggccggcacga (SEQ ID NO: 75) and IR042.REV acatgattacgaattccgacaccatcaccgcccacaa (SEQ ID NO: 76) are used to amplify a region of homology from *Streptomyces violaceusniger* DSM 4137 genomic DNA (prepared using standard techniques) to yield 2032 bp PCR product, IR042. The first 15 bp of primers IR042.FOR ggccagtgccaagcttcccggccggcacga (SEQ ID NO: 75) and IR042.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR042 is ligated with pKC1139 digested with HindIII and EcoRI using Infusion Cloning technology to generate plasmid pIR042. Plasmid pIR042 is transferred to *Streptomyces violaceusniger* DSM 4137 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of nigericin as described in Harvey 2007. Samples of culture broth are mixed with methanol, centrifuged for 5 minutes and samples of the supernatant analysed by HPLC-UV and LCMS for production of nigericin. Those patches showing no production of nigericin (due to primary recombination into the nigericin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Harvey 2007 to assess whether they still produce nigericin (i.e. have reverted to original strain). Among the strains that no longer produce nigericin, strains that produce novel compounds are identified by LCMS and HPLC-UV.

Example 54

Generation of constructs able to induce deletion and/or expansion of the nystatin PKS modules and transfer to *Streptomyces noursei* ATCC 11455. Primers IR043.FOR ggccagtgccaagcttcgccctcagccggg (SEQ ID NO: 77) and IR043.REV acatgattacgaattcggaggtggtgttcggcggt (SEQ ID NO: 78) are used to amplify a region of homology from *Streptomyces noursei* ATCC 11455 genomic DNA (prepared using standard techniques) to yield 2092 bp PCR product, IR043. The first 15 bp of primers IR043.FOR and IR043.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR043 is ligated with pKC1139 digested with HindIII and EcoRI using Infusion Cloning technology to generate plasmid pIR043. Plasmid pIR043 is transferred to *Streptomyces noursei* ATCC 11455 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of nystatin as described in Jonsbu 2002. Samples of culture broth are mixed with methanol, centrifuged for 5 minutes and samples of the supernatant analysed by HPLC-UV and LCMS for production of nystatin. Those patches showing no production of nystatin (due to primary recombination into the nystatin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Jonsbu 2002 to assess whether they still produce nystatin (i.e. have reverted to original strain). Among the strains that no longer produce nystatin, strains that produce novel compounds are identified by LCMS and HPLC-UV.

Example 55

Generation of constructs able to induce deletion and/or expansion of the oligomycin PKS modules and transfer to *Streptomyces avermitilis* ATCC 31267. Primers IR044.FOR ggccagtgccaagcttcaccgccacctccgtg (SEQ ID NO: 79) and IR044.REV acatgattacgaattccggcactcgcaccct (SEQ ID NO: 80) are used to amplify a region of homology from *Streptomyces avermitilis* ATCC 31267 genomic DNA (prepared using standard techniques) to yield 2167 bp PCR product, IR044. The first 15 bp of primers IR044.FOR and IR044.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR044 is ligated with pKC1139 digested with HindIII and EcoRI using Infusion Cloning technology to generate plasmid pIR044. Plasmid pIR044 is transferred to *Streptomyces avermitilis* ATCC 31267 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of oligomycin as described in Visser 1960.

Samples of culture broth are mixed with methanol, centrifuged for 5 minutes and samples of the supernatant analysed by HPLC-UV and LCMS for production of oligomycin. Those patches showing no production of oligomycin (due to primary recombination into the oligomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Visser 1960 to assess whether they still produce oligomycin (i.e. have reverted to original strain). Among the strains that no longer produce oligomycin, strains that produce novel compounds are identified by LCMS and HPLC-UV.

Example 56

Generation of constructs able to induce deletion and/or expansion of the phoslactomycin PKS modules and transfer to *Streptomyces* sp. HK803. Primers IR045.FOR ggccagtgccaagcttccggttccagcaggtca (SEQ ID NO: 81) and IR045.REV acatgattacgaattcgctgcgcgccct (SEQ ID NO: 82) are used to amplify a region of homology from *Streptomyces* sp. HK803 genomic DNA (prepared using standard techniques) to yield 2281 bp PCR product, IR045. The first 15 bp of primers IR045.FOR and IR045.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR045 is ligated with pKC1139 digested with HindIII and EcoRI using Infusion Cloning technology to generate plasmid pIR045. Plasmid pIR045 is transferred to *Streptomyces* sp. HK803 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of phoslactomycin as described in Ghatge 2006. Samples of culture broth are mixed with methanol, centrifuged for 5 minutes and samples of the supernatant analysed by HPLC-UV and LCMS for production of phoslactomycin. Those patches showing no production of phoslactomycin (due to primary recombination into the phoslactomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Ghatge 2006 to assess whether they still produce phoslactomycin (i.e. have reverted to original strain). Among the strains that no longer produce phoslactomycin, strains that produce novel compounds are identified by LCMS and HPLC-UV.

Example 57

Generation of constructs able to induce deletion and/or expansion of the piericidin PKS modules and transfer to *Streptomyces piomogenus* var. *Hangzhouwanensis*. Primers IR046.FOR ggccagtgccaagcttcgacatcgtcgacggcgaa (SEQ ID NO: 83) and IR046.REV acatgattacgaattcccggaccgggcctc (SEQ ID NO: 84) are used to amplify a region of homology from *Streptomyces piomogenus* var. *Hangzhouwanensis* genomic DNA (prepared using standard techniques) to yield 1806 bp PCR product, IR046. The first 15 bp of primers IR046.FOR and IR046.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR046 is ligated with pKC1139 digested with HindIII and EcoRI using Infusion Cloning technology to generate plasmid pIR046. Plasmid pIR046 is transferred to *Streptomyces piomogenus* var. *Hangzhouwanensis* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of piericidin as described in Liu 2012. Samples of culture broth are mixed with methanol, centrifuged for 5 minutes and samples of the supernatant analysed by HPLC-UV and LCMS for production of piericidin. Those patches showing no production of piericidin (due to primary recombination into the piericidin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Liu 2012 to assess whether they still produce piericidin (i.e. have reverted to original strain). Among the strains that no longer produce piericidin, strains that produce novel compounds are identified by LCMS and HPLC-UV.

Example 58

Generation of constructs able to induce deletion and/or expansion of the pikromycin PKS modules and transfer to *Streptomyces venezuelae* ATCC 15439. Primers IR047.FOR ggccagtgccaagcttccgacaccaccggcacca (SEQ ID NO: 85) and IR047.REV acatgattacgaattccagaccttcgccagcg (SEQ ID NO: 86) are used to amplify a region of homology from *Streptomyces venezuelae* ATCC 15439 genomic DNA (prepared using standard techniques) to yield 2032 bp PCR product, IR047. The first 15 bp of primers IR047.FOR and IR047.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR047 is ligated with pKC1139 digested with HindIII and EcoRI using Infusion Cloning technology to generate plasmid pIR047. Plasmid pIR047 is transferred to *Streptomyces venezuelae* ATCC 15439 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of pikromycin as described in Xue 1998. Samples of culture broth are mixed with methanol, centrifuged for 5 minutes and samples of the supernatant analysed by HPLC-UV and LCMS for production of pikromycin. Those patches showing no production of pikromycin (due to primary recombination into the pikromycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Xue 1998 to assess whether they still produce pikromycin (i.e. have reverted to original strain). Among the strains that no longer produce pikromycin, strains that produce novel compounds are identified by LCMS and HPLC-UV.

Example 59

Generation of constructs able to induce deletion and/or expansion of the erythromycin PKS modules and transfer to *Saccharopolyspora erythraea* NRRL 2338. Primers IR048.FOR ggccagtgccaagcttgcccaactgggccgc (SEQ ID NO: 87) and IR048.REV acatgattacgaattcgaccttccagtcctgcatcgg (SEQ ID NO: 88) are used to amplify a region of homology from *Saccharopolyspora erythraea* NRRL 2338 genomic DNA (prepared using standard techniques) to yield 2020 bp PCR product, IR048. The first 15 bp of primers IR048.FOR and IR048.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR048 is ligated with pKC1139 digested with HindIII and EcoRI using Infusion Cloning technology to generate plasmid pIR048. Plasmid pIR048 is transferred to *Saccharopolyspora erythraea* NRRL 2338 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of erythromycin as described in WO98/01546. Samples of culture broth are mixed with methanol, centrifuged for 5 minutes and samples of the supernatant analysed by HPLC-UV and LCMS for production of erythromycin. Those patches showing no production of erythromycin (due to primary recombination into the erythromycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in WO98/01546 to assess whether they still produce erythromycin (i.e. have reverted to original strain). Among the strains that no longer produce erythromycin, strains that produce novel compounds are identified by LCMS and HPLC-UV.

Example 60

Generation of constructs able to induce deletion and/or expansion of the pimaracin PKS modules and transfer to *Streptomyces natalensis* ATCC 27448. Primers IR049.FOR ggccagtgccaagcttcggtatcgacccggagtcc (SEQ ID NO: 89) and IR049.REV acatgattacgaattcagacgctcgcggatct (SEQ ID NO: 90) are used to amplify a region of homology from *Streptomyces natalensis* ATCC 27448 genomic DNA (prepared using standard techniques) to yield 1748 bp PCR product, IR049. The first 15 bp of primers IR049.FOR and IR049.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR049 is ligated with pKC1139 digested with HindIII and EcoRI using Infusion Cloning technology to generate plasmid pIR049. Plasmid pIR049 is transferred to *Streptomyces natalensis* ATCC 27448 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of pimaracin as described in Aparicio 1999. Samples of culture broth are mixed with methanol, centrifuged for 5 minutes and samples of the supernatant analysed by HPLC-UV and LCMS for production of pimaracin. Those patches showing no production of pimaracin (due to primary recombination into the pimaracin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Aparicio 1999 to assess whether they still produce pimaracin (i.e. have reverted to original strain). Among the strains that no longer produce pimaracin, strains that produce novel compounds are identified by LCMS and HPLC-UV.

Example 61

Generation of constructs able to induce deletion and/or expansion of the pladienolide PKS modules and transfer to *Streptomyces platensis* Mer-11107. Primers IR050.FOR ggccagtgccaagcttgccggagagcgccaa (SEQ ID NO: 91) and IR050.REV acatgattacgaattcggtgccgctgacccc (SEQ ID NO: 92) are used to amplify a region of homology from *Streptomyces platensis* Mer-11107 genomic DNA (prepared using standard techniques) to yield 2003 bp PCR product, IR050. The first 15 bp of primers IR050.FOR and IR050.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR050 is ligated with pKC1139 digested with HindIII and EcoRI using Infusion Cloning technology to generate plasmid pIR050. Plasmid pIR050 is transferred to *Streptomyces platensis* Mer-11107 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of pladienolide as described in Machida 2008. Samples of culture broth are mixed with methanol, centrifuged for 5 minutes and samples of the supernatant analysed by HPLC-UV and LCMS for production of pladienolide. Those patches showing no production of pladienolide (due to primary recombination into the pladienolide PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Machida 2008 to assess whether they still produce pladienolide (i.e. have reverted to original strain). Among the strains that no longer produce pladienolide, strains that produce novel compounds are identified by LCMS and HPLC-UV.

Example 62

Generation of constructs able to induce deletion and/or expansion of the pyoluteorin PKS modules and transfer to

*Pseudomonas fluorescens* Pf-5. Primers IR051.FOR ggccagtgccaagcttagctccttcgtgctggg (SEQ ID NO: 93) and IR051.REV acatgattacgaattcgttgcgggttgttcgccaga (SEQ ID NO: 94) are used to amplify a region of homology from *Pseudomonas fluorescens* Pf-5 genomic DNA (prepared using standard techniques) to yield 1985 bp PCR product, IR051. The first 15 bp of primers IR051.FOR and IR051.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR051 is ligated with pKC1139 digested with HindIII and EcoRI using Infusion Cloning technology to generate plasmid pIR051. Plasmid pIR051 is transferred to *Pseudomonas fluorescens* Pf-5 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of pyoluteorin as described in Nowak-Thompson 1997. Samples of culture broth are mixed with methanol, centrifuged for 5 minutes and samples of the supernatant analysed by HPLC-UV and LCMS for production of pyoluteorin. Those patches showing no production of pyoluteorin (due to primary recombination into the pyoluteorin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Nowak-Thompson 1997 to assess whether they still produce pyoluteorin (i.e. have reverted to original strain). Among the strains that no longer produce pyoluteorin, strains that produce novel compounds are identified by LCMS and HPLC-UV.

Example 63

Generation of constructs able to induce deletion and/or expansion of the reveromycin PKS modules and transfer to *Streptomyces* sp. SN-593. Primers IR052.FOR ggccagtgccaagcttcgccatcgtgggcatgg (SEQ ID NO: 95) and IR052.REV acatgattacgaattctccgcctgtgccaccg (SEQ ID NO: 96) are used to amplify a region of homology from *Streptomyces* sp. SN-593 genomic DNA (prepared using standard techniques) to yield 2141 bp PCR product, IR052. The first 15 bp of primers IR052.FOR and IR052.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR052 is ligated with pKC1139 digested with HindIII and EcoRI using Infusion Cloning technology to generate plasmid pIR052. Plasmid pIR052 is transferred to *Streptomyces* sp. SN-593 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of reveromycin as described in Takahashi 2011. Samples of culture broth are mixed with methanol, centrifuged for 5 minutes and samples of the supernatant analysed by HPLC-UV and LCMS for production of reveromycin. Those patches showing no production of reveromycin (due to primary recombination into the reveromycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Takahashi 2011 to assess whether they still produce reveromycin (i.e. have reverted to original strain). Among the strains that no longer produce reveromycin, strains that produce novel compounds are identified by LCMS and HPLC-UV.

Example 64

Generation of constructs able to induce deletion and/or expansion of the rifamycin PKS modules and transfer to *Amycolatopsis mediterranei* S699. Primers IR053.FOR ggccagtgccaagcttcacctgaccccggttcgaga (SEQ ID NO: 97) and IR053.REV acatgattacgaattccgtgcttggccgaac (SEQ ID NO: 98) are used to amplify a region of homology from *Amycolatopsis mediterranei* S699 genomic DNA (prepared using standard techniques) to yield 1737 bp PCR product, IR053. The first 15 bp of primers IR053.FOR and IR053.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR053 is ligated with pKC1139 digested with HindIII and EcoRI using Infusion Cloning technology to generate plasmid pIR053. Plasmid pIR053 is transferred to *Amycolatopsis mediterranei* S699 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C.

for pKC1139), at which the plasmid is unable to replicate and the primary integration is selected, before a selection of colonies are transferred again to fresh agar containing apramycin and incubating until good growth is seen. Samples are grown for production of rifamycin as described in August 1998. Samples of culture broth are mixed with methanol, centrifuged for 5 minutes and samples of the supernatant analysed by HPLC-UV and LCMS for production of rifamycin. Those patches showing no production of rifamycin (due to primary recombination into the rifamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in August 1998 to assess whether they still produce rifamycin (i.e. have reverted to original strain). Among the strains that no longer produce rifamycin, strains that produce novel compounds are identified by LCMS and HPLC-UV.

Example 65

Generation of constructs able to induce deletion and/or expansion of the rubradirin PKS modules and transfer to *Streptomyces achromogenes* var. *rubradiris* NRRL3061. Primers IR054.FOR ggccagtgccaagcttggcggaaccgggacatcggcatgg (SEQ ID NO: 99) and IR054.REV acatgattacgaattcagcattggtcccgccgata (SEQ ID NO: 100) are used to amplify a region of homology from *Streptomyces achromogenes* var. *rubradiris* NRRL3061 genomic DNA (prepared using standard techniques) to yield 1879 bp PCR product, IR054. The first 15 bp of primers IR054.FOR and IR054.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR054 is ligated with pKC1139 digested with HindIII and EcoRI using Infusion Cloning technology to generate plasmid pIR054. Plasmid pIR054 is transferred to *Streptomyces achromogenes* var. *rubradiris* NRRL3061 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of rubradirin as described in Sohng 1997. Samples of culture broth are mixed with methanol, centrifuged for 5 minutes and samples of the supernatant analysed by HPLC-UV and LCMS for production of rubradirin. Those patches showing no production of rubradirin (due to primary recombination into the rubradirin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Sohng 1997 to assess whether they still produce rubradirin (i.e. have reverted to original strain). Among the strains that no longer produce rubradirin, strains that produce novel compounds are identified by LCMS and HPLC-UV.

Example 66

Generation of constructs able to induce deletion and/or expansion of the salinomycin PKS modules and transfer to *Streptomyces albus* DSM 41398. Primers IR055.FOR ggccagtgccaagcttcagcgaggggcgcgagaaggccgtcaa (SEQ ID NO: 101) and IR055.REV acatgattacgaattctgagccgccgccaactccc (SEQ ID NO: 102) are used to amplify a region of homology from *Streptomyces albus* DSM 41398 genomic DNA (prepared using standard techniques) to yield 2226 bp PCR product, IR055. The first 15 bp of primers IR055.FOR and IR055.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR055 is ligated with pKC1139 digested with HindIII and EcoRI using Infusion Cloning technology to generate plasmid pIR055. Plasmid pIR055 is transferred to *Streptomyces albus* DSM 41398 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of salinomycin as described in U.S. Pat. No. 4,212,942. Samples of culture broth are mixed with methanol, centrifuged for 5 minutes and samples of the supernatant analysed by HPLC-UV and LCMS for production of salinomycin. Those patches showing no production of salinomycin (due to primary recombination into the salinomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in U.S. Pat. No. 4,212,942 to assess whether they still produce salinomycin (i.e. have reverted to original strain). Among the strains that no longer produce salinomycin, strains that produce novel compounds are identified by LCMS and HPLC-UV.

Example 67

Generation of constructs able to induce deletion and/or expansion of the tautomycetin PKS modules and transfer to Streptomyces sp. CK4412. Primers IR056.FOR ggccagtgc-caagcttggactgggcccggttcgcccc (SEQ ID NO: 103) and IR056.REV acatgattacgaattccgcaccactccgggcg (SEQ ID NO: 104) are used to amplify a region of homology from Streptomyces sp. CK4412 genomic DNA (prepared using standard techniques) to yield 2039 bp PCR product, IR056. The first 15 bp of primers IR056.FOR and IR056.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR056 is ligated with pKC1139 digested with HindIII and EcoRI using Infusion Cloning technology to generate plasmid pIR056. Plasmid pIR056 is transferred to Streptomyces sp. CK4412 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of tautomycetin as described in Park 2009. Samples of culture broth are mixed with methanol, centrifuged for 5 minutes and samples of the supernatant analysed by HPLC-UV and LCMS for production of tautomycetin. Those patches showing no production of tautomycetin (due to primary recombination into the tautomycetin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Park 2009 to assess whether they still produce tautomycetin (i.e. have reverted to original strain). Among the strains that no longer produce tautomycetin, strains that produce novel compounds are identified by LCMS and HPLC-UV.

Example 68

Generation of constructs able to induce deletion and/or expansion of the tautomycin PKS modules and transfer to Streptomyces spiroverticillatus. Primers IR057.FOR ggcca-gtgccaagcttcgctggcccgccaccg (SEQ ID NO: 105) and IR057.REV acatgattacgaattcgacgaactccagtagtcgct (SEQ ID NO: 106) are used to amplify a region of homology from Streptomyces spiroverticillatus genomic DNA (prepared using standard techniques) to yield 2089 bp PCR product, IR057. The first 15 bp of primers IR057.FOR and IR057.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR057 is ligated with pKC1139 digested with HindIII and EcoRI using Infusion Cloning technology to generate plasmid pIR057. Plasmid pIR057 is transferred to Streptomyces spiroverticillatus by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of tautomycin as described in Li 2008. Samples of culture broth are mixed with methanol, centrifuged for 5 minutes and samples of the supernatant analysed by HPLC-UV and LCMS for production of tautomycin. Those patches showing no production of tautomycin (due to primary recombination into the tautomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Li 2008 to assess whether they still produce tautomycin (i.e. have reverted to original strain). Among the strains that no longer produce tautomycin, strains that produce novel compounds are identified by LCMS and HPLC-UV.

Example 69

Generation of constructs able to induce deletion and/or expansion of the tetronomycin PKS modules and transfer to Streptomyces sp. NRRL 11266. Primers IR058.FOR ggcca-gtgccaagcttcagacccggcagcggct (SEQ ID NO: 107) and IR058.REV acatgattacgaattcgcgtgatggccgccag (SEQ ID NO: 108) are used to amplify a region of homology from Streptomyces sp. NRRL 11266 genomic DNA (prepared using standard techniques) to yield 2319 bp PCR product, IR058. The first 15 bp of primers IR058.FOR and IR058.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR058 is ligated with pKC1139 digested with HindIII and EcoRI using Infusion Cloning technology to generate plasmid pIR058. Plasmid pIR058 is transferred to *Streptomyces* sp. NRRL 11266 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of tetronomycin as described in Demydchuk 2008. Samples of culture broth are mixed with methanol, centrifuged for 5 minutes and samples of the supernatant analysed by HPLC-UV and LCMS for production of tetronomycin. Those patches showing no production of tetronomycin (due to primary recombination into the tetronomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Demydchuk 2008 to assess whether they still produce tetronomycin (i.e. have reverted to original strain). Among the strains that no longer produce tetronomycin, strains that produce novel compounds are identified by LCMS and HPLC-UV.

Example 70

Generation of constructs able to induce deletion and/or expansion of the vicenistatin PKS modules and transfer to *Streptomyces halstedii* HC34. Primers IR059.FOR ggccagtgccaagcttcgacgggcatgggcag (SEQ ID NO: 109) and IR059.REV acatgattacgaattcactgcgaaccctgccc (SEQ ID NO: 110) are used to amplify a region of homology from *Streptomyces halstedii* HC34 genomic DNA (prepared using standard techniques) to yield 2240 bp PCR product, IR059. The first 15 bp of primers IR059.FOR and IR059.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR059 is ligated with pKC1139 digested with HindIII and EcoRI using Infusion Cloning technology to generate plasmid pIR059. Plasmid pIR059 is transferred to *Streptomyces halstedii* HC34 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of vicenistatin as described in Ogasawara 2005. Samples of culture broth are mixed with methanol, centrifuged for 5 minutes and samples of the supernatant analysed by HPLC-UV and LCMS for production of vicenistatin. Those patches showing no production of vicenistatin (due to primary recombination into the vicenistatin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Ogasawara 2005 to assess whether they still produce vicenistatin (i.e. have reverted to original strain). Among the strains that no longer produce vicenistatin, strains that produce novel compounds are identified by LCMS and HPLC-UV.

Example 71

Generation of constructs able to induce deletion and/or expansion of the monensin PKS modules and transfer to *Streptomyces cinnamonensis* ATCC 15413. Primers IR060.FOR ggccagtgccaagcttcgcaaccgcctctccac (SEQ ID NO: 111) and IR060.REV acatgattacgaattccctccggcggctcctc (SEQ ID NO: 112) are used to amplify a region of homology from *Streptomyces cinnamonensis* ATCC 15413 genomic DNA (prepared using standard techniques) to yield 1509 bp PCR product, IR060. The first 15 bp of primers IR060.FOR and IR060.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR060 is ligated with pKC1139 digested with HindIII and EcoRI using Infusion Cloning technology to generate plasmid pIR060. Plasmid pIR060 is transferred to *Streptomyces cinnamonensis* ATCC 15413 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of monensin as described in Oliynyk 2003. Samples of culture broth are mixed with methanol, centrifuged for 5 minutes and samples of the supernatant analysed by HPLC-UV and LCMS for production of monensin. Those patches showing no production of monensin(due to primary recombination into the monensin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Oliynyk 2003 to assess whether they still produce monensin (i.e. have reverted to original strain). Among the strains that no longer produce monensin, strains that produce novel compounds are identified by LCMS and HPLC-UV.

Example 72

Generation of constructs able to induce deletion and/or expansion of the spiramycin PKS modules and transfer to Streptomyces ambofaciens. Primers IR061.FOR ggccagtgc-caagcttCTCGACCCCGACCAGGC (SEQ ID NO: 113) and IR061.REV acatgattacgaattcGGCTGCGCAGGGCGAC (SEQ ID NO: 114) are used to amplify a region of homology from Streptomyces ambofaciens genomic DNA (prepared using standard techniques) to yield 2562 bp PCR product, IR061. The first 15 bp of primers IR061.FOR and IR061.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR061 is ligated with pKC1139 digested with HindIII and EcoRI using Infusion Cloning technology to generate plasmid pIR061. Plasmid pIR061 is transferred to Streptomyces ambofaciens by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of spiramycin as described in Lounes 1995. Samples of culture broth are mixed with methanol, centrifuged for 5 minutes and samples of the supernatant analysed by HPLC-UV and LCMS for production of spiramycin. Those patches showing no production of spiramycin (due to primary recombination into the spiramycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Lounes 1995 to assess whether they still produce spiramycin (i.e. have reverted to original strain). Among the strains that no longer produce spiramycin, strains that produce novel compounds are identified by LCMS and HPLC-UV.

Example 73

Generation of constructs able to induce deletion and/or expansion of the spinosyn PKS modules and transfer to Saccharopolyspora spinosa NRRL 18538. Primers IR062.FOR ggccagtgccaagctttgtcgaggcactgcgagc (SEQ ID NO: 115) and IR062.REV acatgattacgaattctccggtcaaggtcga-cacgat (SEQ ID NO: 116) are used to amplify a region of homology from Saccharopolyspora spinosa NRRL 18538 genomic DNA (prepared using standard techniques) to yield 2400 bp PCR product, IR062. The first 15 bp of primers IR062.FOR and IR062.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR062 is ligated with pKC1139 digested with HindIII and EcoRI using Infusion Cloning technology to generate plasmid pIR062. Plasmid pIR062 is transferred to Saccharopolyspora spinosa NRRL 18538 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of spinosyn as described in Waldron 2001. Samples of culture broth are mixed with methanol, centrifuged for 5 minutes and samples of the supernatant analysed by HPLC-UV and LCMS for production of spinosyn. Those patches showing no production of spinosyn (due to primary recombination into the spinosyn PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Waldron 2001 to assess whether they still produce spinosyn (i.e. have reverted to original strain). Among the strains that no longer produce spinosyn, strains that produce novel compounds are identified by LCMS and HPLC-UV.

Example 74

Generation of constructs able to induce deletion and/or expansion of the amphotericin B PKS modules and transfer to *Streptomyces nodosus* ATCC 14899. Primers IR063.FOR ggccagtgccaagcttcaccgatggagtgaccggccac (SEQ ID NO: 117) and IR063.REV acatgattacgaattcacccgatcgtgatcgtcgg (SEQ ID NO: 118) are used to amplify a region of homology from *Streptomyces nodosus* ATCC 14899 genomic DNA (prepared using standard techniques) to yield 1898 bp PCR product, IR063. The first 15 bp of primers IR063.FOR and IR063.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR063 is ligated with pKC1139 digested with HindIII and EcoRI using Infusion Cloning technology to generate plasmid pIR063. Plasmid pIR063 is transferred to *Streptomyces nodosus* ATCC 14899 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of amphotericin B as described in Caffrey 2001. Samples of culture broth are mixed with methanol, centrifuged for 5 minutes and samples of the supernatant analysed by HPLC-UV and LCMS for production of amphotericin B. Those patches showing no production of amphotericin B (due to primary recombination into the amphotericin B PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Caffrey 2001 to assess whether they still produce amphotericin B (i.e. have reverted to original strain). Among the strains that no longer produce amphotericin B, strains that produce novel compounds are identified by LCMS and HPLC-UV.

Example 75

Generation of constructs able to induce deletion and/or expansion of the mycotrienin PKS modules and transfer to *Streptomyces flaveolus* DSM40061. Primers IR064.FOR ggccagtgccaagcttactgcggctccccgc (SEQ ID NO: 119) and IR064.REV acatgattacgaattccgtggcgggttcccc (SEQ ID NO: 120) are used to amplify a region of homology from *Streptomyces flaveolus* DSM40061 genomic DNA (prepared using standard techniques) to yield 1509 bp PCR product, IR064. The first 15 bp of primers IR064.FOR and IR064.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR064 is ligated with pKC1139 digested with HindIII and EcoRI using Infusion Cloning technology to generate plasmid pIR064. Plasmid pIR064 is transferred to *Streptomyces flaveolus* DSM40061 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of mycotrienin as described in Qu et al., 2001. Samples of culture broth are mixed with methanol, centrifuged for 5 minutes and samples of the supernatant analysed by HPLC-UV and LCMS for production of mycotrienin. Those patches showing no production of mycotrienin (due to primary recombination into the mycotrienin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Qu et al., 2001 to assess whether they still produce mycotrienin (i.e. have reverted to original strain). Among the strains that no longer produce mycotrienin, strains that produce novel compounds are identified by LCMS and HPLC-UV.

Example 76

Generation of constructs able to induce deletion and/or expansion of the apoptolidin PKS modules and transfer to *Nocardiopsis* sp. FU40. Primers IR065.FOR ggccagtgccaagcttggattcgagcaaccgggac (SEQ ID NO: 121) and IR065.REV acatgattacgaattcctggctgacctgcccgaa (SEQ ID NO: 122) are used to amplify a region of homology from *Nocardiopsis* sp. FU40 genomic DNA (prepared using standard techniques) to yield 2216 bp PCR product, IR065. The first 15 bp of primers IR065.FOR and IR065.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR065 is ligated with pKC1139 digested with HindIII and EcoRI using Infusion Cloning technology to generate plasmid pIR065. Plasmid pIR065 is transferred to *Nocardiopsis* sp. FU40 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of apoptolidin as described in Du et al., 2011. Samples of culture broth are mixed with methanol, centrifuged for 5 minutes and samples of the supernatant analysed by HPLC-UV and LCMS for production of apoptolidin. Those patches showing no production of apoptolidin (due to primary recombination into the apoptolidin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Du et al., 2011 to assess whether they still produce apoptolidin (i.e. have reverted to original strain). Among the strains that no longer produce apoptolidin, strains that produce novel compounds are identified by LCMS and HPLC-UV.

Example 77

Generation of constructs able to induce deletion and/or expansion of the kendomycin PKS modules and transfer to *Streptomyces violaceoruber*. Primers IR066.FOR ggccagtgccaagcttgaagtggcgtccgaccggc (SEQ ID NO: 123) and IR066.REV acatgattacgaattcgacgccattgacgtcgg (SEQ ID NO: 124) are used to amplify a region of homology from *Streptomyces violaceoruber* genomic DNA (prepared using standard techniques) to yield 1835 bp PCR product, IR066. The first 15 bp of primers IR066.FOR and IR066.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR066 is ligated with pKC1139 digested with HindIII and EcoRI using Infusion Cloning technology to generate plasmid pIR066. Plasmid pIR066 is transferred to *Streptomyces violaceoruber* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of kendomycin as described in Wenzel et al., 2008. Samples of culture broth are mixed with methanol, centrifuged for 5 minutes and samples of the supernatant analysed by HPLC-UV and LCMS for production of kendomycin. Those patches showing no production of kendomycin (due to primary recombination into the kendomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Wenzel et al., 2008 to assess whether they still produce kendomycin (i.e. have reverted to original strain). Among the strains that no longer produce kendomycin, strains that produce novel compounds are identified by LCMS and HPLC-UV.

Example 78

Generation of constructs able to induce deletion and/or expansion of the angolamycin PKS modules and transfer to *Streptomyces eurythermus* ATCC 23956. Primers IR067.FOR ggccagtgccaagcttgtgcacagtgctgcgg (SEQ ID NO: 125) and IR067.REV acatgattacgaattcaggcggccagacgcc (SEQ ID NO: 126) are used to amplify a region of homology from *Streptomyces eurythermus* ATCC 23956 genomic DNA (prepared using standard techniques) to yield 1701 bp PCR product, IR067. The first 15 bp of primers IR067.FOR and IR067.Rev contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR067 is ligated with pKC1139 digested with HindIII and EcoRI using Infusion Cloning technology to generate plasmid pIR067. Plasmid pIR067 is transferred to *Streptomyces eurythermus* ATCC 23956 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of angolamycin as described in U.S. Pat. No. 3,131,127. Samples of culture broth are mixed with methanol, centrifuged for 5 minutes and samples of the supernatant analysed by HPLC-UV and LCMS for production of angolamycin. Those patches showing no production of angolamycin (due to primary recombination into the angolamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in U.S. Pat. No. 3,131,127 to assess whether they still produce angolamycin (i.e. have reverted to original strain). Among the strains that no longer produce angolamycin, strains that produce novel compounds are identified by LCMS and HPLC-UV.

Example 79

Generation of constructs able to induce deletion and/or expansion of the meridamycin PKS modules and transfer to Streptomyces violaceusniger DSM 4137. Primers IR068.FOR ggccagtgccaagcttggctcccgtccgcagg (SEQ ID NO: 127) and IR068.REV acatgattacgaattcccttcggaggcggcca (SEQ ID NO: 128) are used to amplify a region of homology from Streptomyces violaceusniger DSM 4137 genomic DNA (prepared using standard techniques) to yield 2378 bp PCR product, IR068. The first 15 bp of primers IR068.FOR and IR068.Rev contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR068 is ligated with pKC1139 digested with HindIII and EcoRI using Infusion Cloning technology to generate plasmid pIR068. Plasmid pIR068 is transferred to Streptomyces violaceusniger DSM 4137 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of meridamycin as described in Sun 2006. Samples of culture broth are mixed with methanol, centrifuged for 5 minutes and samples of the supernatant analysed by HPLC-UV and LCMS for production of meridamycin. Those patches showing no production of meridamycin (due to primary recombination into the meridamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Sun 2006 to assess whether they still produce meridamycin (i.e. have reverted to original strain). Among the strains that no longer produce meridamycin, strains that produce novel compounds are identified by LCMS and HPLC-UV.

Example 80

Generation of constructs able to induce deletion and/or expansion of the concanamcyin A PKS modules and transfer to Streptomyces neyagawaensis ATCC 27449. Primers IR069.FOR ggccagtgccaagcttcatggacccgcagcagc (SEQ ID NO: 129) and IR069.REV acatgattacgaattcagacccgaccccatcc (SEQ ID NO: 130) are used to amplify a region of homology from Streptomyces neyagawaensis ATCC 27449 genomic DNA (prepared using standard techniques) to yield 1451 bp PCR product, IR069. The first 15 bp of primers IR069.FOR and IR069.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR069 is ligated with pKC1139 digested with HindIII and EcoRI using Infusion Cloning technology to generate plasmid pIR069. Plasmid pIR069 is transferred to Streptomyces neyagawaensis ATCC 27449 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of concanamcyin A as described in Haydock 2005. Samples of culture broth are mixed with methanol, centrifuged for 5 minutes and samples of the supernatant analysed by HPLC-UV and LCMS for production of concanamcyin A. Those patches showing no production of concanamcyin A (due to primary recombination into the concanamcyin A PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Haydock 2005 to assess whether they still produce concanamcyin A (i.e. have reverted to original strain). Among the strains that no longer produce concanamcyin A, strains that produce novel compounds are identified by LCMS and HPLC-UV.

Example 81

Generation of constructs able to induce deletion and/or expansion of the complestatin NRPS modules and transfer to Streptomyces lavendulae. Primers IR070.FOR ggccagtgccaagcttccgccttcgtcgtgctc (SEQ ID NO: 131) and IR070.REV acatgattacgaattcgcgagcgcgatgc (SEQ ID NO: 132) are used to amplify a region of homology from Streptomyces lavendulae genomic DNA (prepared using standard techniques) to yield 2016 bp PCR product, IR070. The first 15 bp of primers IR070.FOR and IR070.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR070 is ligated with pKC1139 digested with HindIII and EcoRI using Infusion Cloning technology to generate plasmid pIR070. Plasmid pIR070 is transferred to *Streptomyces lavendulae* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of complestatin as described in Kaneko 1989. Samples of culture broth are mixed with methanol, centrifuged for 5 minutes and samples of the supernatant analysed by HPLC-UV and LCMS for production of complestatin. Those patches showing no production of complestatin (due to primary recombination into the complestatin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kaneko 1989 to assess whether they still produce complestatin (i.e. have reverted to original strain). Among the strains that no longer produce complestatin, strains that produce novel compounds are identified by LCMS and HPLC-UV.

Example 82

Generation of constructs able to induce deletion and/or expansion of the triostin NRPS modules and transfer to *Streptomyces triostinicus*. Primers IR071.FOR Acatgattacgaattctcgcgcggtgcgg (SEQ ID NO: 133) and IR071.REV Ggccagtgccaagcttttccctctcttacgcgcag (SEQ ID NO: 134) are used to amplify a region of homology from *Streptomyces triostinicus* genomic DNA (prepared using standard techniques) to yield 1361 bp PCR product, IR071. The first 15 bp of primers IR071.FOR and IR071.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR071 is ligated with pKC1139 digested with HindIII and EcoRI using Infusion Cloning technology to generate plasmid pIR071. Plasmid pIR071 is transferred to *Streptomyces triostinicus* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of Triostin as described in Praseuth et al., 2008. Samples of culture broth are mixed with methanol, centrifuged for 5 minutes and samples of the supernatant analysed by HPLC-UV and LCMS for production of Triostin. Those patches showing no production of Triostin (due to primary recombination into the Triostin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Praseuth et al., 2008 to assess whether they still produce Triostin (i.e. have reverted to original strain). Among the strains that no longer produce Triostin, strains that produce novel compounds are identified by LCMS and HPLC-UV.

Example 83

Generation of constructs able to induce deletion and/or expansion of the ambruticin PKS modules and transfer to *Sorangium cellulosum* So ce10. Primers IR072.FOR ggccagtgccaagcttGCGGTCACGCACGG (SEQ ID NO: 135) and IR072.REV acatgattacgaattcTCCGTGCGCGGCCAC (SEQ ID NO: 136) are used to amplify a region of homology from *Sorangium cellulosum* So ce10 genomic DNA (prepared using standard techniques) to yield 2055 bp PCR product, IR072. The first 15 bp of primers IR072.FOR and IR072.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR072 is ligated with pKC1139 digested with HindIII and EcoRI using Infusion Cloning technology to generate plasmid pIR072. Plasmid pIR072 is transferred to *Sorangium cellulosum* So ce10 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of ambruticin as described in Hopf 1990. Samples of culture broth are mixed with methanol, centrifuged for 5 minutes and samples of the supernatant analysed by HPLC-UV and LCMS for production of ambruticin. Those patches showing no production of ambruticin (due to primary recombination into the ambruticin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Hopf 1990 to assess whether they still produce ambruticin (i.e. have reverted to original strain). Among the strains that no longer produce ambruticin, strains that produce novel compounds are identified by LCMS and HPLC-UV.

Example 84

Generation of constructs able to induce deletion and/or expansion of the difficidin PKS modules and transfer to *Bacillus amyloliquefaciens* Strain FZB42. Primers IR073.FOR ggccagtgccaagcttATTTATGGATGTTTATGCAGCCCGCCGGA (SEQ ID NO: 137) and IR073.REV acatgattacgaattcCCGGCTTTTGATAAGCGCTTTTCA (SEQ ID NO: 138) are used to amplify a region of homology from *Bacillus amyloliquefaciens* strain FZB42 genomic DNA (prepared using standard techniques) to yield 1613 bp PCR product, IR073. The first 15 bp of primers IR073.FOR and IR073.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR073 is ligated with pKC1139 digested with HindIII and EcoRI using Infusion Cloning technology to generate plasmid pIR073. Plasmid pIR073 is transferred to *Bacillus amyloliquefaciens* strain FZB42 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of difficidin as described in Arguelles-Arias 2009. Samples of culture broth are mixed with methanol, centrifuged for 5 minutes and samples of the supernatant analysed by HPLC-UV and LCMS for production of difficidin. Those patches showing no production of difficidin (due to primary recombination into the difficidin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Arguelles-Arias 2009 to assess whether they still produce difficidin (i.e. have reverted to original strain). Among the strains that no longer produce difficidin, strains that produce novel compounds are identified by LCMS and HPLC-UV.

Example 85

Generation of constructs able to induce deletion and/or expansion of the filipin PKS modules and transfer to *Streptomyces avermitilis*. Primers IR074.FOR ggccagtgccaagcttcggcaccatgaccgagg (SEQ ID NO: 139) and IR074.REV acatgattacgaattcgccagcgcttcgaggat (SEQ ID NO: 140) are used to amplify a region of homology from *Streptomyces avermitilis* genomic DNA (prepared using standard techniques) to yield 1822 bp PCR product, IR074. The first 15 bp of primers IR074.FOR and IR074.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR074 is ligated with pKC1139 digested with HindIII and EcoRI using Infusion Cloning technology to generate plasmid pIR074. Plasmid pIR074 is transferred to *Streptomyces avermitilis* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of filipin as described in Miyamoto 2011. Samples of culture broth are mixed with methanol, centrifuged for 5 minutes and samples of the supernatant analysed by HPLC-UV and LCMS for production of filipin. Those patches showing no production of filipin (due to primary recombination into the filipin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Miyamoto 2011 to assess whether they still produce filipin (i.e. have reverted to original strain). Among the strains that no longer produce filipin, strains that produce novel compounds are identified by LCMS and HPLC-UV.

Example 86

Generation of constructs able to induce deletion and/or expansion of the kijanimicin PKS modules and transfer to *Actinomadura kijaniata*. Primers IR075.FOR ggccagtgccaagcttGCCCTGCACCTGGCGATC (SEQ ID NO: 141) and IR075.REV acatgattacgaattcGCCGTTGCTG- GTGGGGA (SEQ ID NO: 142) are used to amplify a region of homology from *Actinomadura kijaniata* genomic DNA (prepared using standard techniques) to yield 1502 bp PCR product, IR075. The first 15 bp of primers IR075.FOR and IR075.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR075 is ligated with pKC1139 digested with HindIII and EcoRI using Infusion Cloning technology to generate plasmid pIR075. Plasmid pIR075 is transferred to *Actinomadura kijaniata* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of kijanimicin as described in Waitz 1981. Samples of culture broth are mixed with methanol, centrifuged for 5 minutes and samples of the supernatant analysed by HPLC-UV and LCMS for production of kijanimicin. Those patches showing no production of kijanimicin (due to primary recombination into the kijanimicin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Waitz 1981 to assess whether they still produce kijanimicin (i.e. have reverted to original strain). Among the strains that no longer produce kijanimicin, strains that produce novel compounds are identified by LCMS and HPLC-UV.

Example 87

Generation of constructs able to induce deletion and/or expansion of the lankamycin PKS modules and transfer to *Streptomyces rochei* plasmid pSLA2-L. Primers IR076.FOR ggccagtgccaagcttGCGCACGGCGCAC (SEQ ID NO: 143) and IR076.REV acatgattacgaattcGGACTGGGCGGCCAG (SEQ ID NO: 144) are used to amplify a region of homology from *Streptomyces rochei* plasmid pSLA2-L genomic DNA (prepared using standard techniques) to yield 1781 bp PCR product, IR076. The first 15 bp of primers IR076.FOR and IR076.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR076 is ligated with pKC1139 digested with HindIII and EcoRI using Infusion Cloning technology to generate plasmid pIR076. Plasmid pIR076 is transferred to *Streptomyces rochei* plasmid pSLA2-L by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of lankamycin as described in Arakawa 2007. Samples of culture broth are mixed with methanol, centrifuged for 5 minutes and samples of the supernatant analysed by HPLC-UV and LCMS for production of lankamycin. Those patches showing no production of lankamycin (due to primary recombination into the lankamycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Arakawa 2007 to assess whether they still produce lankamycin (i.e. have reverted to original strain). Among the strains that no longer produce lankamycin, strains that produce novel compounds are identified by LCMS and HPLC-UV.

Example 88

Generation of constructs able to induce deletion and/or expansion of the macrolactin PKS modules and transfer to *Bacillus amyloliquefaciens* strain FZB42. Primers IR077.FOR ggccagtgccaagcttTTCGGAATCAACTCACT-TATGATCATGTCACT (SEQ ID NO: 145) and IR077.REV acatgattacgaattcAAAGTTCTCAGTTTCTCCTTTAGT-TCCG (SEQ ID NO: 146) are used to amplify a region of homology from *Bacillus amyloliquefaciens* strain FZB42 genomic DNA (prepared using standard techniques) to yield 1807 bp PCR product, IR077. The first 15 bp of primers IR077.FOR and IR077.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR077 is ligated with pKC1139 digested with HindIII and EcoRI using Infusion Cloning technology to generate plasmid pIR077. Plasmid pIR077 is transferred to *Bacillus amyloliquefaciens* strain FZB42 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of macrolactin as described in Schneider 2007. Samples of culture broth are mixed with methanol, centrifuged for 5 minutes and samples of the supernatant analysed by HPLC-UV and LCMS for production of macrolactin. Those patches showing no production of macrolactin (due to primary recombination into the macrolactin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Schneider 2007 to assess whether they still produce macrolactin (i.e. have reverted to original strain). Among the strains that no longer produce macrolactin, strains that produce novel compounds are identified by LCMS and HPLC-UV.

Example 89

Generation of constructs able to induce deletion and/or expansion of the mupirocin PKS modules and transfer to *Pseudomonas fluorescens* NCIMB 10586. Primers IR078.FOR ggccagtgccaagcttCTCGAGCAGTGGCTGCT (SEQ ID NO: 147) and IR078.REV acatgattacgaattcGCTCGACATAGCCCACAT (SEQ ID NO: 148) are used to amplify a region of homology from *Pseudomonas fluorescens* NCIMB 10586 genomic DNA (prepared using standard techniques) to yield 1573 bp PCR product, IR078. The first 15 bp of primers IR078.FOR and IR078.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR078 is ligated with pKC1139 digested with HindIII and EcoRI using Infusion Cloning technology to generate plasmid pIR078. Plasmid pIR078 is transferred to *Pseudomonas fluorescens* NCIMB 10586 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of mupirocin as described in Kassem El-Sayed 2003. Samples of culture broth are mixed with methanol, centrifuged for 5 minutes and samples of the supernatant analysed by HPLC-UV and LCMS for production of mupirocin. Those patches showing no production of mupirocin (due to primary recombination into the mupirocin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kassem El-Sayed 2003 to assess whether they still produce mupirocin (i.e. have reverted to original strain). Among the strains that no longer produce mupirocin, strains that produce novel compounds are identified by LCMS and HPLC-UV.

Example 90

Generation of constructs able to induce deletion and/or expansion of the mycinamicin PKS modules and transfer to *Micromonospora griseorubida*. Primers IR079.FOR ggccagtgccaagcttAGCCGCTCGCTGATCG (SEQ ID NO: 149) and IR079.REV acatgattacgaattcGCCTCCAAACGACCCG (SEQ ID NO: 150) are used to amplify a region of homology from *Micromonospora griseorubida* genomic DNA (prepared using standard techniques) to yield 1753 bp PCR product, IR079. The first 15 bp of primers IR079.FOR and IR079.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR079 is ligated with pKC1139 digested with HindIII and EcoRI using Infusion Cloning technology to generate plasmid pIR079. Plasmid pIR079 is transferred to *Micromonospora griseorubida* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of mycinamicin as described in Takenaka 1998. Samples of culture broth are mixed with methanol, centrifuged for 5 minutes and samples of the supernatant analysed by HPLC-UV and LCMS for production of mycinamicin. Those patches showing no production of mycinamicin (due to primary recombination into the mycinamicin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Takenaka 1998 to assess whether they still produce mycinamicin (i.e. have reverted to original strain). Among the strains that no longer produce mycinamicin, strains that produce novel compounds are identified by LCMS and HPLC-UV.

Example 91

Generation of constructs able to induce deletion and/or expansion of the macbecin PKS modules and transfer to *Actinosynnema pretiosum* subsp. *Pretiosum* ATCC 31280. Primers IR080.FOR ggccagtgccaagcttCCGACCCCGCTG-GACGCGGC (SEQ ID NO: 151) and IR080.REV acatgattacgaattcCCACGACCACGGCCC (SEQ ID NO: 152) are used to amplify a region of homology from *Actinosynnema pretiosum* subsp. *Pretiosum* ATCC 31280 genomic DNA (prepared using standard techniques) to yield 1644 bp PCR product, IR080. The first 15 bp of primers IR080.FOR and IR080.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR080 is ligated with pKC1139 digested with HindIII and EcoRI using Infusion Cloning technology to generate plasmid pIR080. Plasmid pIR080 is transferred to *Actinosynnema pretiosum* subsp. *Pretiosum* ATCC 31280 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of macbecin as described in Zhang 2008. Samples of culture broth are mixed with methanol, centrifuged for 5 minutes and samples of the supernatant analysed by HPLC-UV and LCMS for production of macbecin. Those patches showing no production of macbecin (due to primary recombination into the macbecin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Zhang 2008 to assess whether they still produce macbecin (i.e. have reverted to original strain). Among the strains that no longer produce macbecin, strains that produce novel compounds are identified by LCMS and HPLC-UV.

Example 92

Generation of constructs able to induce deletion and/or expansion of the nemadectin PKS modules and transfer to *Streptomyces cyaneogriseus* subsp. *Noncyanogenus*. Primers IR081.FOR ggccagtgccaagcttGCACGGTAGCCTCCA-GGAACTT (SEQ ID NO: 153) and IR081.REV acatgattacgaattcGGTTCGGTGGGGGGTGT (SEQ ID NO: 154) are used to amplify a region of homology from *Streptomyces cyaneogriseus* subsp. *Noncyanogenus* genomic DNA (prepared using standard techniques) to yield 1988 bp PCR product, IR081. The first 15 bp of primers IR081.FOR and IR081.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR081 is ligated with pKC1139 digested with HindIII and EcoRI using Infusion Cloning technology to generate plasmid pIR081. Plasmid pIR081 is transferred to *Streptomyces cyaneogriseus* subsp. *Noncyanogenus* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of nemadectin as described in US20060234353 A1. Samples of culture broth are mixed with methanol, centrifuged for 5 minutes and samples of the supernatant analysed by HPLC-UV and LCMS for production of nemadectin. Those patches showing no production of nemadectin (due to primary recombination into the nemadectin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in US20060234353 A1 to assess whether they still produce nemadectin (i.e. have reverted to original strain). Among the strains that no longer produce nemadectin, strains that produce novel compounds are identified by LCMS and HPLC-UV.

Example 93

Generation of constructs able to induce deletion and/or expansion of the oleandomycin PKS modules and transfer to *Streptomyces antibioticus*. Primers IR082.FOR ggccagtgccaagcttaccggctcgacaccgcac (SEQ ID NO: 155) and IR082.REV acatgattacgaattcgaccatcaccgcccg (SEQ ID NO: 156) are used to amplify a region of homology from *Streptomyces antibioticus* genomic DNA (prepared using standard techniques) to yield 1651 bp PCR product, IR082. The first 15 bp of primers IR082.FOR and IR082.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR082 is ligated with pKC1139 digested with HindIII and EcoRI using Infusion Cloning technology to generate plasmid pIR082. Plasmid pIR082 is transferred to *Streptomyces antibioticus* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of oleandomycin as described in Kim 2005. Samples of culture broth are mixed with methanol, centrifuged for 5 minutes and samples of the supernatant analysed by HPLC-UV and LCMS for production of oleandomycin. Those patches showing no production of oleandomycin (due to primary recombination into the oleandomycin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Kim 2005 to assess whether they still produce oleandomycin (i.e. have reverted to original strain). Among the strains that no longer produce oleandomycin, strains that produce novel compounds are identified by LCMS and HPLC-UV.

Example 94

Generation of constructs able to induce deletion and/or expansion of the iso-migrastatin PKS modules and transfer to *Streptomyces platensis* NRRL 18993. Primers IR083.FOR ggccagtgccaagcttCTCGACGGCTTCGCATCGA (SEQ ID NO: 157) and IR083.REV acatgattacgaattcTGAACGGGGTGGCCGC (SEQ ID NO: 158) are used to amplify a region of homology from *Streptomyces platensis* NRRL 18993 genomic DNA (prepared using standard techniques) to yield 1467 bp PCR product, IR083. The first 15 bp of primers IR083.FOR and IR083.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR083 is ligated with pKC1139 digested with HindIII and EcoRI using Infusion Cloning technology to generate plasmid pIR083. Plasmid pIR083 is transferred to *Streptomyces platensis* NRRL 18993 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of iso-migrastatin as described in Lim 2009. Samples of culture broth are mixed with methanol, centrifuged for 5 minutes and samples of the supernatant analysed by HPLC-UV and LCMS for production of iso-migrastatin. Those patches showing no production of iso-migrastatin (due to primary recombination into the iso-migrastatin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Lim 2009 to assess whether they still produce iso-migrastatin (i.e. have reverted to original strain). Among the strains that no longer produce iso-migrastatin, strains that produce novel compounds are identified by LCMS and HPLC-UV.

Example 95

Generation of constructs able to induce deletion and/or expansion of the chlorothricin PKS modules and transfer to *Streptomyces antibioticus* DSM 40725. Primers IR084.FOR ggccagtgccaagcttggacctggacgccctctac (SEQ ID NO: 159) and IR084.REV acatgattacgaattccttcggcttcggtggcttggagg (SEQ ID NO: 160) are used to amplify a region of homology from *Streptomyces antibioticus* DSM 40725 genomic DNA (prepared using standard techniques) to yield 1918 bp PCR product, IR084. The first 15 bp of primers IR084.FOR and IR084.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR084 is ligated with pKC1139 digested with HindIII and EcoRI using Infusion Cloning technology to generate plasmid pIR084. Plasmid pIR084 is transferred to *Streptomyces antibioticus* DSM 40725 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of chlorothricin as described in Jia 2006. Samples of culture broth are mixed with methanol, centrifuged for 5 minutes and samples of the supernatant analysed by HPLC-UV and LCMS for production of chlorothricin. Those patches showing no production of chlorothricin (due to primary recombination into the chlorothricin PKS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Jia 2006 to assess whether they still produce chlorothricin (i.e. have reverted to original strain). Among the strains that no longer produce chlorothricin, strains that produce novel compounds are identified by LCMS and HPLC-UV.

Example 96

Generation of constructs able to induce deletion and/or expansion of the quinomycin NRPS modules and transfer to *Streptomyces lasaliensis*. Primers IR085.FOR Ggccagtgccaagcttaacttcttttccgtgggcgga (SEQ ID NO: 161) and IR085.REV Acatgattacgaattcgacgcggttggaccag (SEQ ID NO: 162) are used to amplify a region of homology from *Streptomyces lasaliensis* genomic DNA (prepared using standard techniques) to yield 1699 bp PCR product, IR085. The first 15 bp of primers IR085.FOR and IR085.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR085 is ligated with pKC1139 digested with HindIII and EcoRI using Infusion Cloning technology to generate plasmid pIR085. Plasmid pIR085 is transferred to *Streptomyces lasaliensis* by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of Quinomycin as described in Steinerova et al. 1987. Samples of culture broth are mixed with methanol, centrifuged for 5 minutes and samples of the supernatant analysed by HPLC-UV and LCMS for production of Quinomycin. Those patches showing no production of Quinomycin (due to primary recombination into the Quinomycin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Steinerova et al. 1987 to assess whether they still produce Quinomycin (i.e. have reverted to original strain). Among the strains that no longer produce Quinomycin, strains that produce novel compounds are identified by LCMS and HPLC-UV.

Example 97

Generation of constructs able to induce deletion and/or expansion of the polyoxypeptin NRPS modules and transfer to *Streptomyces* sp. MK498-98 F14. Primers IR086.FOR Ggccagtgccaagcttaccgtgtaggagaagcaccga (SEQ ID NO: 163) and IR086.REV Acatgattacgaattcccagttccggcacggt (SEQ ID NO: 164) are used to amplify a region of homology from *Streptomyces* sp. MK498-98 F14 genomic DNA (prepared using standard techniques) to yield 1413 bp PCR product, IR086. The first 15 bp of primers IR086.FOR and IR086.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR086 is ligated with pKC1139 digested with HindIII and EcoRI using Infusion Cloning technology to generate plasmid pIR086. Plasmid pIR086 is transferred to *Streptomyces* sp. MK498-98 F14 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of Polyoxypeptin as described in Du et al. 2014. Samples of culture broth are mixed with methanol, centrifuged for 5 minutes and samples of the supernatant analysed by HPLC-UV and LCMS for production of Polyoxypeptin. Those patches showing no production of Polyoxypeptin (due to primary recombination into the Polyoxypeptin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Du et al. 2014 to assess whether they still produce Polyoxypeptin (i.e. have reverted to original strain). Among the strains that no longer produce Polyoxypeptin, strains that produce novel compounds are identified by LCMS and HPLC-UV.

Example 98

Generation of constructs able to induce deletion and/or expansion of the enduracidin NRPS modules and transfer to

*Streptomyces fungicidicus* ATCC 21013. Primers IR087.FOR ggccagtgccaagcttcgtccggtcagctcggc (SEQ ID NO: 165) and IR087.REV acatgattacgaattcgccggggcgcatccggaa (SEQ ID NO: 166) are used to amplify a region of homology from *Streptomyces fungicidicus* ATCC 21013 genomic DNA (prepared using standard techniques) to yield 1915 bp PCR product, IR087. The first 15 bp of primers IR087.FOR and IR087.REV contain homology to pKC1139 digested with HindIII and EcoRI. Plasmid pKC1139 (or other temperature sensitive plasmid containing the same polylinker) is digested with HindIII and EcoRI and used as a vector for Infusion cloning. PCR IR087 is ligated with pKC1139 digested with HindIII and EcoRI using Infusion Cloning technology to generate plasmid pIR087. Plasmid pIR087 is transferred to *Streptomyces fungicidicus* ATCC 21013 by conjugation or other standard transformation method (as described in general methods). Plates are incubated until single transformant colonies are visible. Colonies are patched to agar (such as MAM agar) containing apramycin and incubated at a temperature which allows plasmid replication (for example 28° C. for pKC1139) until good growth is seen. Once stabilised, strains are transferred to solid agar containing apramycin and incubated at a higher temperature (for example 37° C. for pKC1139), at which the plasmid is unable to replicate and the primary integration is selected, before a selection of colonies are transferred again to fresh agar containing apramycin and incubating until good growth is seen. Samples are grown for production of enduracidin as described in Higashide 1968. Samples of culture broth are mixed with methanol, centrifuged for 5 minutes and samples of the supernatant analysed by HPLC-UV and LCMS for production of enduracidin. Those patches showing no production of enduracidin (due to primary recombination into the enduracidin NRPS) are then inoculated into liquid media with no antibiotics (such as TSB) and incubated at a lower temperature (for example 28° C. for pKC1139) to force the secondary recombination event with shaking until well grown. A sample is then used to inoculate a second batch of liquid media and incubated with shaking at the lower temperature until well grown. Finally, another sample is then used to inoculate a third sample of liquid media and incubated with shaking until well grown. Samples of this third growth are then diluted and spread onto agar plates to generate single colonies when incubated at this lower temperature. These colonies are patched onto solid agar plates and incubated until good growth is seen. Patches are tested by growing as described in Higashide 1968 to assess whether they still produce enduracidin (i.e. have reverted to original strain). Among the strains that no longer produce enduracidin, strains that produce novel compounds are identified by LCMS and HPLC-UV.

REFERENCES

Marshall, J. A., and Shiping, X. 1995 J. Org. Chem., 60, 7230-7237

Strässler, C., Linden, A., and Heimgartner, H. 1997. Helv. Chim. Acta. 80: 1528-1554

Becker and Rickards, Aust. J. Chem., 1984, 37, 2104

Tyler W A, Gangoli N, Gokina P, Kim H A, Covey M, Levison S W, Wood T L. J Neurosci. 2009 May 13; 29(19):6367-78. doi: 10.1523/JNEUROSCI.0234-09.2009.

Reeves C D, Rodriguez E Methods Enzymol. 2009; 459: 295-318. doi: 10.1016/S0076-6879(09)04613-8.

Staunton J, Weissman K J. Nat Prod Rep. 2001 August; 18(4):380-416.

Koehn F E. Prog Drug Res. 2008; 65:175, 177-210.

Koehn F E, Carter G T. Discov Med. 2005 April; 5(26): 159-64.

Giessen T W, Marahiel M A. FEBS Lett. 2012 Jul. 16; 586(15):2065-75. doi: 10.1016/j.febslet.2012.01.017. Epub 2012 Jan. 21.

Pfeifer B A, Khosla C. Microbiol Mol Biol Rev. 2001 March; 65(1):106-18.

Bierman M, Logan R, O'Brien K, Seno E T, Rao R N, Schoner B E. Gene. 1992 Jul. 1; 116(1):43-9.

Kendrew S G, Petkovic H, Gaisser S, Ready S J, Gregory M A, Coates N J, Nur-E-Alam M, Warneck T, Suthar D, Foster T A, McDonald L, Schlingman G, Koehn F E, Skotnicki J S, Carter G T, Moss S J, Zhang M Q, Martin C J, Sheridan R M, Wilkinson B. Metab Eng. 2013 January; 15:167-73. doi: 10.1016/j.ymben.2012.11.001. Epub 2012 Nov. 17.

Schwecke T, Aparicio J F, Molnár I, König A, Khaw L E, Haydock S F, Oliynyk M, Caffrey P, Cortés J, Lester J B, et al. Proc Natl Acad Sci USA. 1995 Aug. 15; 92(17): 7839-43.

Gaisser S, Kellenberger L, Kaja A L, Weston A J, Lill R E, Wirtz G, Kendrew S G, Low L, Sheridan R M, Wilkinson B, Galloway I S, Stutzman-Engwall K, McArthur H A, Staunton J, Leadlay P F. Org Biomol Chem. 2003 Aug. 21; 1(16):2840-7.

Li J W-H, Vederas J C. Science 2009 325(161) DOI: 10.1126/science.1168243

Cao W, Konsolaki M. J Biosci. 2011 August; 36(3):493-8.

Gerard M, Deleersnijder A, Demeulemeester J, Debyser Z, Baekelandt V. Mol Neurobiol. 2011 August; 44(1):13-27. doi: 10.1007/s12035-011-8184-2. Epub 2011 May 7.

Norville I H, Harmer N J, Harding S V, Fischer G, Keith K E, Brown K A, Sarkar-Tyson M, Titball R W. Infect Immun. 2011 November; 79(11):4299-307. doi: 10.1128/IAI.00134-11. Epub 2011 Aug. 22.

Leuzzi R, Serino L, Scarselli M, Savino S, Fontana M R, Monaci E, Taddei A, Fischer G, Rappuoli R, Pizza M. Mol Microbiol. 2005 November; 58(3):669-81.

Moro A, Ruiz-Cabello F, Fernández-Cano A, Stock R P, González A. EMBO J. 1995 Jun. 1; 14(11):2483-90.

Hoerauf A, Rascher C, Bang R, Pahl A, Solbach W, Brune K, Röllinghoff M, Bang H. Mol Microbiol. 1997 April; 24(2):421-9.

Zang N, Tang D J, Wei M L, He Y Q, Chen B, Feng J X, Xu J, Gan Y Q, Jiang B L, Tang J L. Mol Plant Microbe Interact. 2007 January; 20(1):21-30.

Kang C B, Hong Y, Dhe-Paganon S, Yoon H S. Neurosignals. 2008; 16(4):318-25. doi: 10.1159/000123041. Epub 2008 Jul. 18.

Bové J, Martínez-Vicente M, Vila M. Nat Rev Neurosci. 2011 Jul. 20; 12(8):437-52. doi: 10.1038/nrn3068.

Ruan B, Pong K, Jow F, Bowlby M, Crozier R A, Liu D, Liang S, Chen Y, Mercado M L, Feng X, Bennett F, von Schack D, McDonald L, Zaleska M M, Wood A, Reinhart P H, Magolda R L, Skotnicki J, Pangalos M N, Koehn F E, Carter G T, Abou-Gharbia M, Graziani E I. Proc Natl Acad Sci USA. 2008 Jan. 8; 105(1):33-8. Epub 2007 Dec. 27.

Chambraud B, Sardin E, Giustiniani J, Dounane O, Schumacher M, Goedert M, Baulieu E E. Proc Natl Acad Sci USA. 2010 Feb. 9; 107(6):2658-63. doi: 10.1073/pnas.0914957107. Epub 2010 Jan. 25.

Shim S, Yuan J P, Kim J Y, Zeng W, Huang G, Milshteyn A, Kern D, Muallem S, Ming G L, Worley P F. Neuron. 2009 Nov. 25; 64(4):471-83. doi: 10.1016/j.neuron.2009.09.025.

Labrande C, Velly L, Canolle B, Guillet B, Masmejean F, Nieoullon A, Pisano P. Neuroscience. 2006; 137(1):231-9. Epub 2005 Nov. 10.
Avramut M, Achim C L. Physiol Behav. 2002 December; 77(4-5):463-8.
Deleersnijder A, Van Rompuy A S, Desender L, Pottel H, Buée L, Debyser Z, Baekelandt V, Gerard M. J Biol Chem. 2011 Jul. 29; 286(30):26687-701. doi: 10.1074/jbc.M110.182303. Epub 2011 Jun. 7.
Flett et al., 1997 FEMS Micro Lett 155:223-229
Lotareva O V and Prosorov A A 2005 Doklady Biological Sciences 2006 405:226-228
Desomer J et al., 1990 Appl Environ Microbiol 56(9):2818-2825
Stephenson M and Jarrett P 1991 Biotech Tech 5(1):9-12
Goude R and Parish T 2009 Methods Mol Biol 465:203-215
Wenzel S C et al., 2005 Chem and Biol 12(3):349-356
Pfeifer B A and Khosla C, 2001 Microbiol. Mol. Biol. Rev. 65(1):106-118
Birch A W and Cullum J, 1985 J of Gen Micobiol. 131: 1299-1303
Du et al., 2011 Tetrahedron; 67(35): 6568-6575
Vasant Kumar et al., 1994 Appl Environ Microbiol.; 60(11): 4086-4093
Goh et al., 2007 BMC Biotechnology, 7:72
Garbe et al., 1994 Microbiology 140(1): 133-138
Wenzel et al., 2005 Chemistry and Biology Volume 12, Issue 3, Pages 349-356
Atkins et al., 1987 J Gen Microbiol.; 133(10):2727-31.
Aranda et al., 2010 BMC Microbiology, 10:279
Dhingra et al., 2003 Journal of Industrial Microbiology and Biotechnology, Volume 30, Issue 4, pp 195-204
Choi et al., 2006 J Microbiol Methods.; 64(3):391-7.
Love et al., 1992 Appl Environ Microbiol.; 58(4): 1376-1378.
Kopp et al., 2005 Chembiochem.; 6(7):1277-86.
Hofemeister et al., 1983 Mol Gen Genet. 189:58-68
Lessard et al., 2004 BMC Microbiology 2004, 4 1471-2180/4/15
Youngman et al., 1983 PNAS 80:2305-2309
Chen et al., 2010 Plasmid 64(2):110-7. doi:10.1016/j.plasmid.2010.05.003
Shanks et al., 2010 Plasmid 62(2): 88-97. doi:10.1016/j.plasmid.2009.05.002
Maguin et al., 1992 *J. Bacteriol.* 1992, 174(17):5633.
Sherman et al., 1986 Antibiot. September; 39(9):1270-80.
Jia et al., 2011 Bioresour Technol. November; 102(21): 10147-50
Kudo et al., 2010 ChemBioChem, Volume 11, Issue 11, pages 1574-1582
Chen et al., 2003 Chemistry & Biology, Vol. 10, 1065-1076
Yang et al., 1996 Biotech Bioeng Volume 49, Issue 4, pages 437-444
Hill et al., 2003 Chem. Commun., 1358-1359
Peiru et al., 2007 Biochemistry. July 10; 46(27):8100-9. Epub 2007 Jun. 16.
Otsuka et al., 2000 Tetrahedron 56 (2000) 8281±8286
Chen et al., 2010 Biotechnology and Bioprocess Engineering 15: 969-974 (2010)
Ikeda et al., 1998 Antimicrobial Agents and Chemotherapy, February 1988, p. 282-284
Horbal et al., 2010 Appl Microbiol Biotechnol. 2010 January; 85(4):1069-79
Tohyama et al., 2006 J. Antibiot. 59(1): 44-52
Kelly et al., 2008 Bioorganic Chemistry 36(1):4-15
Zhang et al., 2012 Electron. J. Biotechnol. vol. 15 no. 4
Nadkami et al., 1994 J Antibiot (Tokyo). 47(3):334-41.
Matsuo et al., 1997 FEMS Microbiology Letters 153(1): 83-88
Olano et al., 2004 Chem Biol. 11: 87-97
Yuan et al., 2012 J Agric Food Chem. 28; 60(12):2976-81
Haavik et al., 1978 Acta Pathologica Microbiologica Scandinavica Section B Microbiology, Volume 86B, Issue 1-6, pages 67-70
Zhang et al., 2013 Chembiochem. 14(3): 301-306.
Omura et al., 1979 J Antibiot (Tokyo). 32(4):255-61.
Sun 2002 Microbiology vol. 148 no. 2 361-371
Zhuang et al. 2006 Process Biochemistry Volume 41, Issue 2, February 2006, Pages 405-409
Kavakas et al., 1997 J Bacteriol. December 1997; 179(23): 7515-7522
Harvey et al., 2007 Chemistry & Biology Volume 14, Issue 6, Pages 703-714
Jonsbu et al., 2002 J Biotechnol. 95(2):133-44
Visser et al., 1960 Journal of Biochemical and Microbiological Technology and Engineering 2(1): 31-48
Ghatge et al., 2006 J Ind Microbiol Biotechnol. 33: 589-99
Liu et al., 2012 dx.doi.org/10.1016/j.chembiol.2011.12.018
Xue et al., 1998 Proc Natl Acad Sci USA. 95(21):12111-6.
Aparicio et al., 1999 The Journal of Biological Chemistry, 274, 10133-10139.
Machida et al., 2008 Biosci Biotechnol Biochem. 2008 November; 72(11):2946-52
Nowak-Thomson et al., 1997 Gene. 1997 Dec. 19; 204(1-2):17-24.
Takahashi et al., 2011 Nat Chem Biol. 7(7):461-8
August et al., 1998 Chem Biol. 5(2):69-79
Sohng et al., 1997 Mol Cells. 7(5):674-81
Park et al., 2009 J Ind Microbiol Biotechnol. 36(7):993-8
Li et al., 2008 The Journal of Biological Chemistry, 283, 28607-28617
Demydchuk et al., 2008 Chembiochem. 9(7):1136-45
Ogasawara et al., 2005 J Antibiot (Tokyo). 58(7):468-72
Olinyk et al., 2003 Mol Microbiol. 49(5):1179-90
Lounes et al., 1995 Curr Microbiol. 31(5):304-11
Waldron et al., 2001 Chem Biol. 8(5):487-99
Caffrey et al., 2001 Chemistry & Biology 8: 713-723
Qu X et al., 2001 Angewandte Chemie International Edition 50(41):9651-9654
Du Y et al., 2011 Tetrahedron 67 (35), 6568-6575
Wenzel et al., 2008 Chembiochem. November 3; 9(16): 2711-21
Sun et al., 2006 Microbiology. 152(Pt 12):3507-15
Haydock et al., 2005 Microbiology. 151(Pt 10):3161
Kaneko et al., 1989 The Journal of Antibiotics. Vol. 42 No. 2 P 236-241
Praseuth et al., 2008 Biotechnol Prog. 2008 November-December; 24(6):1226-31. doi: 10.1002/btpr.34
Hopf et al., 1990 Appl Microbiol Biotechnol. 32(5):499-504
Arguelles-Arias et al., 2009 Microbial Cell Factories 8:63
Miyamoto et al., 2011 Microbiology 157: 2266-2275
Waitz et al., 1981 The Journal of Antibiotics. Vol. 34 No. 9 P 1101-1106
Arawaka et al., 2007 Microbiology vol. 153 no. 6 1817-1827
Schneider et al., 2007 J Nat Prod. 70(9):1417-23
Kassem El-Sayed et al., 2003 Chemistry & Biology Volume 10, Issue 5, Pages 419-430
Takenaka et al., 1998 FEMS Microbiology Letters November 1998; 167(1):95-100
Zhang et al., 2008 J Med Chem. 51(18):5494-7
Kim et al., 2005 J Antibiot (Tokyo). 58(3):196-201
Lim et al., 2009 The Journal of Biological Chemistry, 284, 29746-29756.

Jia et al., 2006 Chemistry & Biology. Volume 13, Issue 6, Pages 575-585

Steinerova et al. 1987 Folia Microbiol (Praha). 1987; 32(1): 1-5.

Du et al. 2014 BMC Microbiology 2014, 14:30 www.biomedcentral.com/1471-2180/14/30

Higashide et al., 1968 J Antibiot 21, 126-137

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps. All patents and patent applications referred to herein are incorporated by reference in their entirety.

The invention claimed is:

1. A process for producing a library of two or more mutant modular polyketide synthase encoding strains of cells which express mutant functional polyketide synthases having an increased or reduced number of modules and which have been formed by recombination events which process comprises the steps of:
   (i) contacting a modular polyketide synthase encoding host strain of cells which is a homologous host for the polyketide synthase with a vector which includes a selectable marker, an inducible origin of replication and a portion of DNA homologous to a portion of DNA within the polyketide synthase, thereby to integrate the vector into cells of the strain within the polyketide synthase encoding gene cluster of the genome of said cells, such that the vector integrates into cells of the strain within the polyketide synthase encoding gene cluster via a single crossover event;
   (ii) applying selective pressure to the cells into which the vector has been integrated by inducing the origin of replication so that the cells eliminate the selectable marker through one or more recombination events leading to a mixture of strains of cells in which the cells of the strains express mutant functional polyketide synthases having an increased or reduced number of modules as compared with the strain of step (i); and
   (iii) screening for or selecting two or more strains of cells that lack the selectable marker and which express mutant functional polyketide synthases having an increased or reduced number of modules.

2. A process according to claim 1 which is a process for producing a library of three or more mutant modular polyketide synthase encoding strains of cells and wherein step (iii) consists of screening for or selecting three or more strains of cells that lack the selectable marker and which express mutant functional polyketide synthases having an increased or reduced number of modules.

3. A process according to claim 1 wherein the inducible origin of replication is a temperature sensitive origin of replication.

4. A process according to claim 1 wherein the strain of cells of step (i) expresses one or more post polyketide synthase (PKS) genes.

5. A process according to claim 1 wherein the strain of cells of step (i) is an actinomycete strain.

6. A process according to claim 1 wherein the polyketide synthase of step (i) is a polyketide synthase capable of producing rapamycin.

7. A process according to claim 1 wherein the vector includes a portion of DNA homologous to a portion of DNA within the polyketide synthase such that the vector integrates into the strain within a linker region between modules.

8. A process according to claim 1 wherein the vector includes a portion of DNA homologous to a portion of DNA within the polyketide synthase such that the vector integrates into the strain within a module.

9. A process according to claim 8 wherein the vector includes a portion of DNA homologous to a portion of DNA within the polyketide synthase such that the vector integrates into the strain within the ketosynthase (KS) or acyl carrier protein (ACP) domains of a module.

10. A process according to claim 1 wherein the vector is a plasmid.

11. A process according to claim 1 wherein the selectable marker is an antibiotic resistance gene.

12. A process according to claim 1 which is a process for producing a library of two or more mutant modular polyketide synthase encoding strains of cells which express mutant functional polyketide synthases having a reduced number of modules.

13. A process according to claim 1 which is a process for producing a library of two or more mutant modular polyketide synthase encoding strains of cells which express mutant functional polyketide synthases having an increased number of modules.

14. A process according to claim 1 further comprising the step of isolating at least one cell that lacks the selectable marker and which expresses a mutant functional polyketide synthase having an increased or reduced number of modules and culturing that at least one cell to obtain a strain.

15. A process according to claim 1 wherein the polyketide synthase is a rapamycin synthase.

16. A process for producing a polyketide which comprises culturing a polyketide synthase expressing strain obtained or obtainable according to the process of claim 1, in the presence of one or more starter acids and other necessary feed materials and optionally isolating the polyketide.

17. A process according to claim 1 wherein the portion of DNA which is homologous is at least 500 base pairs in length.

18. A non-natural, polyketide synthase producing strain obtained or obtainable according to the process of claim 1, wherein the polyketide synthase has an increased or reduced number of modules as compared to a wild type polyketide synthase.

* * * * *